(12) United States Patent
Langenfeld et al.

(10) Patent No.: US 11,254,901 B2
(45) Date of Patent: Feb. 22, 2022

(54) SYSTEM AND METHOD FOR PRINTING TISSUE

(71) Applicant: DEKA Products Limited Partnership, Manchester, NH (US)

(72) Inventors: Christopher C. Langenfeld, Nashua, NH (US); David D. B. Cannan, Manchester, NH (US); Dirk A. van der Merwe, Canterbury, NH (US); Jonathan Parker, Henniker, NH (US); John C. Anastasiou, New Boston, NH (US); Michael C. Tilley, Amherst, NH (US); David Blumberg, Jr., Deerfield, NH (US)

( * ) Notice: Subject to any disclaimer, the term of this patent is extended or adjusted under 35 U.S.C. 154(b) by 318 days.

(21) Appl. No.: 15/648,391

(22) Filed: Jul. 12, 2017

(65) Prior Publication Data

US 2017/0369827 A1    Dec. 28, 2017
US 2020/0325430 A9    Oct. 15, 2020

Related U.S. Application Data

(60) Provisional application No. 62/361,214, filed on Jul. 12, 2016, provisional application No. 62/361,209, filed on Jul. 12, 2016.

(51) Int. Cl.
*C12M 3/00* (2006.01)
*C12M 1/32* (2006.01)
(Continued)

(52) U.S. Cl.
CPC .............. *C12M 21/08* (2013.01); *A61F 2/06* (2013.01); *A61L 27/222* (2013.01);
(Continued)

(58) Field of Classification Search
CPC ........ C12M 21/08; C12M 33/00; C12M 1/26; C12M 3/00; C12M 33/06; B33Y 80/00;
(Continued)

(56) References Cited

U.S. PATENT DOCUMENTS

| 5,156,053 A | 10/1992 | Shiraishi et al. |
| 6,053,052 A | 4/2000 | Starastovic |

(Continued)

FOREIGN PATENT DOCUMENTS

| CA | 2685964 | 5/2011 |
| EP | 2679669 | 1/2014 |

(Continued)

OTHER PUBLICATIONS

PCT/US2017/041791, Notification Concerning Transmittal of International Preliminary Report on Patentability (Chapter I of the Patent Cooperation Treaty), dated Jan. 24, 2019.

(Continued)

*Primary Examiner* — Michael M. Robinson
(74) *Attorney, Agent, or Firm* — Kathleen Chapman

(57) ABSTRACT

A system and method for printing cells in a medium. A multi-dimensional printer, stably constructed of low-mass parts, can include a computer numerically controlled system that can enable motors driving delivery systems. The motors can include encoders that can enable achieving arbitrary resolution. The motors can drive ballscrews to enable linear motion of delivery systems, and the delivery systems can enable printing of a biological material in a pre-selected pattern in a petri dish. The petri dish can accommodate a medium such as a gel, and can further accommodate a vision system that can detect actual position and deflection of the delivery system needle. The printer can accommodate multiple delivery systems and therefore multiple needles of various sizes.

8 Claims, 165 Drawing Sheets

(51) Int. Cl.

| | | |
|---|---|---|
| C12N 5/071 | (2010.01) | |
| A61L 27/22 | (2006.01) | |
| A61L 27/36 | (2006.01) | |
| A61L 27/38 | (2006.01) | |
| A61F 2/06 | (2013.01) | |
| C12M 1/26 | (2006.01) | |
| B01L 3/00 | (2006.01) | |
| B01L 3/02 | (2006.01) | |
| B29C 67/00 | (2017.01) | |
| B33Y 10/00 | (2015.01) | |
| B33Y 70/00 | (2020.01) | |
| B29C 64/106 | (2017.01) | |
| B33Y 80/00 | (2015.01) | |
| G01N 35/10 | (2006.01) | |
| B29L 31/00 | (2006.01) | |
| B29C 64/393 | (2017.01) | |
| G06F 113/10 | (2020.01) | |

(52) U.S. Cl.
CPC ......... *A61L 27/225* (2013.01); *A61L 27/3633* (2013.01); *A61L 27/3808* (2013.01); *A61L 27/3813* (2013.01); *A61L 27/3826* (2013.01); *B01L 3/0268* (2013.01); *B01L 3/502761* (2013.01); *B29C 64/106* (2017.08); *B29C 67/00* (2013.01); *B33Y 10/00* (2014.12); *B33Y 70/00* (2014.12); *B33Y 80/00* (2014.12); *C12M 1/26* (2013.01); *C12M 3/00* (2013.01); *C12M 33/00* (2013.01); *C12M 33/06* (2013.01); *C12N 5/0671* (2013.01); *A61L 2430/34* (2013.01); *B29C 64/393* (2017.08); *B29L 2031/7532* (2013.01); *G01N 2035/1041* (2013.01); *G06F 2113/10* (2020.01)

(58) Field of Classification Search
CPC ....... B33Y 70/00; B33Y 10/00; B29C 64/106; B29C 67/00; B01L 3/0268; B01L 3/502761; A61F 2/06; A61L 27/3826; A61L 27/3813; A61L 27/3808; A61L 27/3633; A61L 27/225; A61L 27/222; A61L 2430/34; C12N 5/0671; B29L 2031/7532; G01N 2035/1041
See application file for complete search history.

(56) References Cited

U.S. PATENT DOCUMENTS

| | | | |
|---|---|---|---|
| 6,103,528 A | 8/2000 | An et al. | |
| 6,470,225 B1 | 10/2002 | Yutkowitz | |
| 6,767,928 B1 | 7/2004 | Murphy et al. | |
| 6,936,311 B2 | 8/2005 | Ringeisen et al. | |
| 6,942,830 B2 | 9/2005 | Mulhaupt et al. | |
| 6,986,739 B2 | 1/2006 | Warren et al. | |
| 6,993,406 B1 | 1/2006 | Cesarano, III et al. | |
| 7,051,654 B2 | 5/2006 | Boland et al. | |
| 7,174,282 B2 | 2/2007 | Hollister et al. | |
| 7,445,441 B2 | 11/2008 | West et al. | |
| 7,509,183 B2 | 3/2009 | Lin et al. | |
| 7,615,373 B2 | 11/2009 | Simpson et al. | |
| 7,625,198 B2 | 12/2009 | Lipson et al. | |
| 7,780,897 B2 | 8/2010 | Wicker et al. | |
| 7,857,756 B2 | 12/2010 | Warren et al. | |
| 8,143,055 B2 | 3/2012 | Forgacs et al. | |
| 8,197,743 B2 | 6/2012 | Wicker et al. | |
| 8,198,086 B2 | 6/2012 | Koga et al. | |
| 8,241,905 B2 | 8/2012 | Forgacs et al. | |
| 8,507,263 B2 | 8/2013 | Asnaghi et al. | |
| 8,579,620 B2 | 11/2013 | Wu | |
| 8,586,345 B2 | 11/2013 | Simpson et al. | |
| 8,639,484 B2 | 1/2014 | Sun et al. | |
| 8,691,274 B2 | 4/2014 | Xu et al. | |
| 8,691,974 B2 | 4/2014 | Gatenholm et al. | |
| 8,728,807 B2 | 5/2014 | Forgacs et al. | |
| 8,747,880 B2 | 6/2014 | Forgacs et al. | |
| 8,817,332 B2 | 8/2014 | Wu | |
| 8,852,932 B2 | 10/2014 | Forgacs et al. | |
| 8,931,880 B2 | 1/2015 | Murphy et al. | |
| 9,005,972 B2 | 4/2015 | Xu et al. | |
| 9,011,754 B2 | 4/2015 | Leong et al. | |
| 9,039,998 B2 | 5/2015 | Guillemot et al. | |
| 9,149,952 B2 | 10/2015 | Murphy et al. | |
| 9,222,932 B2 | 12/2015 | Shepherd et al. | |
| 9,227,339 B2 | 1/2016 | Murphy et al. | |
| 9,242,031 B2 | 1/2016 | Bonassar et al. | |
| 9,301,925 B2 | 4/2016 | Xu et al. | |
| 9,303,245 B2 | 4/2016 | Rivron et al. | |
| 9,315,043 B2 | 4/2016 | Murphy et al. | |
| 9,442,105 B2 | 9/2016 | Shepherd et al. | |
| 9,499,779 B2 | 11/2016 | Murphy et al. | |
| 9,556,415 B2 | 1/2017 | Forgacs et al. | |
| 2003/0120183 A1 | 6/2003 | Simmons | |
| 2004/0219668 A1 | 11/2004 | Frei | |
| 2004/0253365 A1* | 12/2004 | Warren ................ | A61B 5/0066 427/2.1 |
| 2005/0079620 A1 | 4/2005 | Eberhard et al. | |
| 2005/0230557 A1 | 10/2005 | Aghili | |
| 2007/0216334 A1 | 9/2007 | Jones | |
| 2007/0227270 A1 | 10/2007 | Mennenga | |
| 2008/0192104 A1* | 8/2008 | Nye ...................... | B41J 3/4073 347/110 |
| 2008/0281533 A1 | 11/2008 | Galiot et al. | |
| 2009/0142836 A1 | 6/2009 | Wang et al. | |
| 2009/0208466 A1 | 8/2009 | Yoo et al. | |
| 2010/0190254 A1 | 7/2010 | Chian et al. | |
| 2011/0091926 A1 | 4/2011 | Frerich | |
| 2011/0177590 A1 | 7/2011 | Clyne et al. | |
| 2011/0319868 A1 | 12/2011 | Hiles | |
| 2012/0022441 A1 | 1/2012 | Kelly et al. | |
| 2012/0116568 A1* | 5/2012 | Murphy .................. | B41J 3/407 700/118 |
| 2013/0164339 A1 | 6/2013 | Murphy et al. | |
| 2013/0177972 A1 | 7/2013 | Green et al. | |
| 2013/0190210 A1 | 7/2013 | Murphy et al. | |
| 2013/0238257 A1 | 9/2013 | Rajamani et al. | |
| 2013/0304233 A1 | 11/2013 | Dean et al. | |
| 2013/0345794 A1 | 12/2013 | Khatiwala et al. | |
| 2014/0012225 A1 | 1/2014 | Yoo et al. | |
| 2014/0052285 A1 | 2/2014 | Butcher et al. | |
| 2014/0099709 A1 | 4/2014 | Presnell et al. | |
| 2014/0228970 A1 | 8/2014 | Boland | |
| 2014/0330418 A1 | 11/2014 | Wu | |
| 2014/0330421 A1 | 11/2014 | Wu | |
| 2015/0004273 A1 | 1/2015 | Forgacs et al. | |
| 2015/0017140 A1 | 1/2015 | Bhatia et al. | |
| 2015/0037445 A1 | 2/2015 | Murphy et al. | |
| 2015/0084956 A1 | 3/2015 | Wu | |
| 2015/0088291 A1 | 3/2015 | Wu | |
| 2015/0105891 A1* | 4/2015 | Golway ................. | G06F 17/50 700/98 |
| 2015/0119994 A1 | 4/2015 | Kang et al. | |
| 2015/0224226 A1 | 8/2015 | Bhatia et al. | |
| 2015/0282885 A1 | 10/2015 | King et al. | |
| 2015/0307728 A1 | 10/2015 | Omenetto et al. | |
| 2015/0335417 A1 | 11/2015 | Birla | |
| 2015/0342720 A1 | 12/2015 | Koç et al. | |
| 2015/0344828 A1 | 12/2015 | Forgacs et al. | |
| 2015/0351896 A1 | 12/2015 | D'lima et al. | |
| 2015/0376560 A1 | 12/2015 | Finlay et al. | |
| 2016/0024461 A1 | 1/2016 | Sun et al. | |
| 2016/0040132 A1 | 2/2016 | Sears et al. | |
| 2016/0046832 A1 | 2/2016 | Wroblesky et al. | |
| 2016/0083681 A1* | 3/2016 | Tavana .................. | C12M 21/08 264/308 |
| 2016/0136895 A1 | 5/2016 | Beyer et al. | |
| 2017/0198252 A1* | 7/2017 | Mironov ................ | C12N 5/00 |

(56) References Cited

U.S. PATENT DOCUMENTS

2018/0169947 A1* 6/2018 Jessen .................. B29C 64/188
2019/0162777 A1  5/2019 Chiang

FOREIGN PATENT DOCUMENTS

| EP | 3190171 | 7/2017 |
|---|---|---|
| GB | 2478801 | 5/2012 |
| WO | WO 2005/081970 | 9/2005 |
| WO | WO 2008/069759 | 6/2008 |
| WO | WO 2009/154466 | 12/2009 |
| WO | WO 2011/097330 | 8/2011 |
| WO | WO 2011/107599 | 9/2011 |
| WO | WO 2011/116125 | 9/2011 |
| WO | WO 2012/122105 | 9/2012 |
| WO | WO 2013/096741 | 6/2013 |
| WO | WO 2013/158508 | 10/2013 |
| WO | WO 2013/192290 | 12/2013 |
| WO | WO 2014/039427 | 3/2014 |
| WO | WO 2014/085725 | 6/2014 |
| WO | WO 2014/110590 | 7/2014 |
| WO | WO 2014/151921 | 9/2014 |
| WO | WO 2014/194180 | 12/2014 |
| WO | WO 2014/197999 | 12/2014 |
| WO | WO 2015/054577 | 4/2015 |
| WO | WO 2015/129881 | 9/2015 |
| WO | WO 2015/158700 | 10/2015 |
| WO | WO 2015/168528 | 11/2015 |
| WO | WO 2015/173020 | 11/2015 |
| WO | WO 2015/198025 | 12/2015 |
| WO | WO 2016/012583 | 1/2016 |
| WO | WO 2016/019078 | 2/2016 |
| WO | WO 2016/022830 | 2/2016 |
| WO | WO 2016/036275 | 3/2016 |

OTHER PUBLICATIONS

International Search Report, Int. App. # PCT/US2017/041791, dated Dec. 15, 2017.
Leak Testing Case Studies: Small Medical Device Leak Test Machine, http://tqc.co.uk/leak-testing/leak-testing-small-medical-device-leak-test-machine.php, Jun. 29, 2017.

* cited by examiner

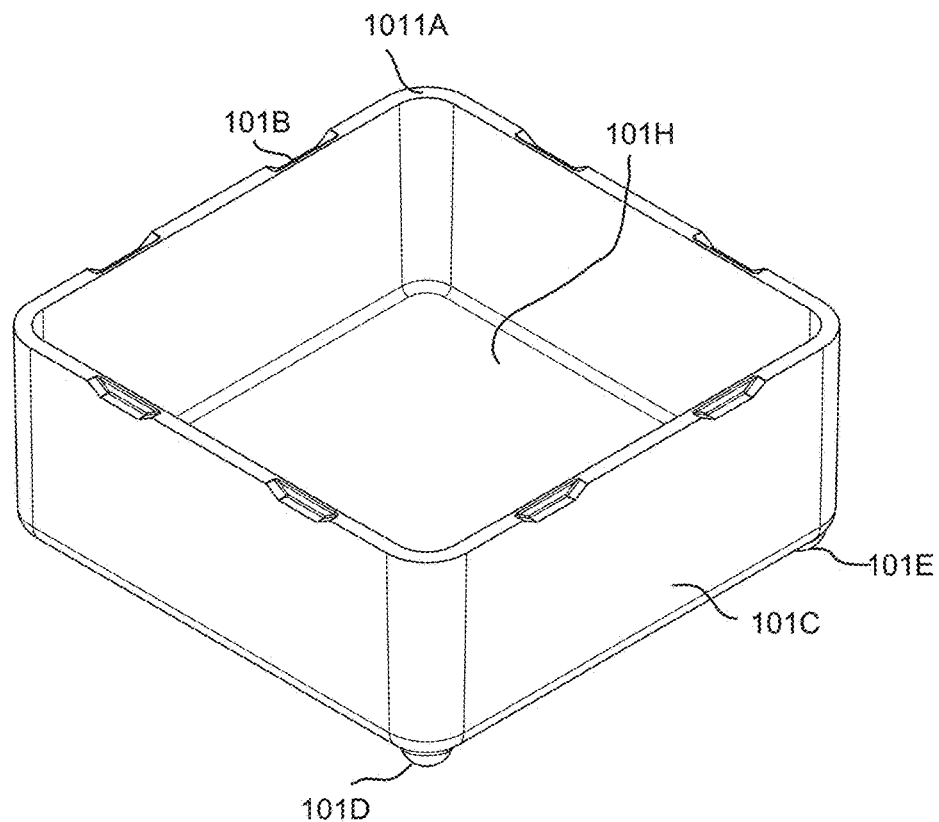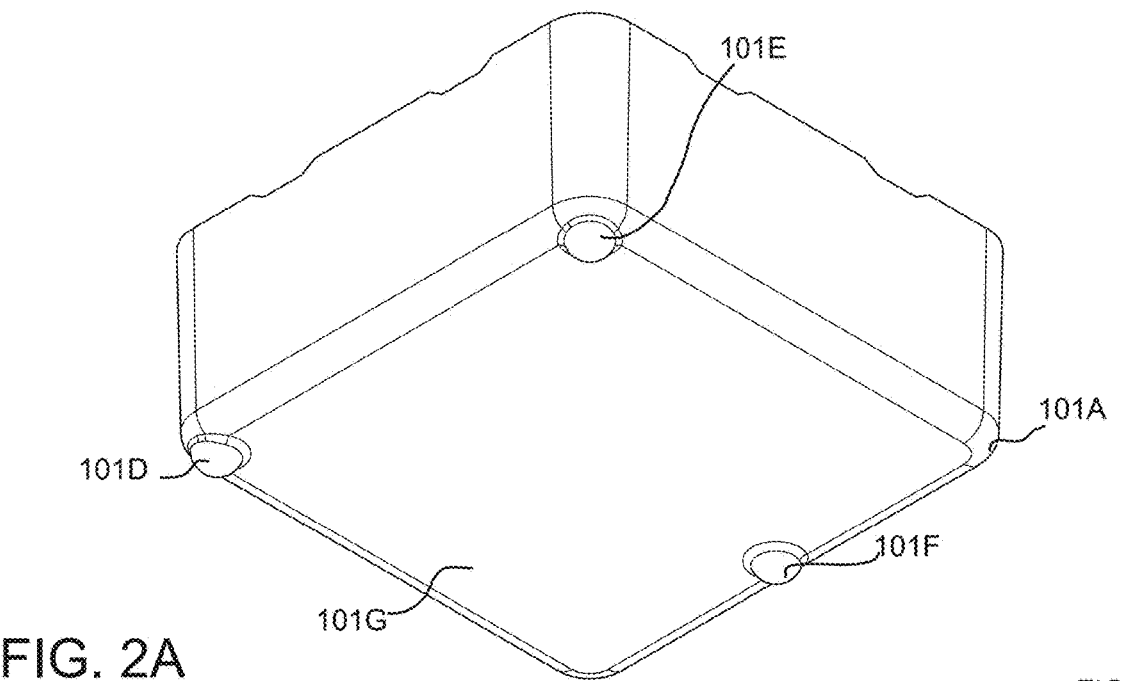
FIG. 2A
FIG. 2A

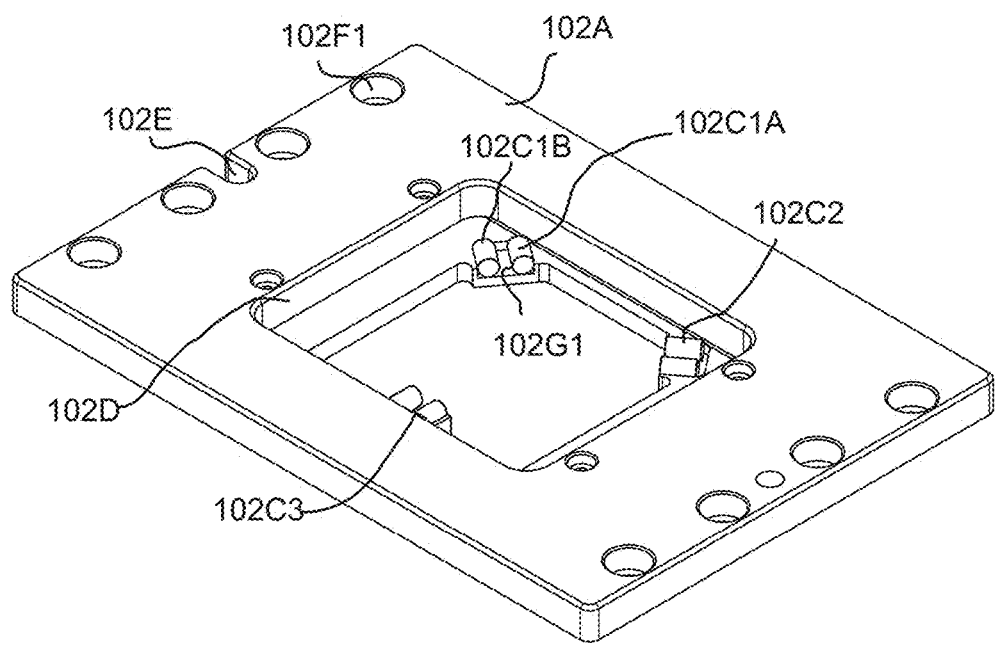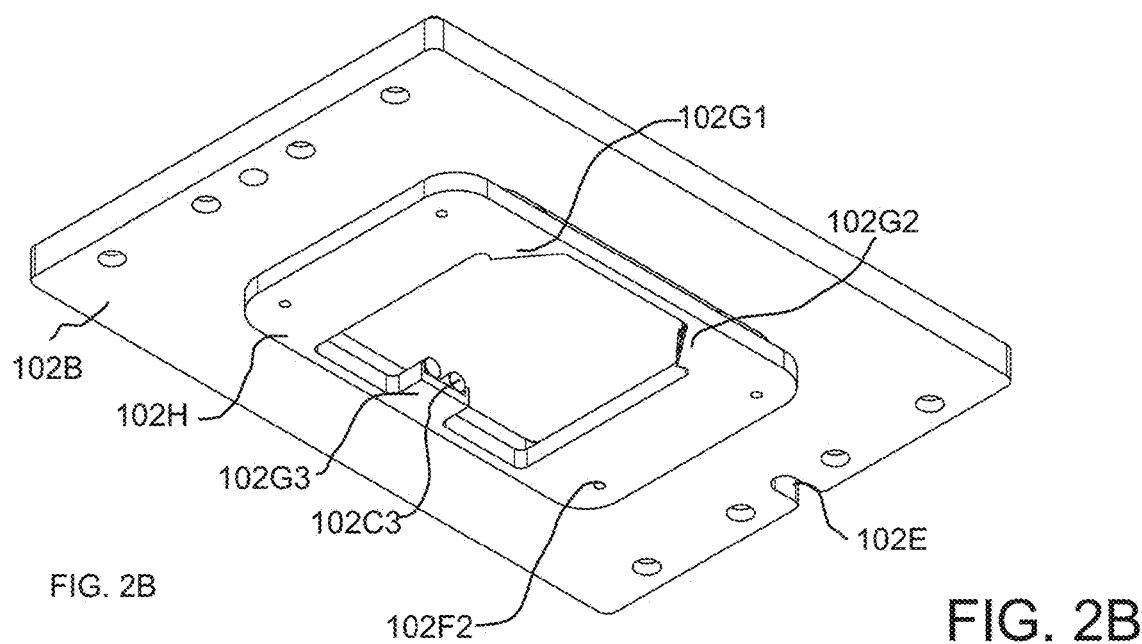
FIG. 2B

109A-C2
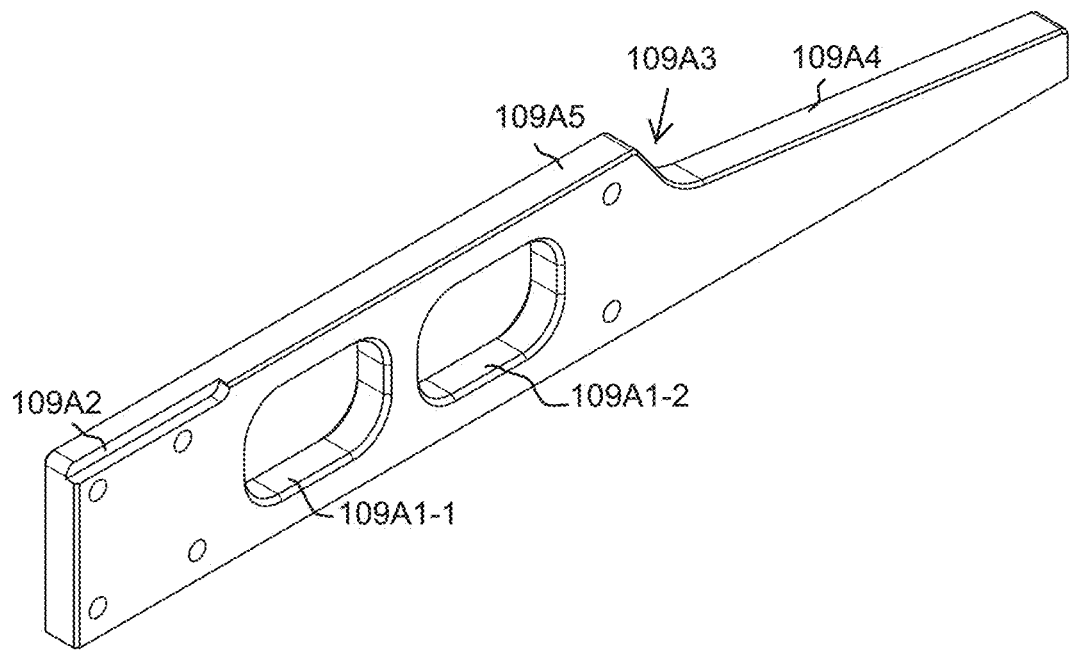
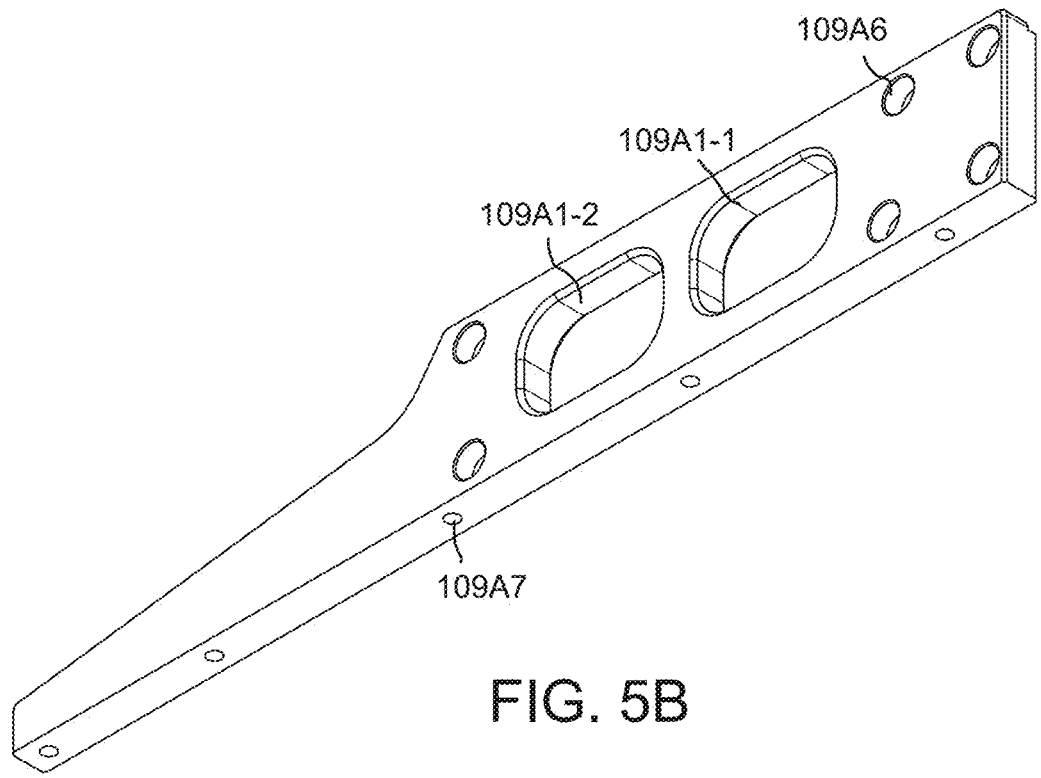
FIG. 5B

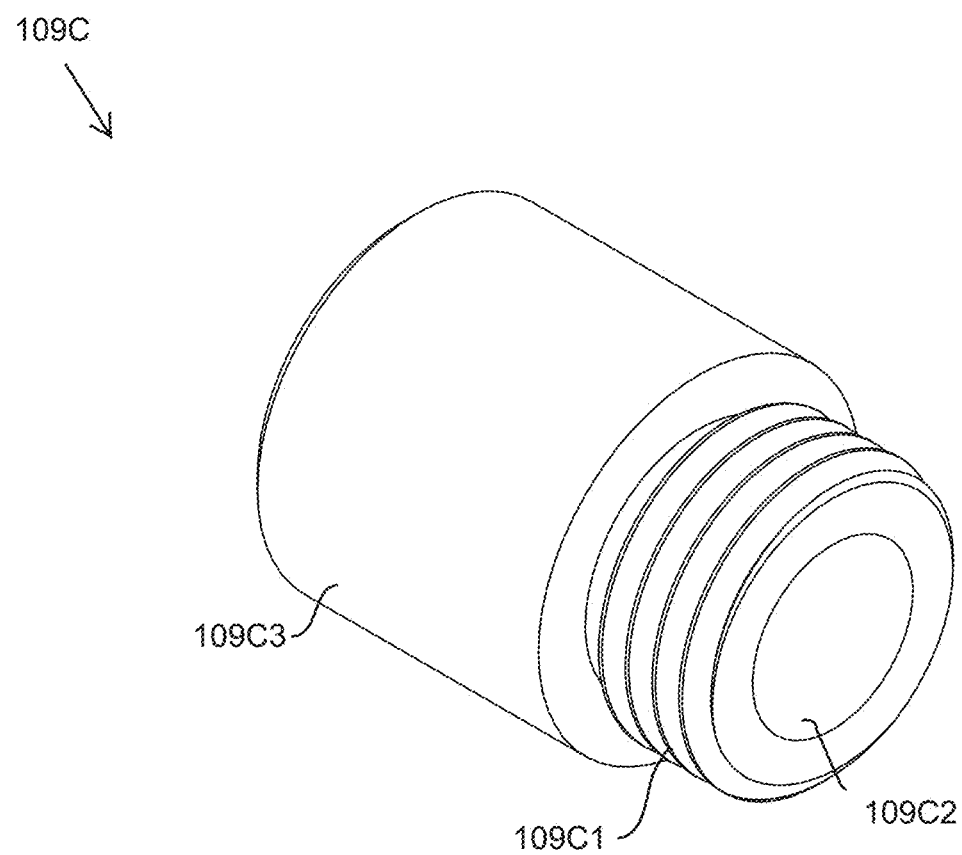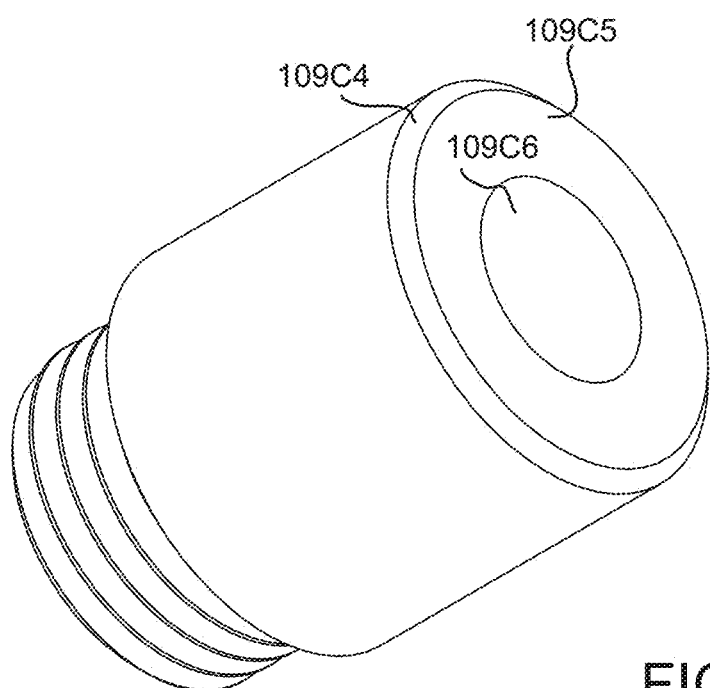
FIG. 8

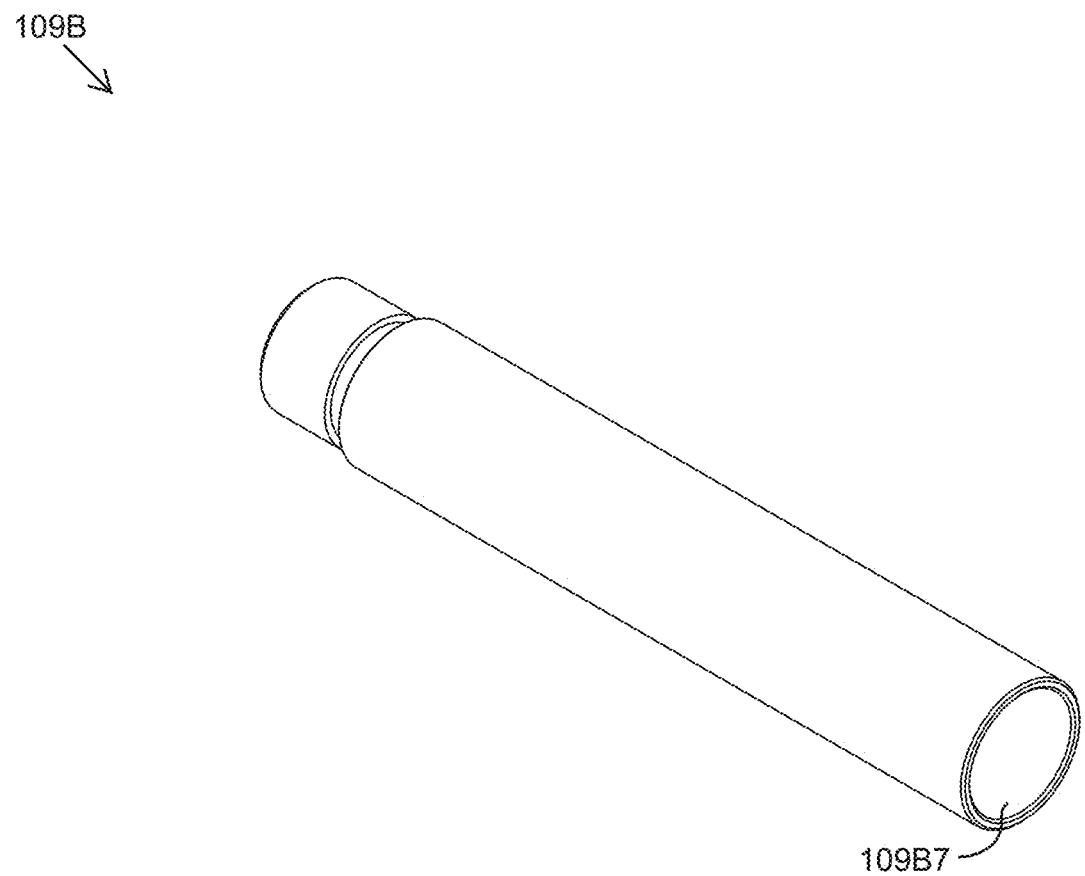
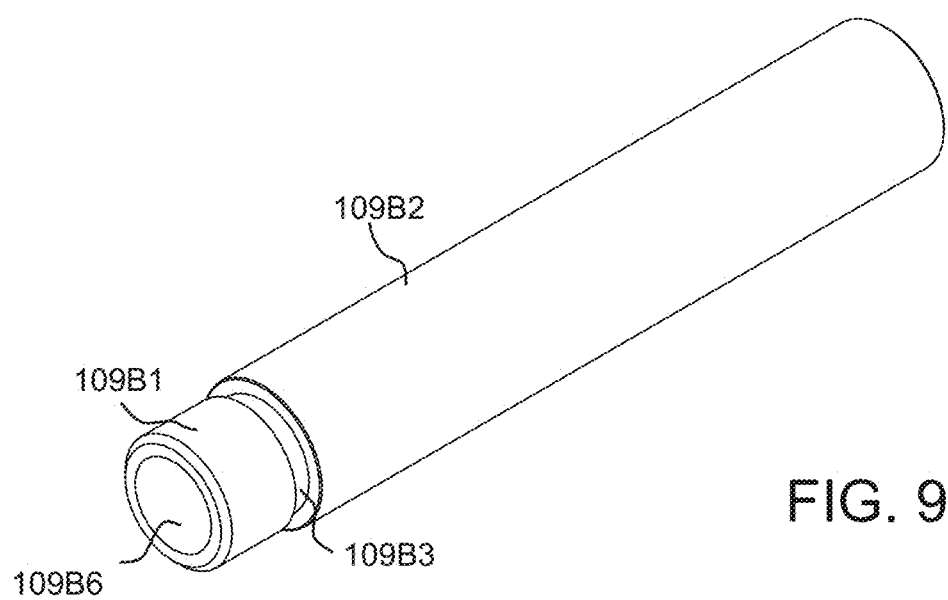
FIG. 9

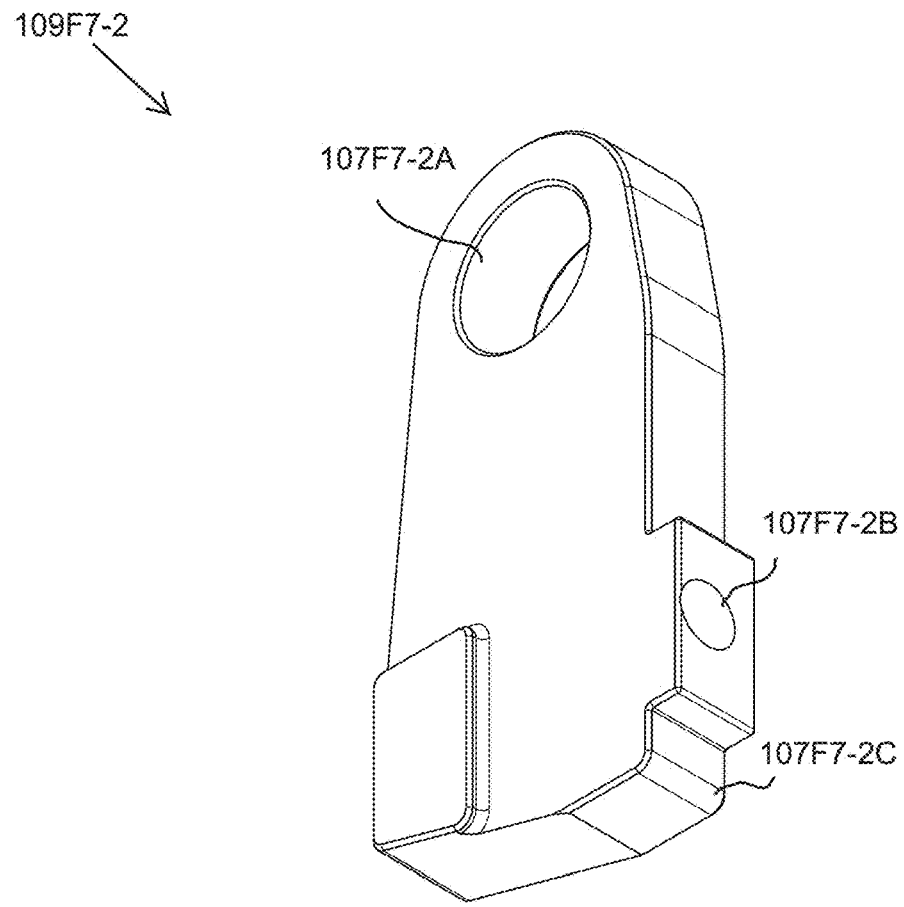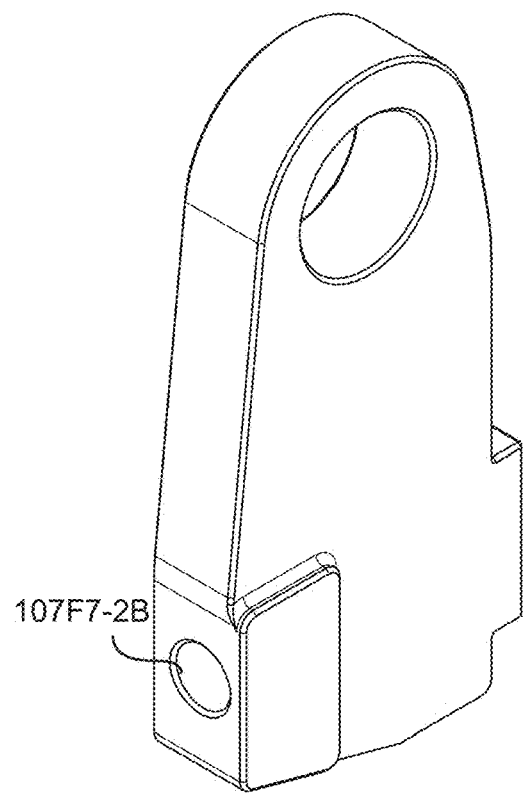
FIG. 12A

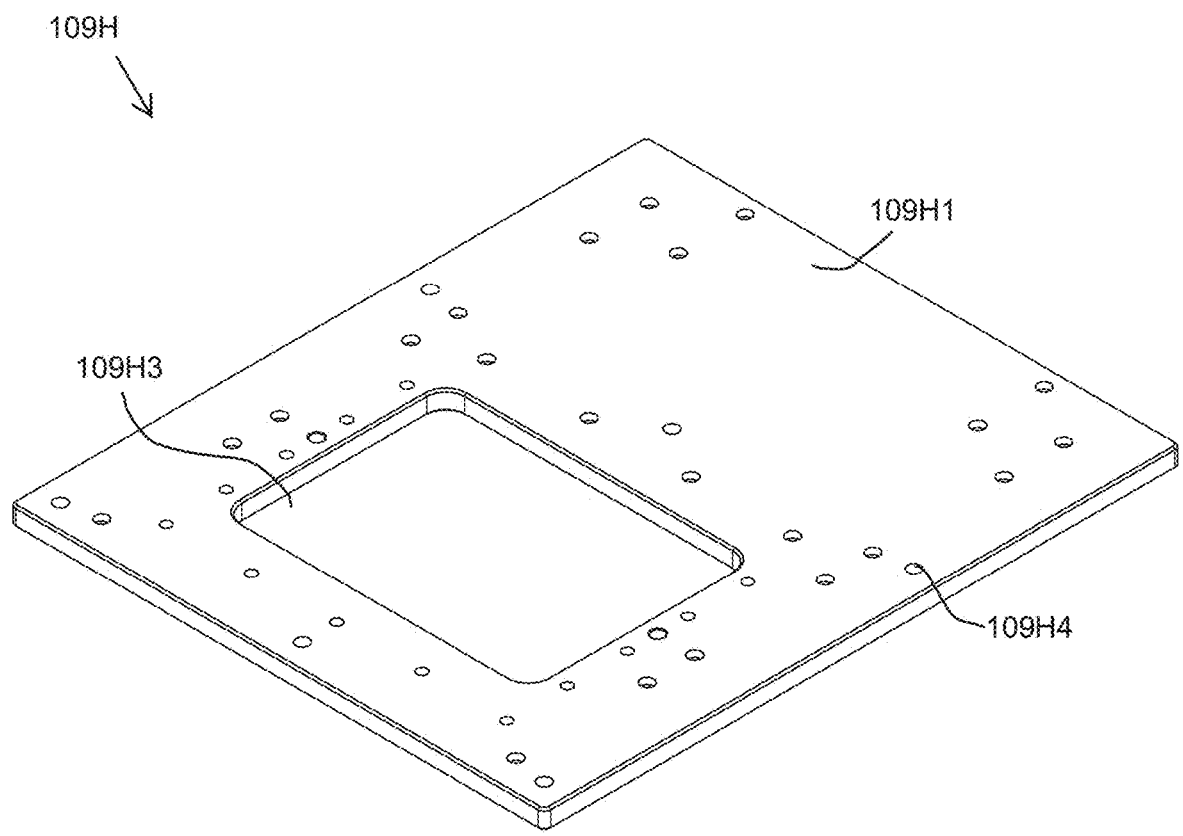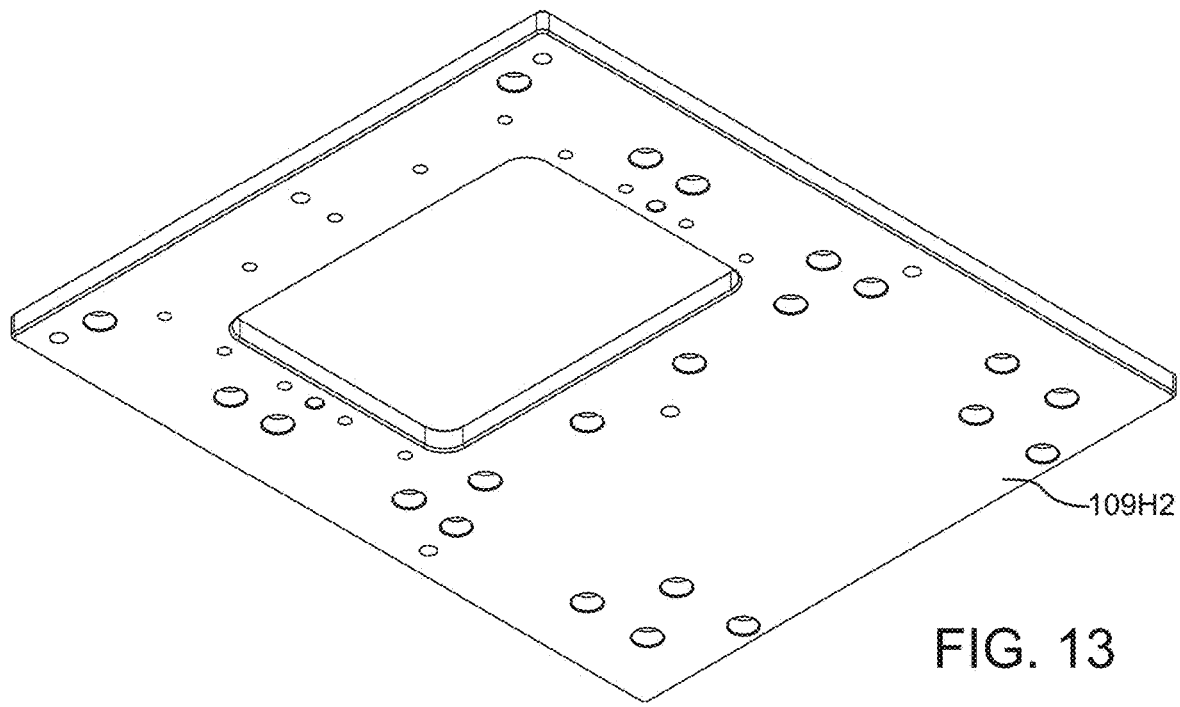
FIG. 13

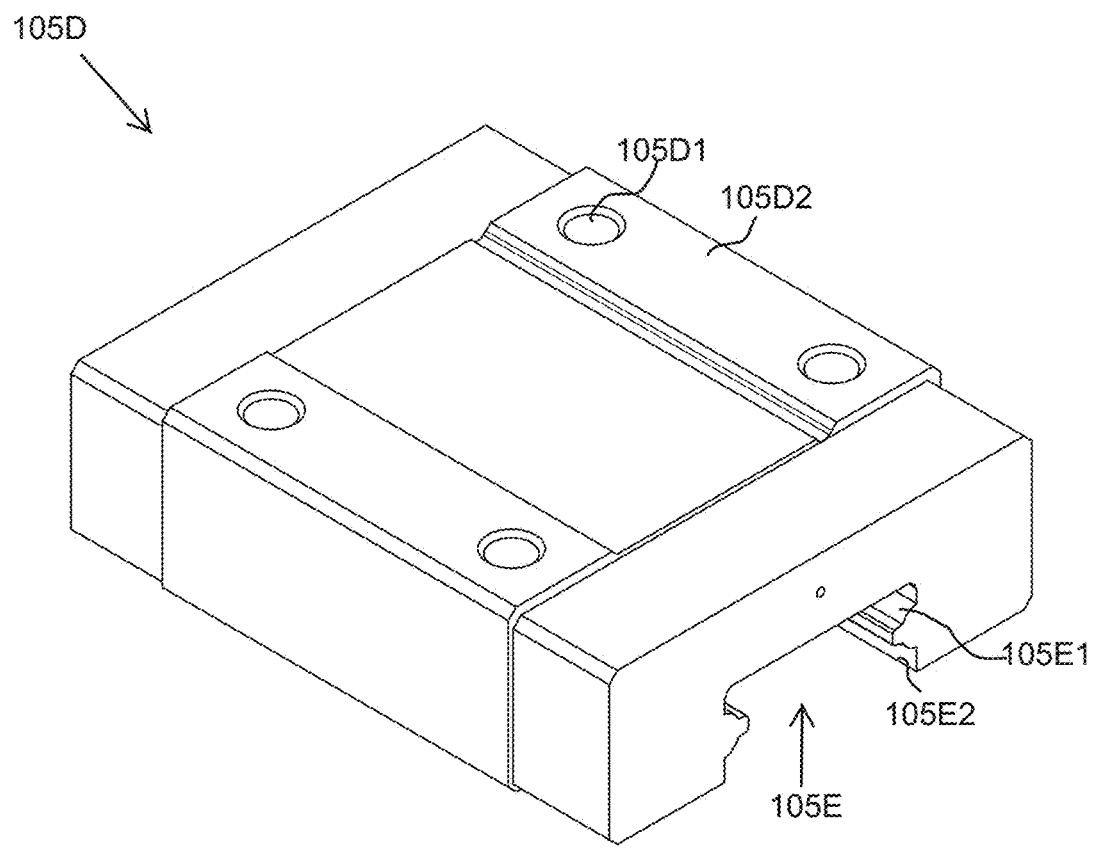
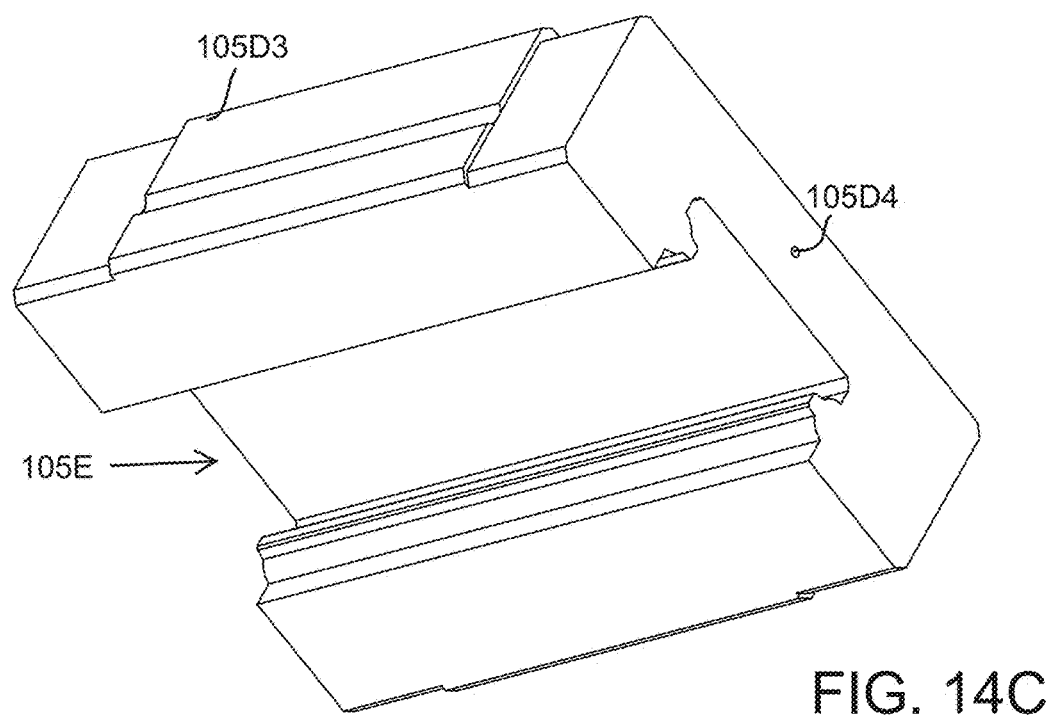
FIG. 14C

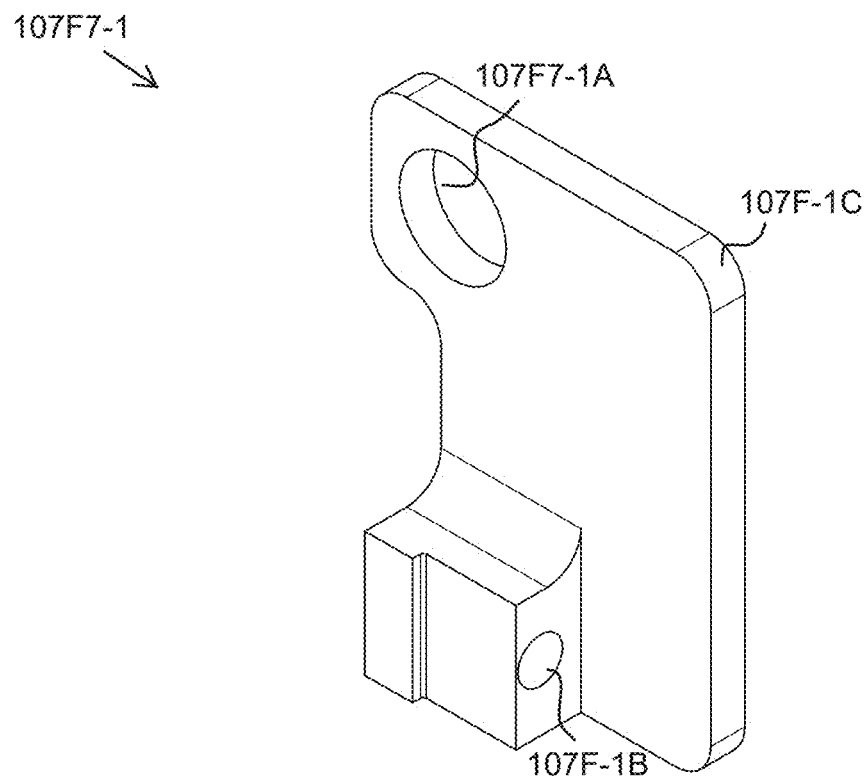
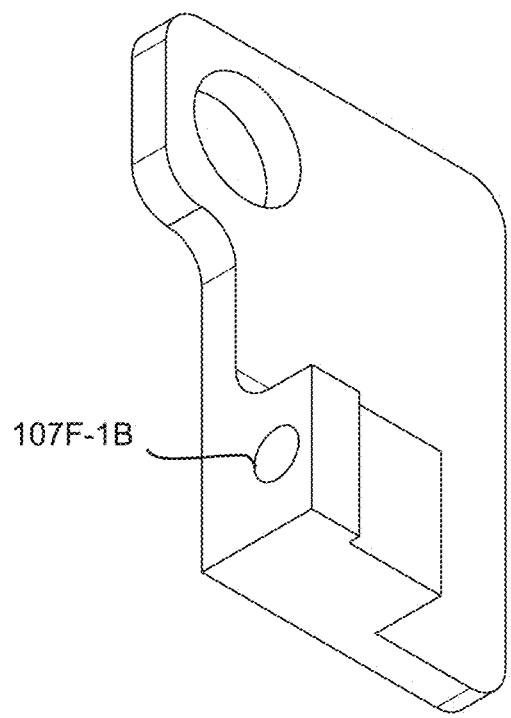
FIG. 16A

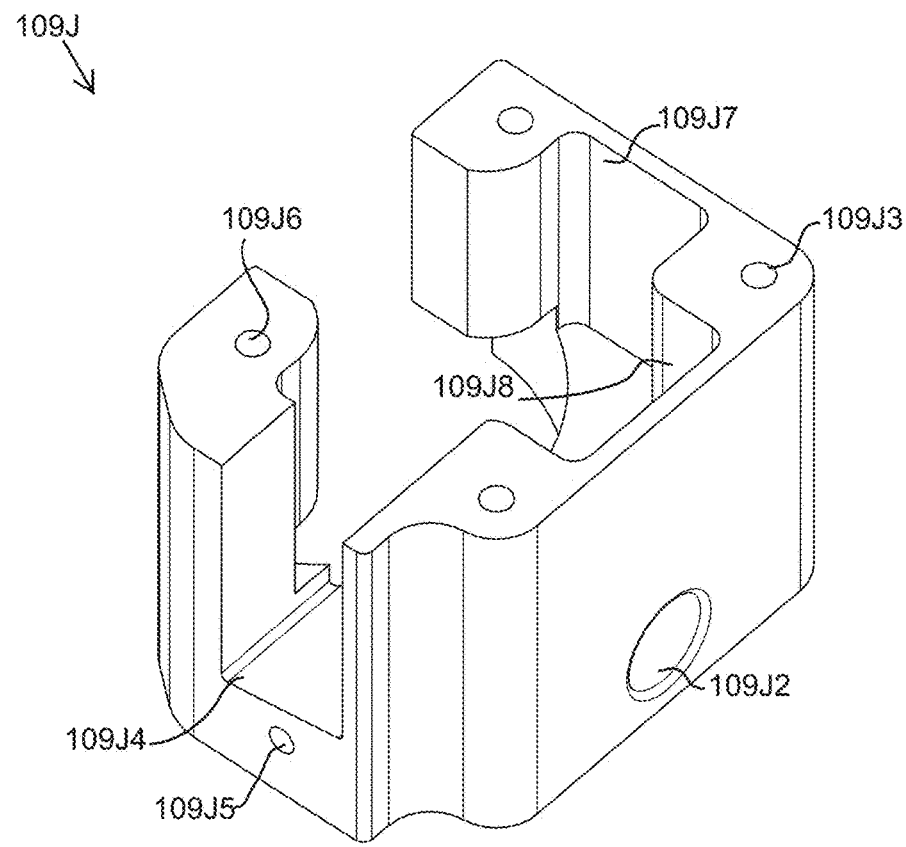
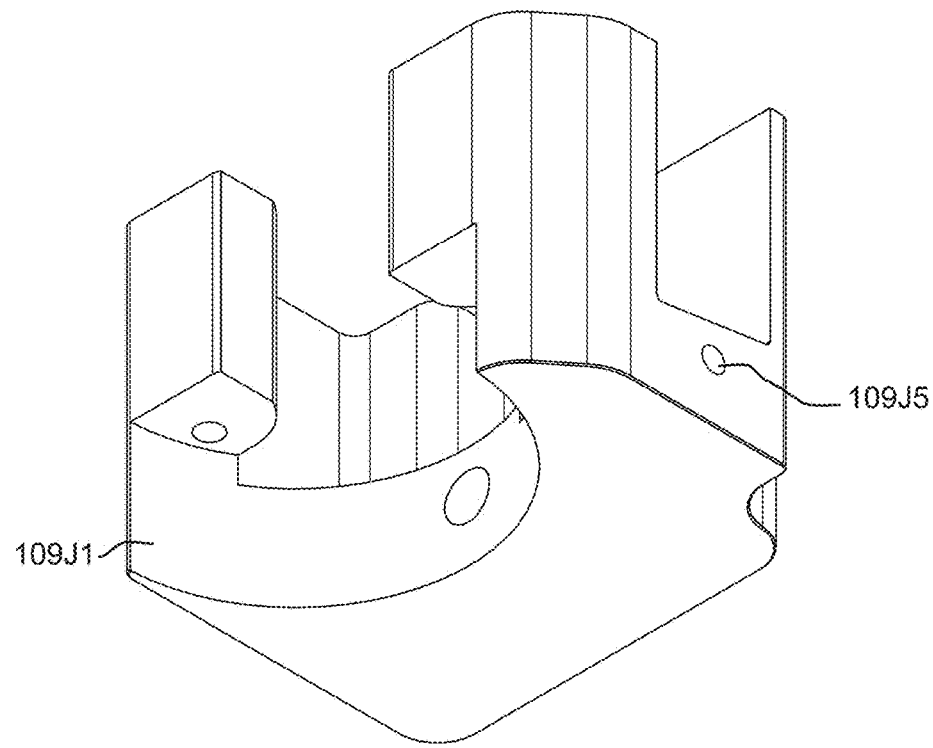
FIG. 20

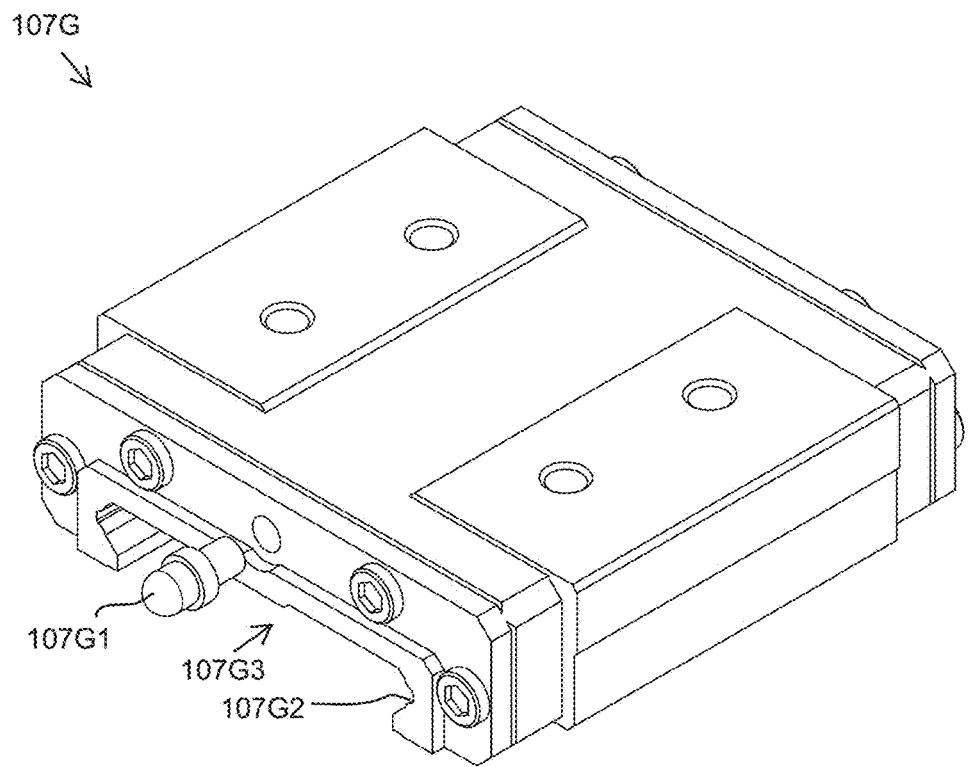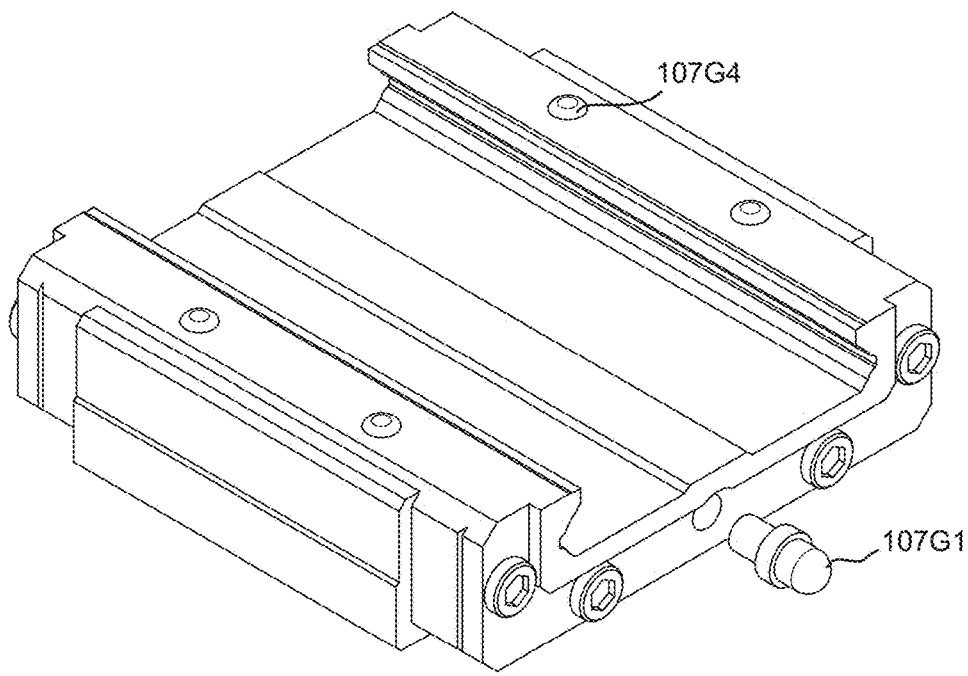
FIG. 21A

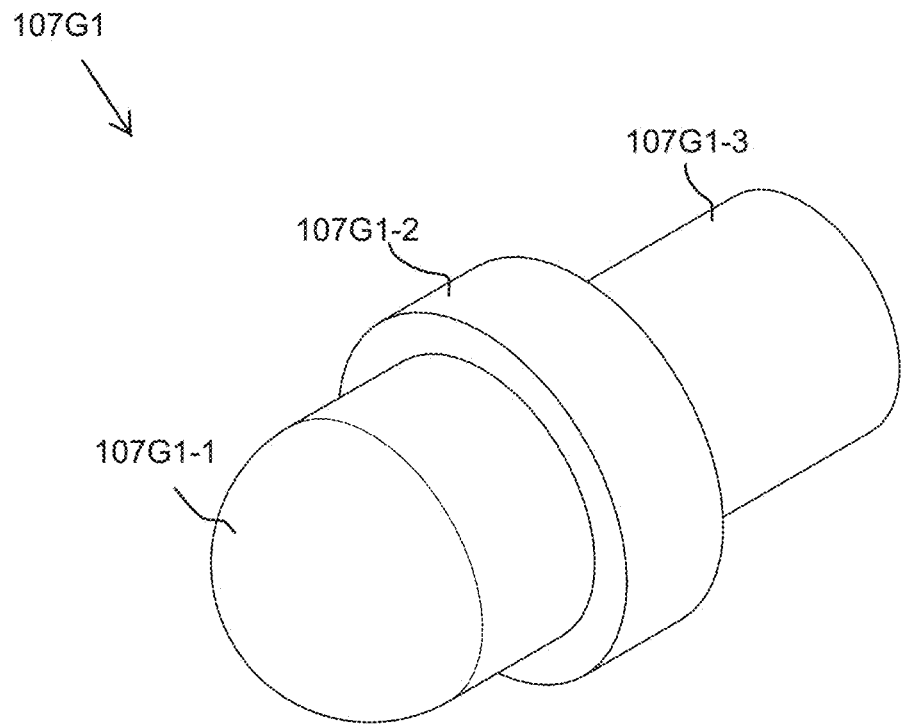
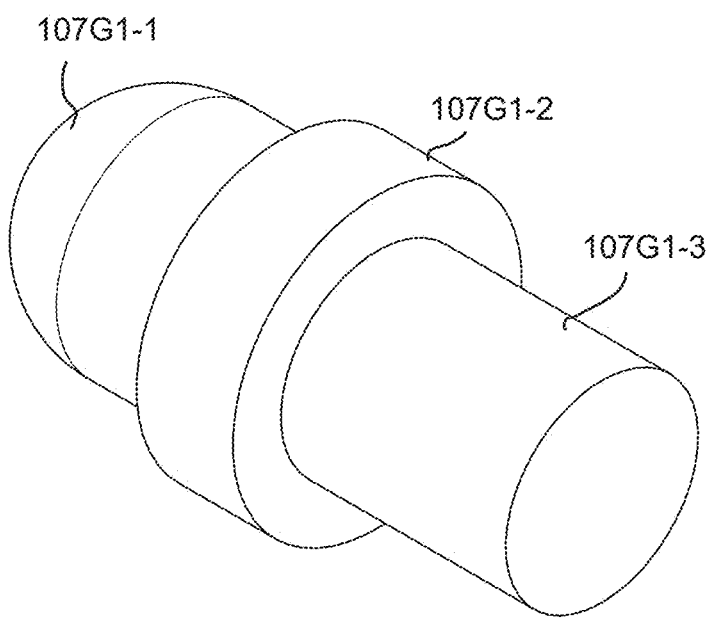
FIG. 21B

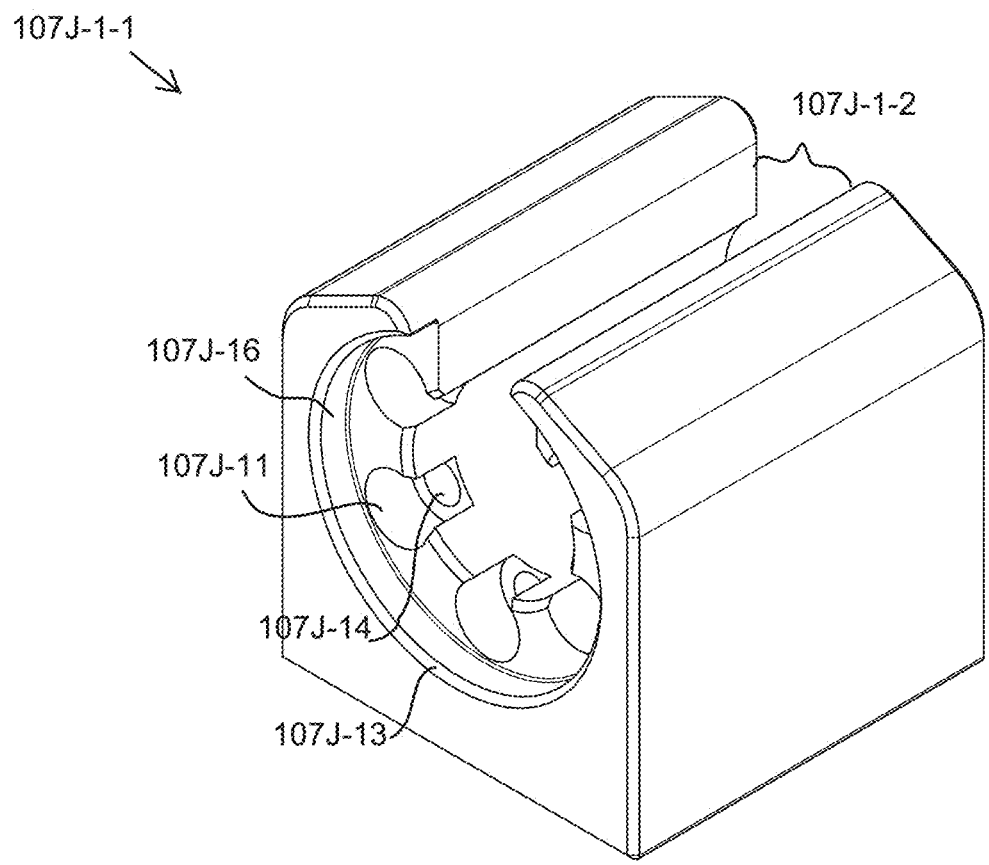
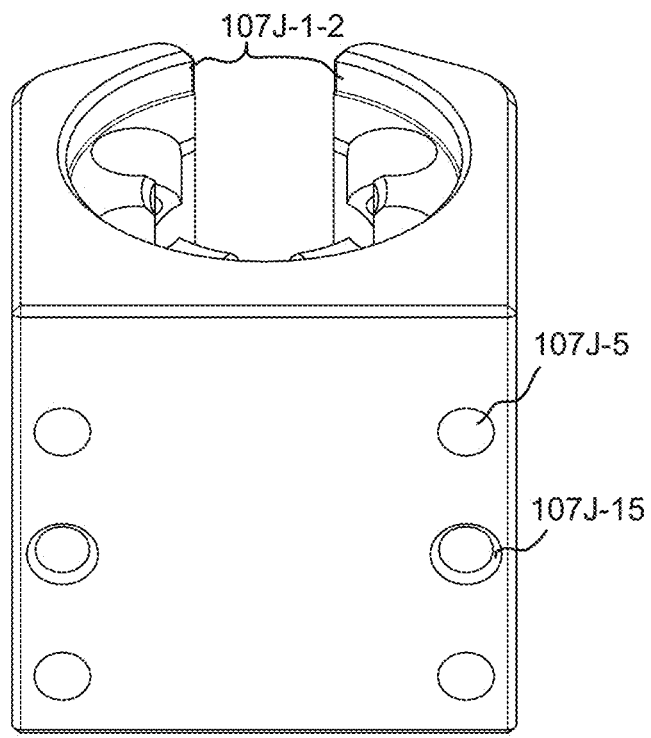
FIG. 23C

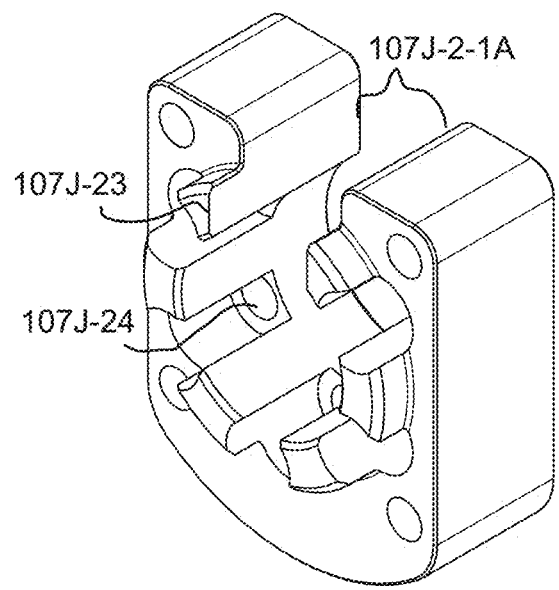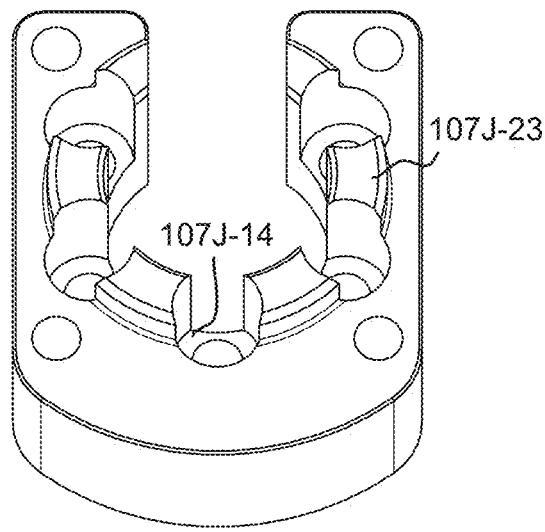
FIG. 24C

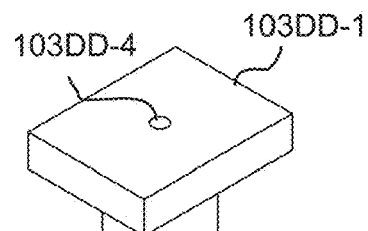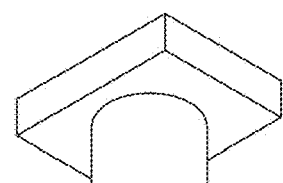
FIG. 26B

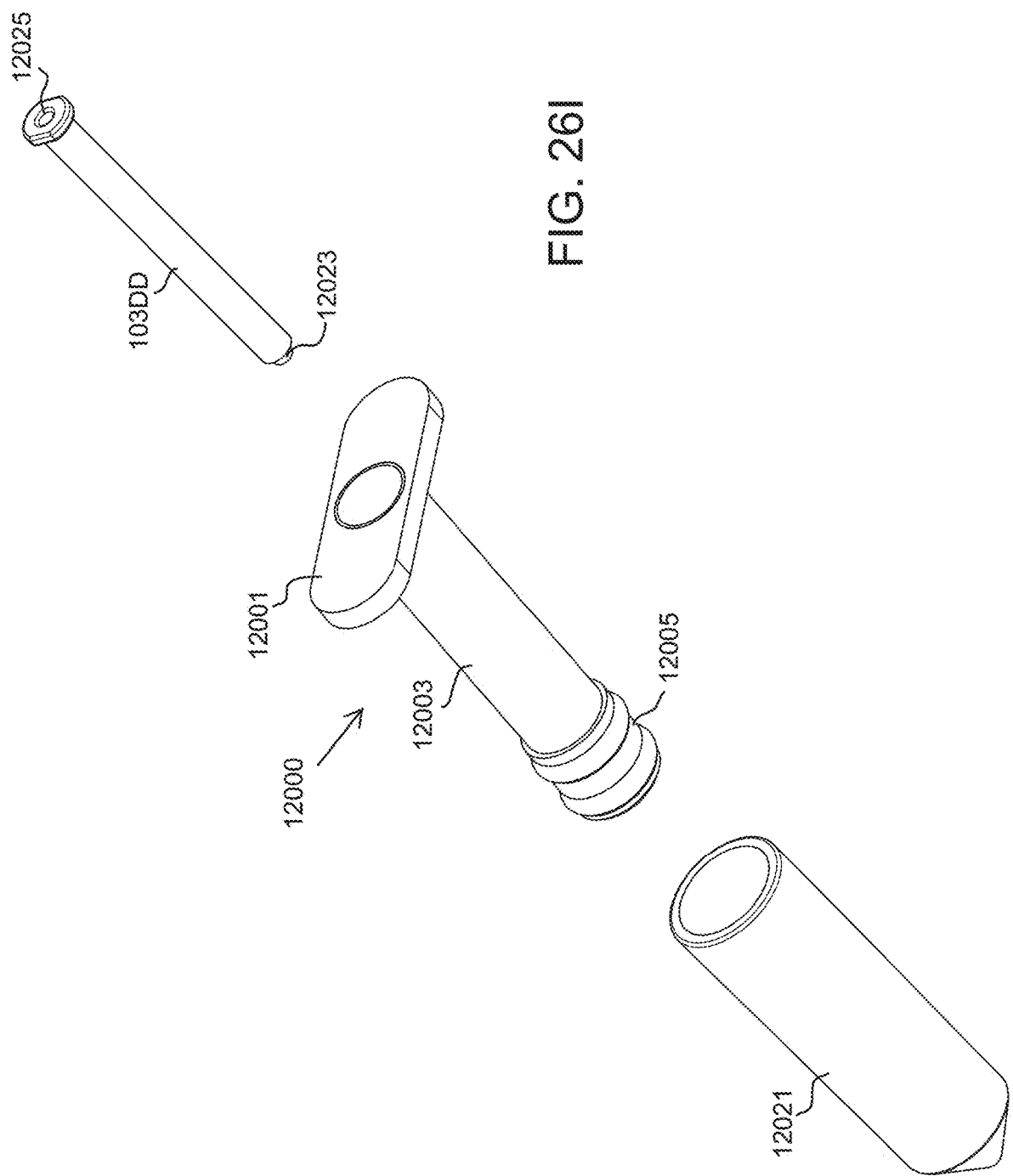

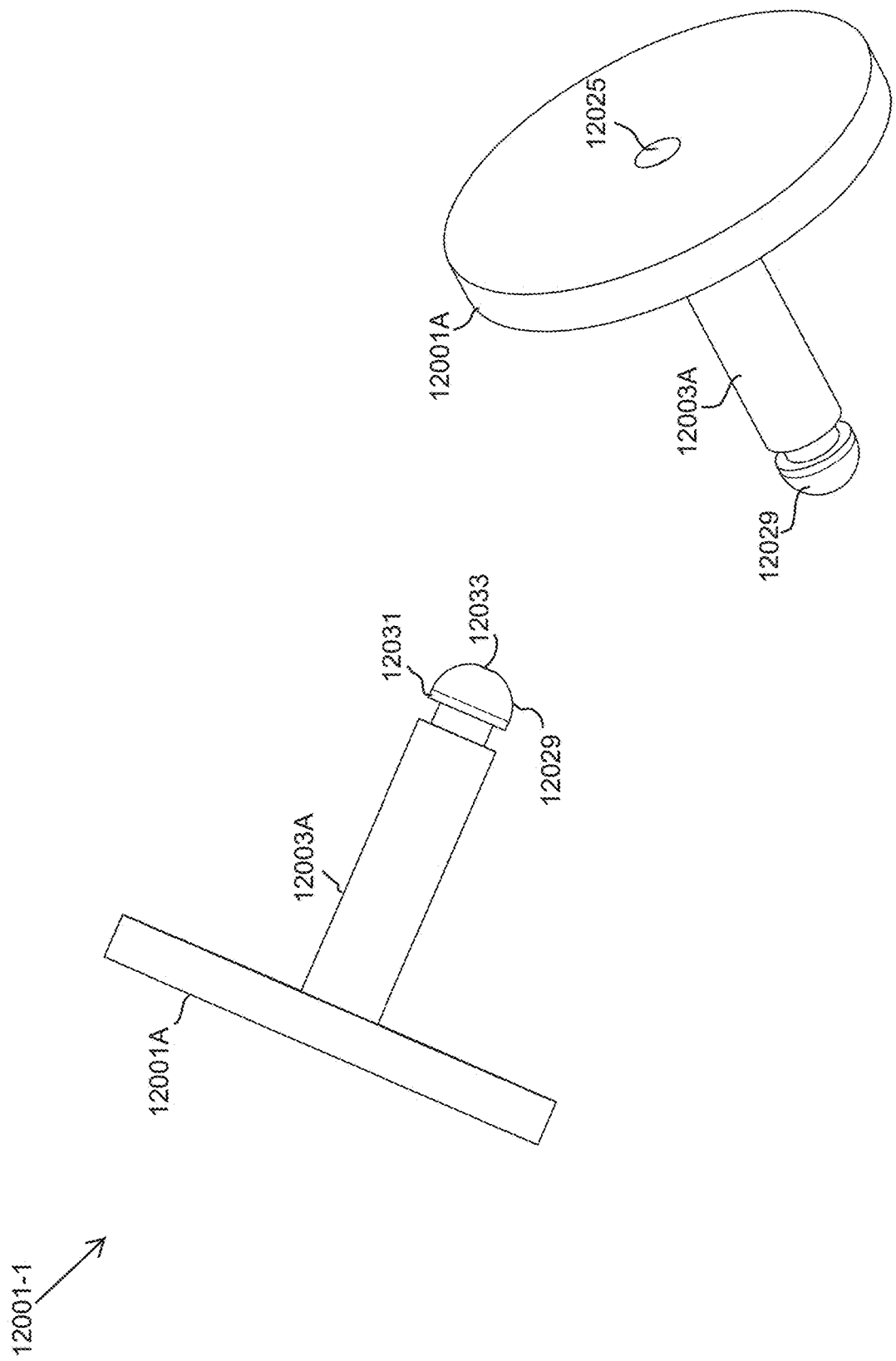

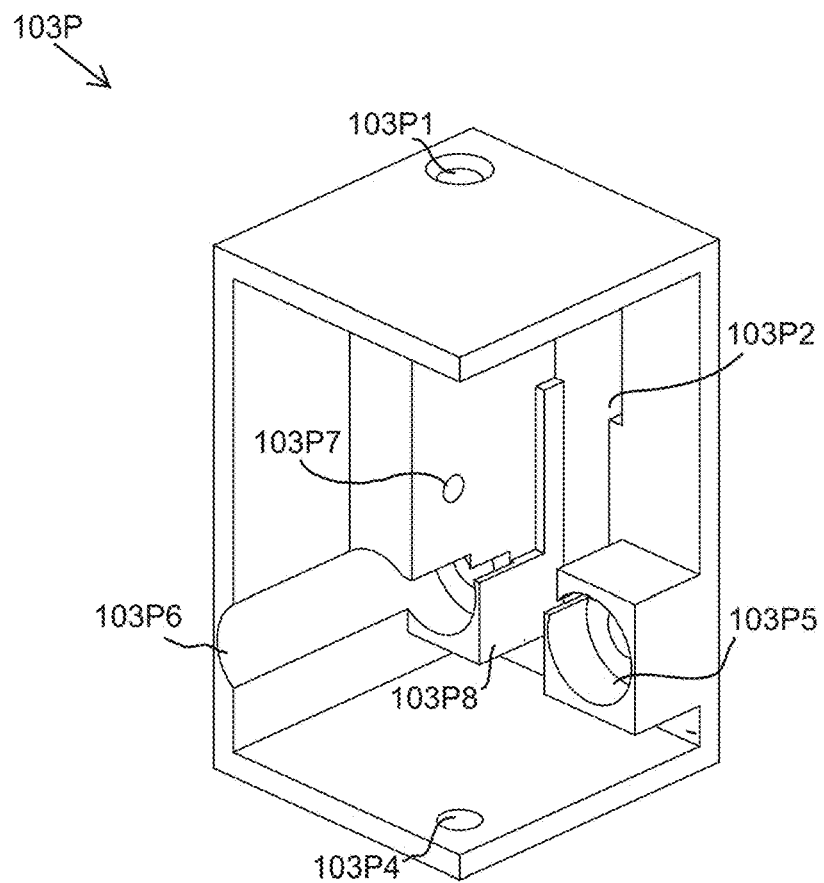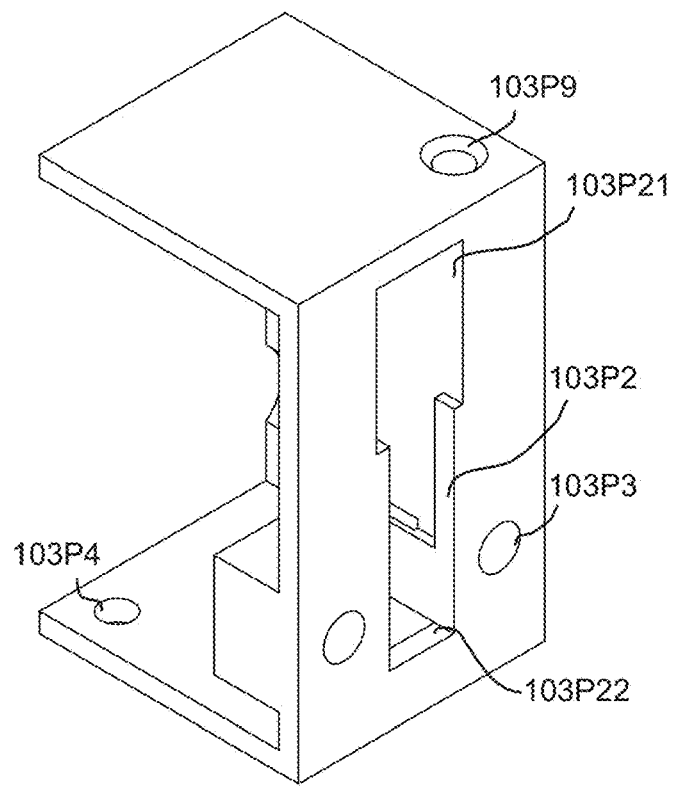
FIG. 27A

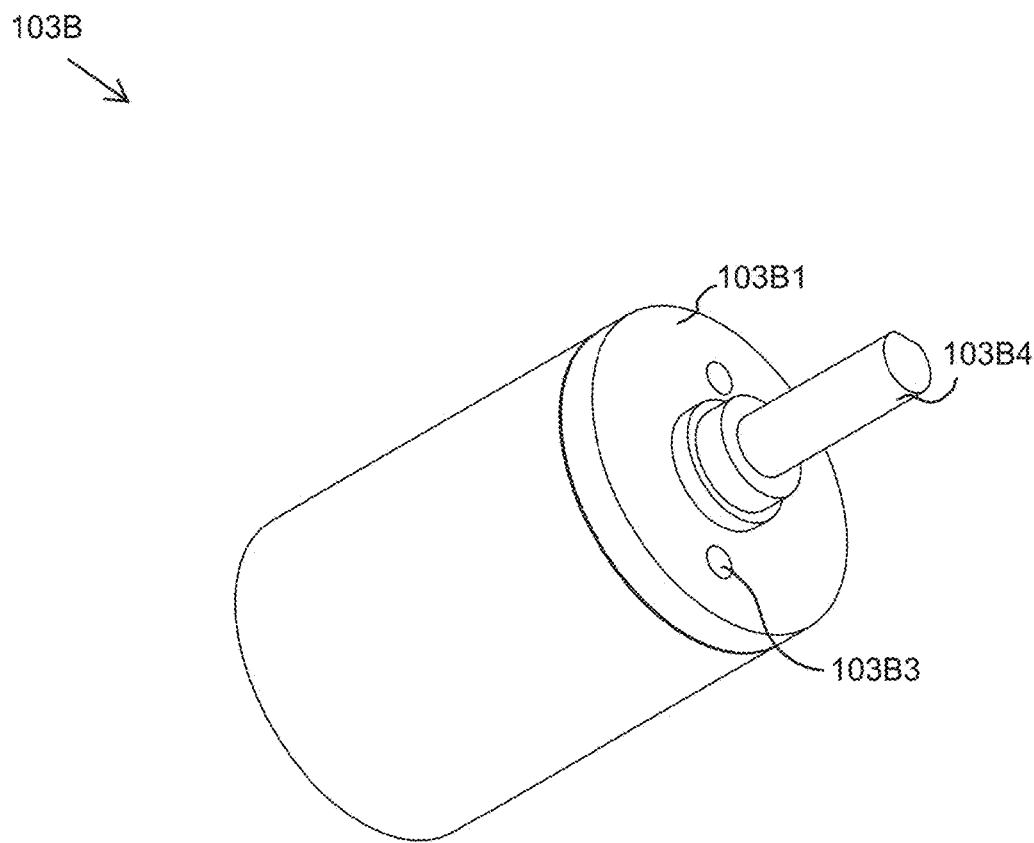
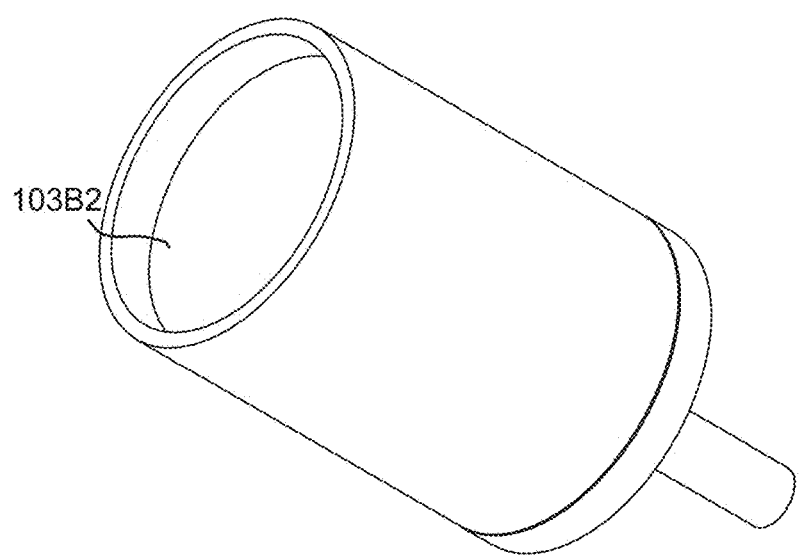
FIG. 29

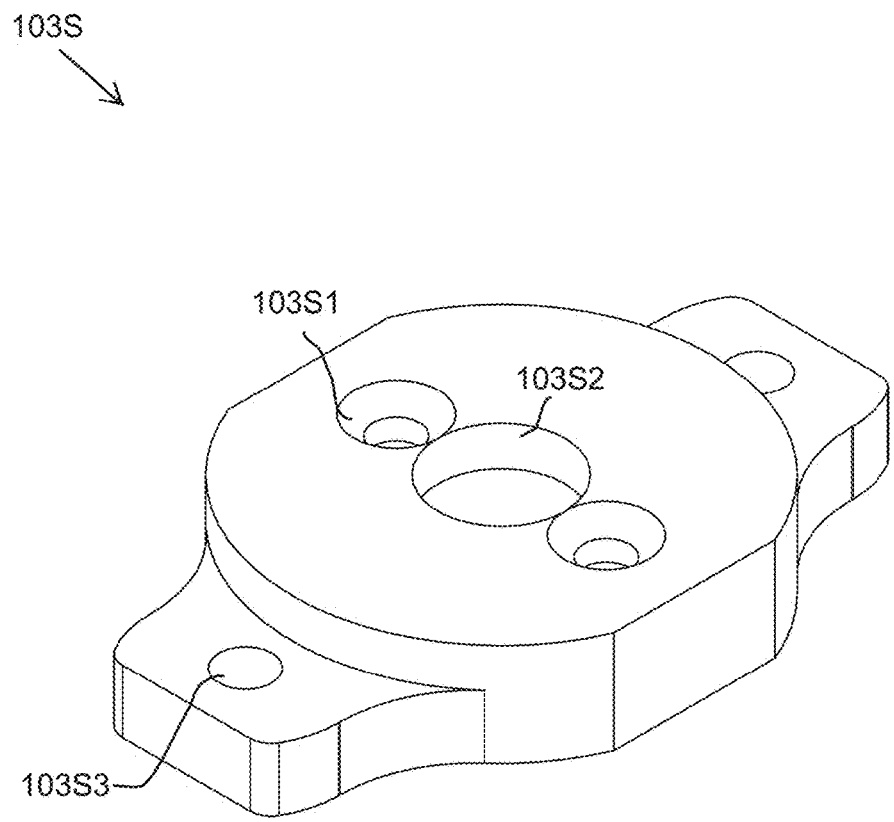
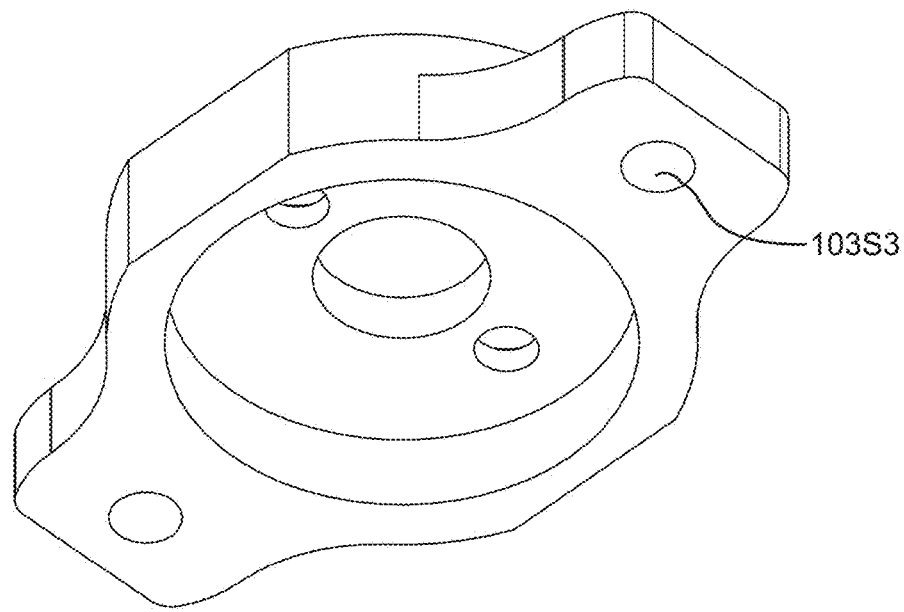
FIG. 30

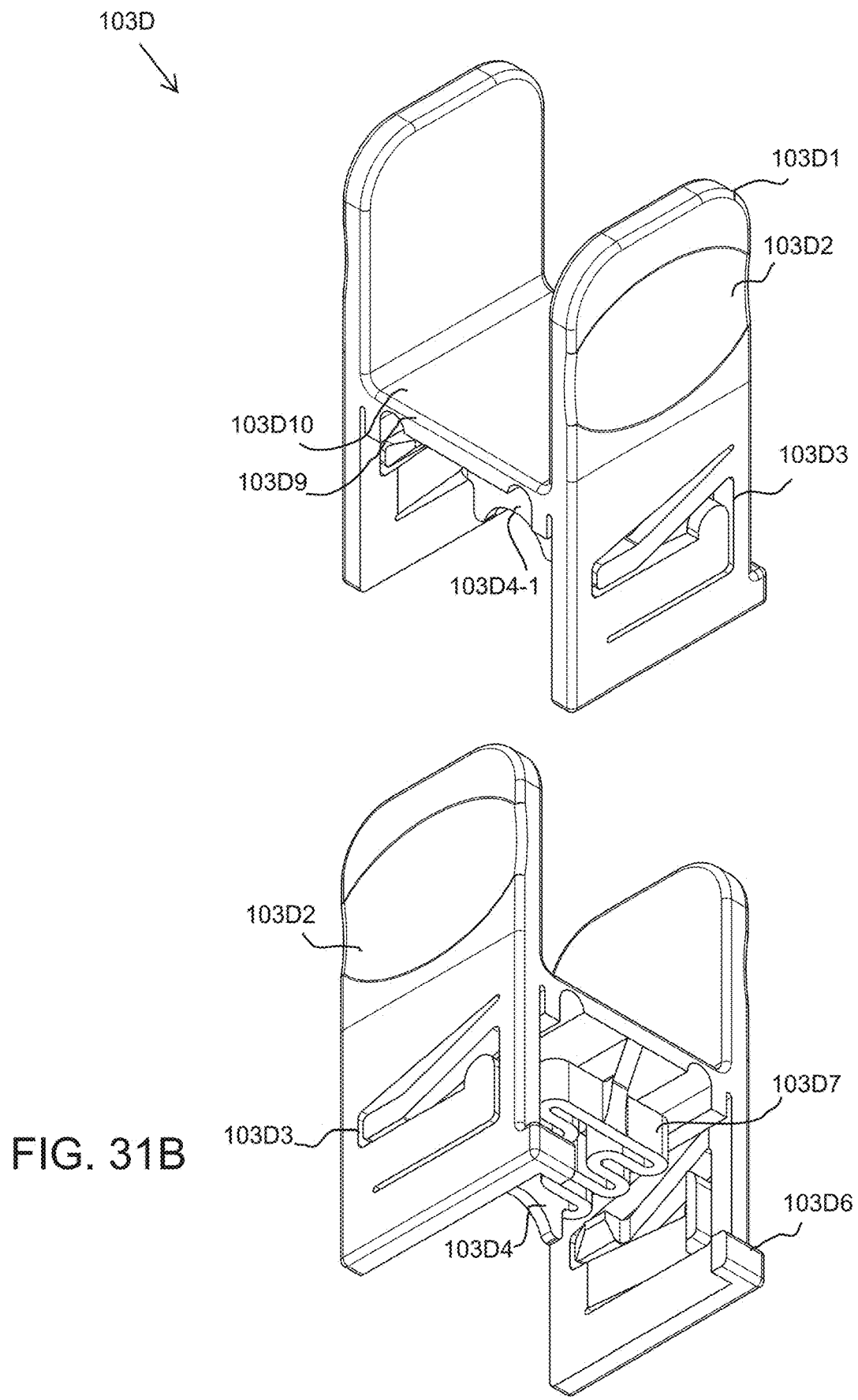

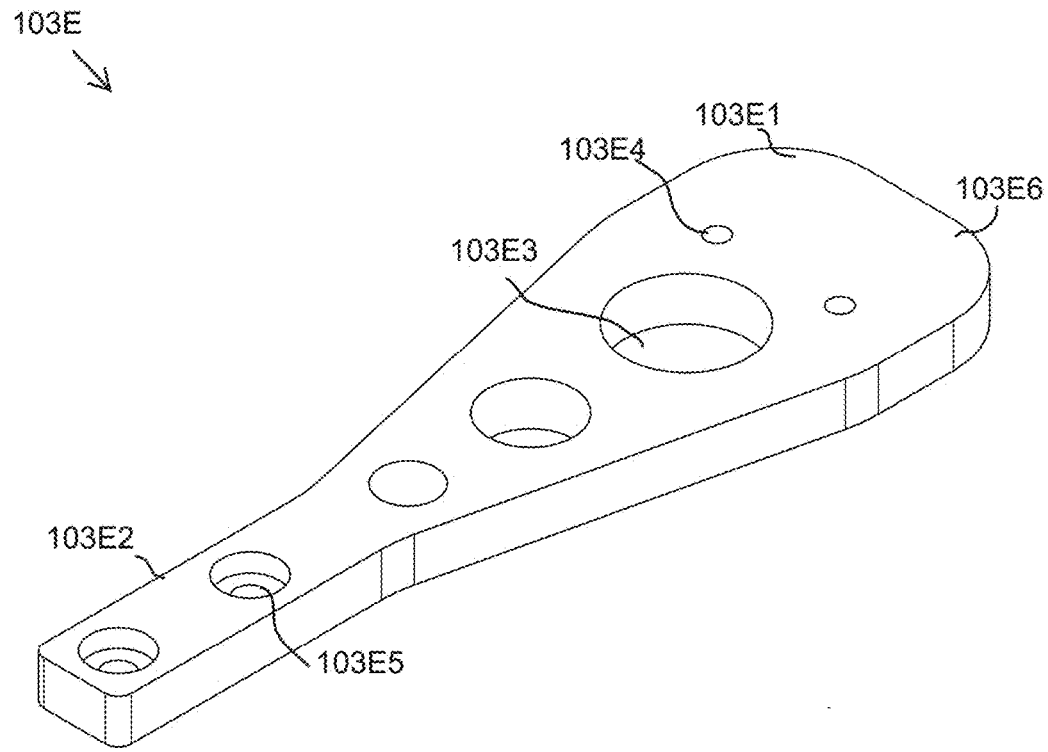
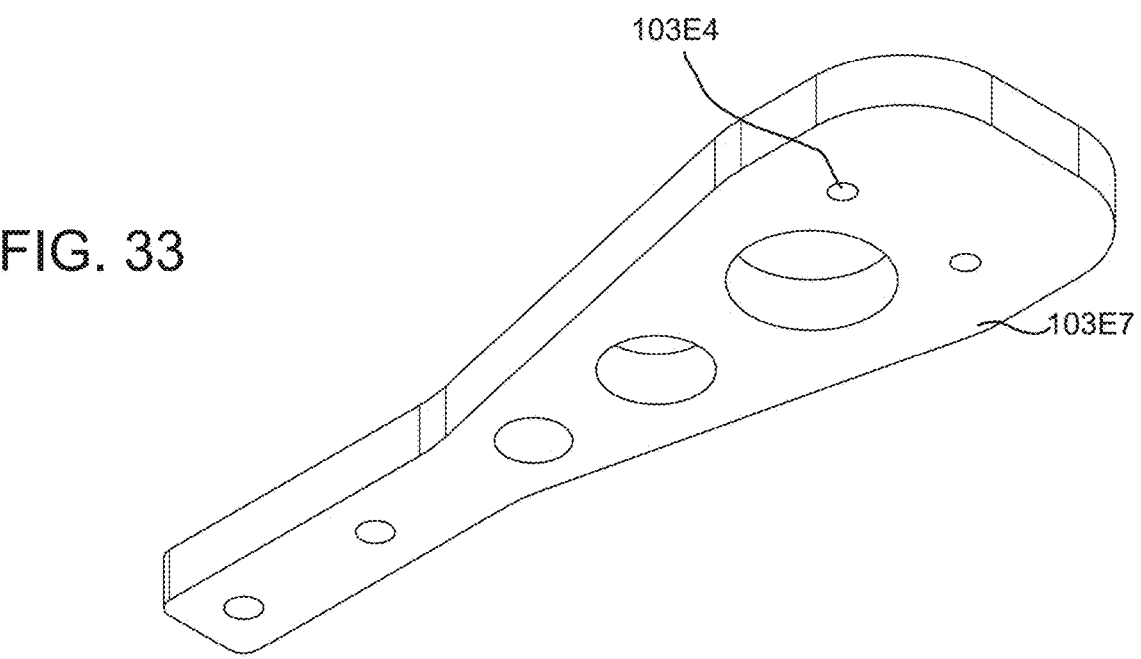
FIG. 33

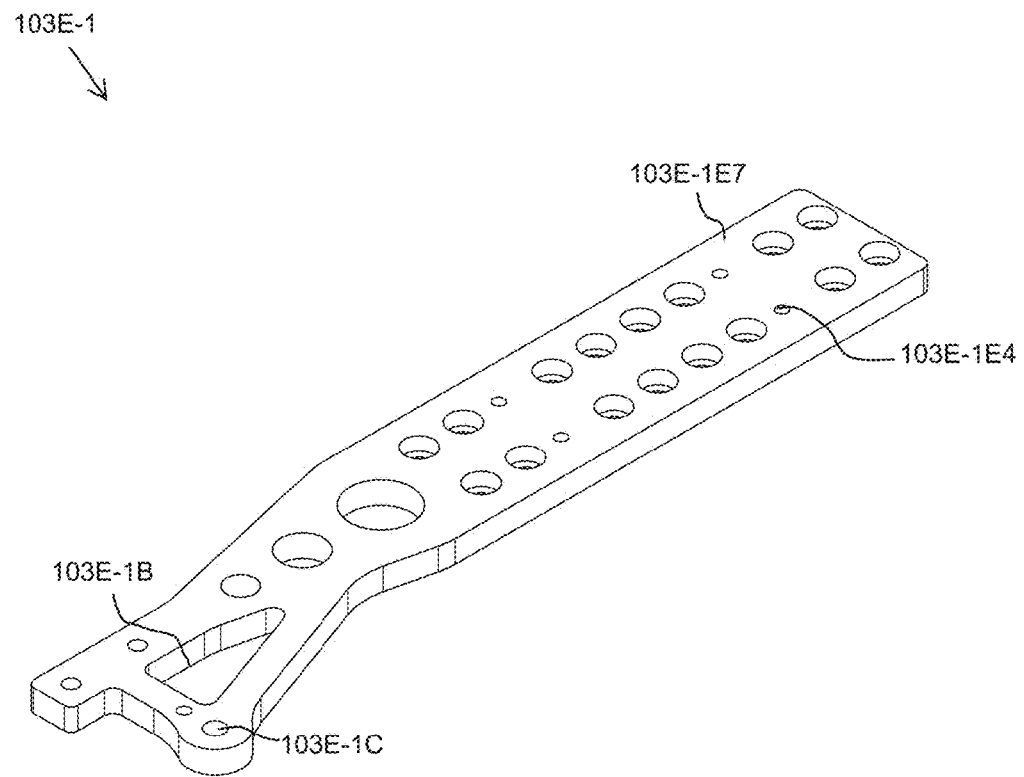
FIG. 33A
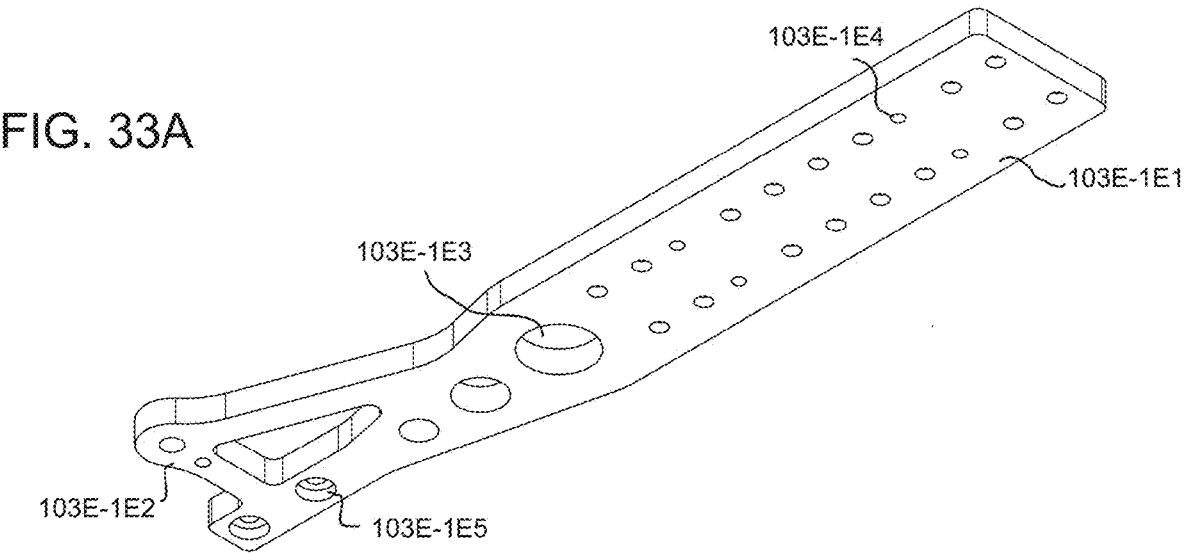

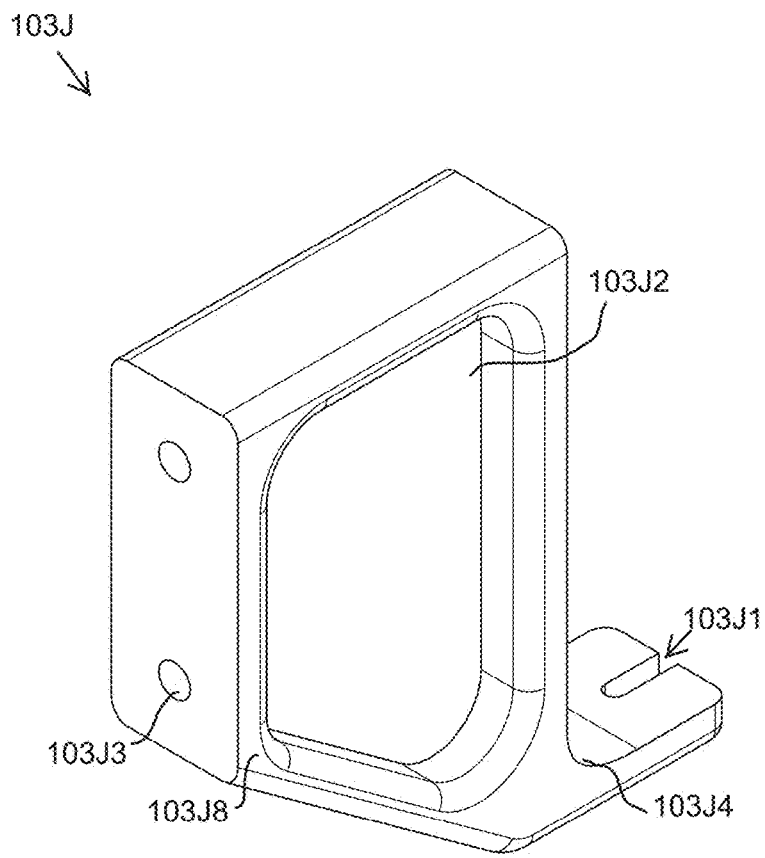
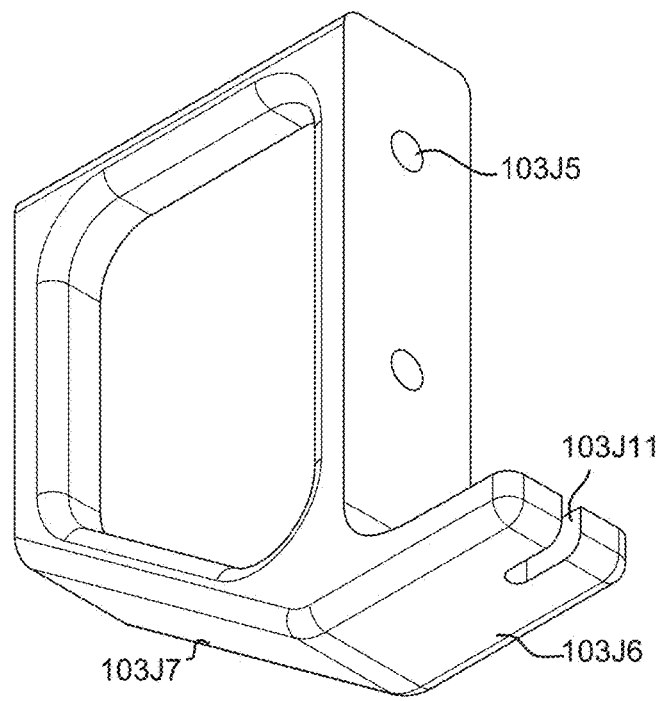
FIG. 34

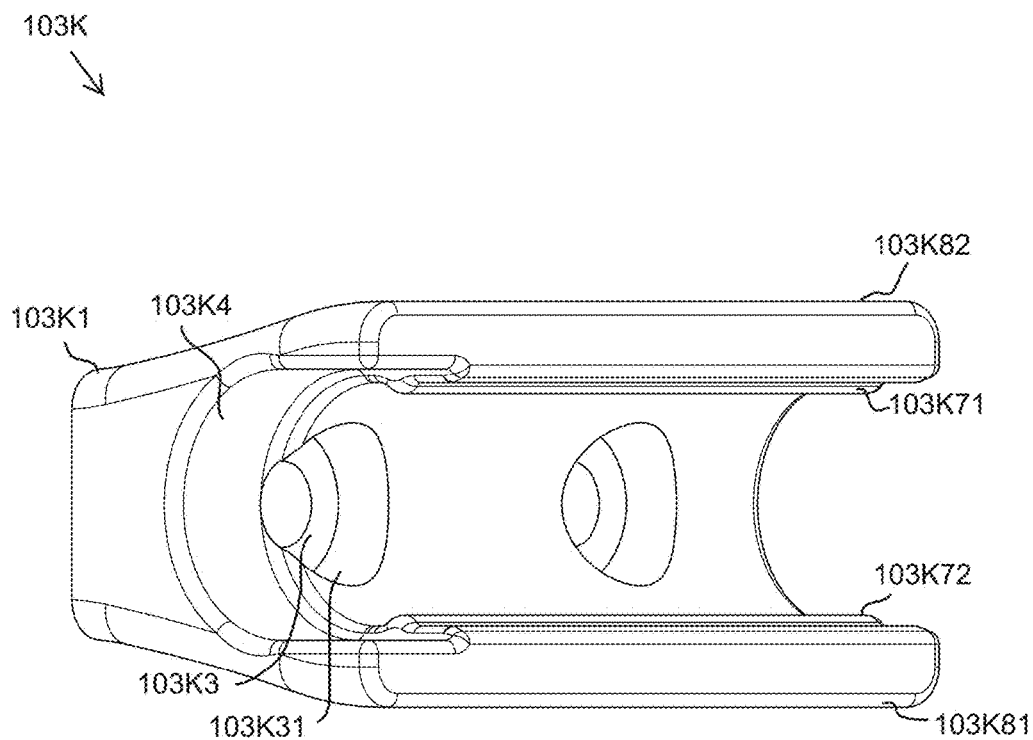
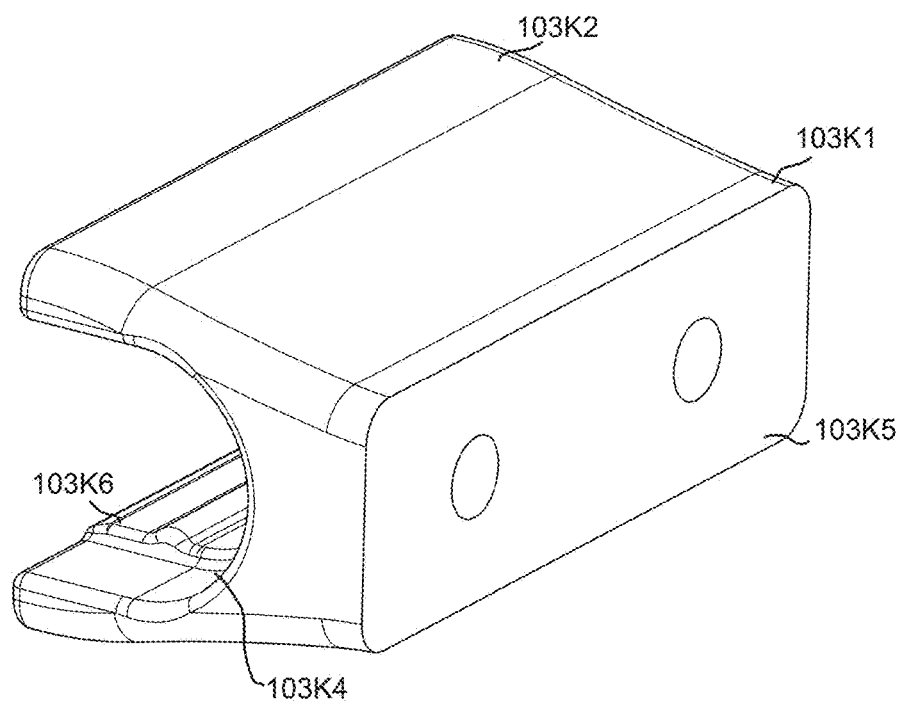
FIG. 35

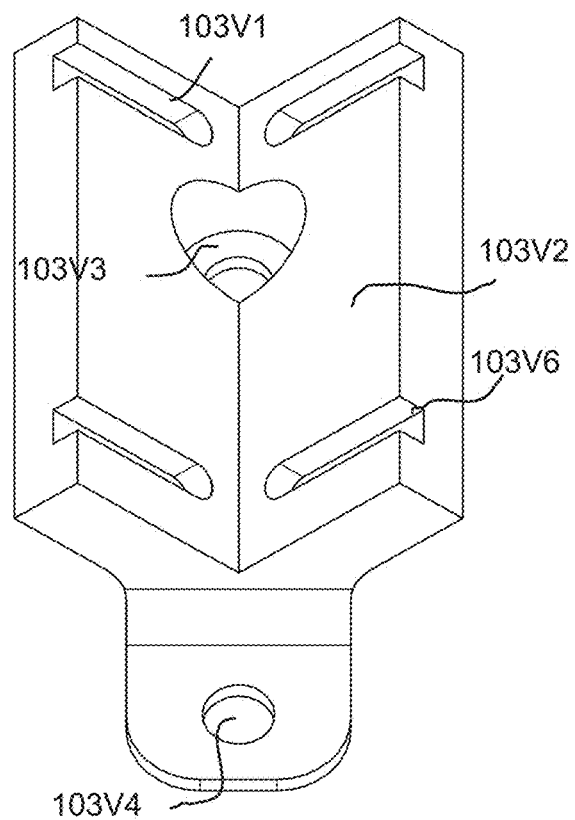
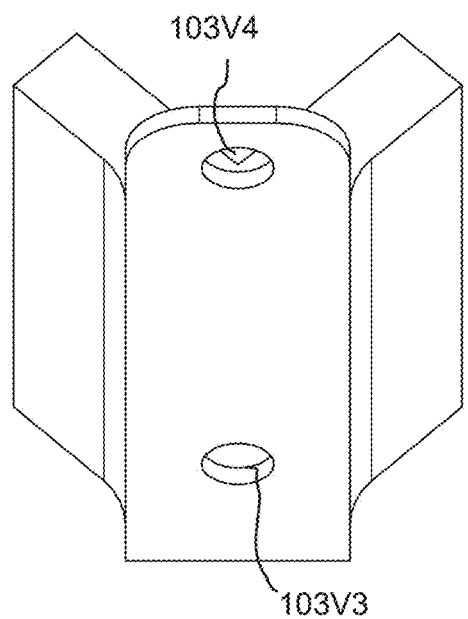
FIG. 35A

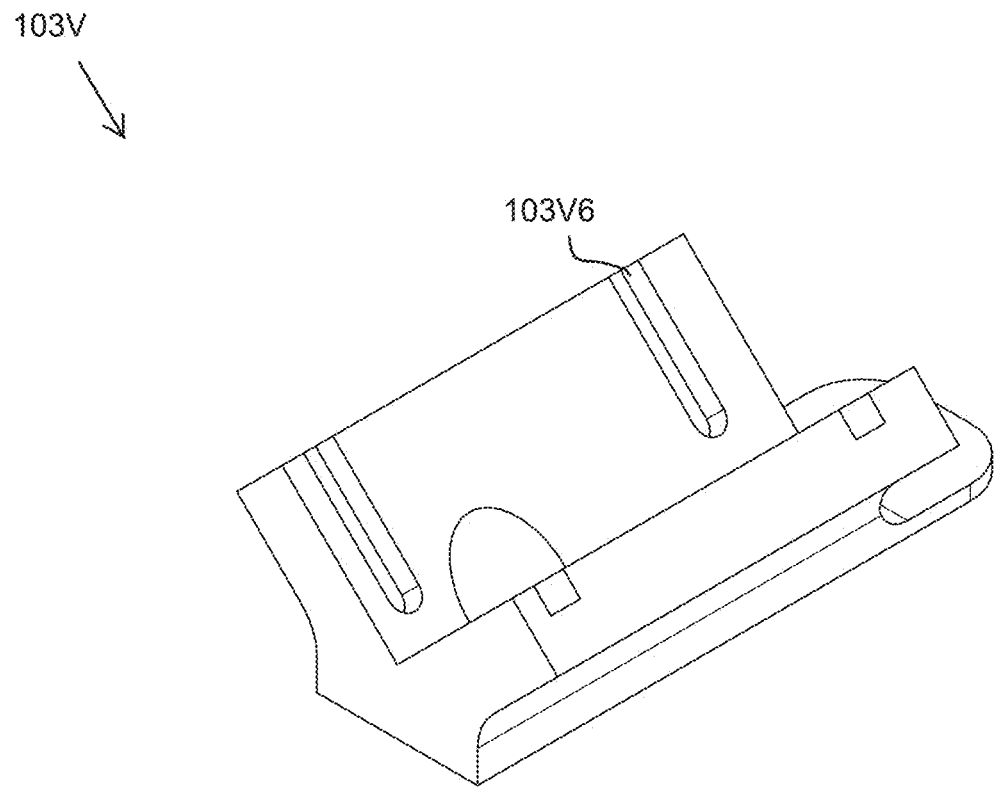
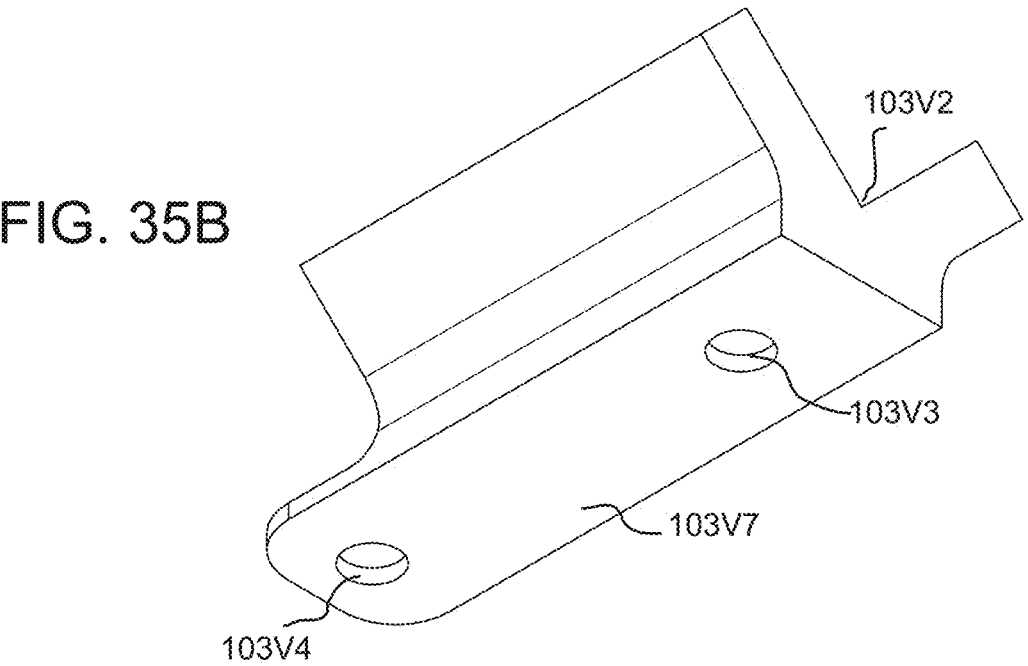
FIG. 35B

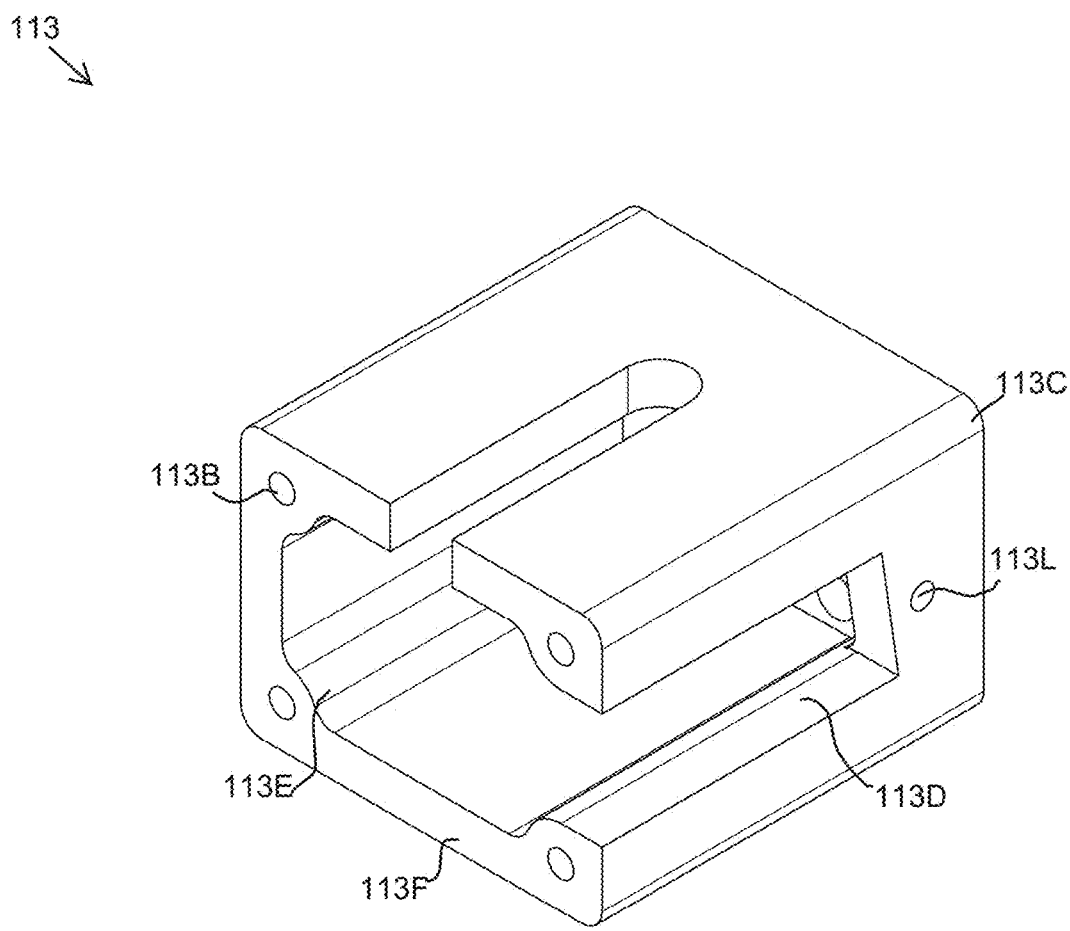
FIG. 37D
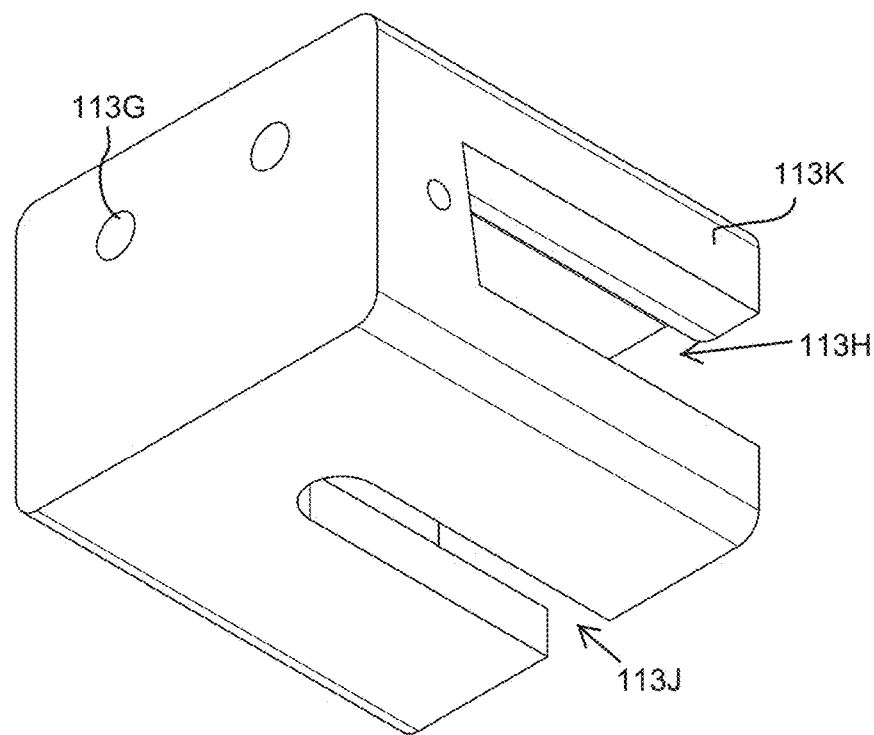

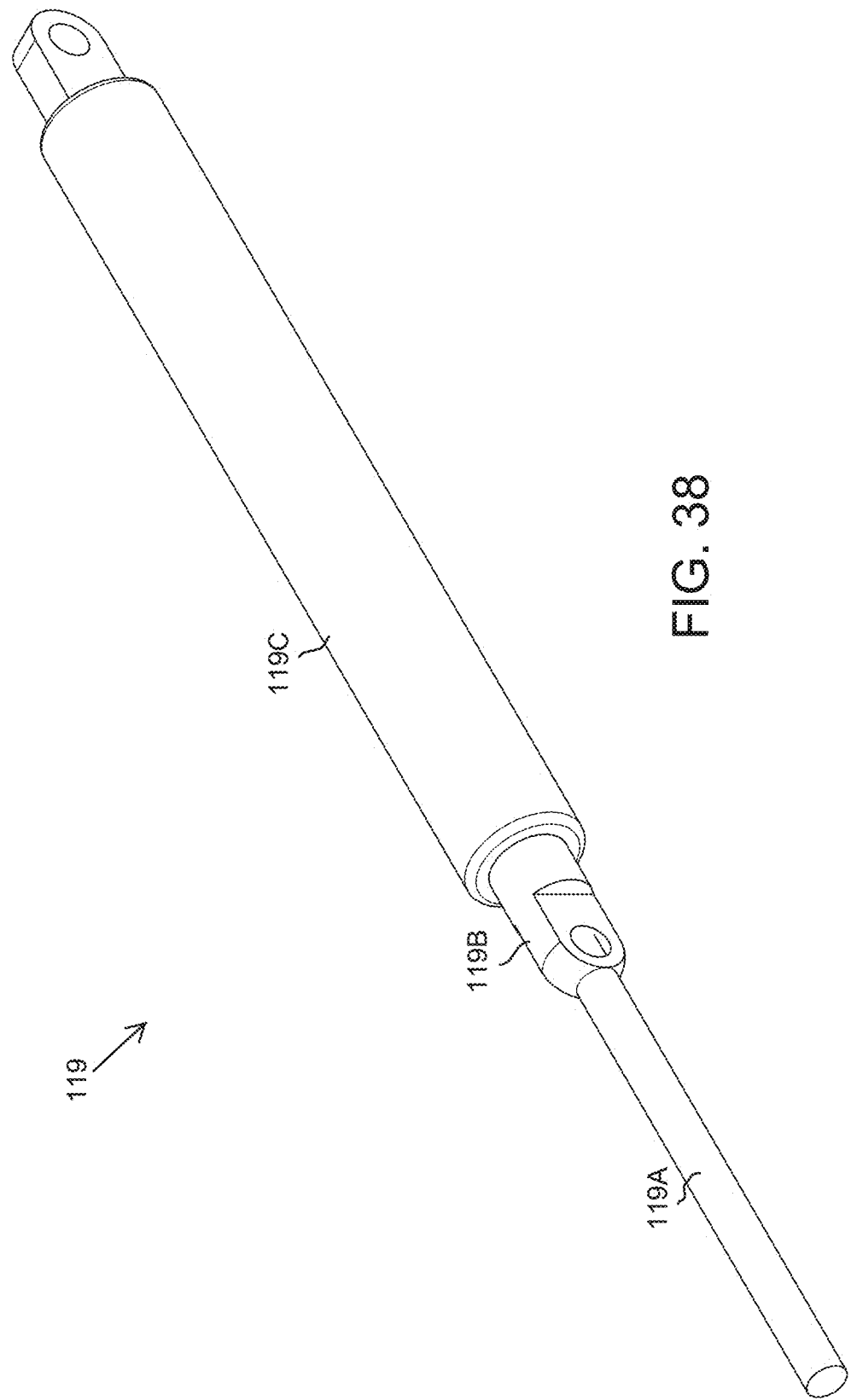

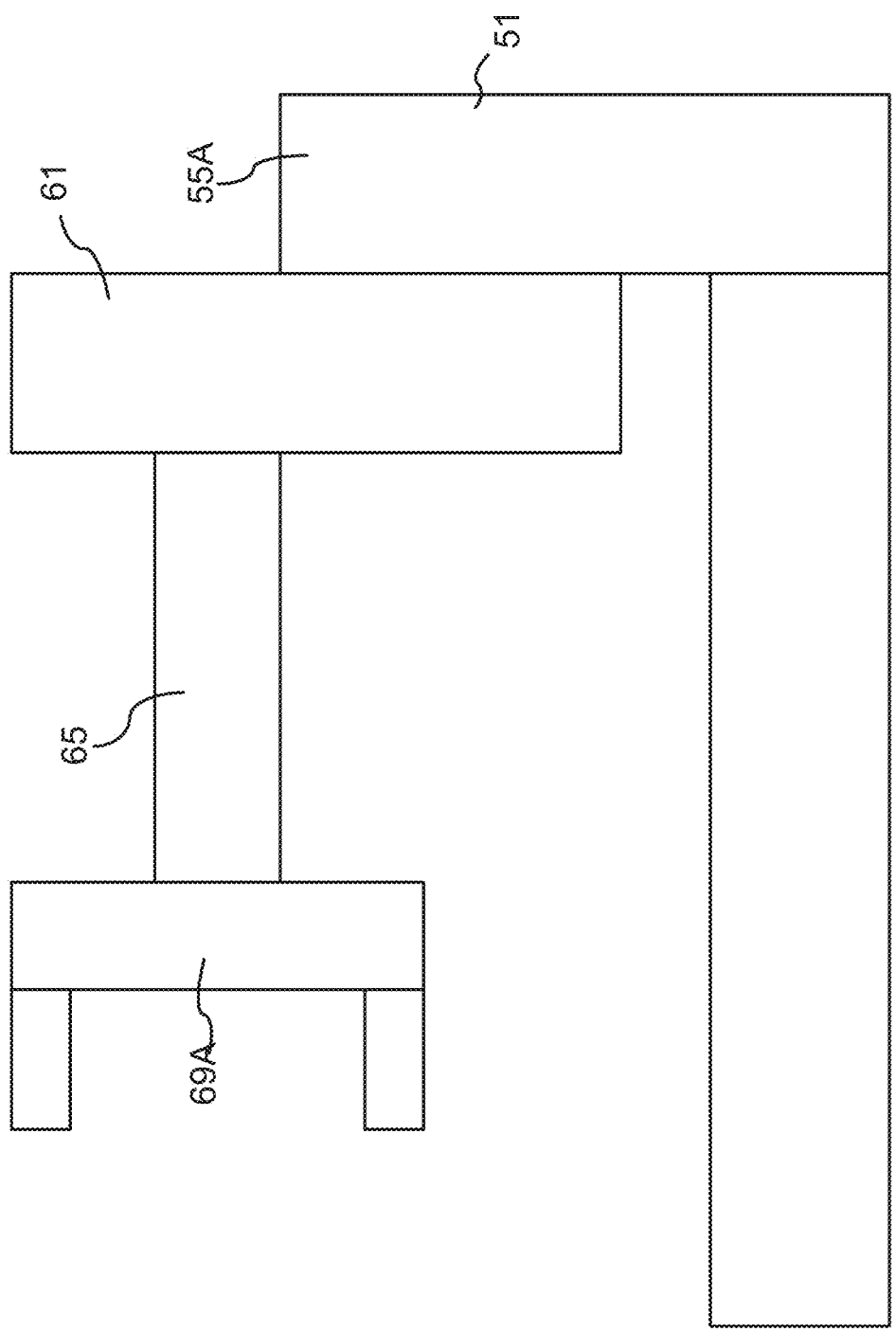

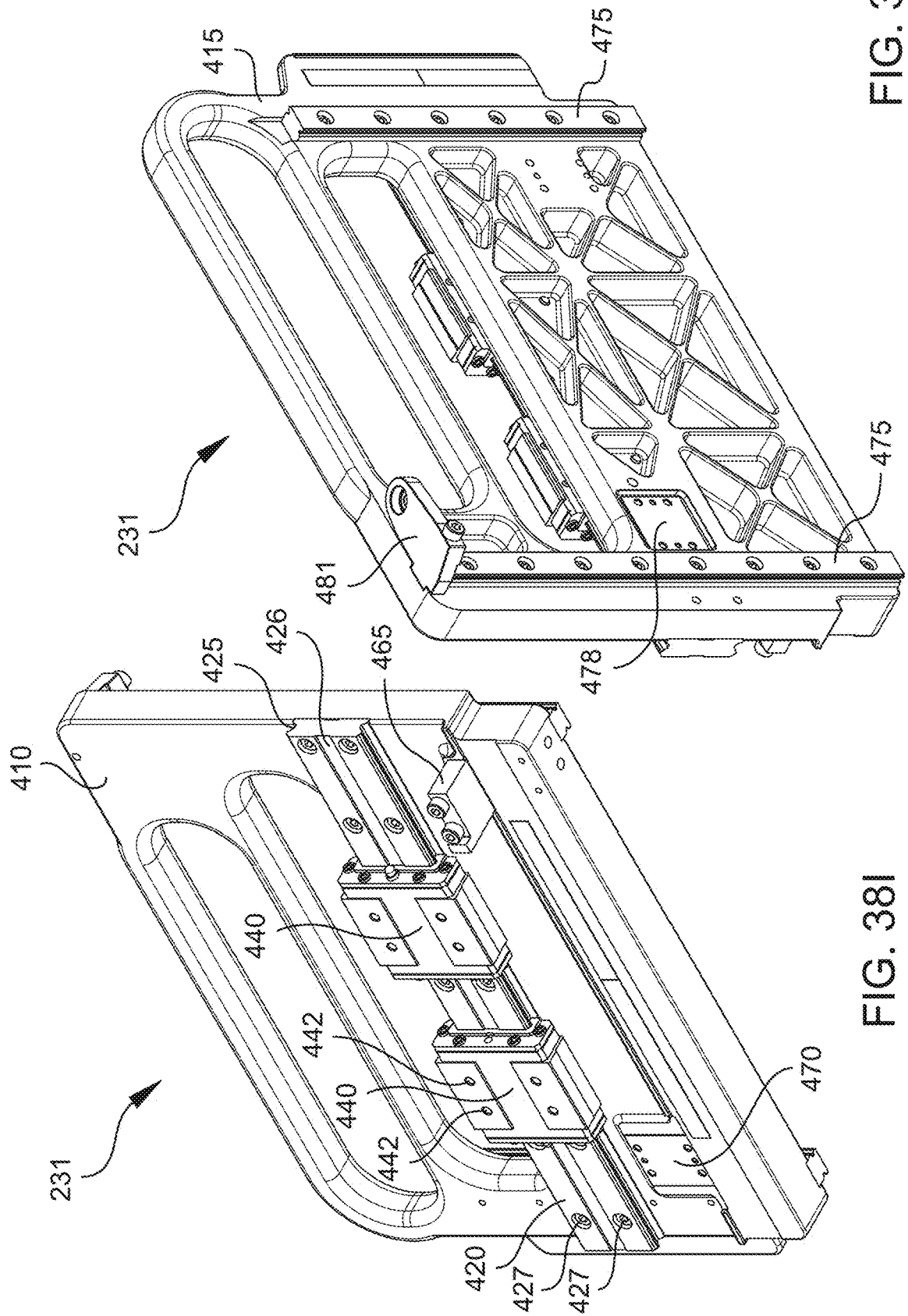

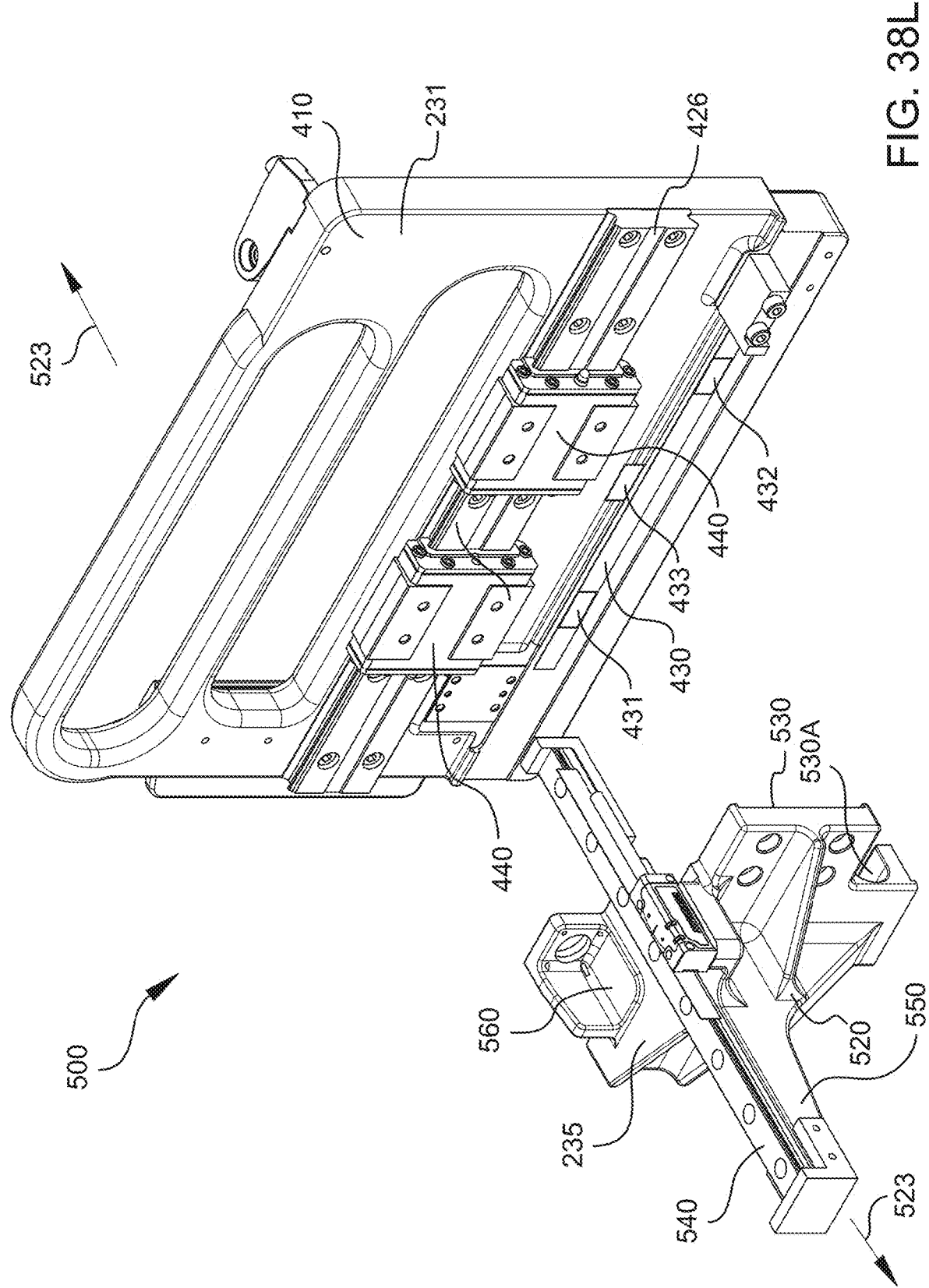

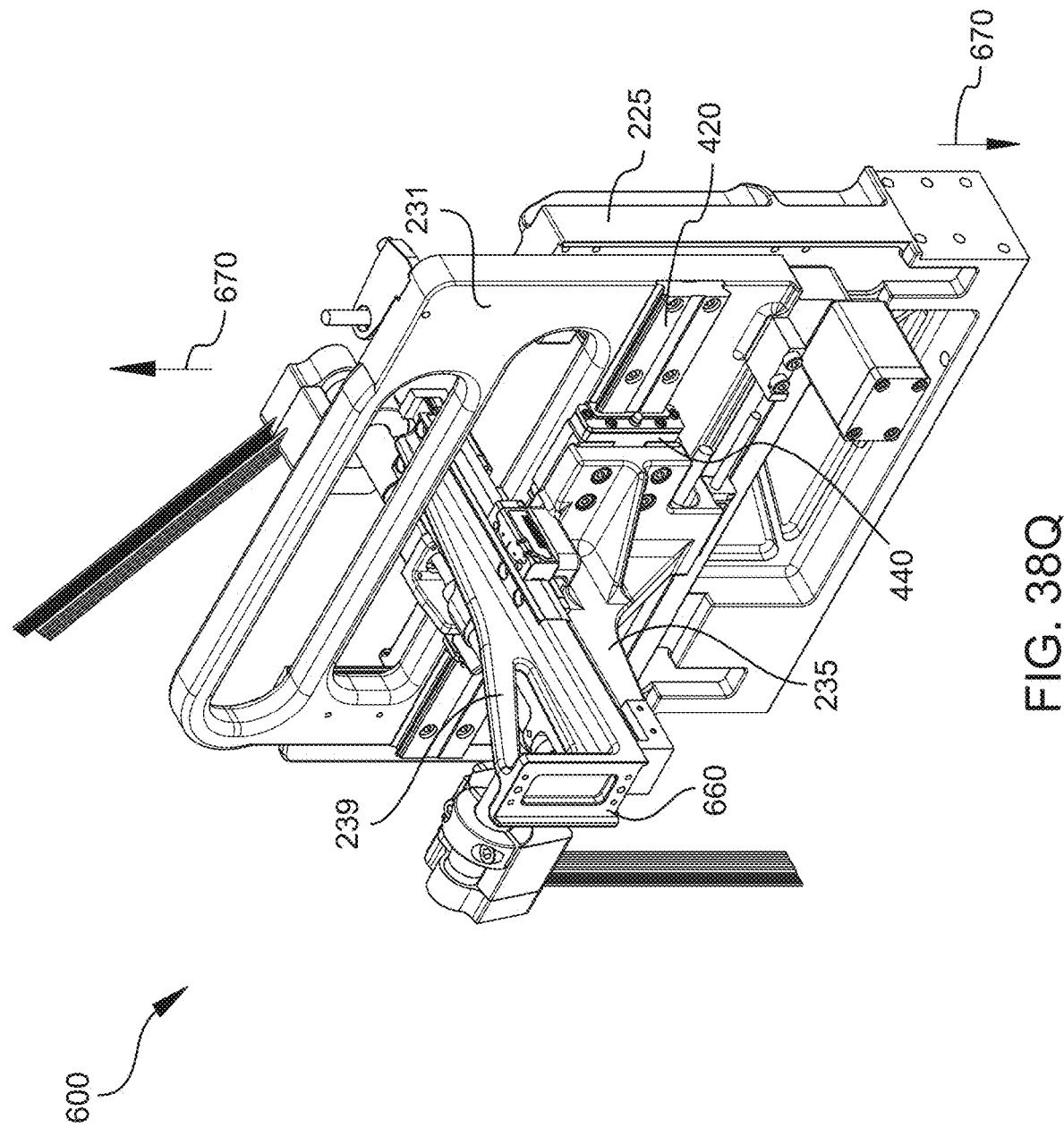

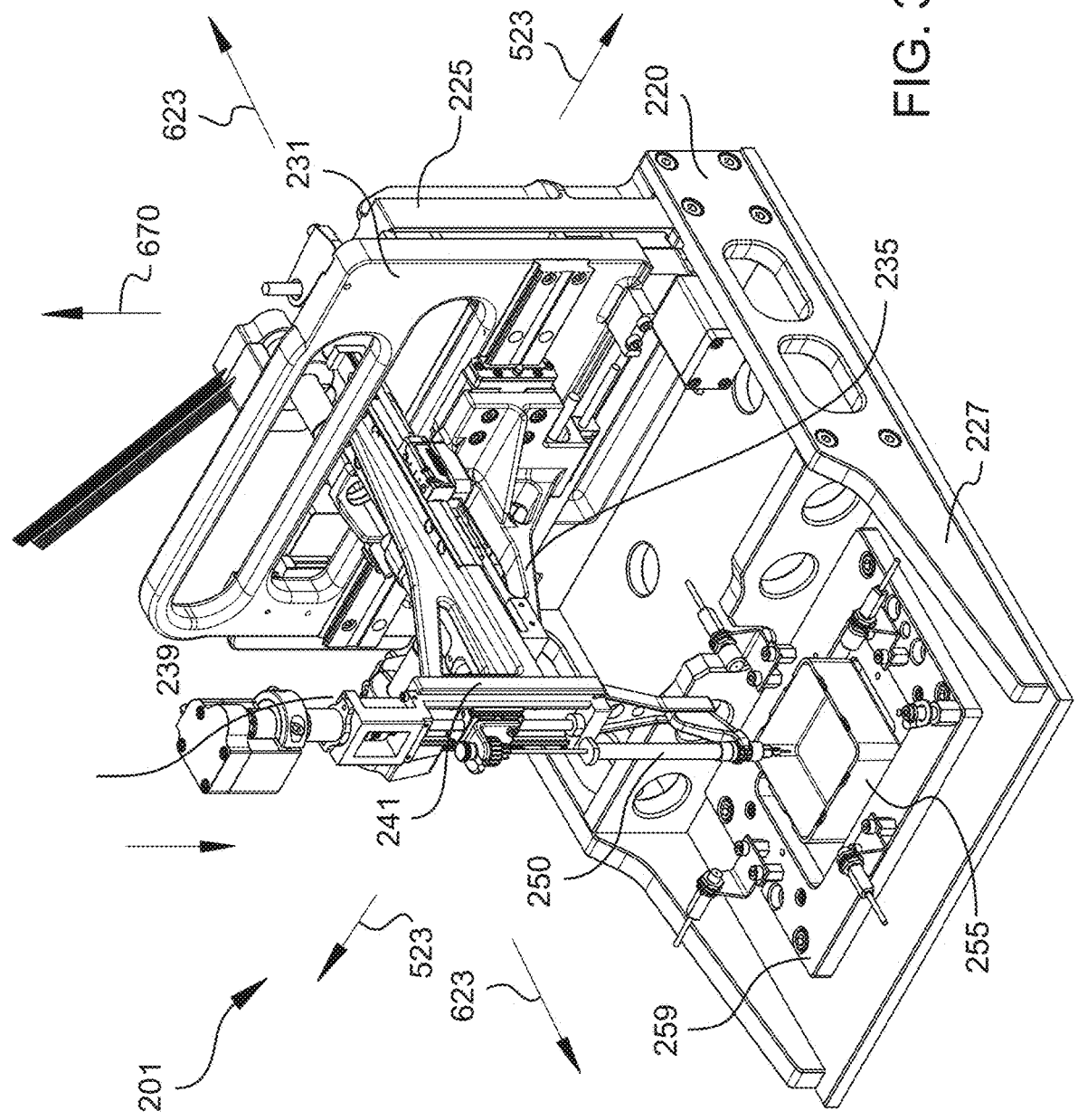

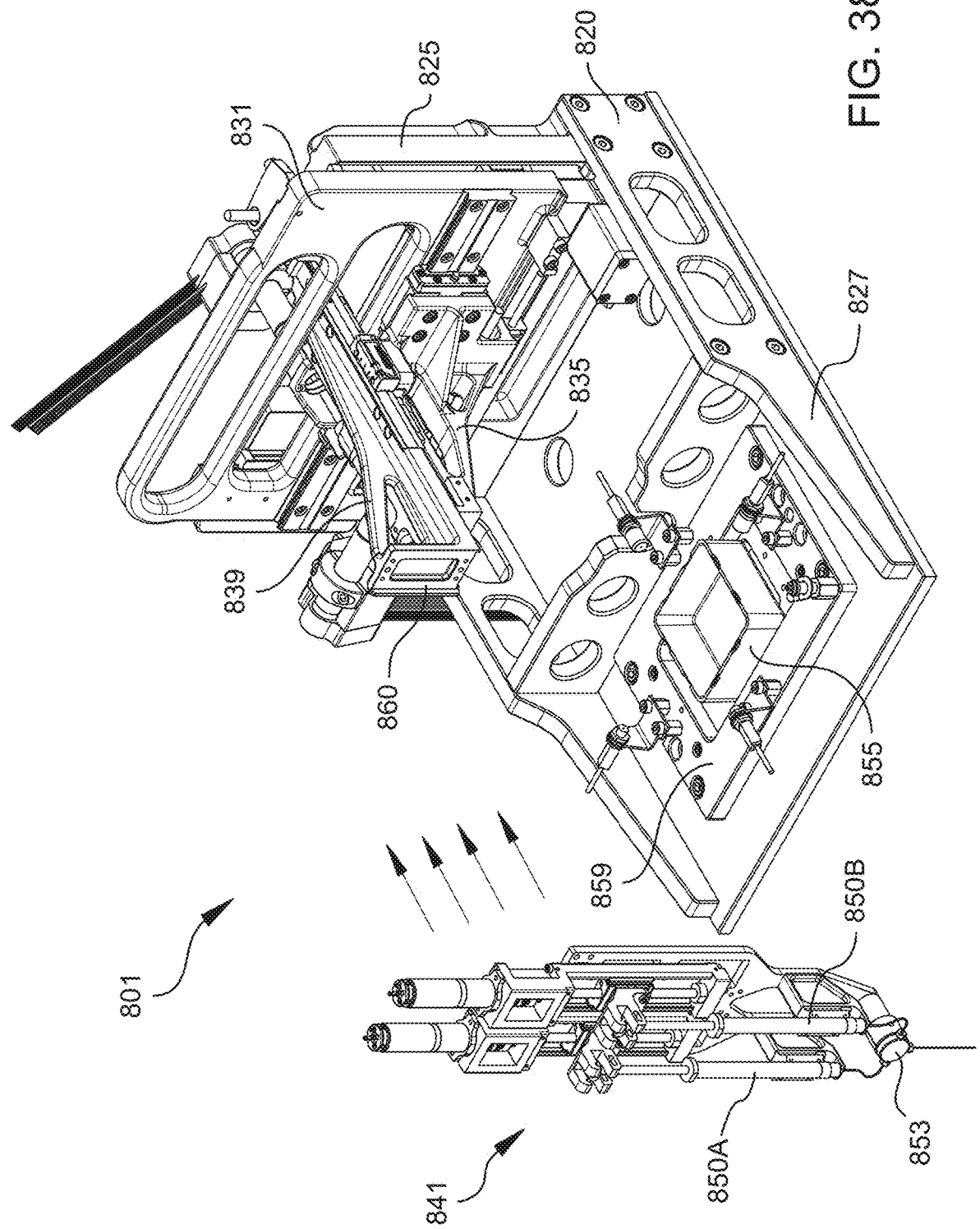

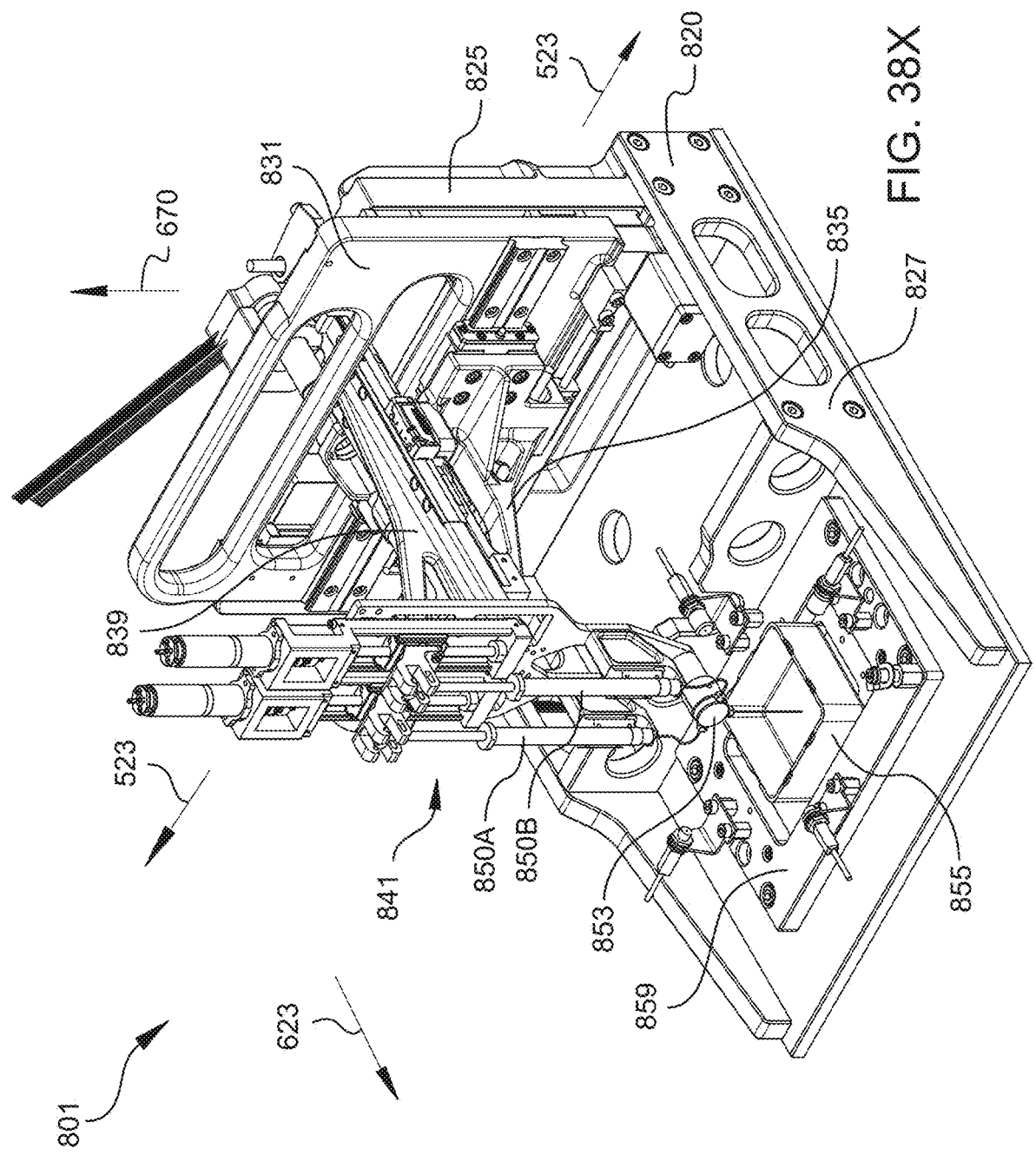

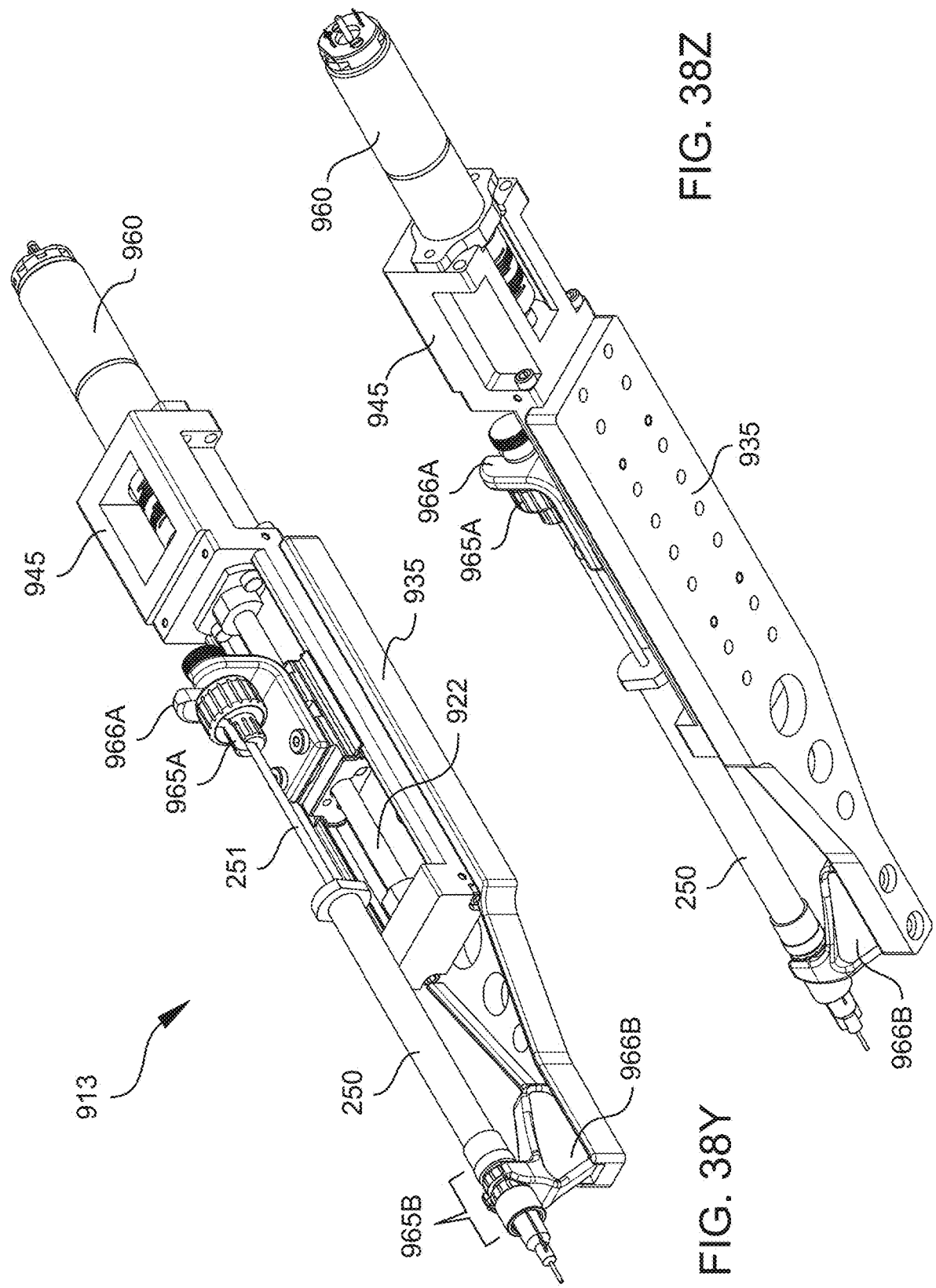

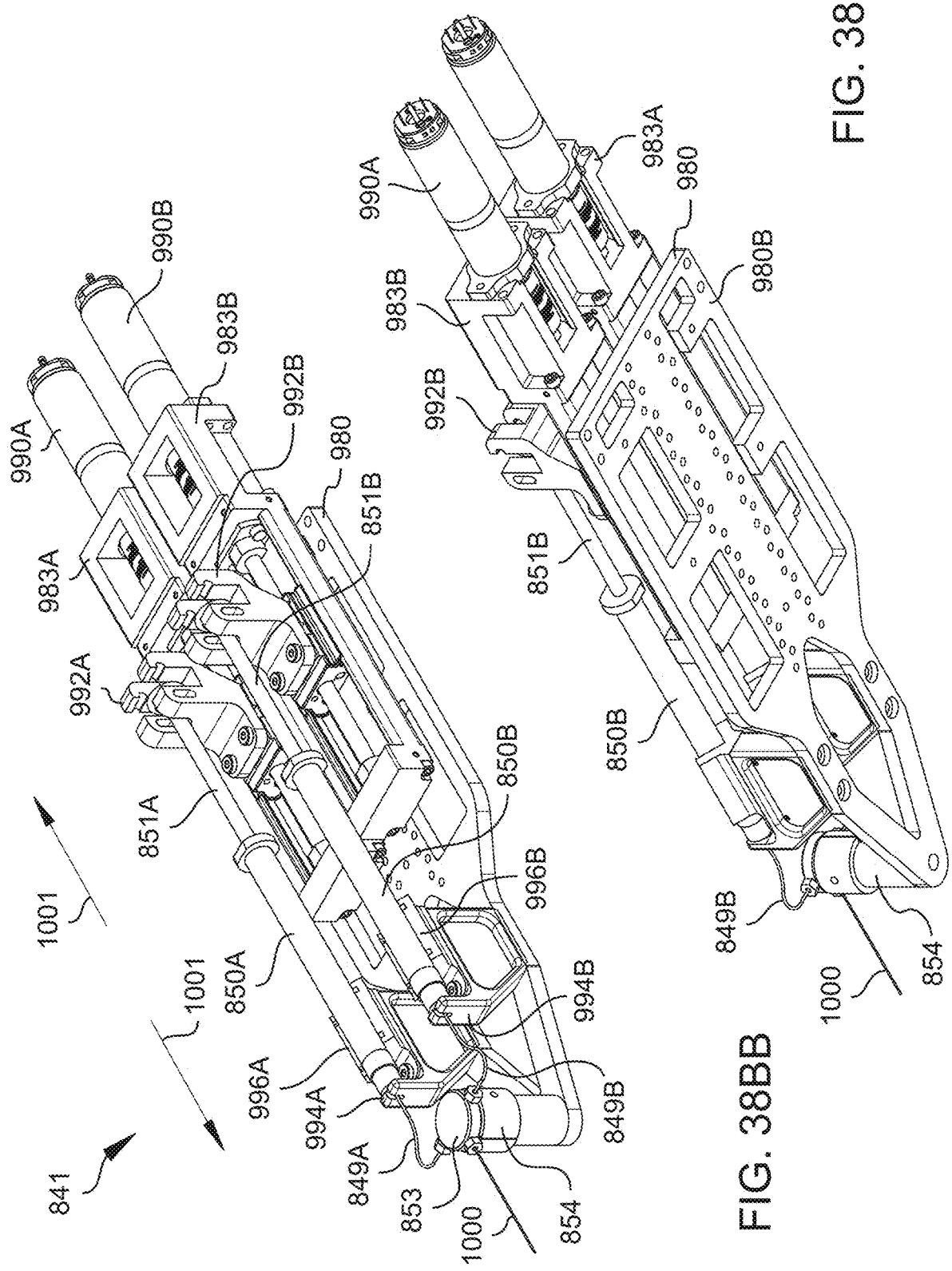

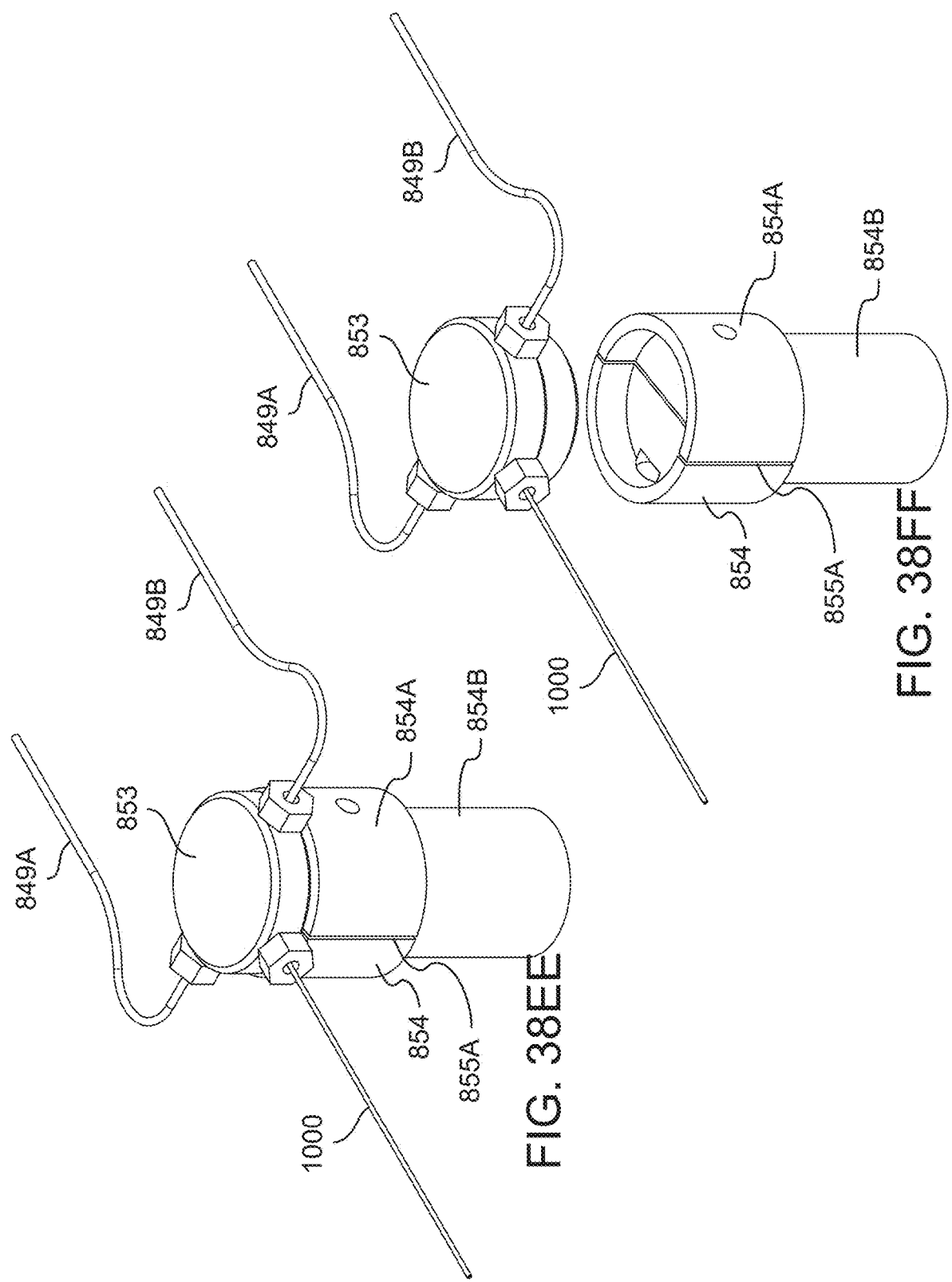

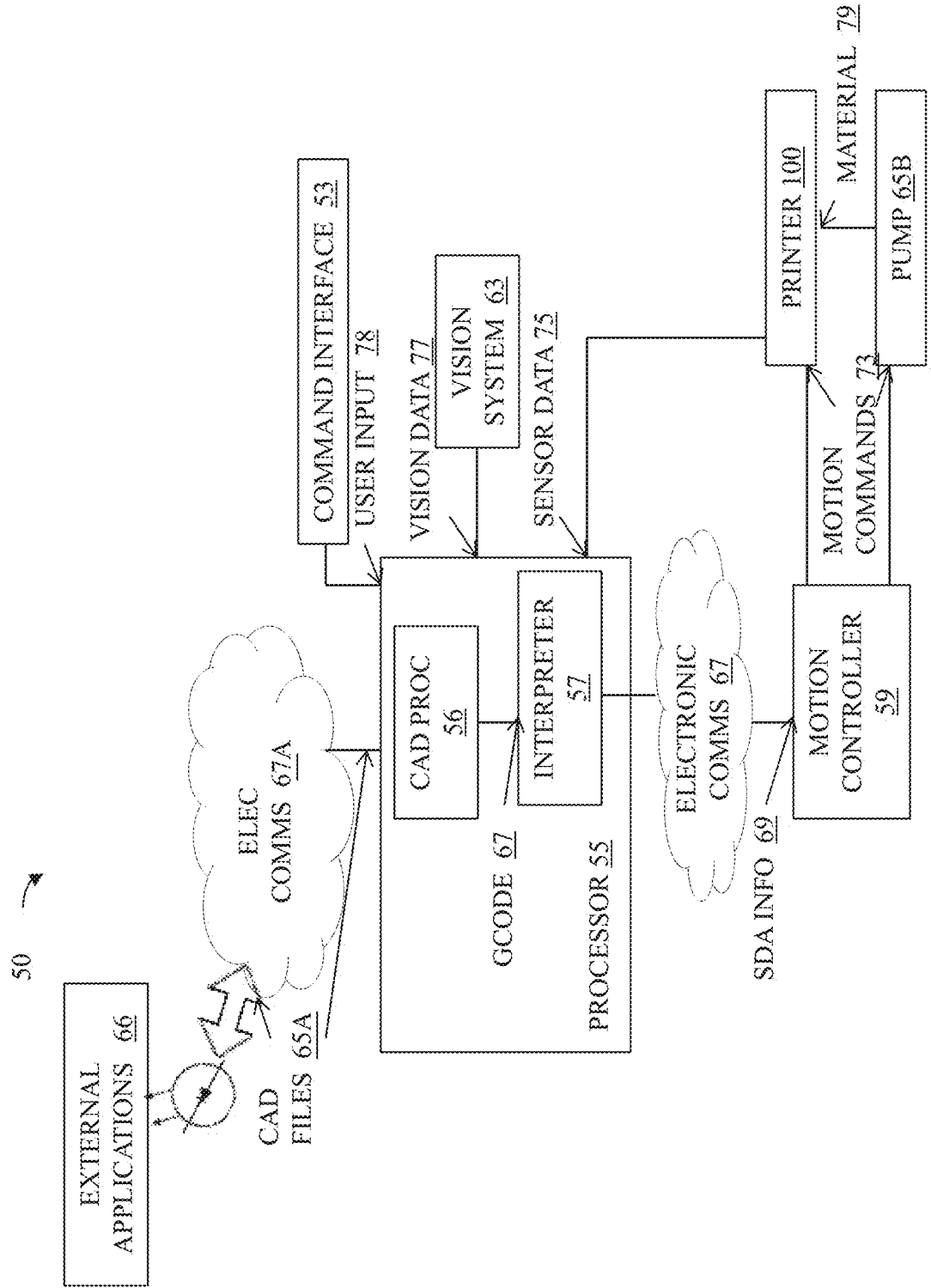

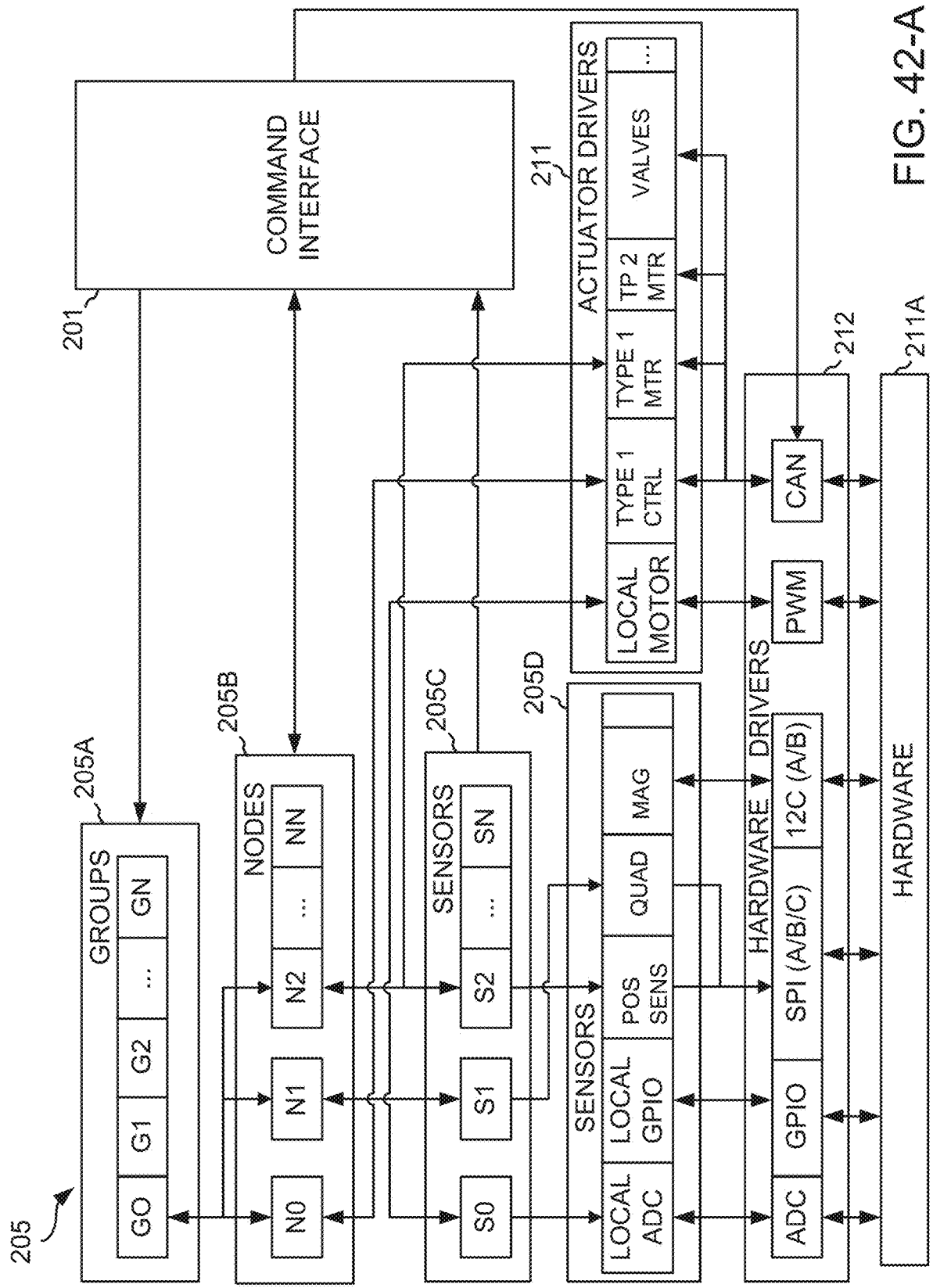
FIG. 42-A

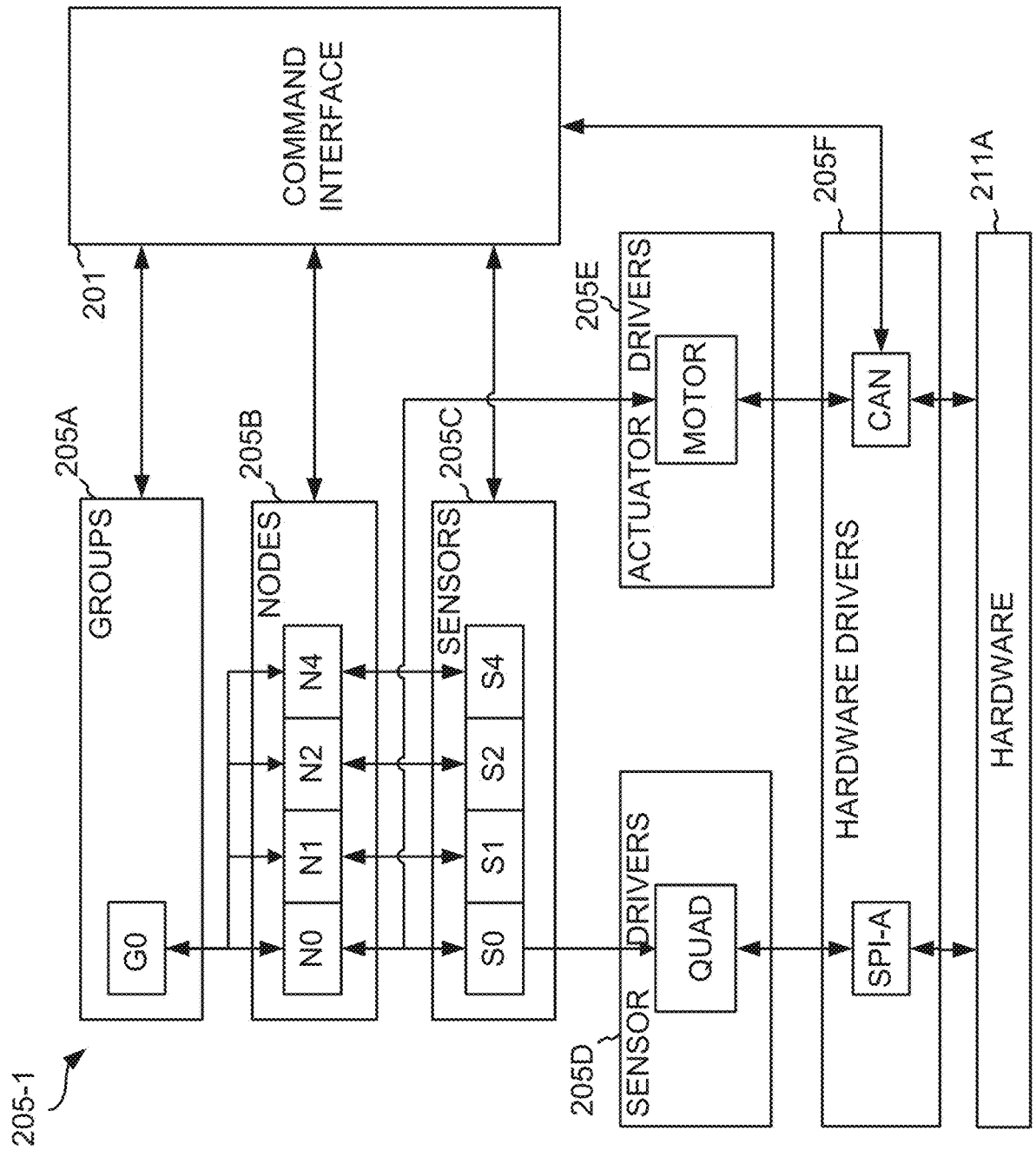
FIG. 42-B

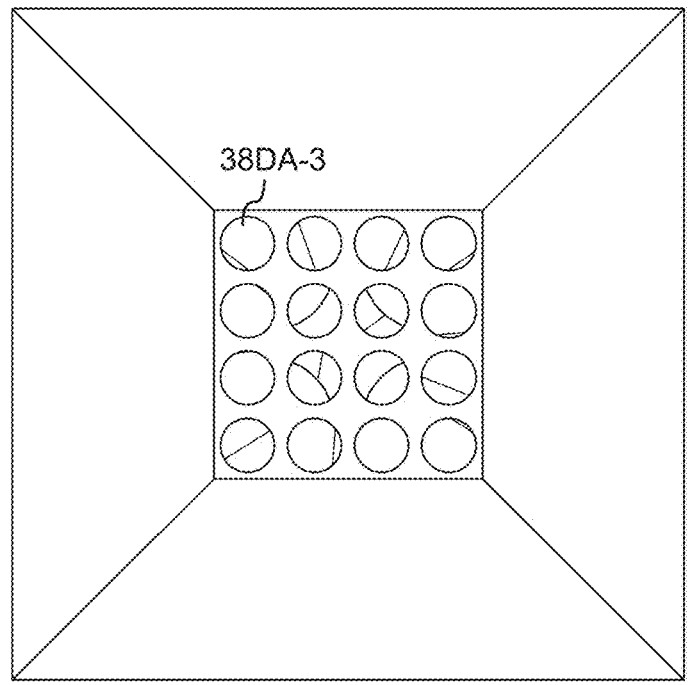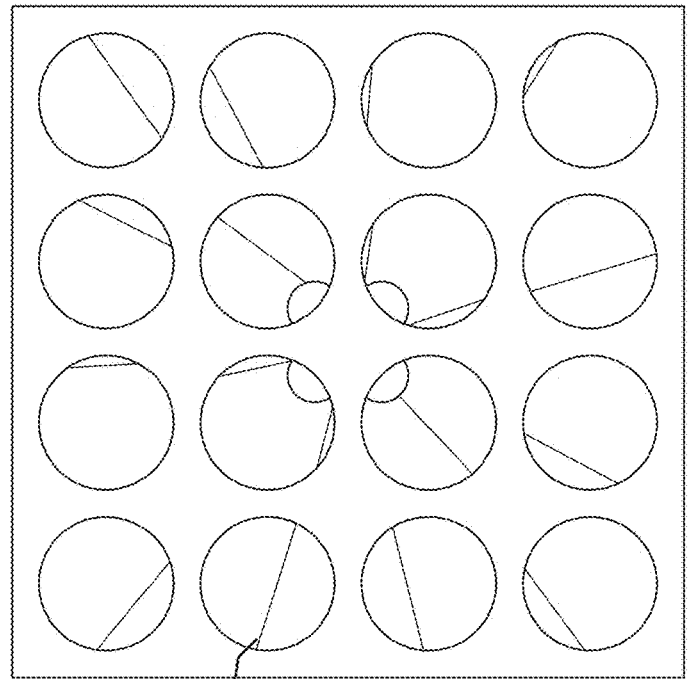
FIG. 53

SYSTEM AND METHOD FOR PRINTING TISSUE

CROSS REFERENCE TO RELATED APPLICATIONS

This utility patent application claims the benefit of U.S. Provisional Patent Application Ser. No. 62/361,214 filed Jul. 12, 2016, entitled System and Method for Creating Tissue, and U.S. Provisional Patent Application Ser. No. 62/361,209 filed Jul. 12, 2016, entitled System and Method for Controlling Motion, which are incorporated herein by reference in their entirety.

BACKGROUND

The present teachings relate generally to multi-dimensional printing, and more specifically to printing to enable tissue creation.

Three-dimensional printers have been developed that can use living cells as the printer "ink". Bioprinters have been used to print miniature and/or replicas of tissues for research purposes. Building structures that incorporate a complete set of elements that keep tissues alive, such as blood vessels and vascular structures to maintain oxygen flow, has been accomplished by combining living cells with special types of plastics and gels that can mimic biological tissues, muscle, and cartilage. As the cells divide and multiply, they secrete a supporting matrix that can maintain the structure's shape. What is needed is a multi-dimensional printer and an associated motion controller that that can dispense material into a biologic printing environment in a pre-designed configuration, where the pre-designed configuration and the biologic environment can promote organized cell division and therefore tissue creation.

Tissue modeling/robotic bioassembly systems can combine tools to design and print volumetric models of biological constructs by extruding a boundary to form a model volumetric object, sketching a 2-dimensional bounded construct on at least two different planes, and connecting the boundaries of the constructs. Such bioassembly systems dispense material through extrusion syringe dispensers adapted for direct-writing of a biomaterial onto a substrate. The dispensing apparatus is a robotic arm that has a robotic arm end effector that grips a syringe barrel. The robotic arm provides movement of a syringe along several axes, and dispenses biomaterials onto a print substrate by non-sequential planar layering, oblique-angle printing, and printing on print substrates having variable surface topographies. What is needed, however, is a system that can provide constrained printing inside a tissue enclosure, and can print multi-dimensional shapes without traditional slicing. What is further needed is a system that can convert a design sketched on a computer user interface to robot commands that can create the design within the tissue enclosure.

SUMMARY

The multi-dimensional printer of the present teachings, stably constructed of low-mass parts, can include a computer numerically controlled system that can enable motors driving delivery systems. The motors can include encoders that can enable achieving arbitrary resolution. The motors can drive ballscrews to enable linear motion of the delivery systems, and the delivery systems can enable printing of a biological material in a pre-selected pattern in a tissue enclosure such as, for example, but not limited to, a petri dish or an enclosed tissue enclosure. The tissue enclosure can accommodate a medium such as, for example, a biological gel, and can further accommodate a vision system such as, for example, a laser micrometer that can detect actual position of a delivery device. The printer can accommodate multiple delivery devices, multiple types of delivery devices, multiple materials, and multiple types of materials.

The motors can be controlled by a motion controller that can accommodate an arbitrary number of actuators, and multiple axes. The motion controller can interface with a processor via, for example, but not limited to, an Ethernet connection, and/or the motion controller can execute on the processor itself. The motion controller can include, among other control types, pass-through commands, control loops, and configurable control loops for multiple inputs. The processor/motion controller, as well as power and safety features, can be housed in an enclosure that can include start, stop, and emergency stop switches.

The system of the present teachings for creating tissue can include, but is not limited to including, at least one positional interface that can receive positional information related to creating the tissue. The positional interface can compute motion information based at least on the positional information. At least one motion controller can compute at least one motion command based at least on the motion information. A multi-dimensional printer can include at least one delivery system, and at least one hardware device. At least one of the hardware devices can receive sensor data, and at least one of the hardware devices can include at least one motor. The printer can drive at least one motor based at least on at least one motion command and the sensor data. The motors can drive at least one delivery system based at least on the sensor data. At least one delivery system can be associated with at least one printing environment, and can create the tissue by delivering at least one material into the at least one printing environment.

The printer can optionally print a three-dimensional structure. The printer can optionally be constructed of low-mass materials. The printer can optionally include a kinematic mount receptacle for the printing environment. The at least one sensor can optionally include a vision system sensing delivery system characteristics of the at least one delivery system. The vision system can provide the delivery system characteristics to the motion controller. The at least one delivery system can optionally include multiple needles of various sizes. The motion controller can optionally include a sensor processor, a group processor, and a node processor. The group processor can manage at least one group, and the at least one group can include at least one node. The at least one node can be associated with at least one actuator. The node processor can manage the at least one actuator, and the sensor processor can manage at least one sensor hardware through at least one sensor driver. The sensor processor can communicate the sensor data to the group processor and the node processor.

The motion controller can optionally include at least one actuator driver driving the at least one actuator, at least one hardware driver that can drive the at least one hardware device, and an error processor that can track errors encountered by the motion controller. The motion controller can optionally include multiple control types.

The method of the present teachings for controlling at least one actuator in any configuration can include, but is not limited to including, linking each of the at least one actuator to at least one sensor, controlling each of the at least one actuator in a control loop, grouping the at least one actuator to accomplish coordinated/synchronized motion, and establishing communications among the at least one actuator. The communications can optionally include a network (CANbus, EtherCAT). The at least one actuator can optionally include a group consisting of rotational motion, linear motion, binary valves, pneumatic compressor, pneumatics valves, and heating element. The at least one sensor can optionally include a group consisting of motor encoder, linear position, pressure sensor, gyroscope, accelerometer, and temperature sensor.

The bioprinting system for printing tissue into a tissue enclosure of the present teachings can include, but is not limited to including, a multi-dimensional printer, a delivery device operably coupled to the multi-dimensional printer, a motion controller commanding the delivery device to print the tissue, and a delivery device locating subsystem returning the delivery device to selected locations within the printed tissue. The delivery device locating subsystem can optionally include a mounting plate including kinematic positioning features, a tissue enclosure being a repository for the printed tissue, the tissue enclosure including kinematic mounting features matably couplable with the kinematic positioning features the mounting features and the positioning features insuring consistent between mounting and remounting of the tissue enclosure, and at least one sensor enabling determining the position of the delivery device within the tissue enclosure. The delivery device locating subsystem can optionally include at least one delivery device fiducial operably coupled with the delivery device.

The at least one sensor can optionally determine the position of the delivery device based at least on the at least one delivery device fiducial. The printer can optionally be constructed of low-mass materials. The at least one sensor can optionally include a vision system sensing delivery system characteristics of the at least one delivery system. The vision system can provide the delivery system characteristics to the motion controller. The motion controller can optionally include a sensor processor, a group processor, and a node processor. The group processor can manage at least one group, and the at least one group including at least one node. The at least one node can be associated with at least one actuator. The node processor can manage the at least one actuator, and the sensor processor can manage at least one sensor hardware through at least one sensor driver. The sensor processor can communicate the sensor data to the group processor and the node processor. The motion controller can optionally include at least one actuator driver driving the at least one actuator, at least one hardware driver driving the at least one hardware device, and an error processor tracking errors encountered by the motion controller. The delivery device can optionally include bi-directional fluid control between the delivery device and the tissue enclosure. The delivery device can optionally accommodate a plurality of input materials, and can include a mixing valve receiving the plurality of input materials. The mixing valve can extrude a single stream of the input materials as the printed tissue.

The system of the present teachings for returning a delivery device of a bioprinter to a specific location in a tissue enclosure after tissue has been printed by the bioprinter, where the bioprinter includes a motion controller, the system can include, but is not limited to including, a kinetic mount means coupling the tissue enclosure with the bioprinter, and a calibration system determining origin coordinates of a reference point of the delivery device within the tissue enclosure. The calibration system can provide the reference point to the motion controller. The system can include a delivery device locating system determining location coordinates of the delivery device as the motion controller commands the delivery device to print the tissue. The kinematic mount means can optionally include mounting features affixed to the tissue enclosure, and positioning features associated with the bioprinter. The mounting features can operably couple with the positioning features to consistently position the tissue enclosure between removal and replacement of the tissue enclosure between printing sessions. The calibration system can optionally include at least one sensor operably coupled with the motion controller. The at least one sensor can enable automatic calibration of the delivery system within the tissue enclosure. The delivery device locating system can optionally include at least one fiducial associated with the delivery device, and at least one sensor sensing the location of the delivery device based on the at least one fiducial.

The method of the present teachings for returning to a specific location in a tissue enclosure after tissue has been printed by a multi-dimensional printer, where the multi-dimensional printer include a delivery device and a motion controller, the method can include, but is not limited to including, coupling the tissue enclosure with the multi-dimensional printer with a kinematic mount means, determining origin coordinates of a reference point of the delivery device within the tissue enclosure, providing the reference point to the motion controller, locating coordinates of the delivery device as the motion controller commands the delivery device to print the tissue, and returning to the delivery device coordinates after the printing of the tissue is complete.

The motion controller can optionally control at least one actuator including linking each of the at least one actuator to at least one sensor, controlling each of the at least one actuator in a PID loop, grouping the at least one actuator to accomplish coordinated/synchronized motion, and establishing communications among the at least one actuator. The communications can optionally include a communications network. The at least one actuator can optionally be selected from a group consisting of rotational motion, linear motion, binary valves, pneumatic compressor, and heating element. The at least one sensor can optionally be selected from a group consisting of motor encoder, linear position, pressure sensor, gyroscope, accelerometer, and temperature sensor.

The bioprinting system of the present teachings for multi-dimensional printing of tissue into a tissue enclosure can include, but is not limited to including, a multi-axis, multi-dimensional printer including a robot controller controlling the motion of the printer, and a delivery device operably coupled with the printer. The delivery device can deliver the tissue. The system can include a tissue enclosure that can include a space for the printed tissue. The tissue enclosure can receive the delivered tissue, and the tissue enclosure can include a plurality of control points that can enable entry of the delivery device. The tissue enclosure can include production line mounting features. The system can include a computer that can access a design of the tissue to be printed. The computer can convert the design to coordinates that the multi-dimensional printer can use to print tissue into the tissue enclosure. The computer can execute computer commands including, but not limited to, accessing parameters associated with the computer commands, and pathing of the design based at least on the parameters. The pathing can produce robot coordinates of the design. The computer can execute commands including transferring the robot coordinates from the computer to the multi-dimensional printer. The system can include a robot controller that can process the robot coordinates including converting the robot coordinates to robot points, an approach vector, an orientation vector, and at least one path, choosing a robot figure for each path based on a desired robot position and range of motion, determining a translation data type based on the approach vector, the orientation vector, and the robot figure, creating at least one motion command based on the translation data type and the robot points, and printing the tissue into the tissue enclosure by commanding the printer based on the at least one motion command.

The method of the present teachings for printing tissue into a tissue enclosure using a robot can include, but is not limited to including, accessing a design of the tissue by a computer, converting the design to robot coordinates that the robot can use to print tissue into the tissue enclosure including, but not limited to including, initializing a multi-axis, multi-dimensional printing system including, but not limited to including, establishing offset parameters for a robot tool, the robot tool enabling printing of the tissue into the tissue enclosure, locating at least one control point used in pathing, and creating at least one path point to be pathed in part space. The pathing can include, but is not limited to including, converting the at least one control point and the at least one path point to robot coordinates, and determining robot orientations. The transferring of the robot coordinates from the computer to the robot can include, but is not limited to including, creating batches of data, setting a pose for the robot for each of the batches, sending the batches to the robot using a communications network protocol, and processing the batches in the robot can include, but is not limited to including, converting the data in each of the batches to robot points, an approach vector, and an orientation vector, choosing a robot figure for each path based on a desired robot position and range of motion, determining a translation data type based on the vector components and the robot figure, and creating a motion command based on the translation data type and the robot points. The method can include executing the motion command to print the tissue in the tissue enclosure.

The method of the present teachings for filling a syringe with a material housed in a container, where the syringe includes a syringe barrel and a plunger, the method can include, but is not limited to including, inserting the syringe barrel into a syringe filler. The syringe barrel can include a plunger end and a coupling end. The syringe filler can include a syringe coupler at a first end of the syringe filler, and a flange at a second end of the syringe filler. The syringe coupler can include a contact end having an opening. The method can include operably coupling the coupling end of the syringe barrel with the syringe coupler, and depressing the flange and the syringe barrel into the container until the material enters the opening and until the material emerges from the syringe plunger end of the syringe barrel.

The method can optionally include removing the plunger from the syringe barrel before inserting the syringe barrel into the syringe filler, and replacing the plunger into the syringe barrel after the syringe barrel is removed from the syringe filler. The material can optionally include a gel-like substance. The method can optionally include homogenizing the material by centrifugation or speed mixing. The syringe coupler can optionally include threading. The threading can matingly couple the syringe barrel with the syringe coupler. The opening size can optionally be based at least on a desired flow rate of the material into the syringe coupler and a desired normal force on the flange required to transfer the material to the syringe barrel.

The syringe filler of the present teachings for filling a syringe barrel with a material, where the syringe barrel includes a plunger end and a coupling end, the syringe filler system can include, but is not limited to including, a filler body including enough space to accept the syringe barrel, and a flange operably coupled with filler body. The flange can enable a substantially normal force to be exerted against the filler body. The substantially normal force can push the syringe filler into a container containing the material. The syringe filler can include a syringe coupler that can include a syringe coupling and a material tube. The syringe coupling can matably connect with the filler body. The material can travel through the material tube from the container to the syringe barrel. The filler body can optionally include a diameter accommodating the size of the syringe barrel and the diameter of the container. The syringe coupler can optionally include at least one protrusion providing at least one seating position for at least one gasket. The at least one gasket can enable the syringe coupler to tightly couple with the container as the syringe coupler moves into the container.

The printing device of the present teachings for printing in a gel-like material can include, but is not limited to including, at least one chassis composed of a base structure and a chassis upright and further comprising a first region and a second region. The first region can be partitioned from the second region through a barrier on base structure of the chassis. The printing device can include at least one primary carriage operatively coupled with the chassis upright and performing a first set of at least one guided motion along at least one fixed path on the plane of the chassis upright. The printing device can include at least one first sub-carriage providing an engaging feature and a pathway operatively coupled with the at least one primary carriage to perform a second set of at least one guided motion. The printing device can include at least one second sub-carriage configured to travel along the pathway of the first sub-carriage to perform a third set of at least one guided motion. The printing device can include at least one delivery system engaged with one of the carriages through a common base plate. The at least one delivery system can perform a resultant motion from combination of first, second and third sets of guided motions. The delivery system can engage one or more printing cartridges at more than one engaging points to exhibit bi-directional material flow in the one or more cartridges. The delivery system can include at least one vessel comprising the gel-like material wherein the printing device prints, the at least one vessel further arrested by a vessel adaptor configured to accommodate vessels of varying dimensions. The printing device can optionally include at least one referencing system. The printing device can optionally include at least one monitoring system that can operate in conjunction with the at least one referencing system.

The method of the present teachings for manufacturing a printing system for printing a specimen in a gel-like material can include, but is not limited to including, providing a chassis with a base structure and an upright body. The base structure can house one or more vessel adaptors to arrest one or more vessels of varying dimensions. The method can include engaging the chassis with at least one primary carriage performing a first set of at least one guided motion along plane of the chassis, and engaging the at least one primary carriage with at least one first sub-carriage comprising an engaging portion and a pathway. The first sub-carriage can provide a second set of at least one guided motion. The method can include engaging the first sub-carriage with a second sub-carriage comprising an engaging portion and a second pathway. The second sub-carriage can perform a third set of at least one guided motion. The method can include engaging at least one delivery assembly with the second sub-carriage. The delivery assembly can include, but is not limited to including, a base plate engaging a lower end of at least one printing cartridge. The base plate engage the at least one delivery assembly with at least one of the carriages such that a combined motion of the first, second and third sets of guided motion is advanced to the delivery assembly. The delivery assembly can include at least one actuating plate engaging at least one plunger end of the printing cartridge such that one or more travel features on the at least one actuating plate can bi-directionally actuate the at least one plunger of the printing cartridge. The at least one actuating plate can be partially engaged with the base plate. The delivery assembly can include at least one printing cartridge that can include a body portion with print material and a delivery needle and a plunger portion that can actuate the print material therein. The at least one printing cartridge can be partially held between the base plate and the at least one actuating plate such that the plunger portion is bi-directionally actuated.

BRIEF DESCRIPTION OF THE DRAWINGS

The present teachings will be more readily understood by reference to the following description, taken with the accompanying drawings, in which:

FIG. 2A-1 is a schematic diagram of first and second views of the petri dish first configuration dish lid of the present teachings;

FIG. 2A-2 is a schematic diagram of first and second views of the petri dish second configuration dish lid of the present teachings;

FIG. 2B is a schematic diagram of first and second views of the petri dish mounting plate of the present teachings;

FIG. 5B is a schematic diagram of first and second views of the support rails second configuration of the present teachings;

FIG. 8 is a schematic diagram of first and second views of the ball nut of the present teachings;

FIG. 9 is a schematic diagram of first and second views of the screw cover tube of the present teachings;

FIG. 12A is a schematic diagram of first and second views of the z-axis stop bearing of the present teachings;

FIG. 13 is a schematic diagram of first and second views of the microscope plate adapter of the present teachings;

FIG. 14C is a schematic diagram of the y-axis linear bearing of the present teachings;

FIG. 16A is a schematic diagram of first and second views of the block z-axis stop bearing of the present teachings;

FIG. 20 is a schematic diagram of first and second views of the motor junction box of the present teachings;

FIG. 21A is a schematic diagram of first and second views of the x-axis linear bearing of the present teachings;

FIG. 21B is a schematic diagram of first and second views of the bumper of the present teachings;

FIG. 23C is a schematic diagram of first and second views of the spindle adapter second configuration of the present teachings;

FIG. 23B is a schematic diagram of first and second views of the spindle adapter third configuration of the present teachings;

FIG. 25C-1 is a schematic diagram of the delivery system second configuration of the present teachings;

FIG. 25C-1A is a schematic diagram of first and second views of the plunger fit of the present teachings;

FIG. 25C-2 is a schematic diagram of an exploded view of the delivery system second configuration of the present teachings;

FIGS. 25F-1A and 25F-1B are schematic diagrams of first and second views of the plunger extension adapter of the present teachings;

FIG. 25F-2 is a schematic diagram of first and second views of the syringe swing clamp of the present teachings;

FIG. 25F-3 is a schematic diagram of first and second views of the bumper of the present teachings;

FIG. 26B is a schematic diagram of first and second views of the barrel third configuration of the present teachings;

FIGS. 26F-26J are schematic diagrams of the syringe filler of the present teachings;

FIG. 26K is a schematic diagram of a second configuration syringe filler of the present teachings;

FIG. 27A is a schematic diagram of first and second views of the switch housing of the present teachings;

FIG. 29 is a schematic diagram of first and second views of the gearbox of the present teachings;

FIG. 30 is a schematic diagram of first and second views of the motor nut adapter of the present teachings;

FIGS. 31A and 31B are schematic diagrams of various views of the barrel slide clip of the present teachings;

FIG. 33 is a schematic diagram of first and second views of the delivery system connector of the present teachings;

FIG. 33A is a schematic diagram of first and second views of the delivery system connector second configuration of the present teachings;

FIG. 34 is a schematic diagram of first and second views of the needle guide of the present teachings;

FIG. 35 is a schematic diagram of first and second views of the barrel holder of the present teachings;

FIGS. 35A and 35B are schematic diagrams of various views of the barrel holder second configuration of the present teachings;

FIG. 37D is a schematic diagram of first and second views of the junction box lower assembly of the present teachings;

FIG. 38 is a schematic diagram of the gas spring of the present teachings;

FIG. 38I is a front bottom right-side perspective view of primary carriage belonging to exemplary printer of the present teachings;

FIG. 38J is a rear top left-side perspective view of primary carriage belonging to exemplary printer of the present teachings;

FIG. 38L is a front top right-side exploded view depicting engagement of primary carriage and first sub-carriage of the exemplary printer;

FIG. 38Q depicts a front top right-side perspective view depicting engagement of primary carriage, first and second sub-carriages and chassis upright of the exemplary printer;

FIG. 38U is a front top right side perspective view depicting engagement of a single cartridge delivery system with the remainder of exemplary printing device;

FIG. 38V is a front top right side partially assembled view depicting engagement of a dual cartridge delivery system with the remainder of exemplary printing device;

FIG. 38X is a front top right side perspective view depicting assembly comprising a dual cartridge delivery system with remainder of exemplary printing device;

FIGS. 38Y and 38Z are perspective views of an exemplary single cartridge delivery system;

FIG. 38AA is an exploded view of an exemplary single cartridge delivery system;

FIGS. 38BB and 38CC are perspective views of an exemplary dual cartridge delivery system;

FIG. 38DD is an exploded view of an exemplary dual cartridge delivery system;

FIG. 38EE is perspective view of an exemplary mixing valve and valve mount;

FIG. 38FF is a partially exploded view depicting engagement of exemplary mixing valve and valve mount;

FIG. 38GG is a cross section view depicting engagement of exemplary mixing valve and valve mount;

FIG. 39 is a schematic block diagram of the architecture of the control system of the present teachings;

FIGS. 42-A and 42-B are schematic block diagrams of exemplary configurations of the architecture of the motion controller of the present teachings;

Figure 43:
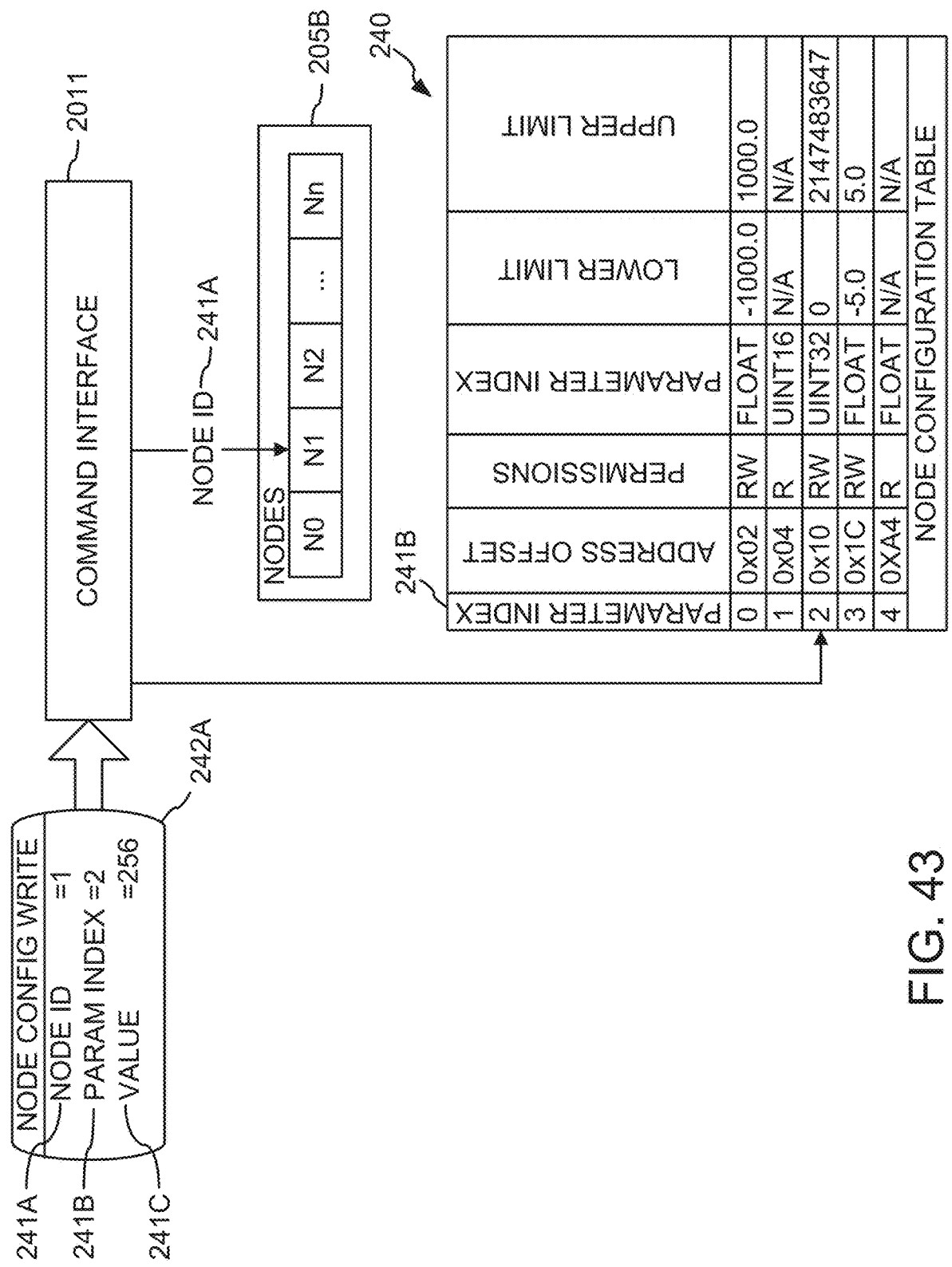
Figure 44A:
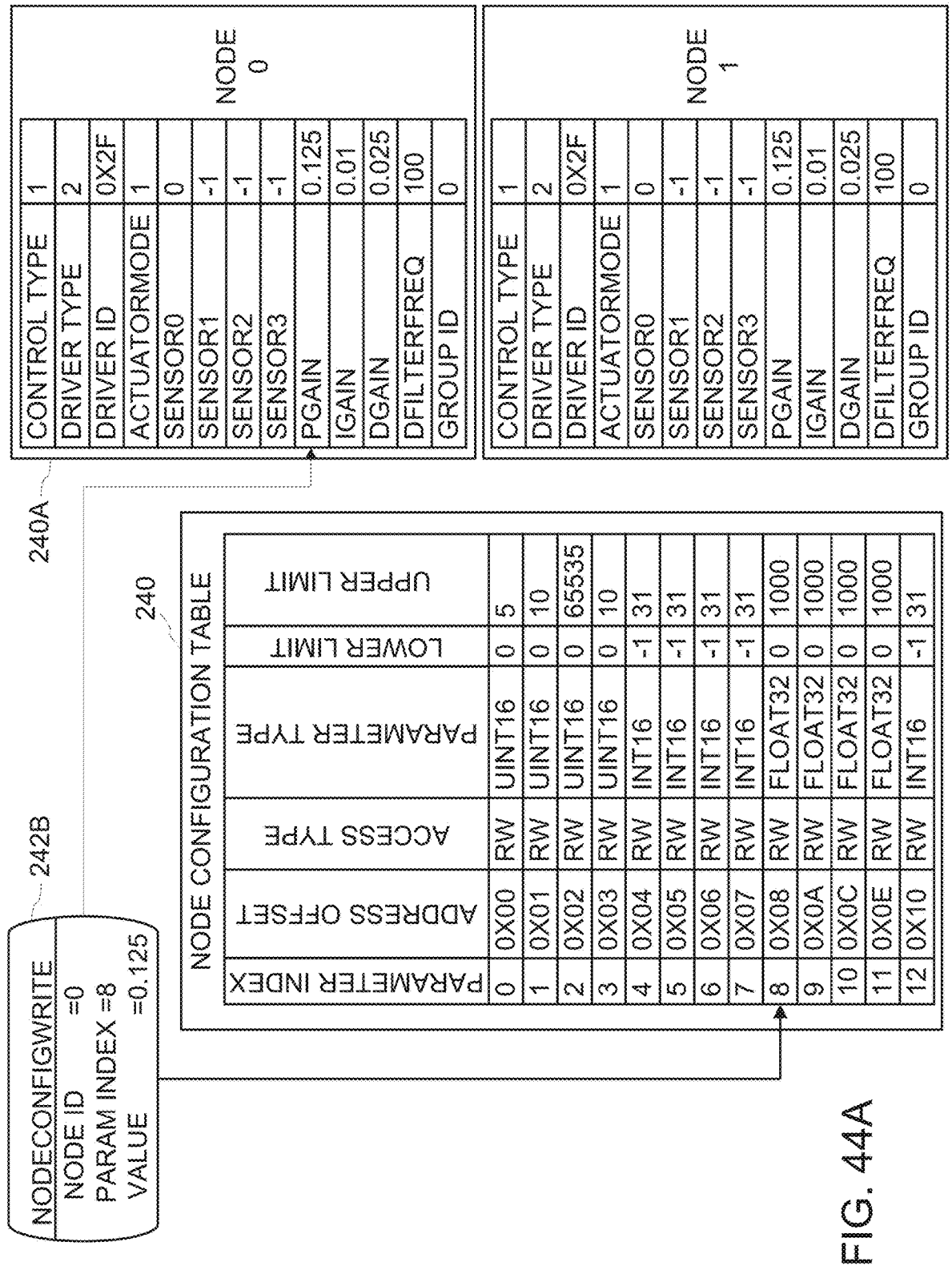
Figure 44B:
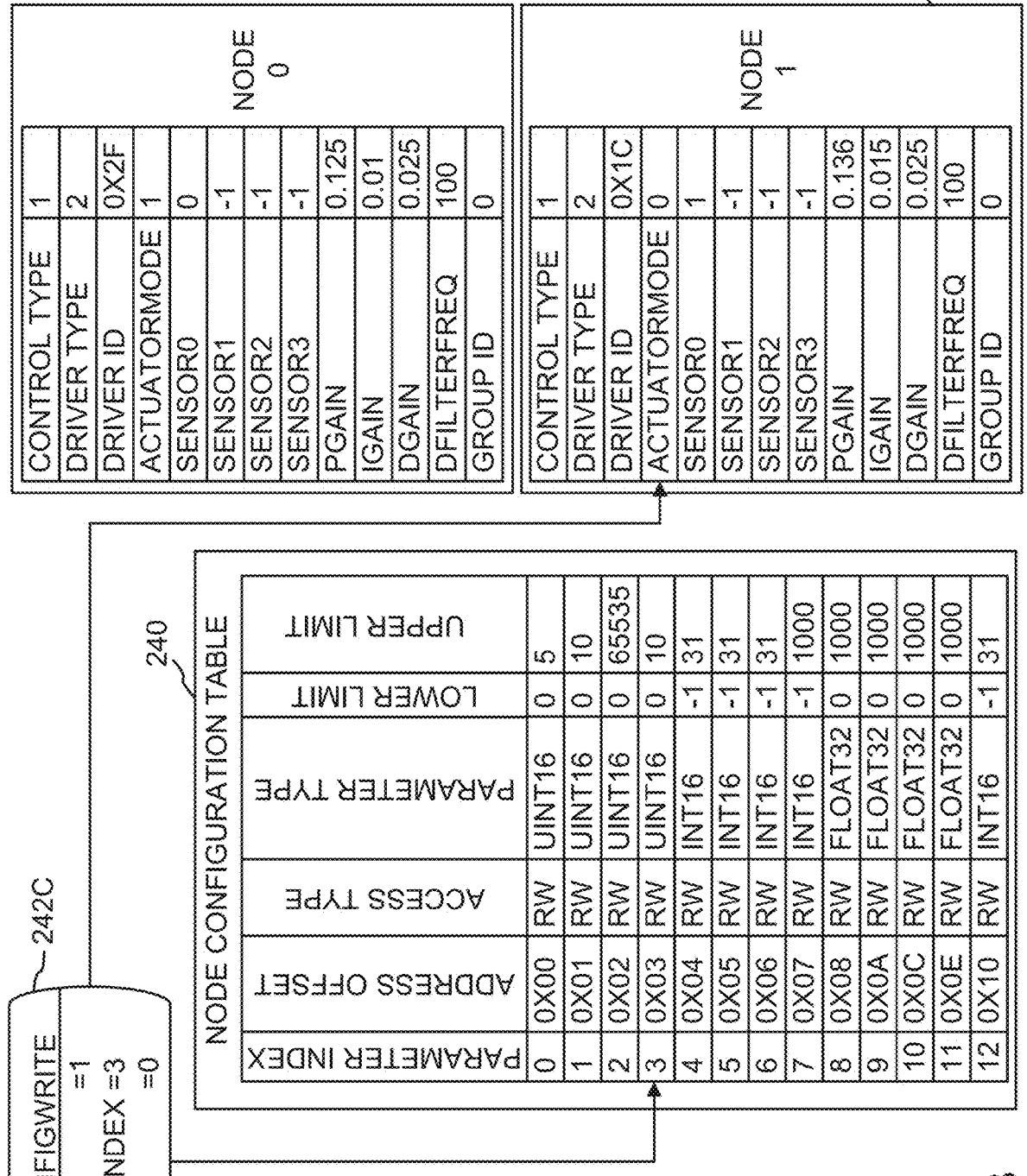
Figure 44C:
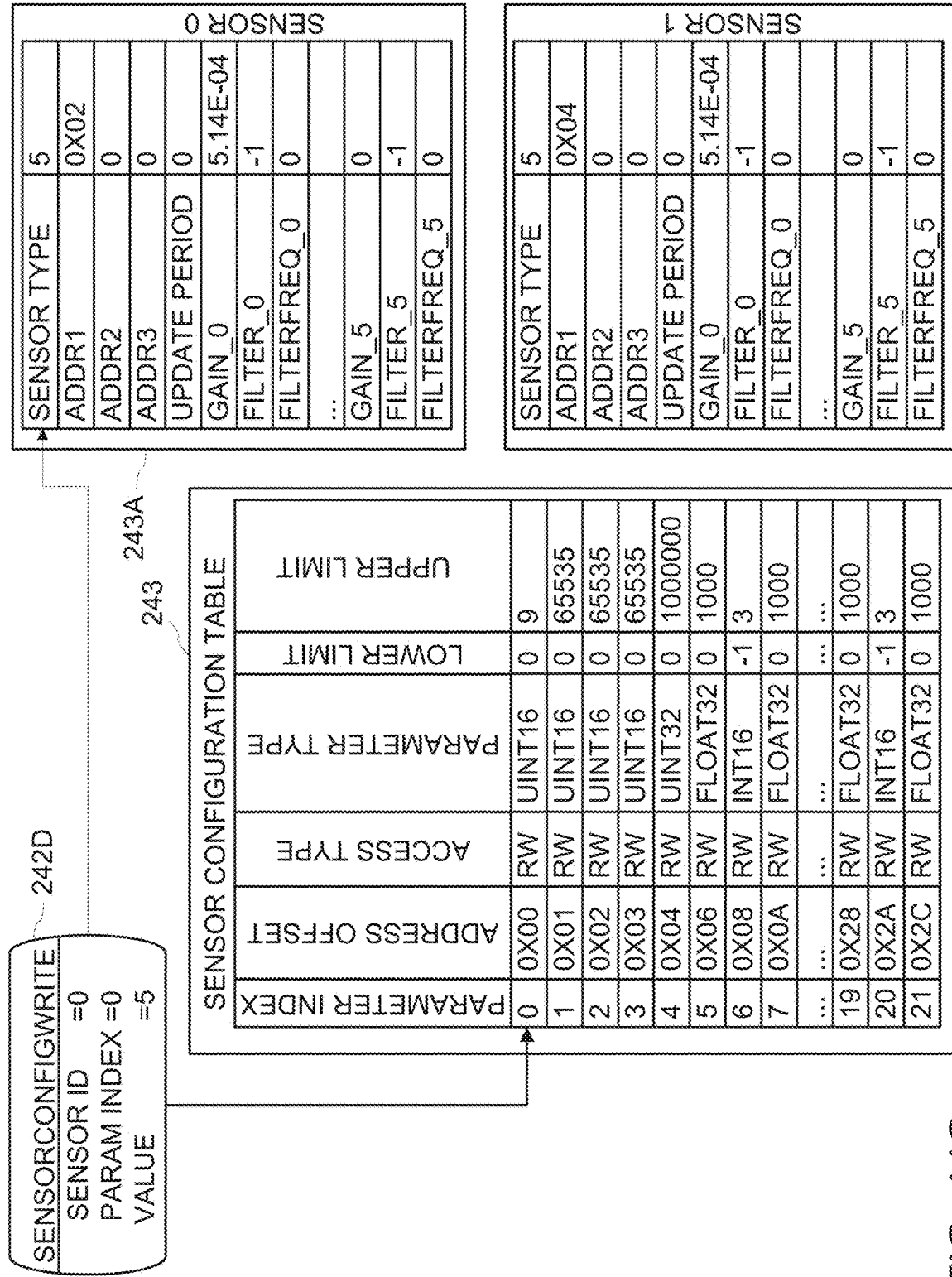
Figure 44D:
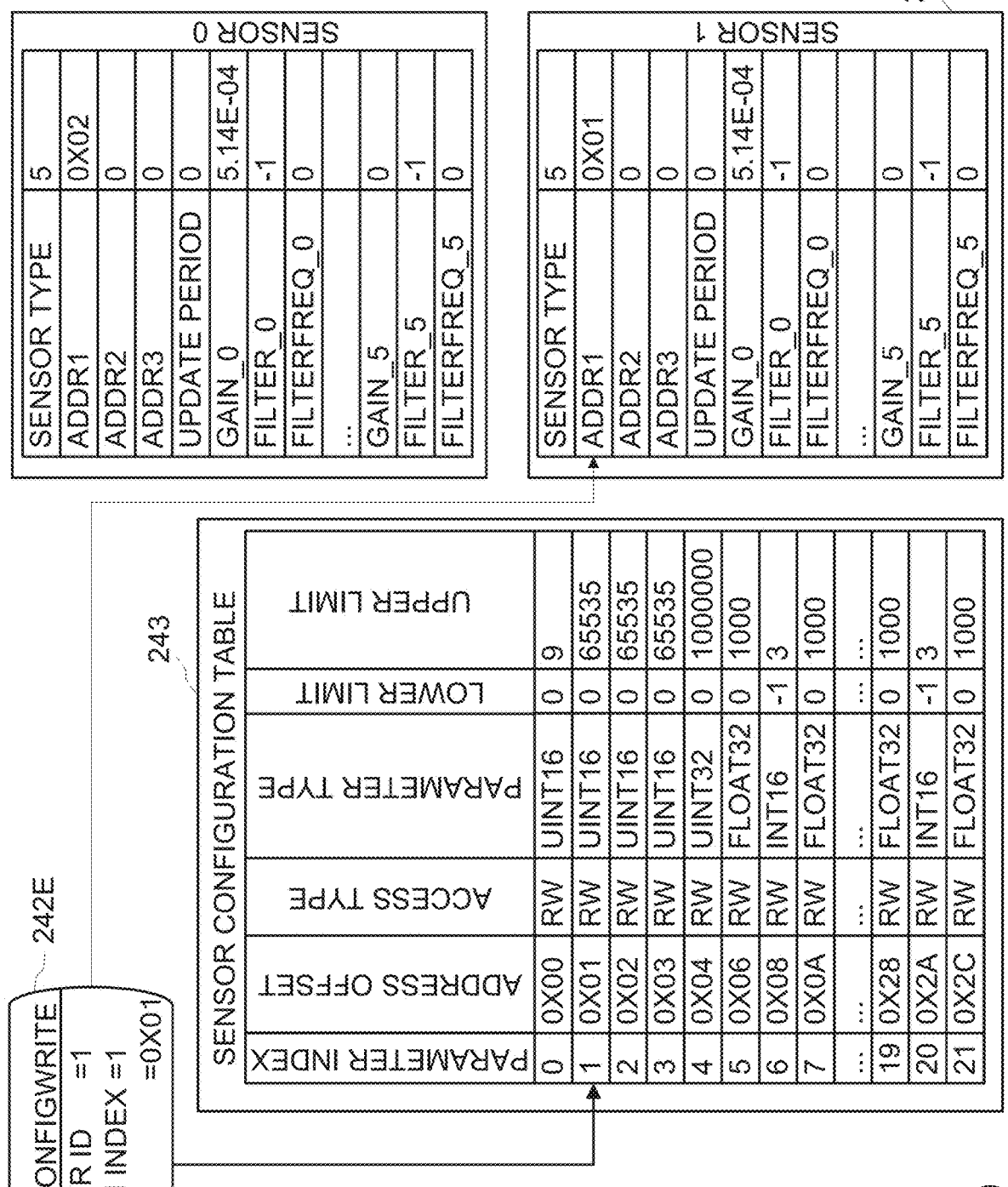
Figure 45:
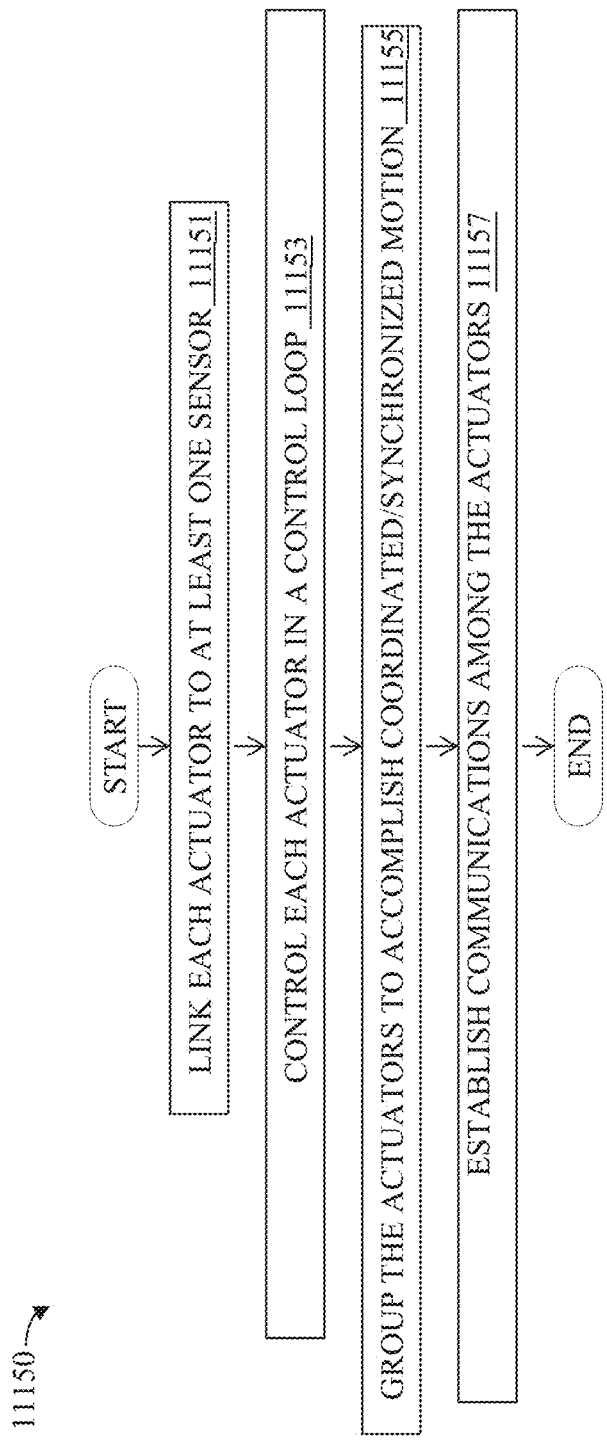
Figure 46:
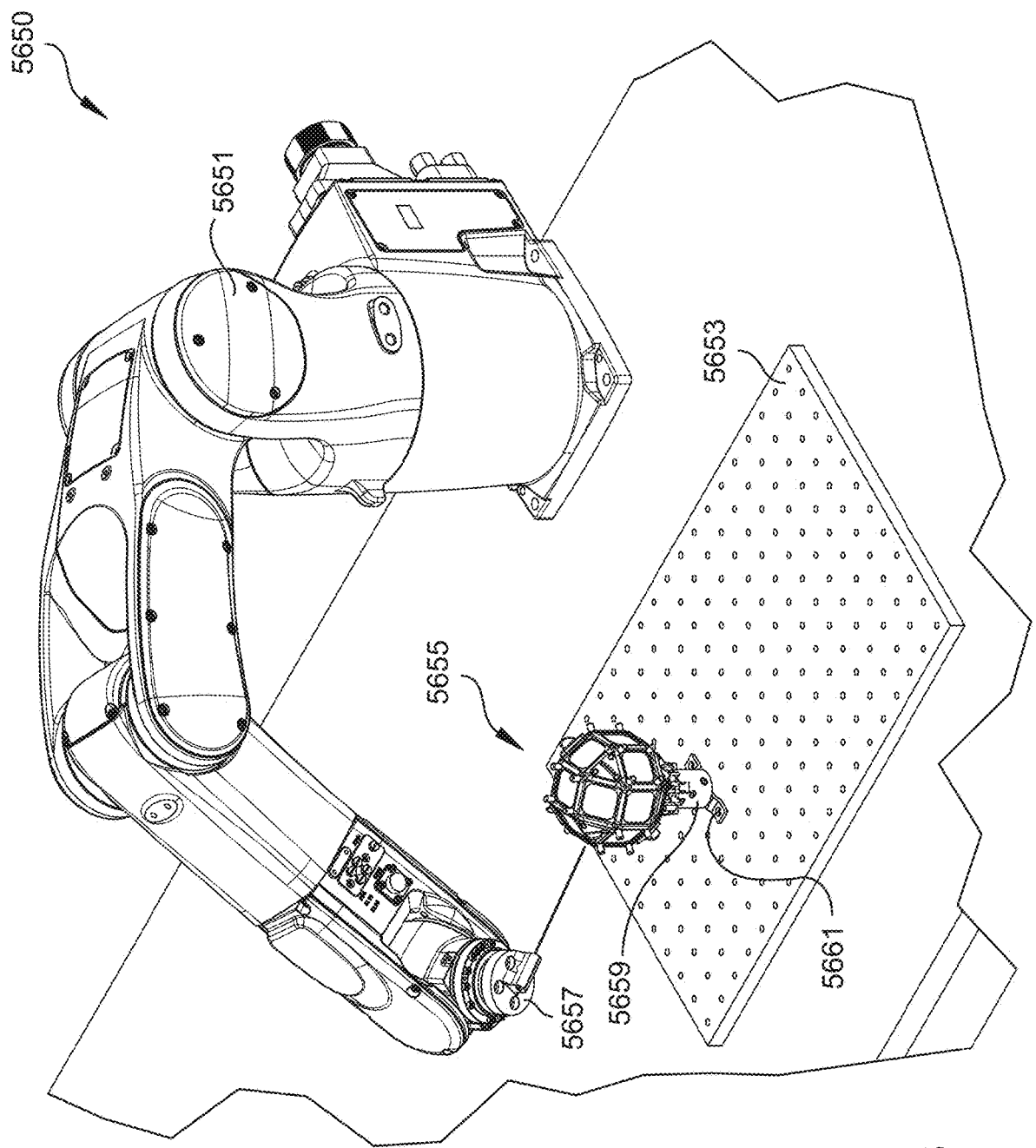
Figure 47:
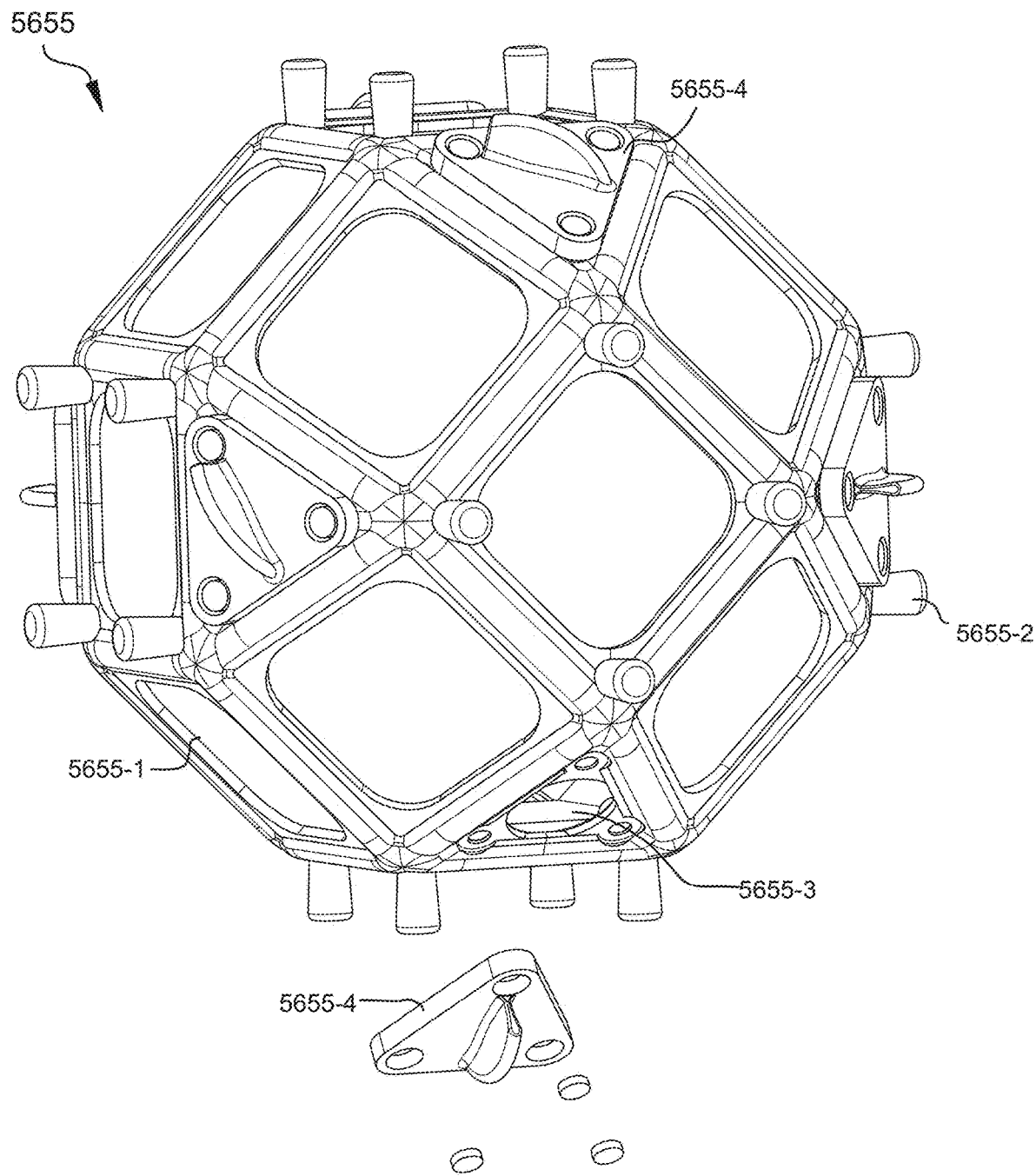
Figure 48:
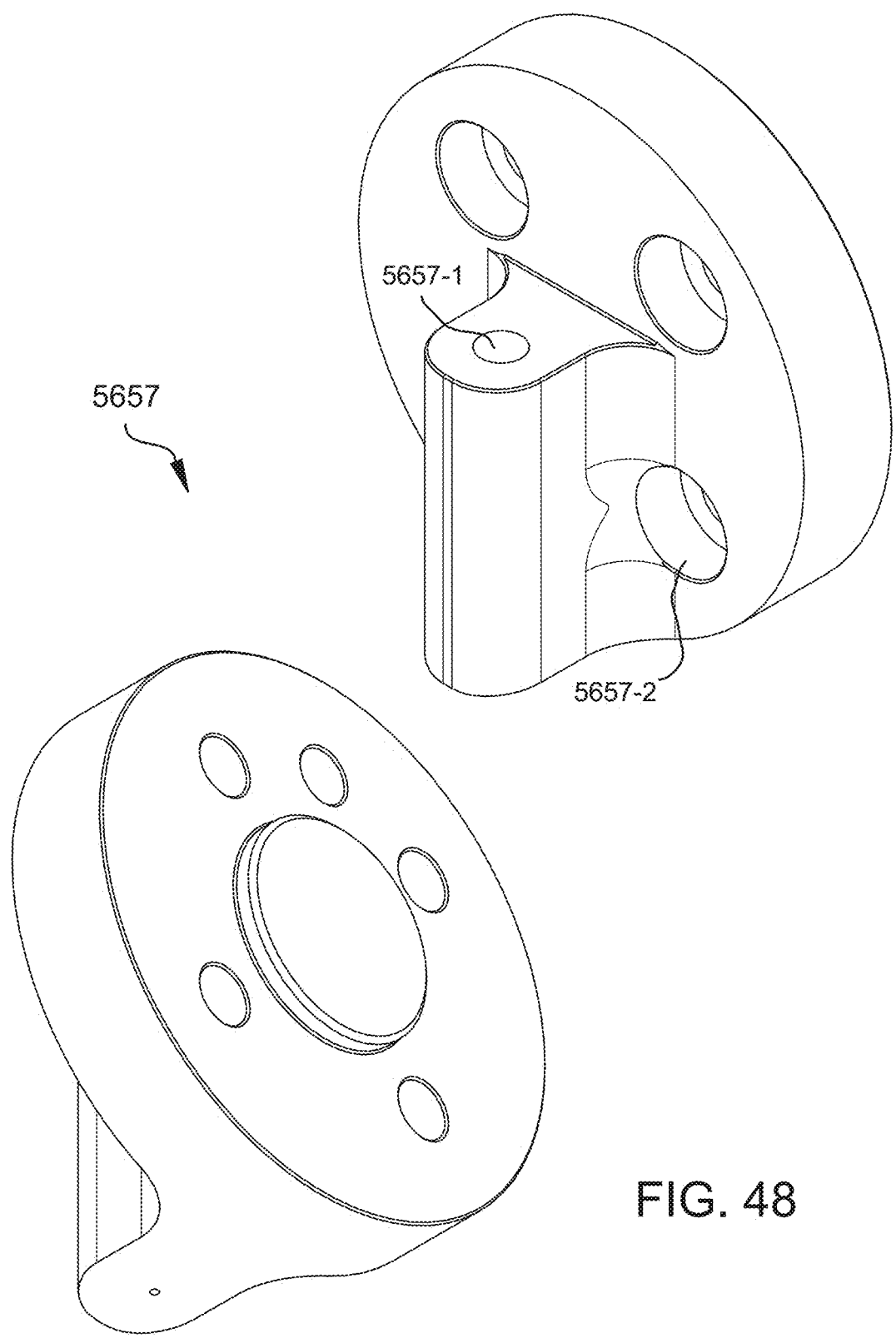
Figure 49A:
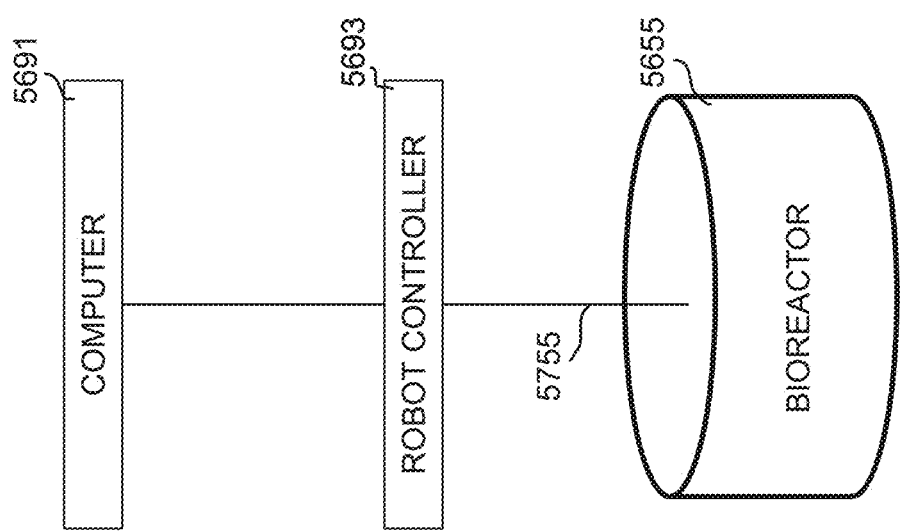
Figure 49B:
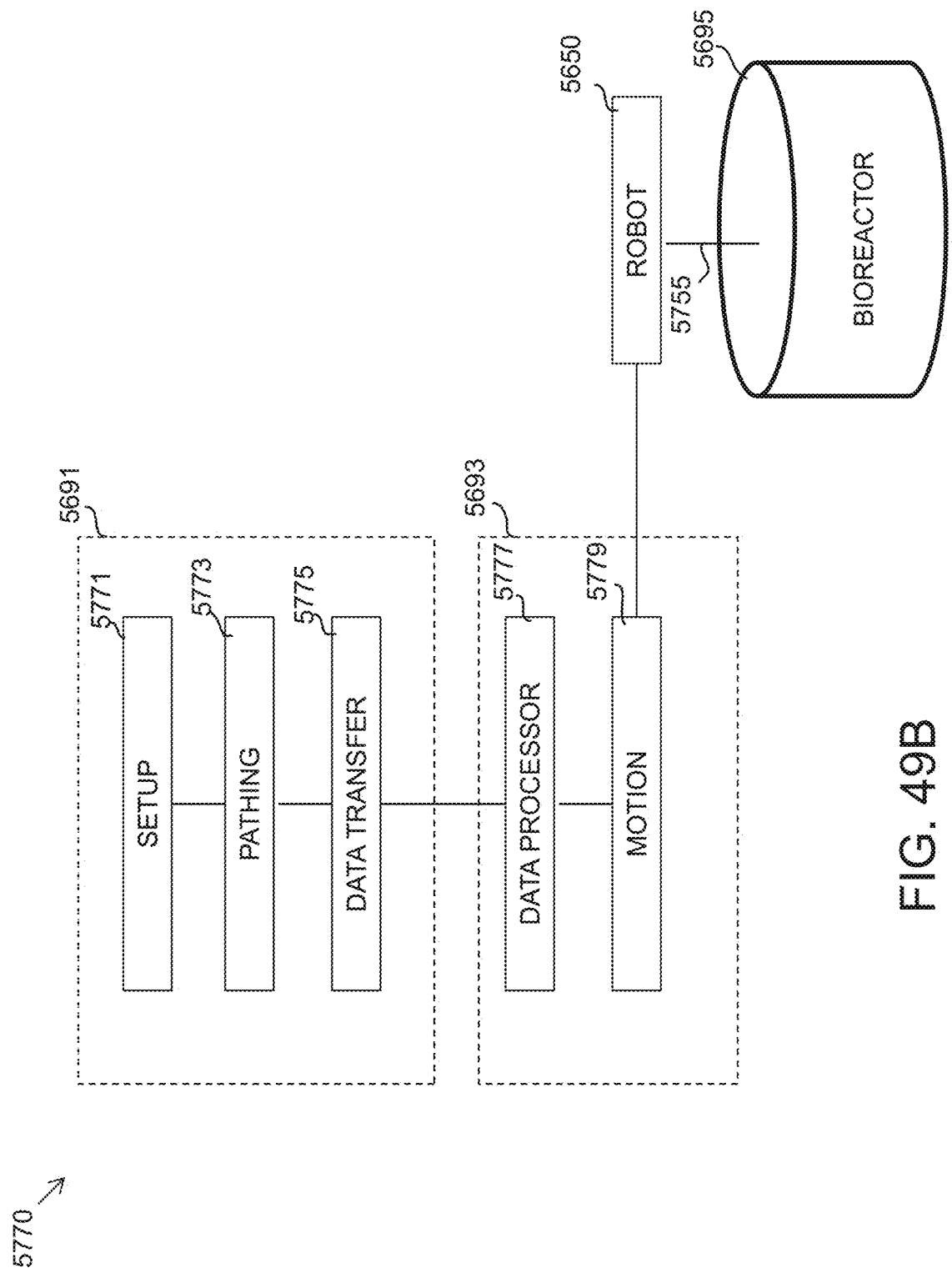
Figure 50:
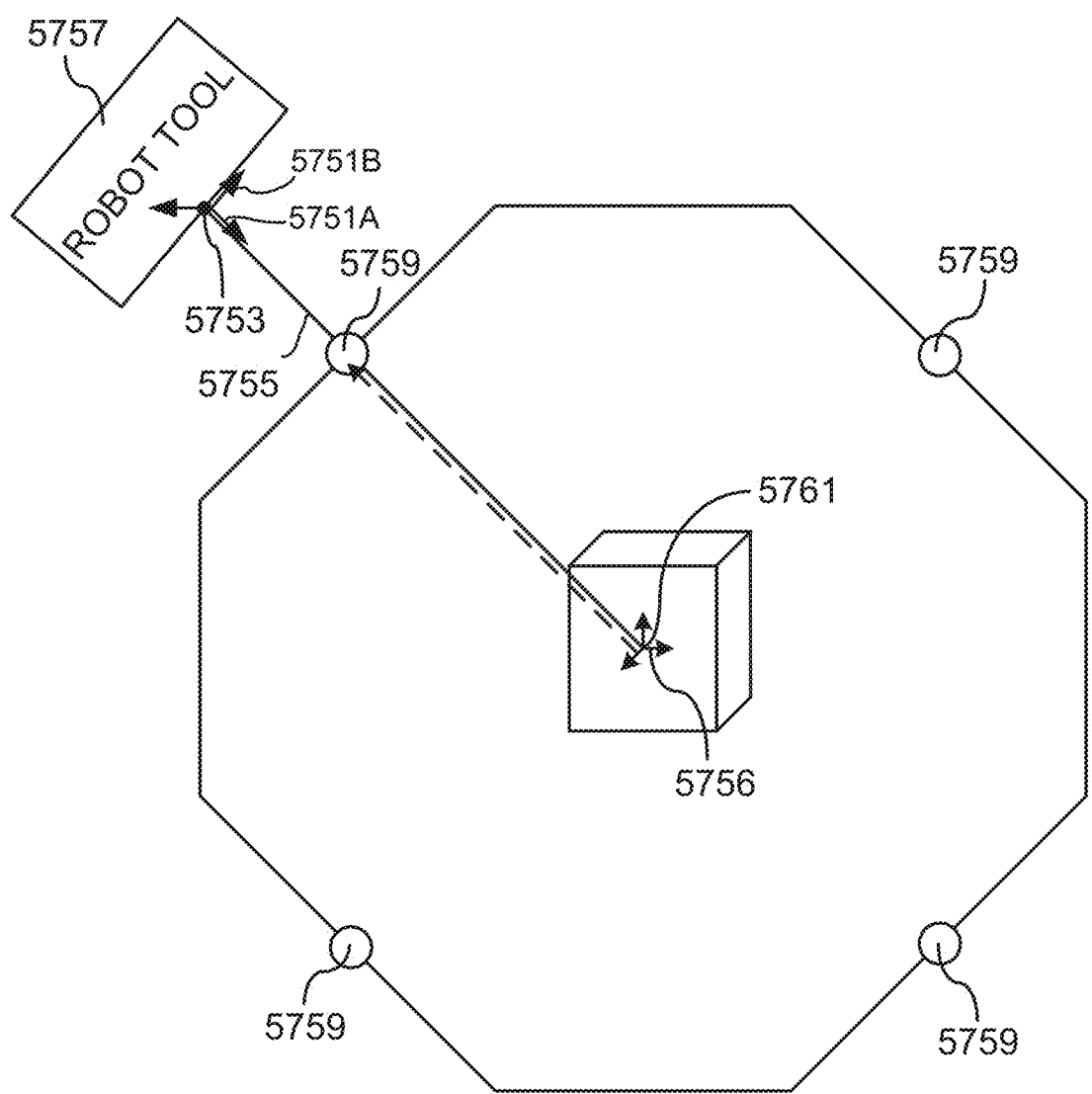
Figure 51:
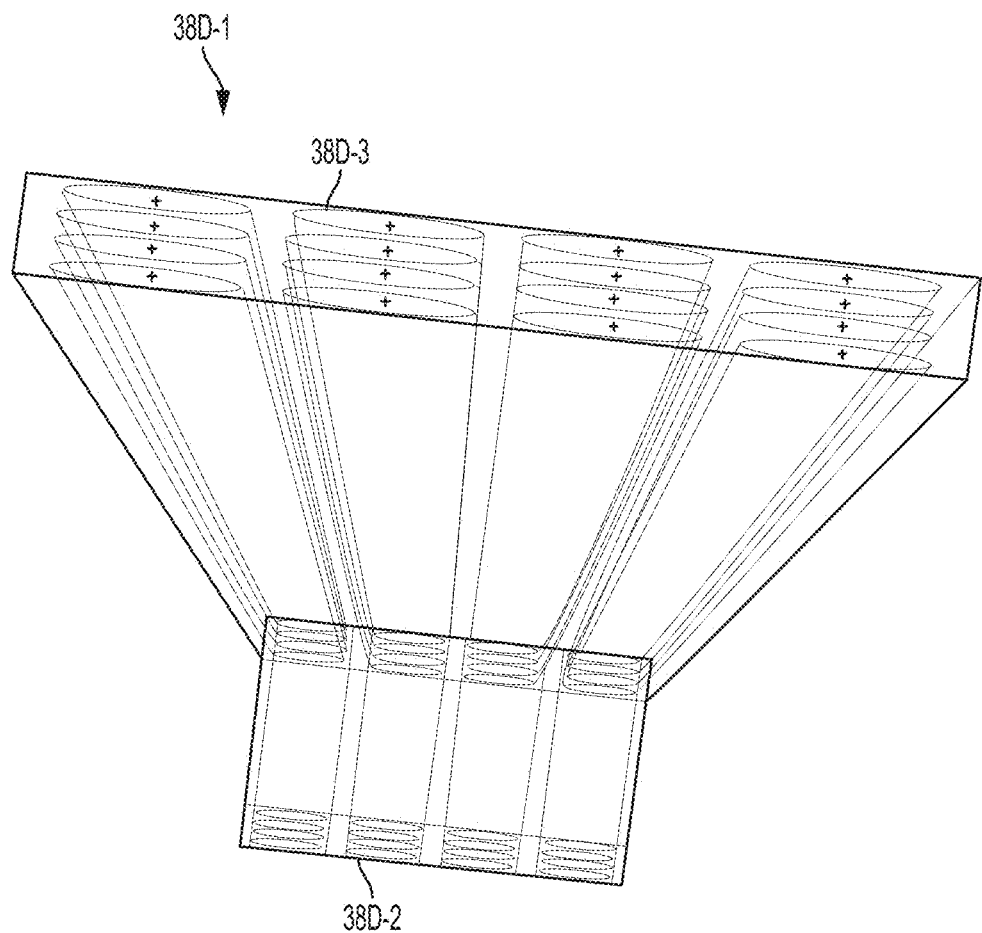
Figure 52:
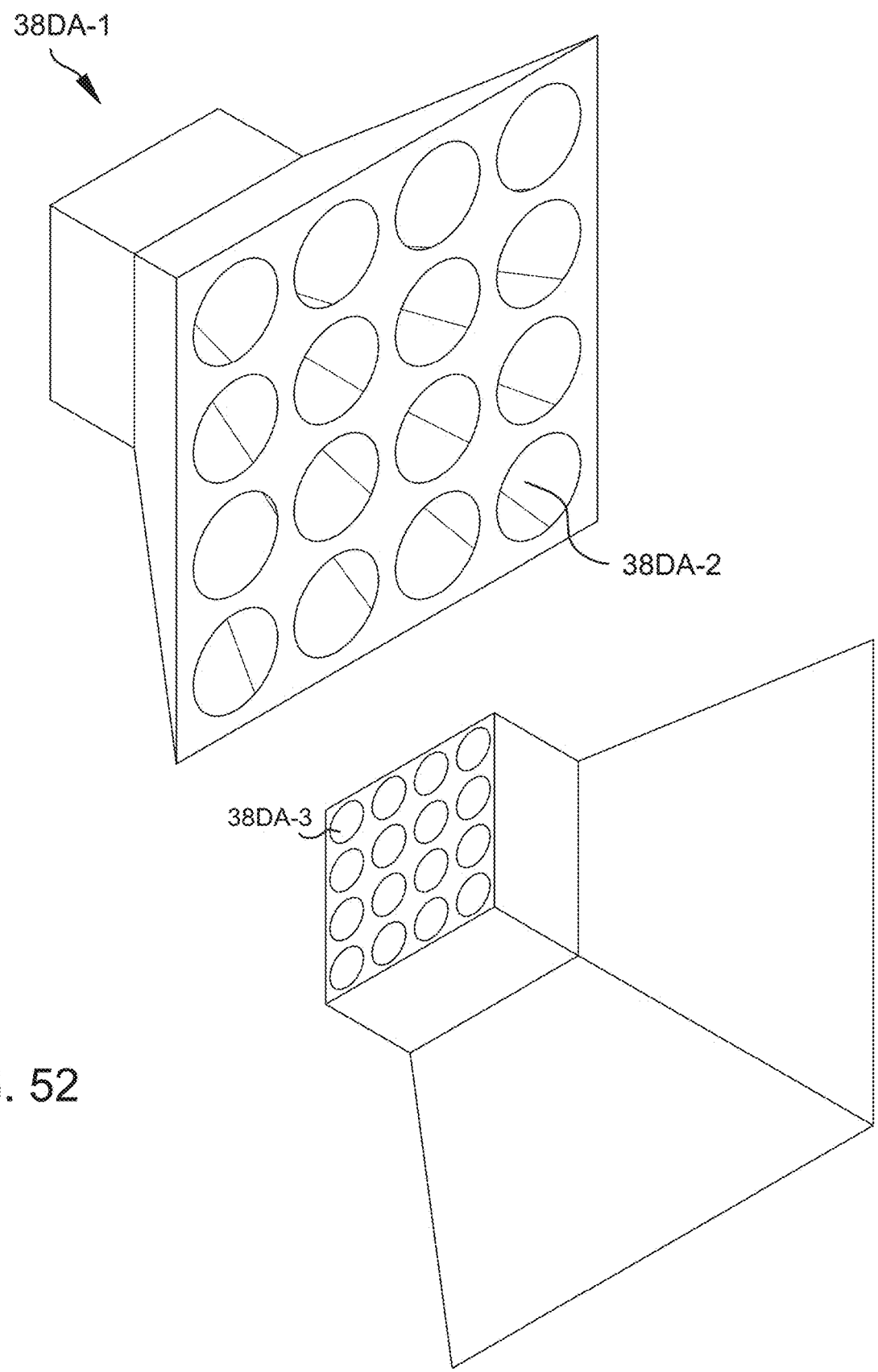
Figure 54:
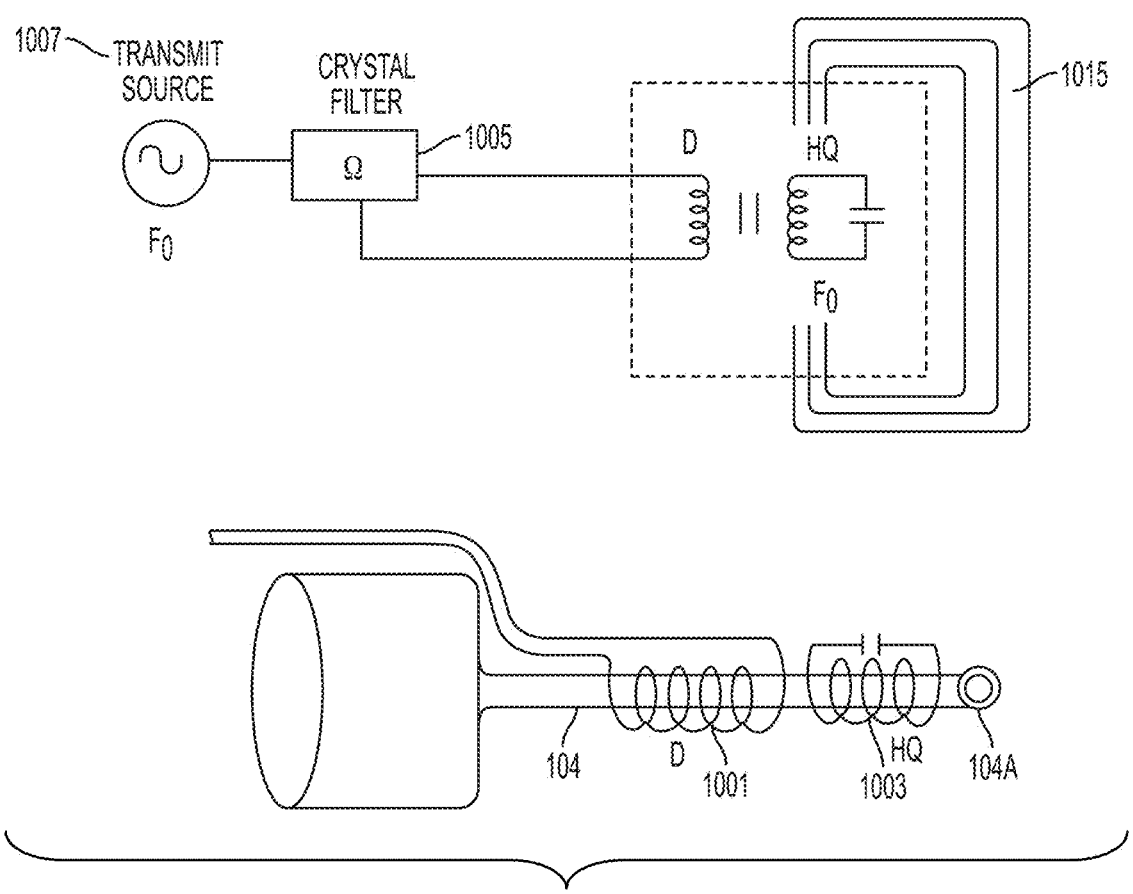
Figure 55:
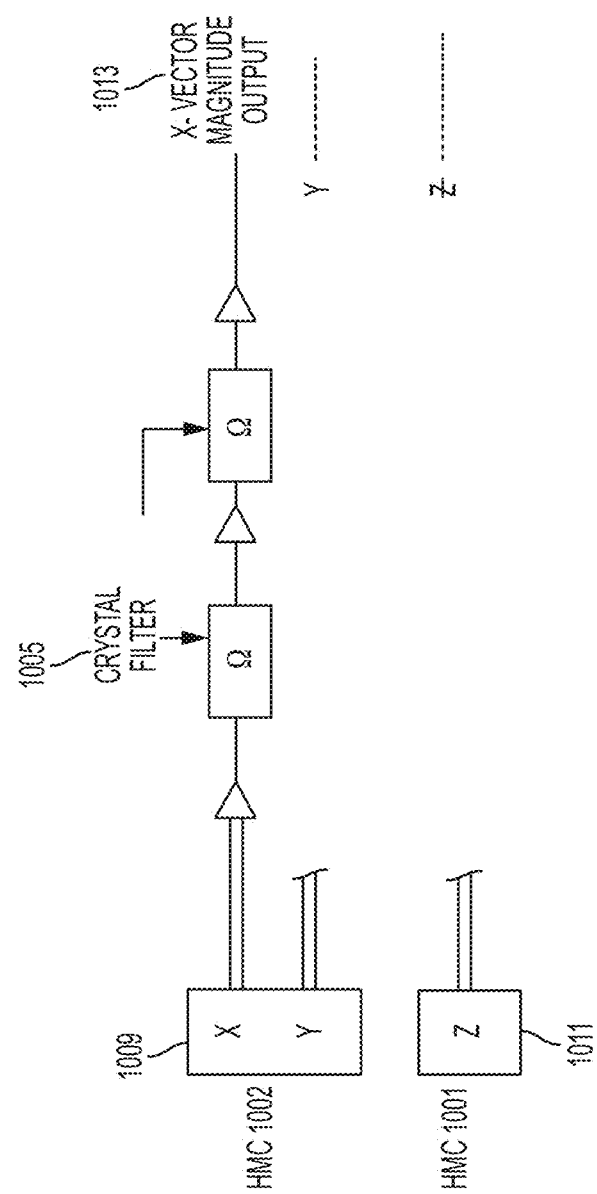
Figure 56:
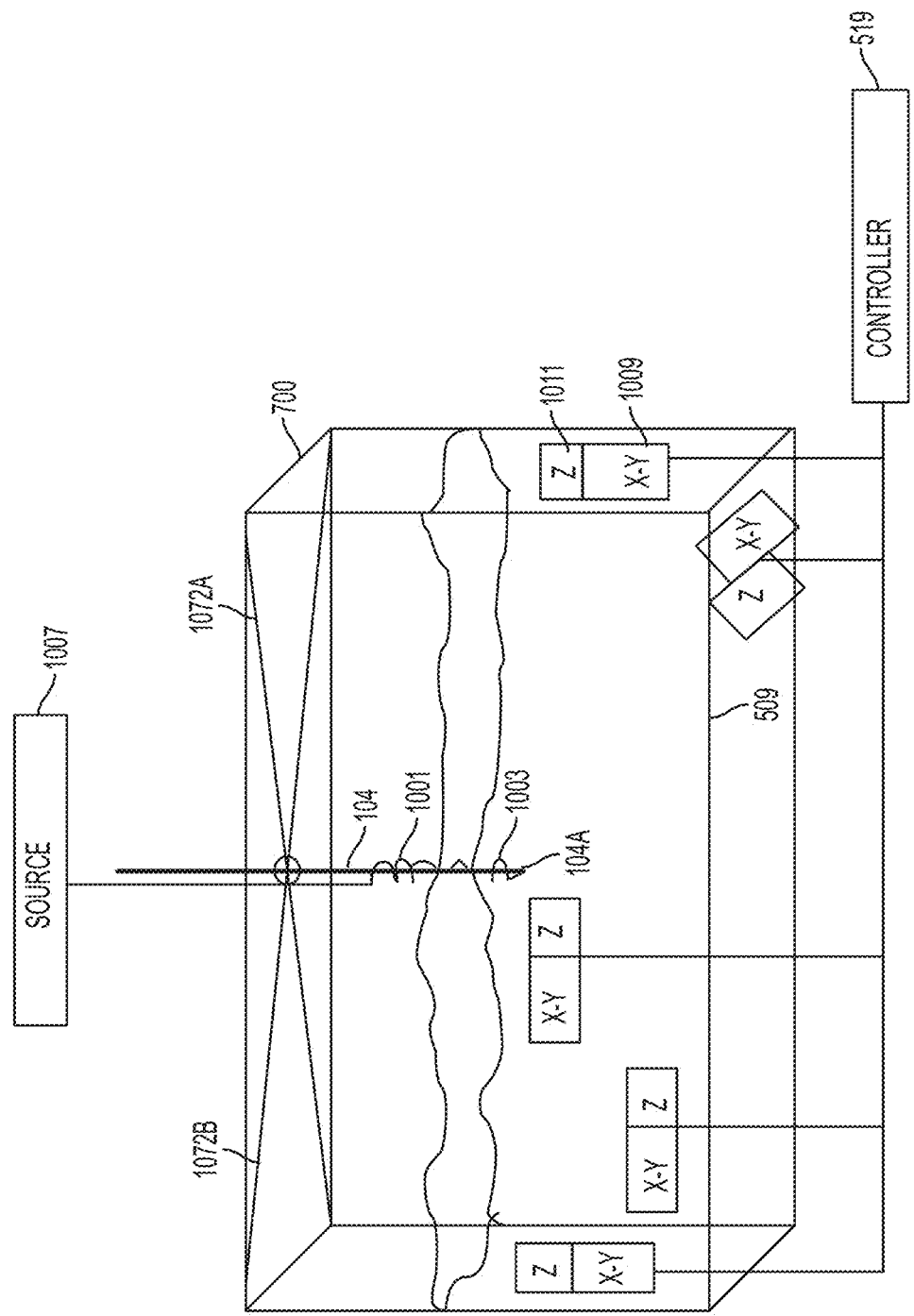
Figure 57:
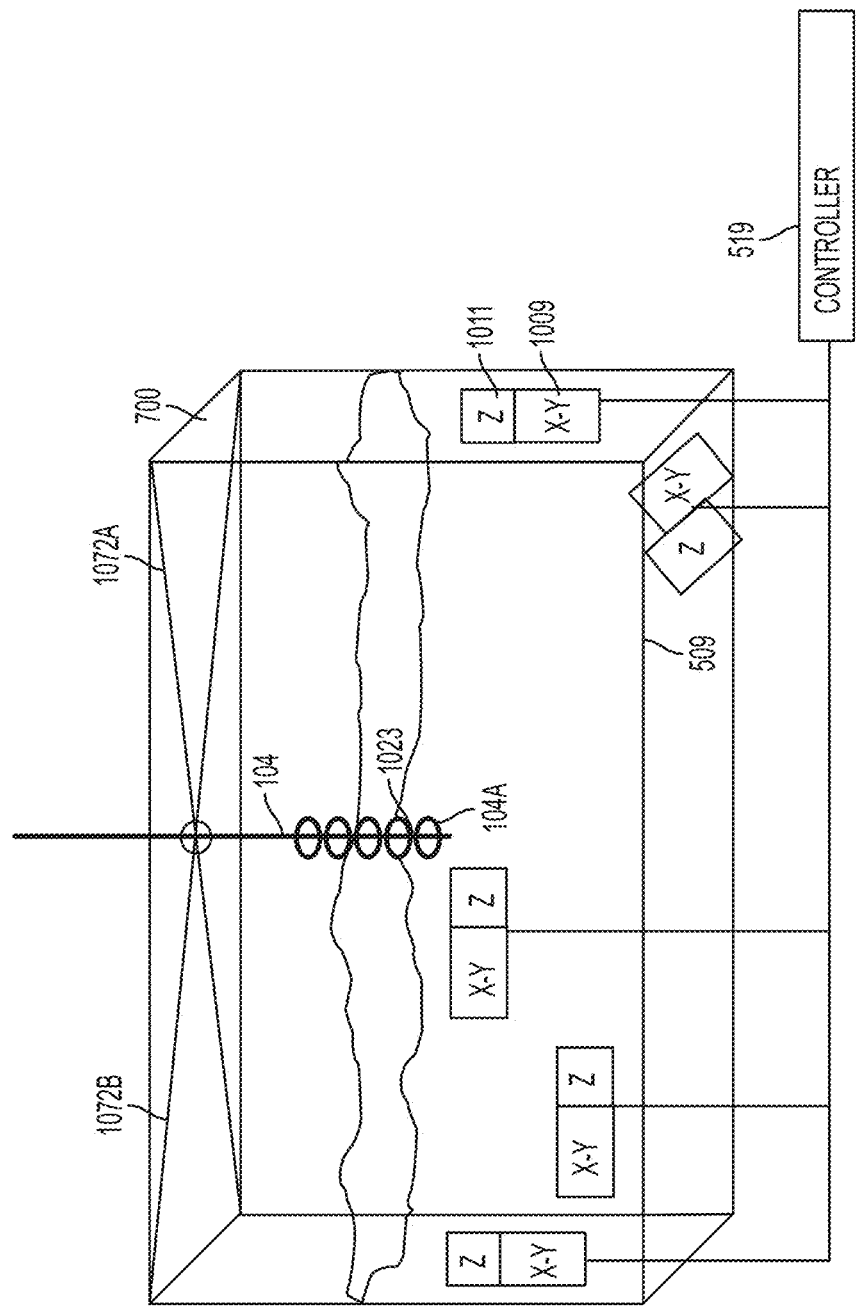
Figure 58:
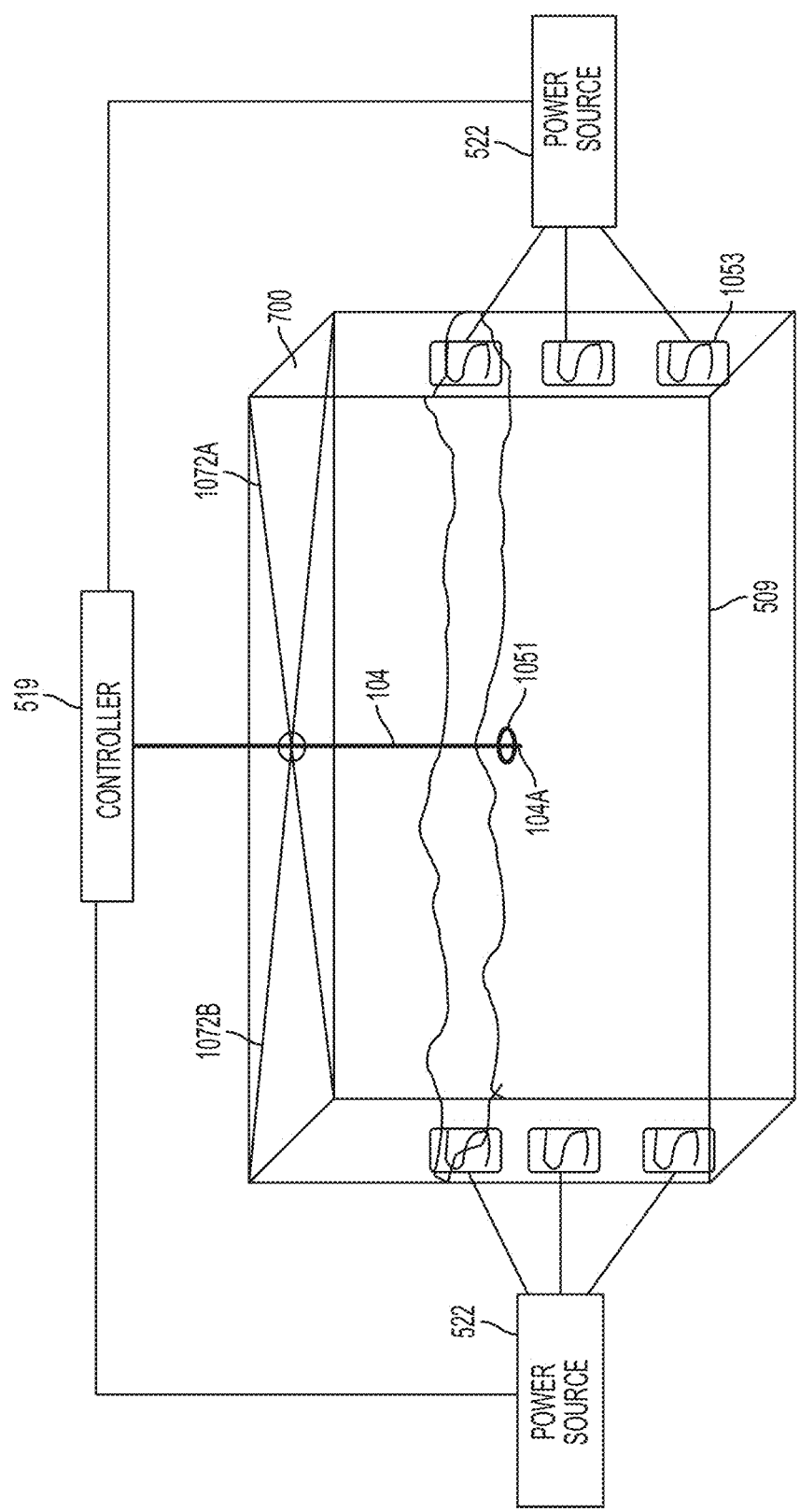
Figure 59:
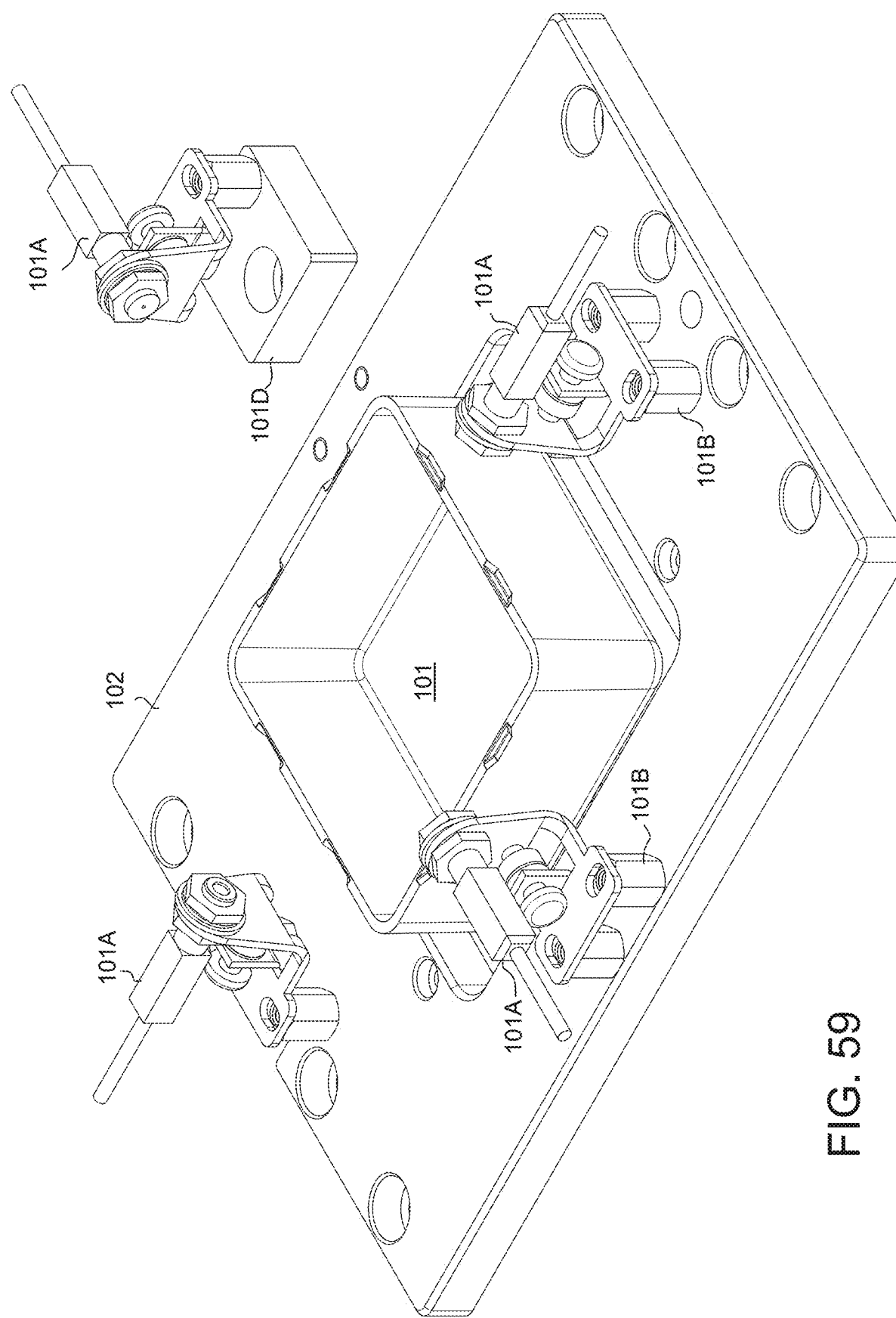
Figure 60:
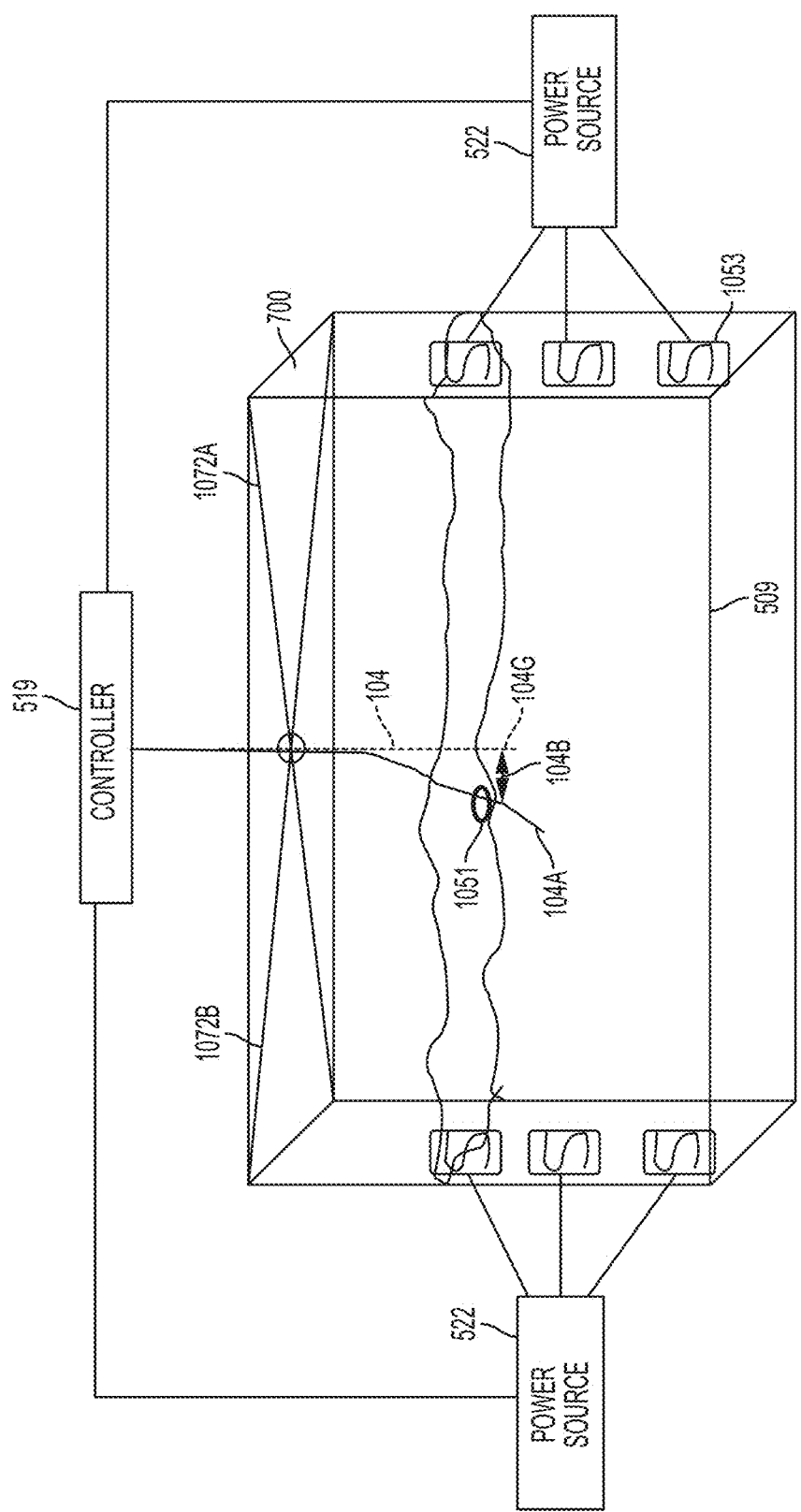
Figure 61:
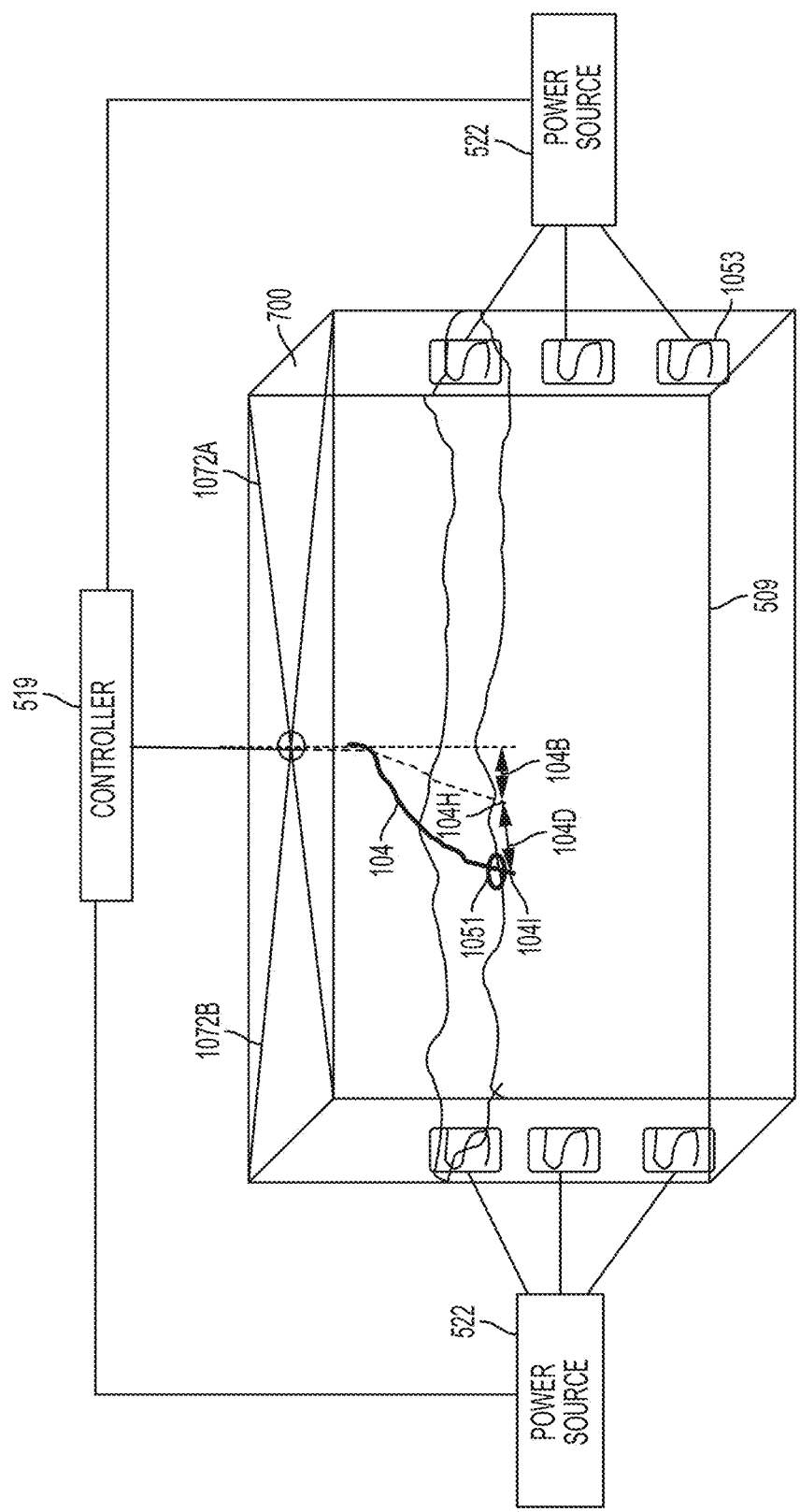
Figure 62:
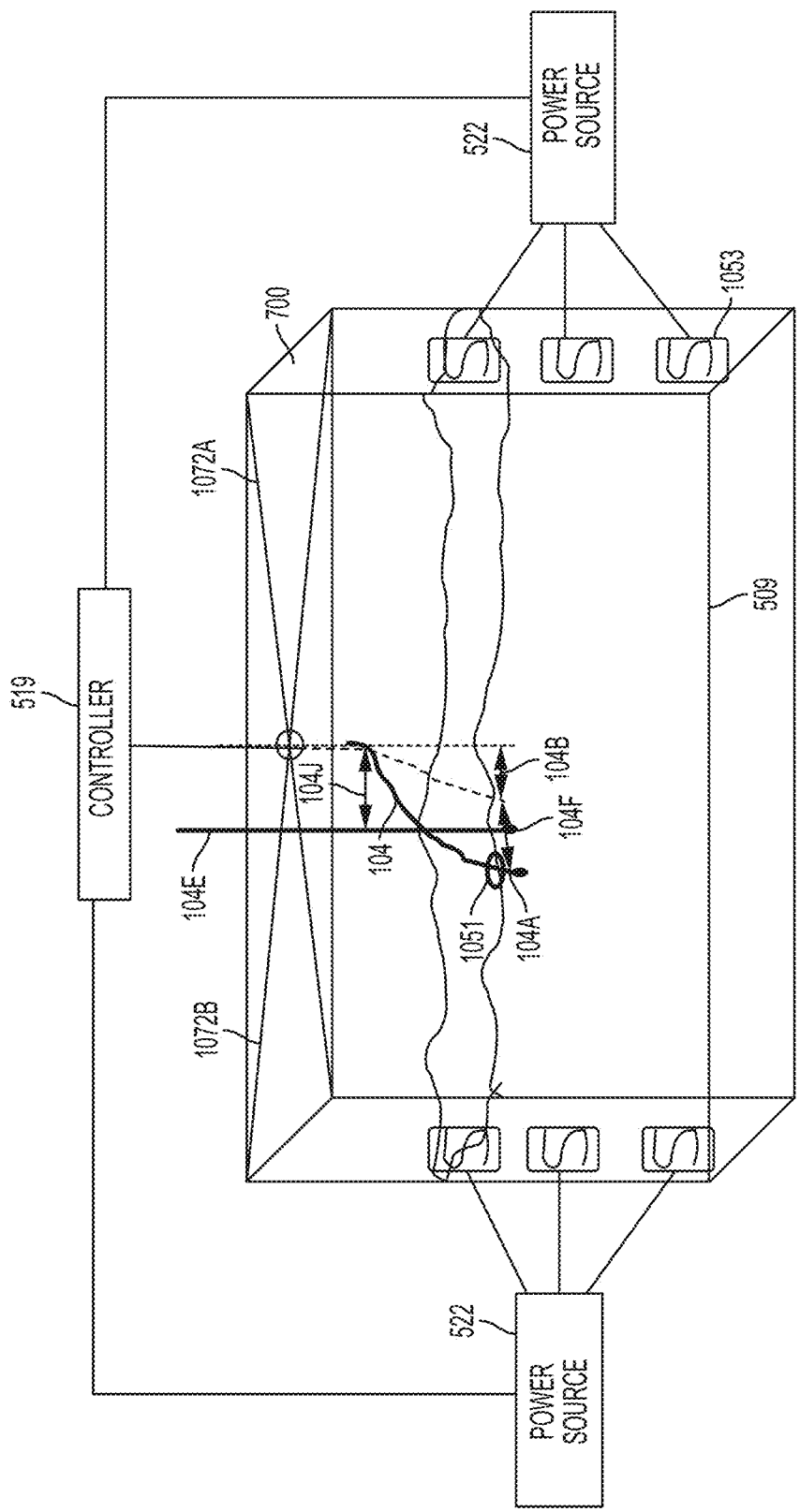
Figure 63:
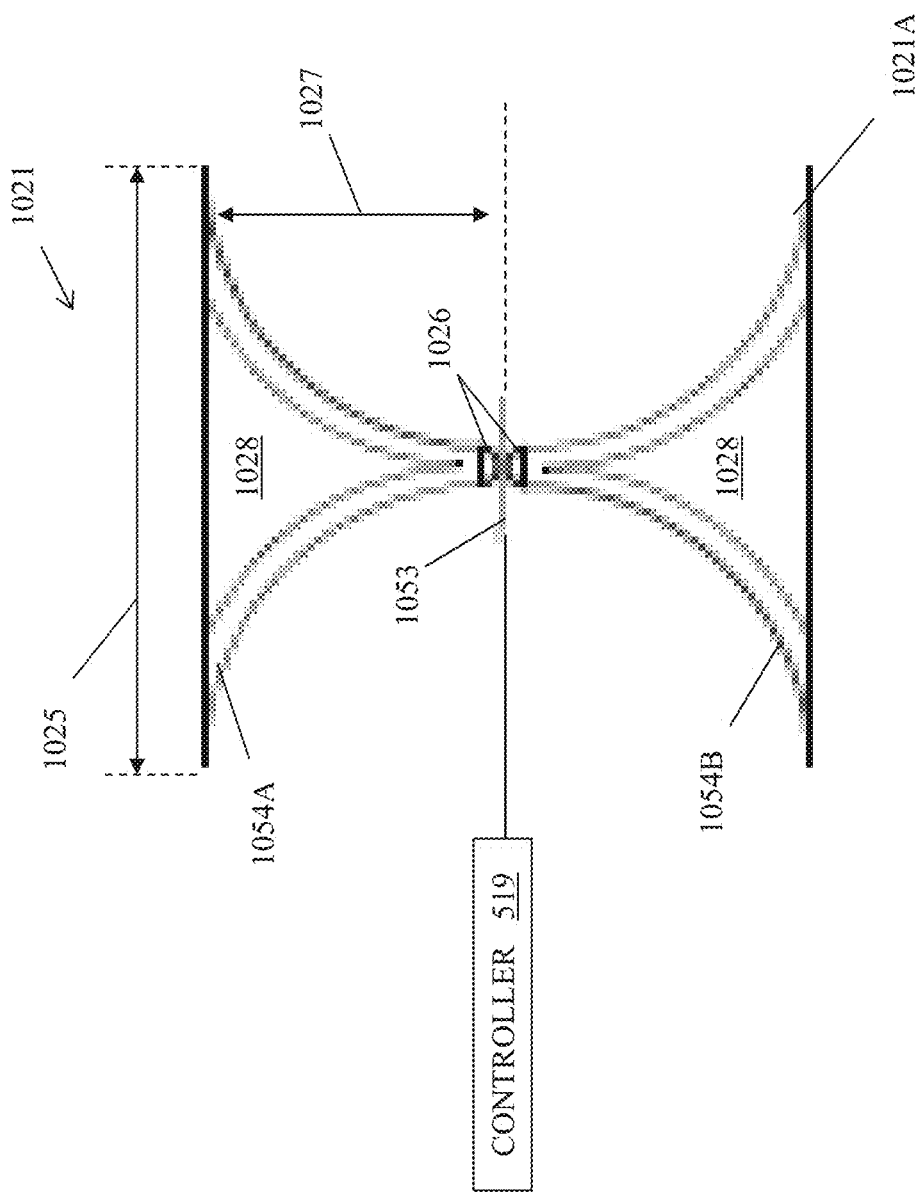
Figure 64:
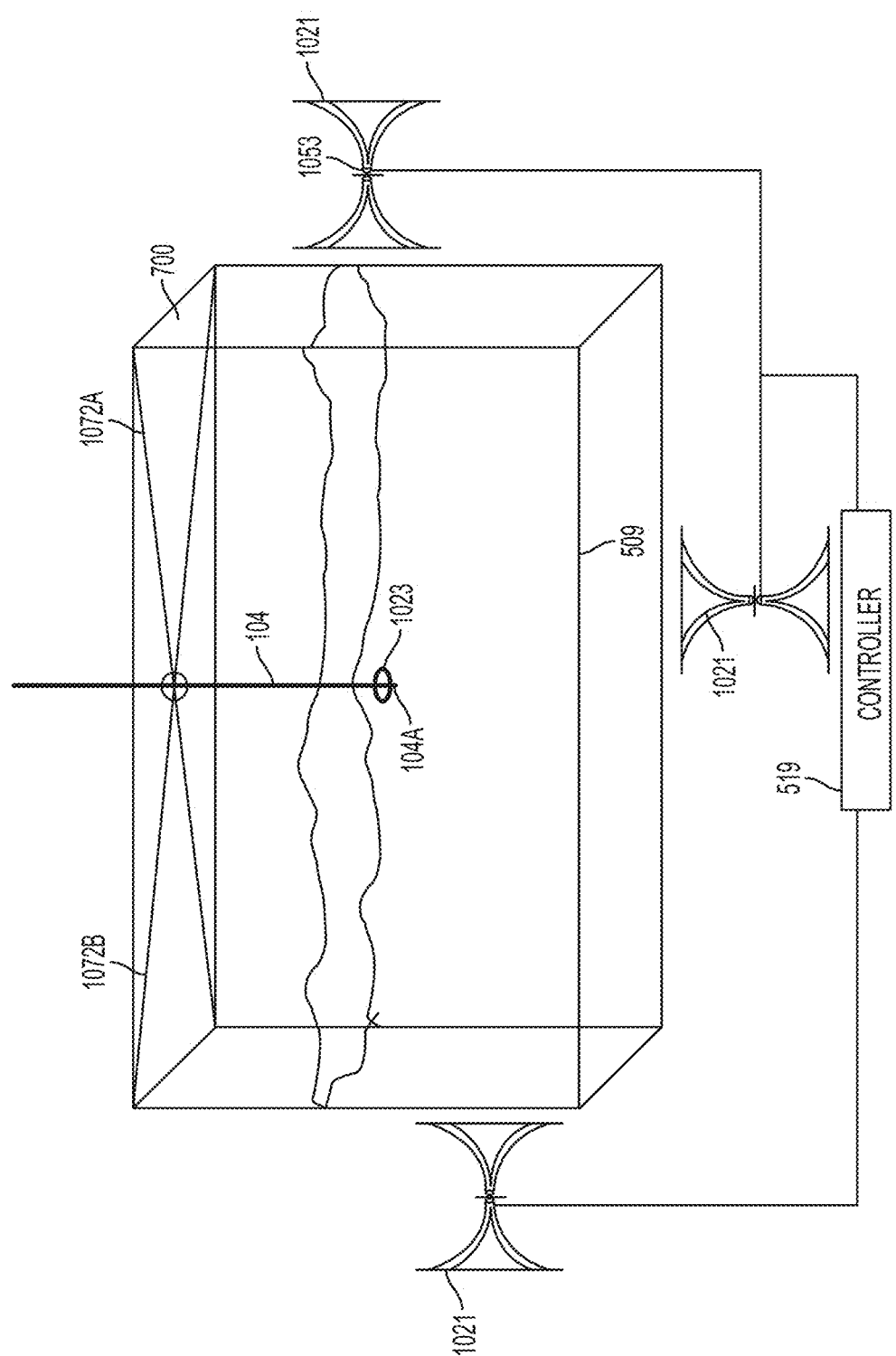
Figure 65:
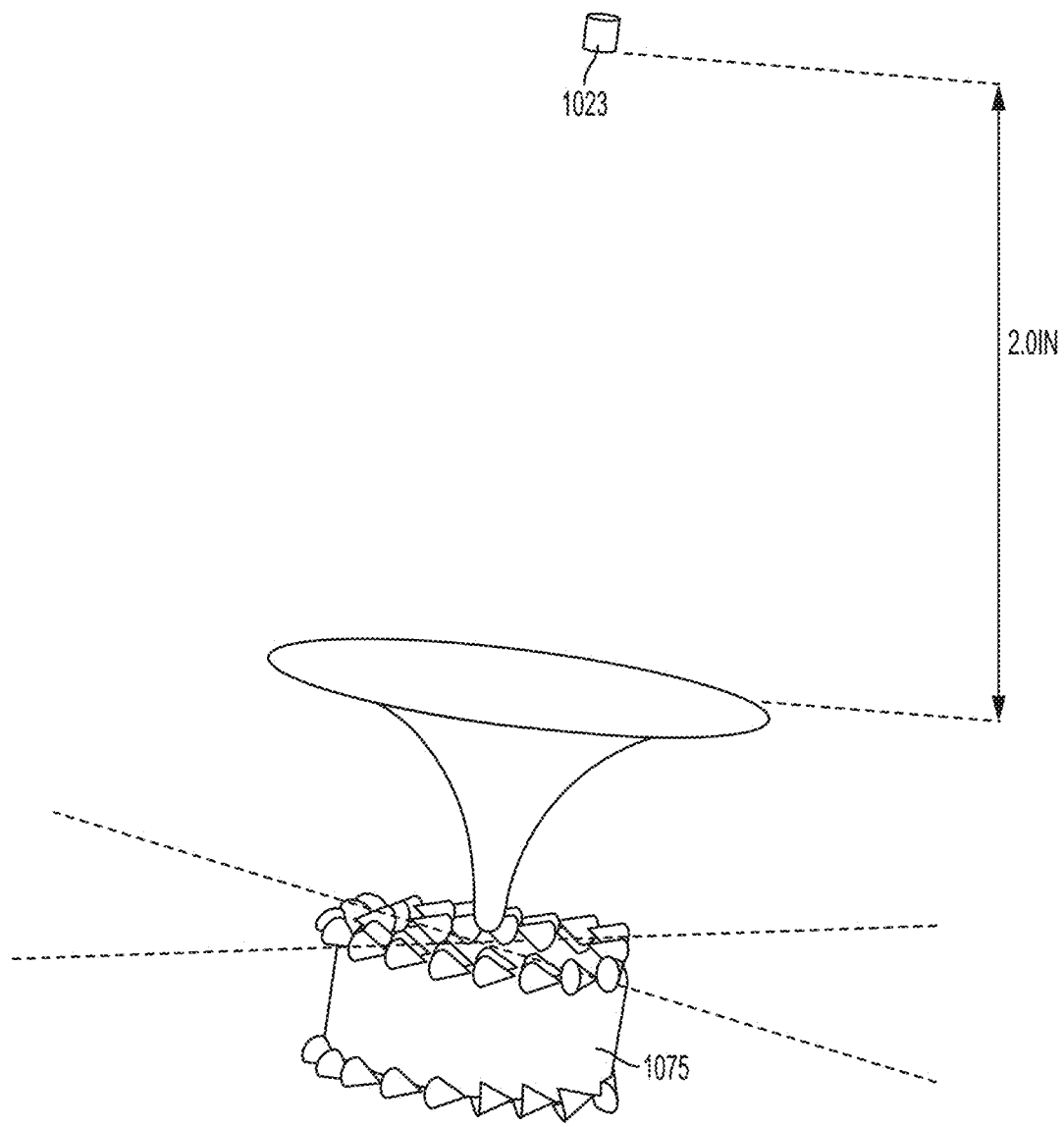
Figure 66:
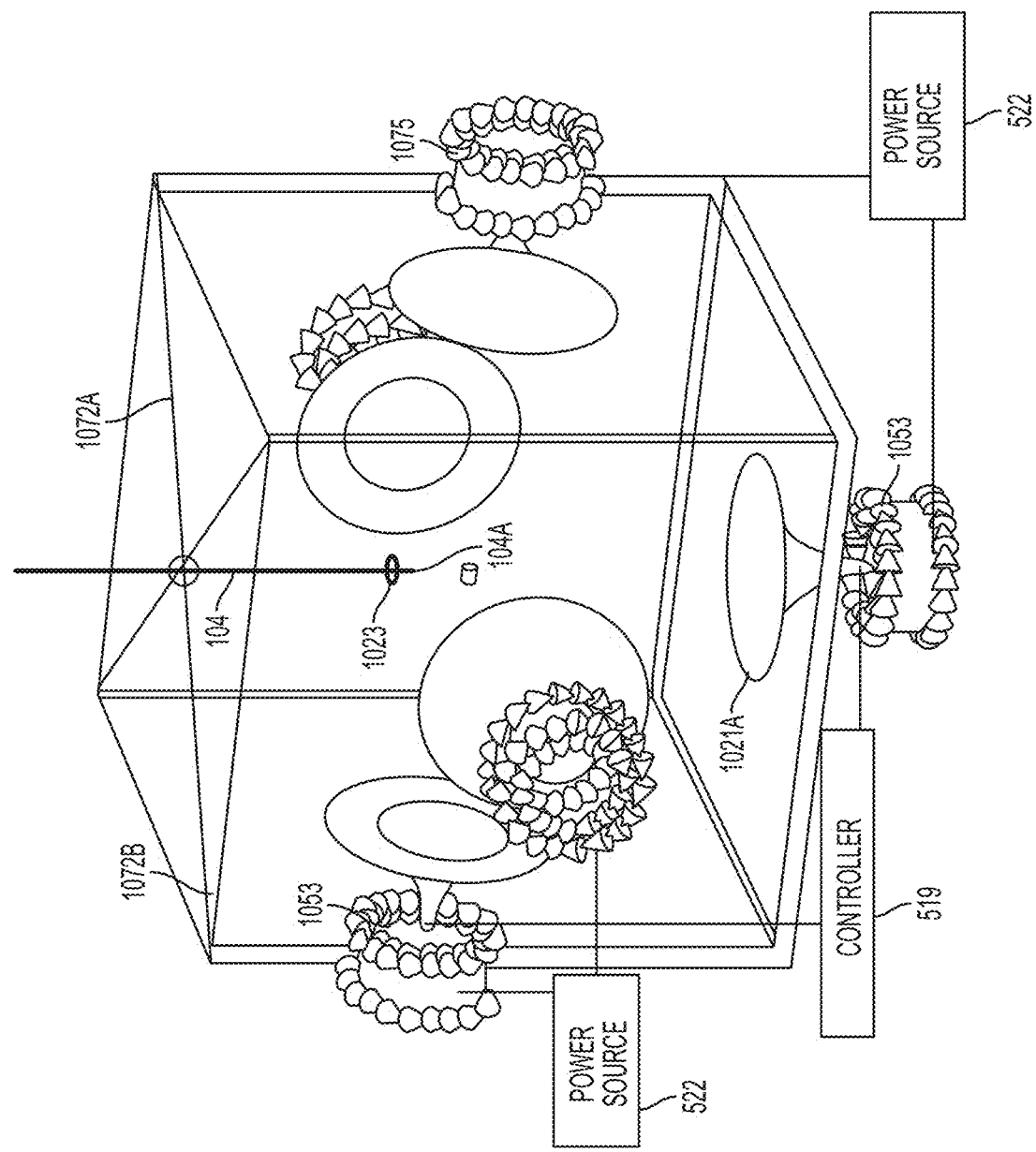
Figure 67:
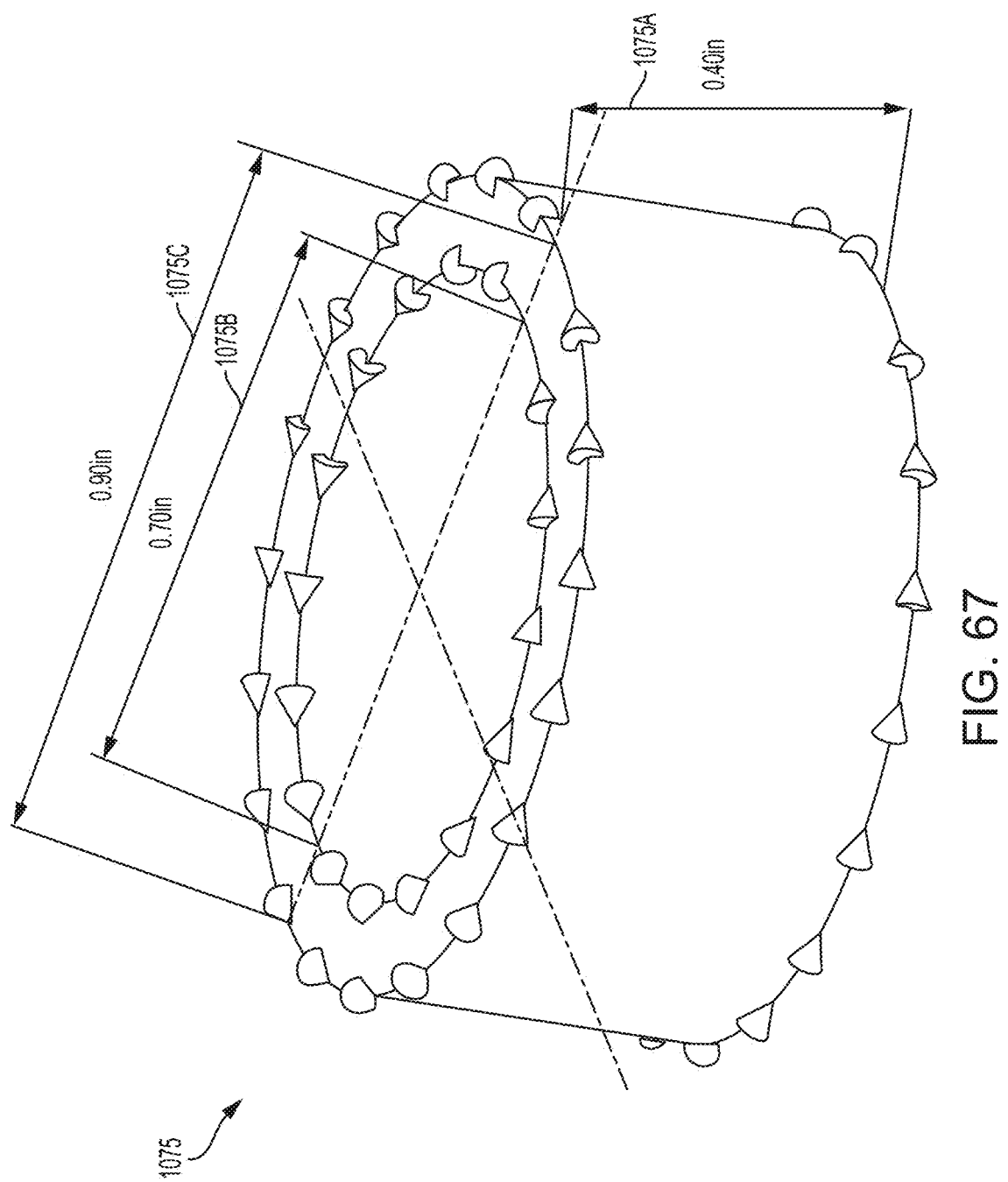
Figure 68:
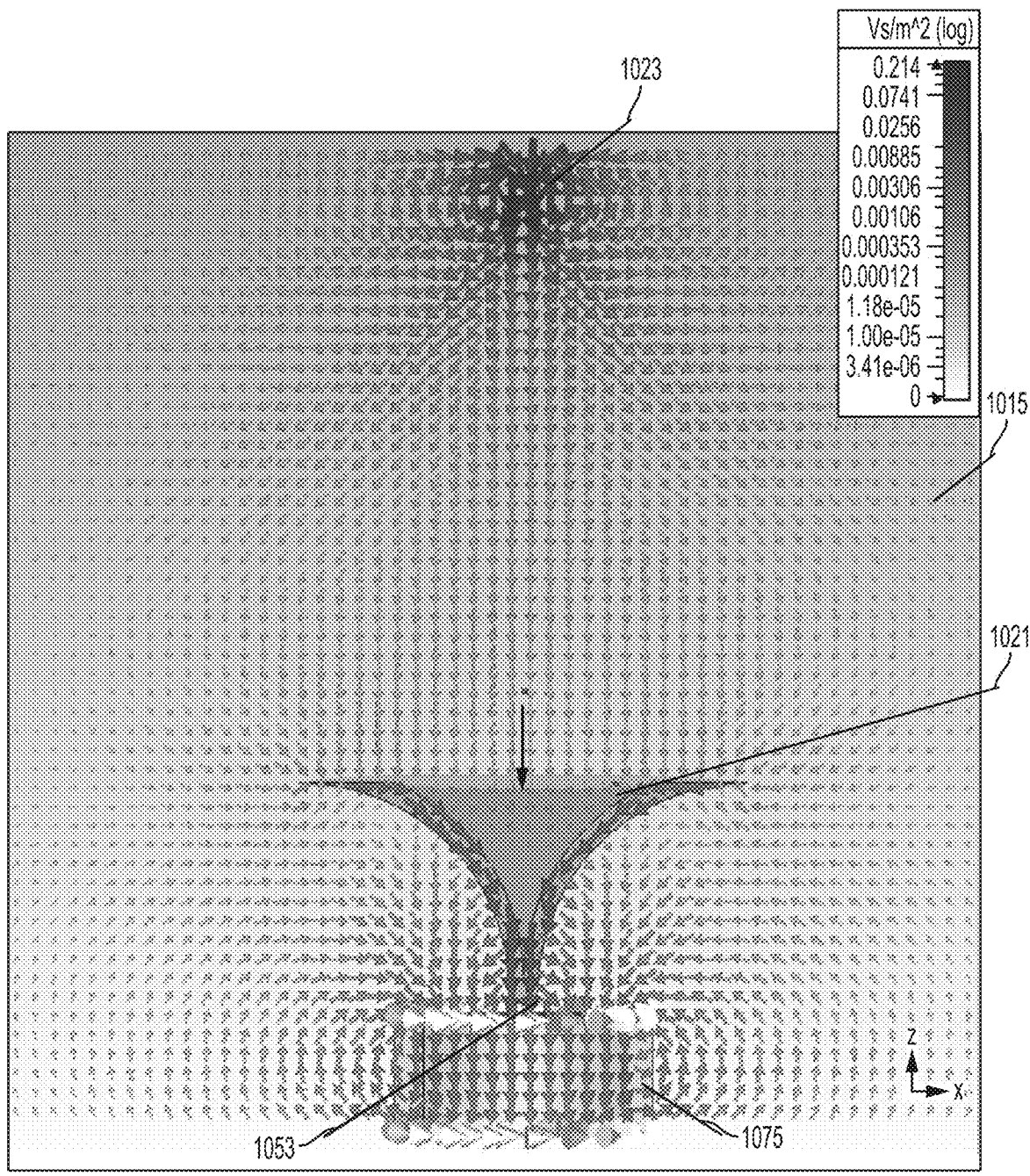

FIGS. 43, 44A, and 44B are schematic block diagrams of the node configuration system of the present teachings;

FIGS. 44C and 44D are schematic block diagrams of the sensor configuration system of the present teachings;

FIG. 45 is a flowchart of the method of the motion controller of the present teachings;

FIG. 46 is a schematic diagram of the bioprinting system of the present teachings;

FIG. 47 is a schematic diagram of the target tissue enclosure of the bioprinting system of FIG. 46;

FIG. 48 is a schematic diagram of the robot tool of the present teachings;

FIGS. 49A and 49B are schematic block diagrams of the control system for the bioprinting system of FIG. 46;

FIG. 50 is a pictorial diagram of the coordinate point conversion of the present teachings;

FIG. 51 is a pictorial representation of the side views of the first configuration of print nozzles of the present teachings;

FIG. 52 is a pictorial representation of the front and rear views of the first configuration of print nozzles of the present teachings;

FIG. 53 is a pictorial representation of the first configuration of print nozzles of the present teachings;

FIG. 54 is a pictorial representation of the tool tip sensor of the present teachings;

FIG. 55 is a pictorial representation of the tool tip sensor configuration of the present teachings;

FIG. 56 is a pictorial representation of the tool tip and sensors of the tissue enclosure of the present teachings;

FIG. 57 is a pictorial representation of another configuration of the tool tip and sensors of the tissue enclosure of the present teachings;

FIG. 58 is a pictorial representation of the third configuration of the tool tip and sensors of the tissue enclosure of the present teachings;

FIG. 59 is a perspective schematic view of the tool touch-off configuration of the tissue enclosure of the present teachings;

FIGS. 60-62 are pictorial representations the process of compliant tool calibration of the tissue enclosure of the present teachings;

FIG. 63 is a pictorial representation of the spreader of the present teachings;

FIG. 64 is a pictorial representation of the spreaders of the present teachings mounted with respect to the tissue enclosure of the present teachings;

FIG. 65 is a pictorial representation of the spreader and magnetic valve of the present teachings;

FIG. 66 is a pictorial representation of the spreader and magnetic valve of the present teachings mounted with respect to the tissue enclosure and tool of the present teachings;

FIG. 67 is a pictorial representation of the magnetic valve of the present teachings;

FIG. 68 is a pictorial representation of the magnetic field sensed by the spreader and magnetic valve of the present teachings;

DETAILED DESCRIPTION

Printing biological material and supporting structures can include (a) simultaneously printing of material (b) precise printing of material and (c) printing particular elements, for example, but not limited to, bio-ink. Methods to print biological material can include printing layers of cells, for example, in a holding container, shaping the tissue by etching fine details using, for example, but not limited to, laser and/or water jet. In some configurations, a mesh structure can underlie the etched tissue, and the method can include lifting the mesh and etched tissue into a tissue enclosure. In some configurations, structure maintenance material 509 (FIG. 56) can be printed into the holding container, structure maintenance (FIG. 56) can be printed along with tissue, or gel can be automatically dispensed through an appropriately-sized extrusion device. In some configurations, a printing method can include printing the biological material and supporting structures onto a drum-like structure, unrolling the drum-like structure and biological material into growth media, and optionally vibrating the drum-like structure to release the biological material and supporting structures from the drum-like structure. In some configurations, the method can optionally include scraping the drum-like structure to release the biological material and supporting structures with, for example, but not limited to, a wire. In some configurations, the method can include printing a layer of structure maintenance material 509 (FIG. 56) onto the drum-like structure, printing a layer of biological material onto the drum-like structure, and scraping a layer of printed material from the drum-like structure. In some configurations, the method can include loading a holding container with fluid, printing a layer of cells on the fluid, dipping the tissue into the layer of cells, and extracting the layer of cells that adhere to the tissue. In some configurations, the method can include loading the holding container with tissue, and lowering the layer of cells onto the tissue in the holding container where the layer of cells can adhere to the tissue in the holding container.

Precisely printing biological material can include providing laminar streams of different bio-inks under conditions that inhibit mixing of the bio-inks. For example, a number of reasonably sized tubes can be placed in a nozzle that will be used to provide bio-ink to a printing device. The tubes can maintain laminar flow in the streams. The size of the tubes can be continually reduced so that a small nozzle at the termination of the printing device includes all the different bio-inks.

Choosing appropriate bio-inks can include, for example, if optical sensing technology is being used, choosing materials that include indices of refraction that differ from the background in which the bio-ink is printed. In some configurations, air or any kind of gas can be appropriate, and multiple different types of gases can be printed to accommodate variations in fluorescence. Quantum dots and nanoparticle/fluorescent beads can be printed as probes/markers. Entire additional structures that may support tissue generation may be printed along with cells that can ultimately grow into tissue, or that can accompany tissue to, for example, monitor and/or sustain the tissue. The additional structures can be placed in a tissue enclosure after being printed, for example, but not limited to, outside a tissue enclosure. The additional structures can include, but are not limited to including, photodetectors, silicon or other semiconductors, electronics, and sensors that can be collocated with tissue. Feedback on growth and topology of the tissue can be accommodated by, for example, printing and/or placing grid patterns/optical gratings in the vicinity of the inside and/or outside of the tissue and monitoring the contours of the tissue. Marker patterns can be placed around the tissue by depositing ink into media or by cutting out bits of gel. In some configurations, photodetectors can be placed in the gel and can be powered by connecting leads and/or inductive coupling that can power the photodetectors without leads.

A configuration of the printer and control system of the present teachings is discussed in detail herein in relation to an inverted microscope. However, various types of microscopes may be used. The printer of the present teachings can be controlled by the controller of the present teachings to print cells in, for example, a gel-like material. Throughout the following description, references to fasteners can include any type of fastening mechanism including, but not limited to, glue, bolts, screws, nails, and hook-and-eye devices.

Figure 1A:
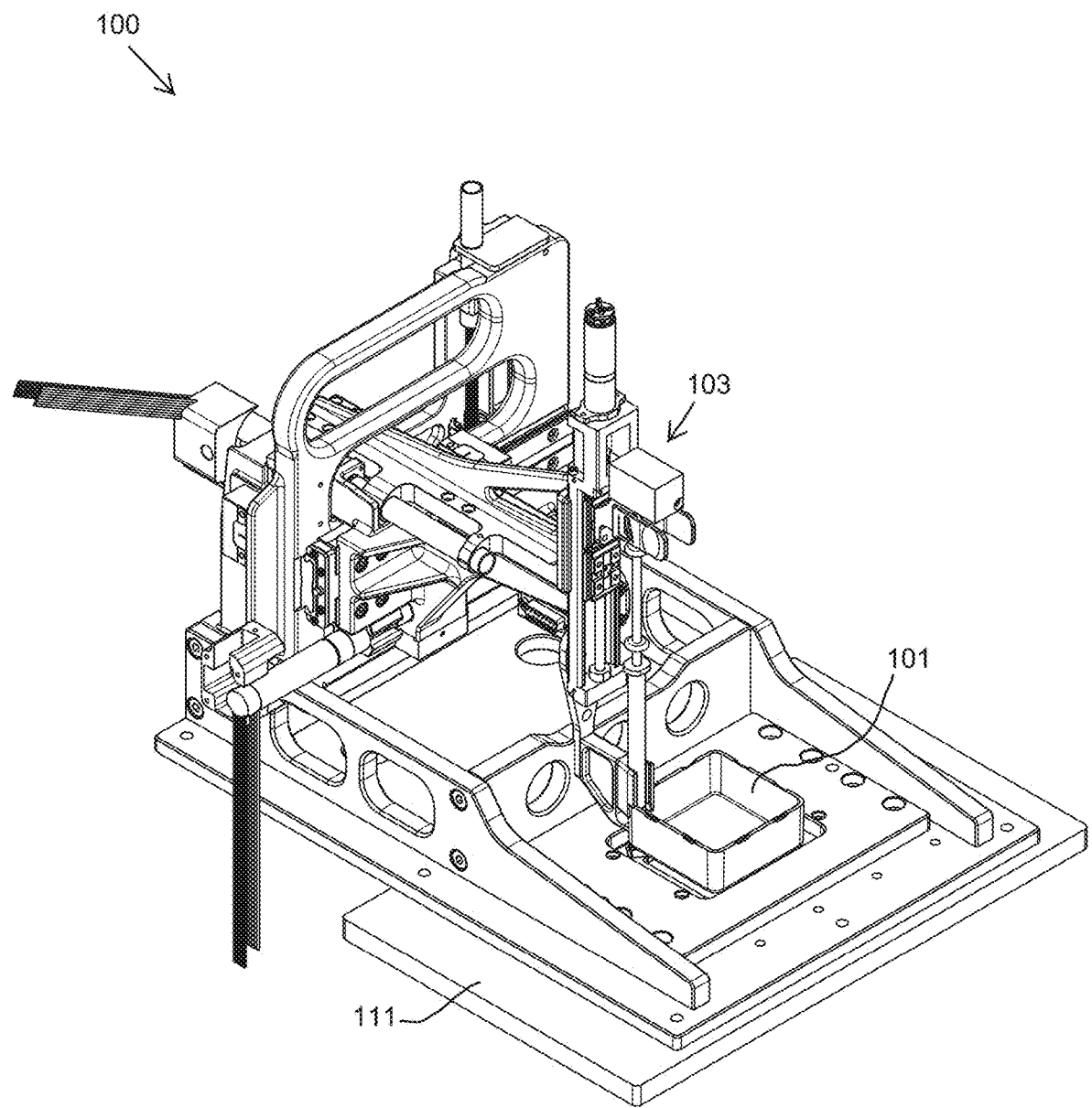
FIGS. 1A and 1B are schematic diagrams of first and second views of the first configuration system of the present teachings.
Figure 1B:
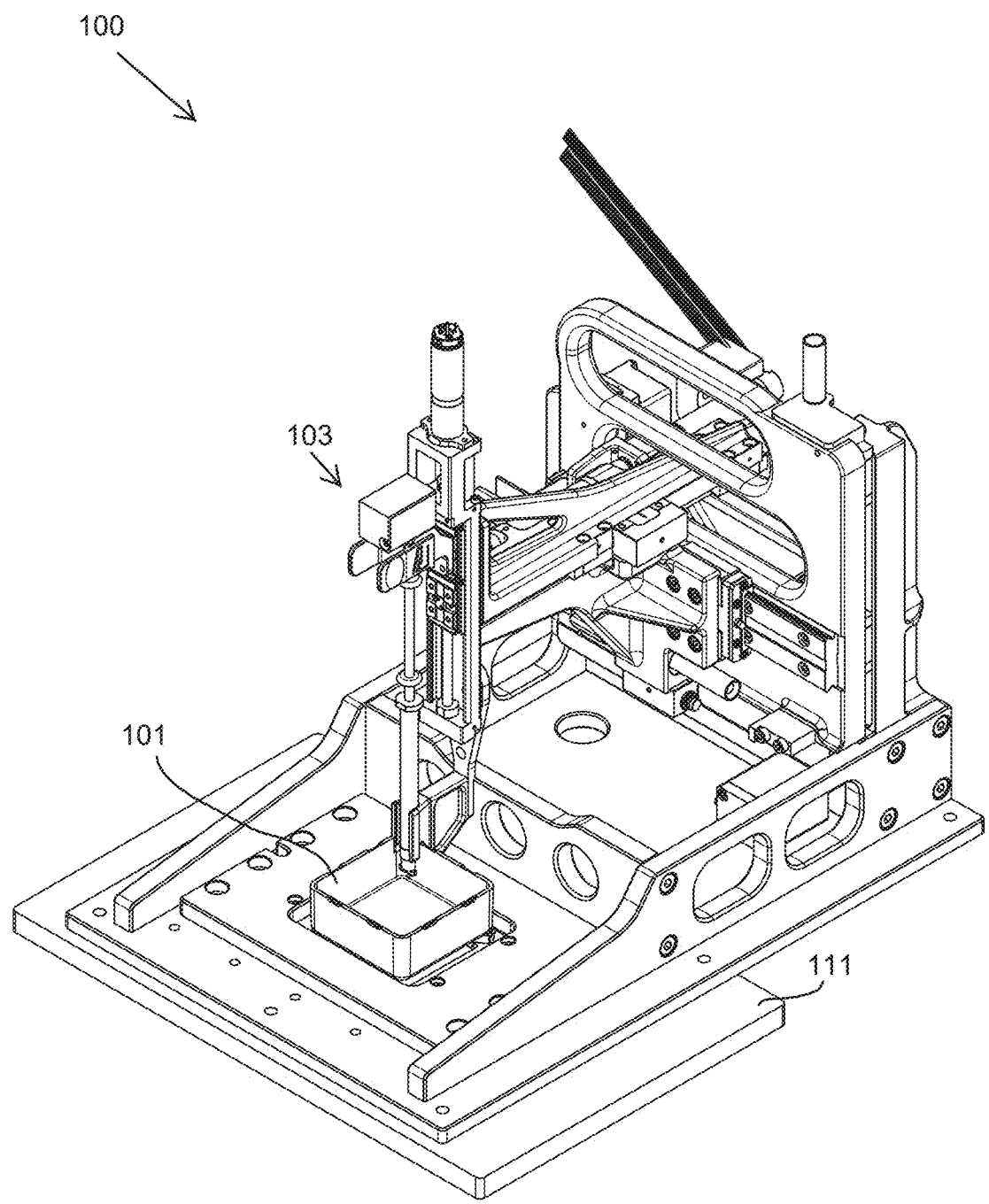

Referring now primarily to FIGS. 1A and 1B, printer 100 of the present teachings can print a multi-dimensional article made of at least one first material. Printer 100 can print the multi-dimensional article by using at least one delivery system 103 that can deposit the at least one first type of material(s) into at least one second material(s) resting in at least one tissue enclosure 101. Information about the multi-dimensional article can be gathered during the printing process from a microscope (not shown) having optical access to tissue enclosure 101 through microscope top plate 111. The at least one second material can reach a pre-selected depth in at least one tissue enclosure 101, the pre-selected depth accommodating a size, shape, and depth of the multi-dimensional article. At least one tissue enclosure 101 can be positioned to accommodate at least one vision system 63 (FIG. 39). At least one vision system 63 (FIG. 39) can be, for example, but not limited to, mounted alongside of at least one tissue enclosure 101. At least one vision system 63 (FIG. 39) can, for example, but not limited to, track the position of at least one needle 103H (FIG. 1C).

Figure 1C:
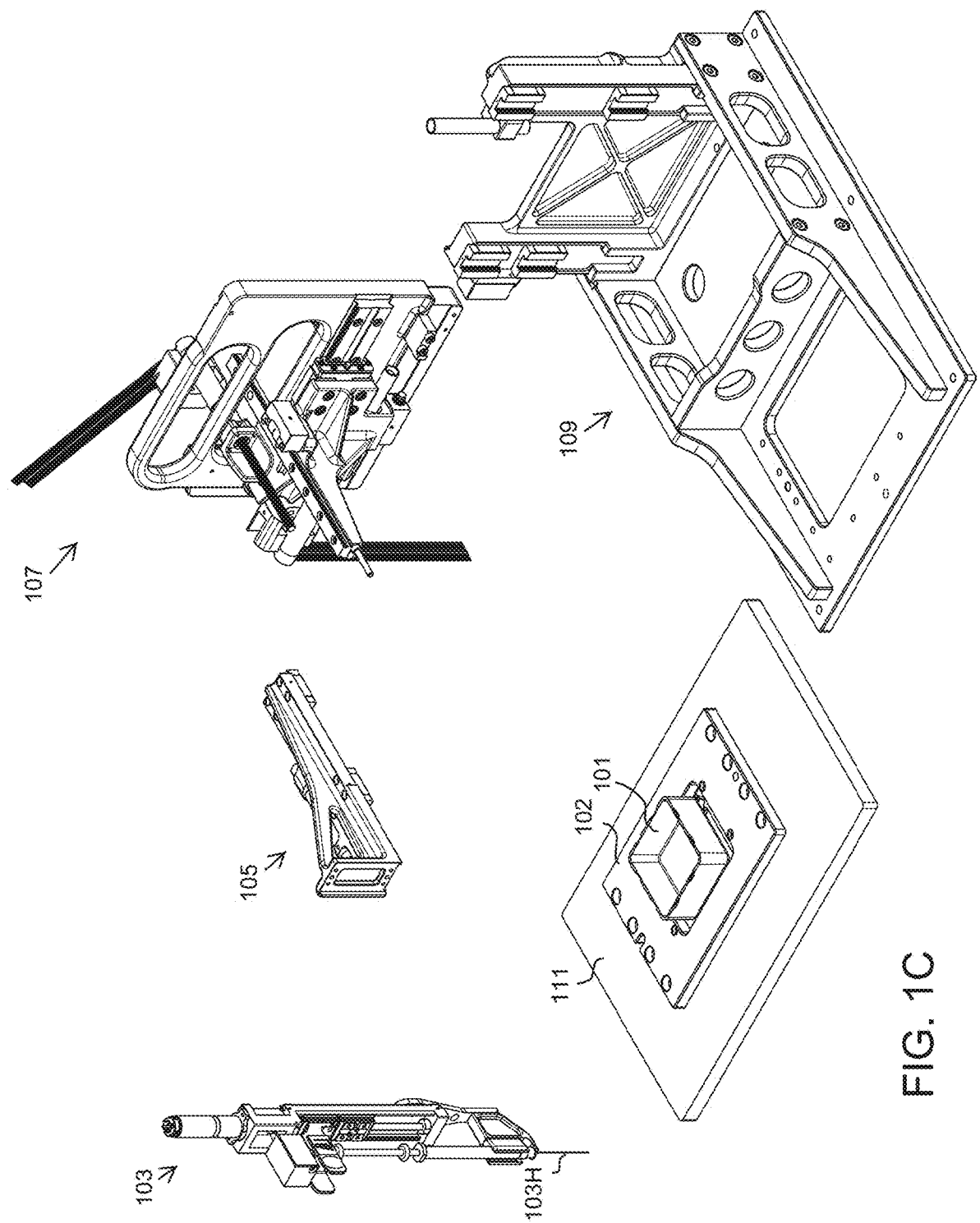
FIG. 1C is a schematic diagram of an exploded view of the first configuration system of the present teachings.

Referring now primarily to FIG. 1C, printer 100 can include, but is not limited to including, at least one delivery system 103, y-axis block 105, x-axis block 107, and z-axis baseplate 109, all resting upon microscope top plate 111. Delivery system 103 can be moved according to at least one motion command 73 (FIG. 39) sent to components described herein with respect to x-axis block 107. Moving delivery system 103 can move needle 103H to a position within a second material resting in tissue enclosure 101. Delivery system 103 can also be directed according to at least one pump command 81 (FIG. 39) to deposit at least one first material 79 (FIG. 39) at the position. When multiple delivery systems 103 are used, in some configurations, a manifold (not shown) can connect a plurality of barrels 103G (FIG. 25B) to a single output port (and single needle 103H). In some configurations, a plurality of delivery systems 103 can be mounted, for example, side-by-side and can print cooperatively and/or asynchronously.

Figure 2A:
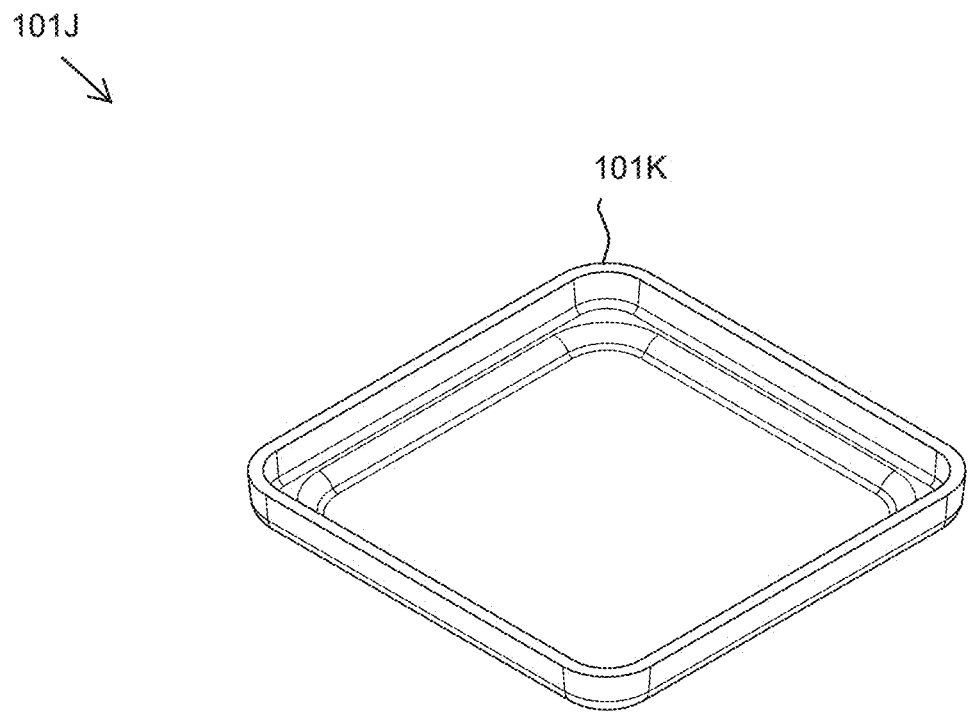
FIG. 2A is a schematic diagram of first and second views of the petri dish of the present teachings.
Figure 1:
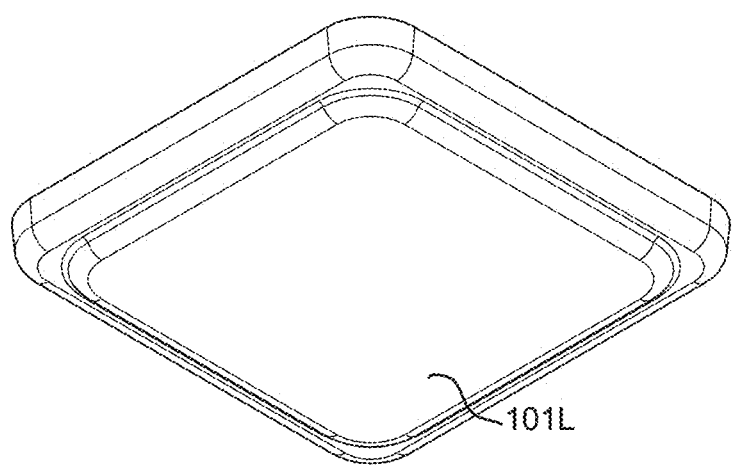

Referring now primarily to FIG. 2A, tissue enclosure 101 can include, but is not limited to including, dish cavity 101H, dish sides 101C, dish first support 101D, dish second support 101E, and dish third support 101F. Dish cavity 101H can be formed of, for example, four sides 101C, joined with, for example, filet edges 1011A that can enable aligned placement of first configuration dish lid 101J (FIG. 2A-1) with lid edges 101K (FIG. 2A-1). Dish sides 101C can include dish divots 101B that can enable venting of tissue enclosure 101 when first configuration dish lid 101J (FIG. 2A-1) is in place. First configuration dish lid 101J (FIG. 2A-1) can include floor 101L (FIG. 2A-1) that can enable stacking of multiple of petri dishes 101. Second configuration dish lid 101J-1 (FIG. 2A-2) can include stacking sides 101J-1A (FIG. 2A-2) and stacking floor 101J-1B (FIG. 2A-2) that can enable stacking of multiple of petri dishes 101. Second configuration dish lid 101J-1 (FIG. 2A-2) can include standoffs 101J-1D (FIG. 2A-2) that can, in conjunction with thin rim 101J-1F (FIG. 2A-2), channel condensate from dish adjacent surface 101J-1E (FIG. 2A-2) to outside of tissue enclosure 101, can prevent contamination of the contents of tissue enclosure 101 by condensate. Dish sides 101C can be any height and width, and can, in some configurations, be flat to accommodate viewing of the contents of petri dish 101 through dish sides 101C. Dish first support 101D, dish second support 101E, and dish third support 101F can, for example, provide resting feet on dish bottom 101G that can support tissue enclosure 101. The locations of dish first support 101D, dish second support 101E, and dish third support 101F can form a kinematic mount that can enable removal of tissue enclosure 101 at a first orientation and replacement of tissue enclosure 101 at the same first orientation. Any configuration of supports can be used to form the kinematic mount.

Referring now primarily to FIG. 2B, petri dish mounting plate 102 can include, but is not limited to including, plate first rest 102C1, plate second rest 102C2, and dish third rest 102C3. Dish first support 101D can rest on platform 102G1 between alignment features 102C1A and 102C1B of plate first rest 102C1. Dish second support 101E can rest on platform 102G2 between the alignment features of plate second rest 102C2, and dish third support 101F can rest on platform 102G3 between the alignment features of plate third rest 102C3. Petri dish mounting plate 102 can be any size and shape, and plate thickness 102D can be, for example, based on how much side viewing through petri dish side 101C (FIG. 2A) can be accommodated in a particular configuration. In some configurations, kinematic plate 102H and mounting plate second side 102B can be attached through fasteners accommodated by fastening cavities 102F1/102F2 to microscope plate adapter 109H (FIG. 13). In some configurations, alignment divot 102E can be use to insure proper placement of petri dish mounting plate 102. In some configurations, standoffs (not shown) can be used to lift petri disk mounting plate 102 to accommodate various microscope configurations.

Figure 3:
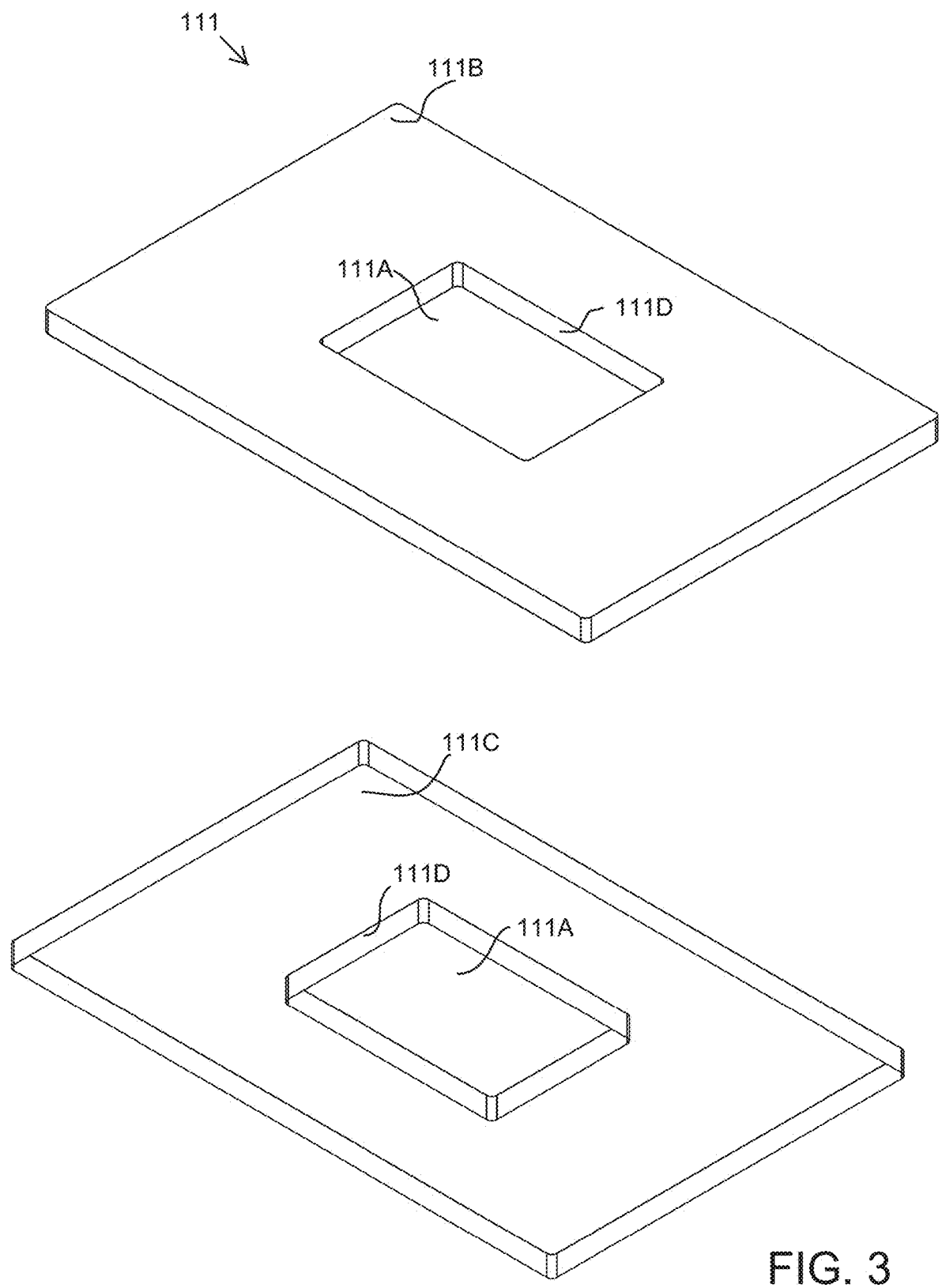
FIG. 3 is a schematic diagram of first and second views of the microscope top plate of the present teachings.
Figure 4A:
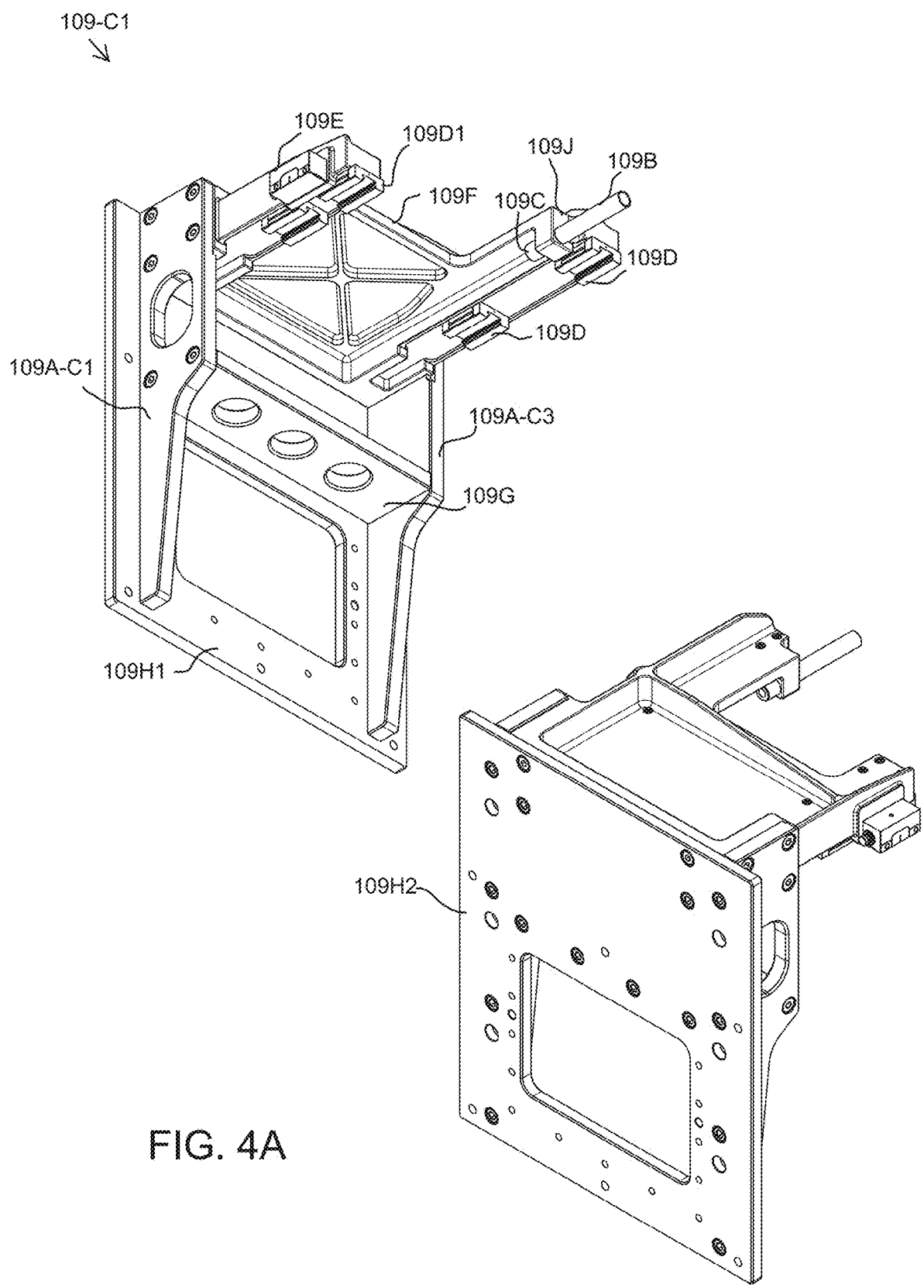
FIG. 4A is a schematic diagram of first and second views of the z-axis baseplate first configuration the present teachings.

Referring now to FIG. 3, microscope top plate 111 can include, but is not limited to including, microscope top plate first side 111B, microscope top plate second side 111C, and microscope top plate dish cavity 111A. Microscope top plate 111 can be any shape and size, and can be constructed of any material having characteristics such as, but not limited to, rigidity. Dish cavity 111A can be any shape, size, and depth. In some configurations, dish cavity 111A can be sized according to the size of tissue enclosure 101, for example, larger than tissue enclosure 101. In some configurations, dish cavity 111A can be sized according to the size of the viewing means (not shown) of the microscope (not shown) mounted in conjunction with microscope top plate 111. Cavity edges 111D can be any shape, size, and depth, and can accommodate the mounting of tissue enclosure 101 within cavity edges 111D, and/or can accommodate the viewing means (not shown) within cavity edges 111D. In some configurations, microscope top plate first side 111B can be mounted adjacent to microscope plate adapter second side 109H2 (FIG. 4A). In some configurations, microscope top plate second side 111C can be mounted adjacent to a microscope (not shown).

Referring now to FIG. 4A, z-axis baseplate first configuration 109 (FIG. 1C) can be configured in several ways. For example, z-axis baseplate first configuration 109-C1 can include, but is not limited to including, support rails 109A-C1, screw cover tube 109B, screw/tube guide 109J, ball nut 109C, carriage 109D, and optical encoder 109E. Z-axis baseplate first configuration 109-C1 can also include baseplate side 109F, mount crossbar 109G, and microscope plate adapter first side 109H1. Screw cover tube 109B can accommodate lead/ball screw 107A (FIG. 15A), and can be held in place by screw/tube guide 109J. Ball nut 109C can form, along with lead/ball screw 107A (FIG. 15A), a lead/ball screw configuration to enable linear motion of a print head. Z-axis baseplate first configuration 109-C1 can be mounted flush with microscope top plate first side 111B (FIG. 3).

Figure 4B:
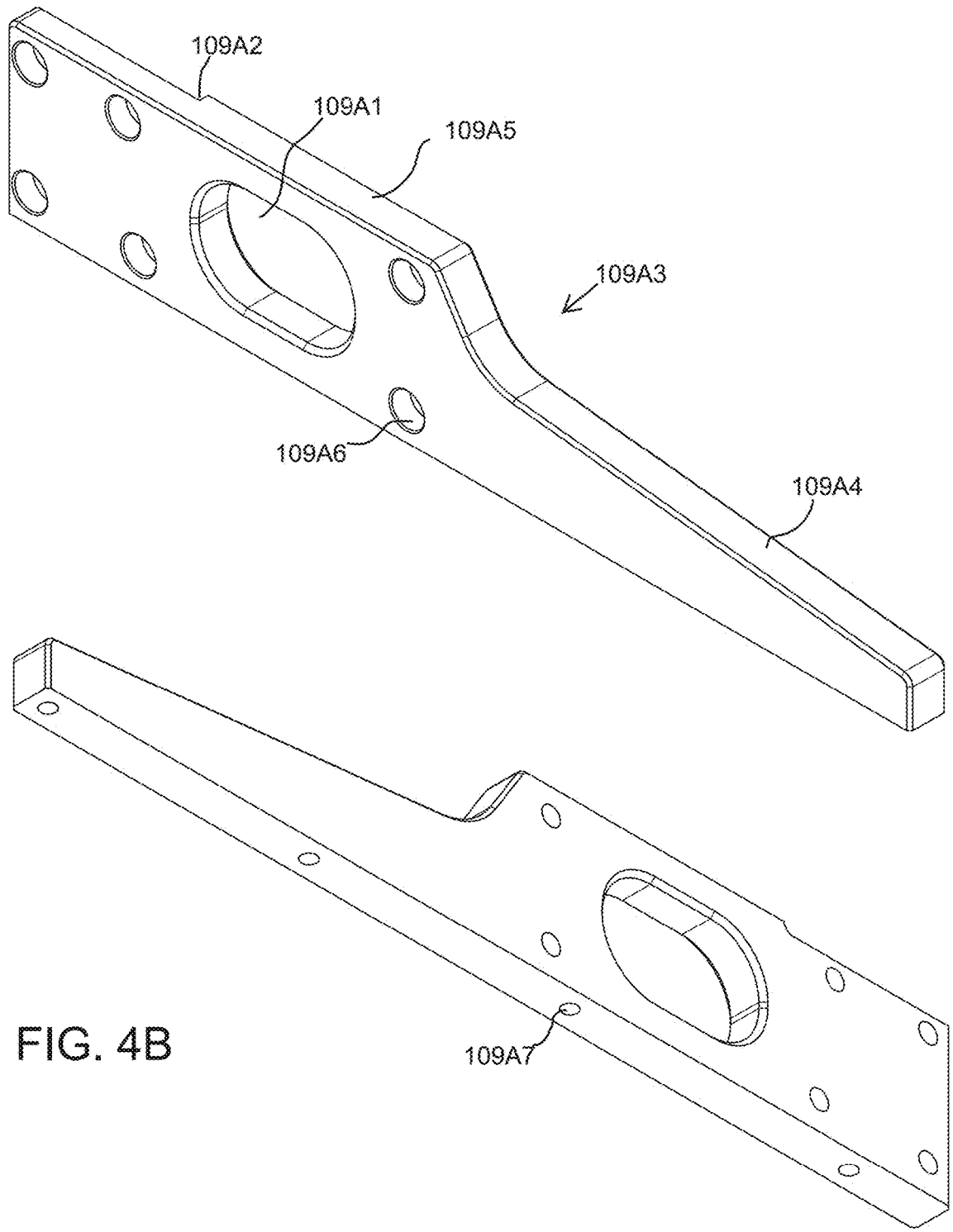
FIG. 4B is a schematic diagram of first and second views of the support rails first configuration of the present teachings.

Referring now primarily to FIG. 4B, in some configurations, support rails first configuration 109A-C1 can include, but are not limited to including, cavities 109A1 and divot 109A2 to accommodate the structure of z-axis baseplate 109-C1. Cavities 109A1 can be sized and shaped to maintain strength and stability in printer 100 (FIG. 2A) while reducing the weight of printer 100 (FIG. 2A), and can accommodate cable runs. Support rails first configuration 109A-C1 can be tapered 109A3 between rail first end 109A4 and rail second end 109A5, where rail first end 109A4 and rail second end 109A5 can be different sizes relative to each other. Support rails first configuration 109A-C1 can be tapered to, for example, but not limited to, provide viewing access to tissue enclosure 101 (FIG. 2A). Support rails first configuration 109A-C1 can be any shape, size, and depth depending on weight requirements of printer 100 (FIG. 2A), viewing requirements, if any, of the contents of tissue enclosure 101 (FIG. 2A), and fastening requirements of z-axis baseplate first configuration 109-C1 (FIG. 4A). Support rails first configuration 109A-C1 can include fastening cavities 109A6 which can be any shape, size, and depth, and can occur in any quantity sufficient to maintain the structural integrity of printer 100 (FIG. 2A), and to insure that printer 100 (FIG. 2A) has positional stability. In some configurations, each of support rails first configuration 109A-C1 can include six fastening cavities 109A6 that can mate support rails 109A to baseplate side 109F (FIG. 4A) and mount crossbar 109G (FIG. 4A), for example. Support rails first configuration 109A-C1 can also include fastening bores 109A7 to accommodate fastening support rails first configuration 109A-C1 to microscope plate adapter 109H (FIG. 13), for example.

Figure 5A:
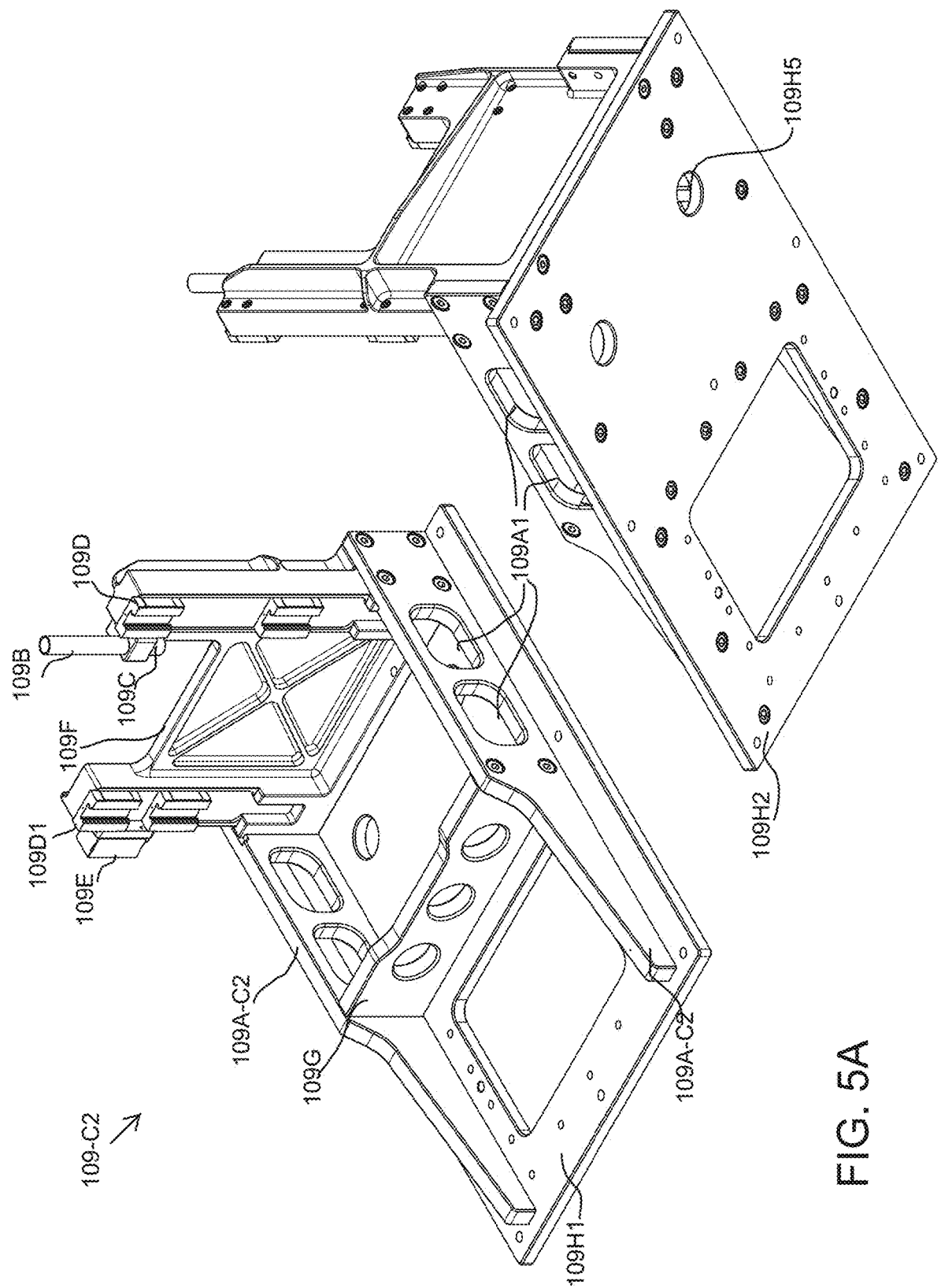
FIG. 5A is a schematic diagram of first and second views of the z-axis baseplate second configuration of the present teachings.

Referring now to FIG. 5A, z-axis baseplate second configuration 109-C2 can include, but is not limited to including, support rails 109A-C2, screw cover tube 109B, ball nut 109C, carriage 109D, and optical encoder 109E. Z-axis baseplate second configuration 109-C2 can also include baseplate side 109F, mount crossbar 109G, and microscope plate adapter first side 109H1 (FIG. 4A). Z-axis baseplate second configuration 109-C2 can be mounted flush with microscope top plate first side 111B (FIG. 3). Optical encoder 109E can track the motion of lead/ball screw 107A (FIG. 15A) and provide that information to processor 55 (FIG. 39). Optical encoder 109E can be wired or wireless, and can include, for example, but not limited to, an absolute or incremental encoder. In some configurations, a RENISHAW® L-9517-9524-03-B optical encoder can be used.

Referring now primarily to FIG. 5B, in some configurations, support rails second configuration 109A-C2 can include, but are not limited to including, cavities 109A1-1, 109A1-2, and divot 109A2 to accommodate the structure of z-axis baseplate 109-C2. Cavities 109A1 and 109A1-2 can be sized and shaped to maintain strength and stability in printer 100 (FIG. 2A) while reducing the weight of printer 100 (FIG. 2A), and can accommodate cable runs. Support rails second configuration 109A-C2 can be tapered 109A3 between rail first end 109A4 and rail second end 109A5, where rail first end 109A4 and rail second end 109A5 can be different sizes relative to each other. Support rails second configuration 109A-C2 can be tapered to, for example, but not limited to, provide viewing access to tissue enclosure 101 (FIG. 2A). Support rails second configuration 109A-C2 can be any shape, size, and depth depending on weight requirements of printer 100 (FIG. 2A), viewing requirements, if any, of the contents of tissue enclosure 101 (FIG. 2A), and fastening requirements of z-axis baseplate 109-C2 (FIG. 5A). Support rails second configuration 109A-C2 can include fastening cavities 109A6 which can be any shape, size, and depth, and can occur in any quantity sufficient to maintain the structural integrity of printer 100 (FIG. 2A), and to insure that printer 100 (FIG. 2A) has positional stability. In some configurations, each of support rails second configuration 109A-C2 can include six fastening cavities 109A6 that can mate support rails second configuration 109A to baseplate side 109F (FIG. 5A) and mount crossbar 109G (FIG. 5A), for example. Support rails second configuration 109A-C2 can also include fastening bores 109A7 to accommodate fastening support rails second configuration 109A-C2 to microscope plate adapter 109H (FIG. 13), for example.

Figure 6A:
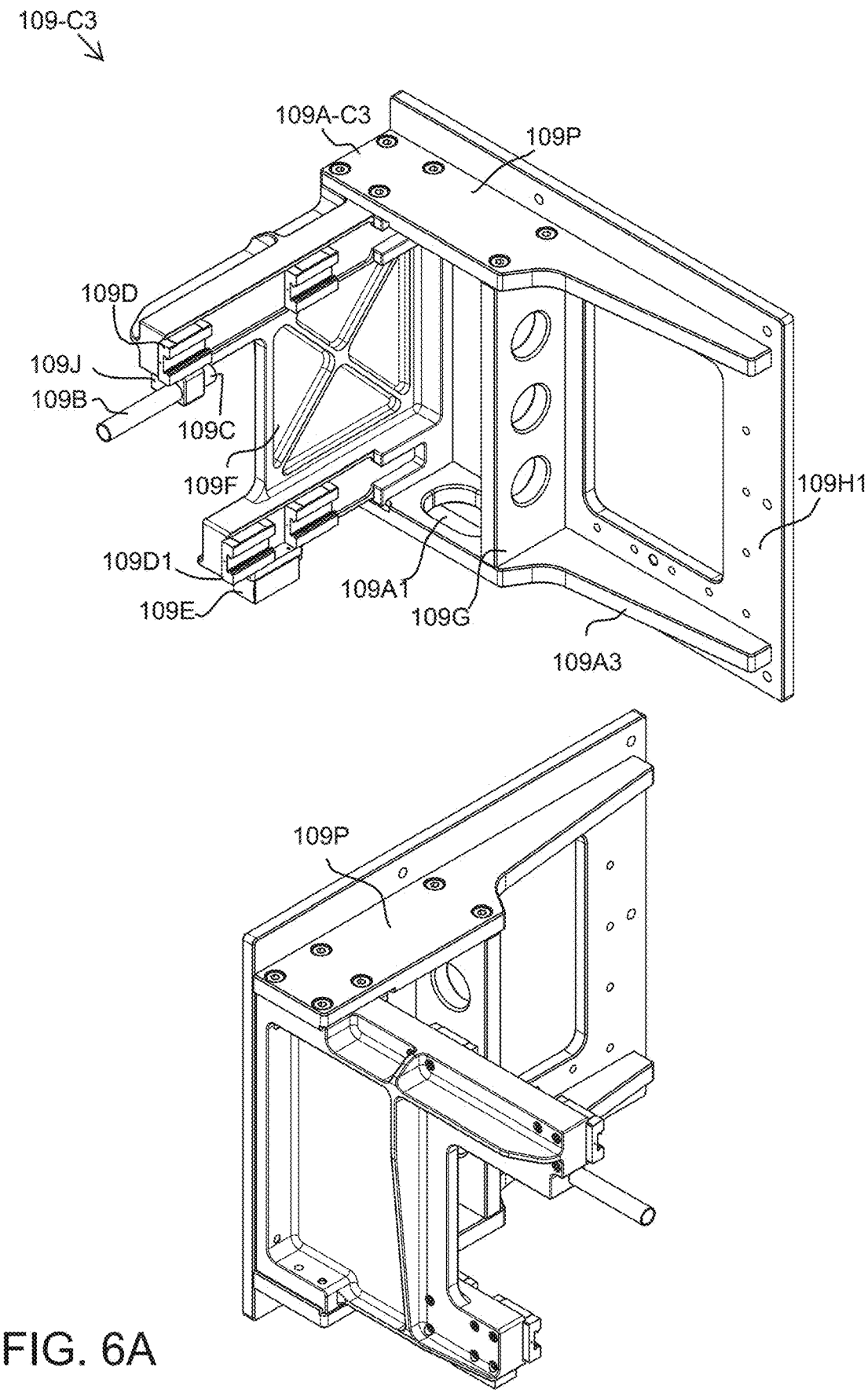
FIG. 6A is a schematic diagram of first and second views of the z-axis baseplate third configuration of the present teachings.

Referring now to FIG. 6A, z-axis baseplate third configuration 109-C3 can include, but is not limited to including, support rails third configuration 109A-C3, screw cover tube 109B, ball nut 109C, carriage 109D, and optical encoder 109E. Z-axis baseplate third configuration 109-C3 can also include baseplate side 109F, mount crossbar 109G, and microscope plate adapter first side 109H1. Z-axis baseplate third configuration 109-C3 can be mounted flush with microscope top plate first side 111B (FIG. 3).

Figure 6B:
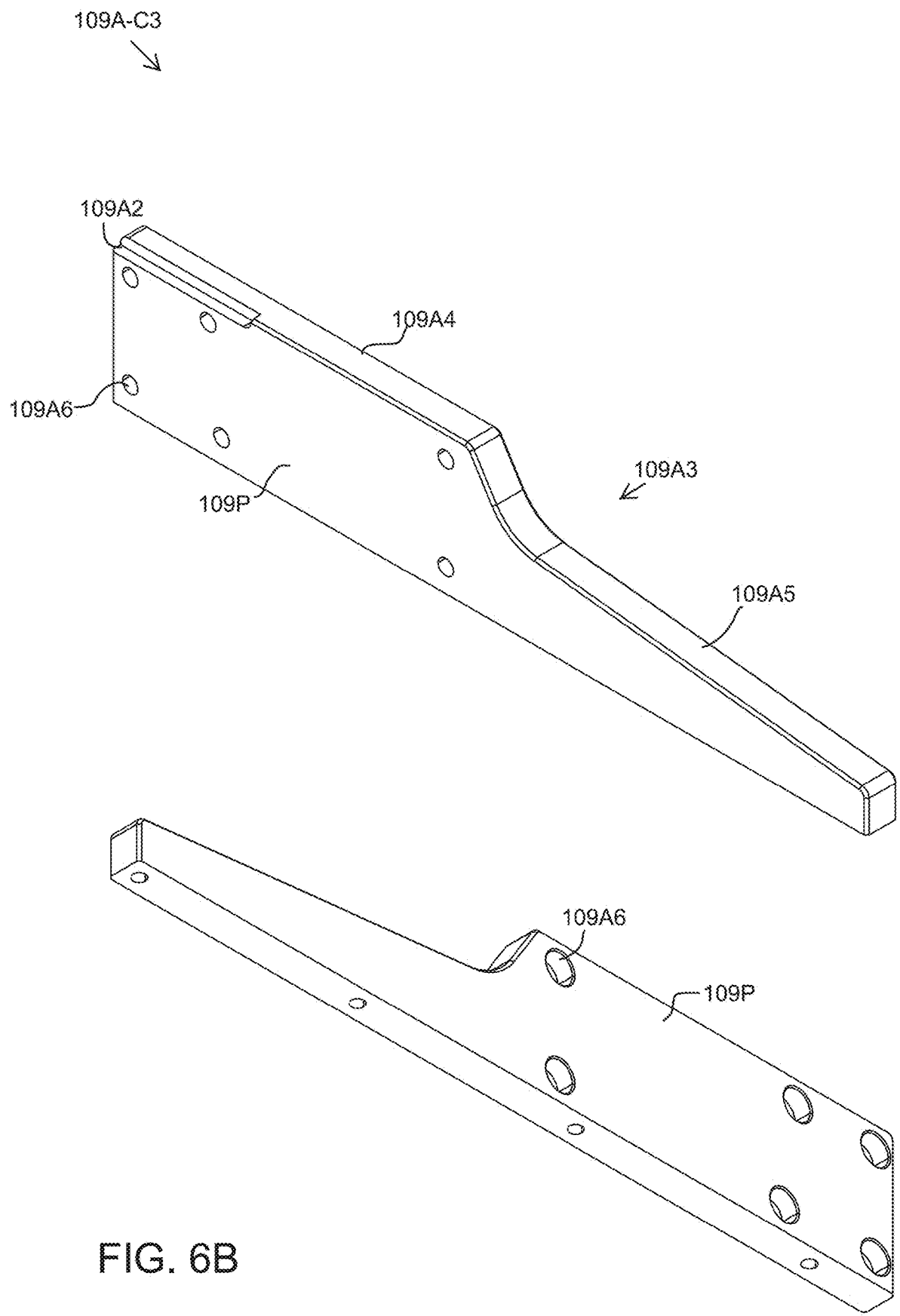
FIG. 6B is a schematic diagram of first and second views of the support rails third configuration of the present teachings.

Referring now primarily to FIG. 6B, in some configurations, support rails third configuration 109A-C3 can include, but are not limited to including, single cavity 109A1 (FIG. 6A) and divot 109A2, and/or or solid face 109P, or a combination of cavities and solid faces. Support rails third configuration 109A-C3 can be tapered 109A3 between rail first end 109A4 and rail second end 109A5, where rail first end 109A4 and rail second end 109A5 can be different sizes relative to each other. Support rails third configuration 109A-C3 can be tapered to, for example, but not limited to, provide viewing access to tissue enclosure 101 (FIG. 2A). Support rails third configuration 109A-C3 can be any shape, size, and depth depending on weight requirements of printer 100 (FIG. 2A), viewing requirements, if any, of the contents of tissue enclosure 101 (FIG. 2A), and fastening requirements of z-axis baseplate third configuration 109-C3 (FIG. 6A). Support rails third configuration 109A-C3 can include fastening cavities 109A6 which can be any shape, size, and depth, and can occur in any quantity sufficient to maintain the structural integrity of printer 100 (FIG. 2A), and to insure that printer 100 (FIG. 2A) has positional stability. In some configurations, each of support rails third configuration 109A-C3 can include six fastening cavities 109A6 that can mate support rails 109A to baseplate side 109F (FIG. 6A) and mount crossbar 109G (FIG. 6A), for example. Support rails third configuration 109A-C3 can also include fastening bores 109A7 to accommodate fastening support rails third configuration 109A-C3 to microscope plate adapter 109H (FIG. 13), for example.

Figure 7:
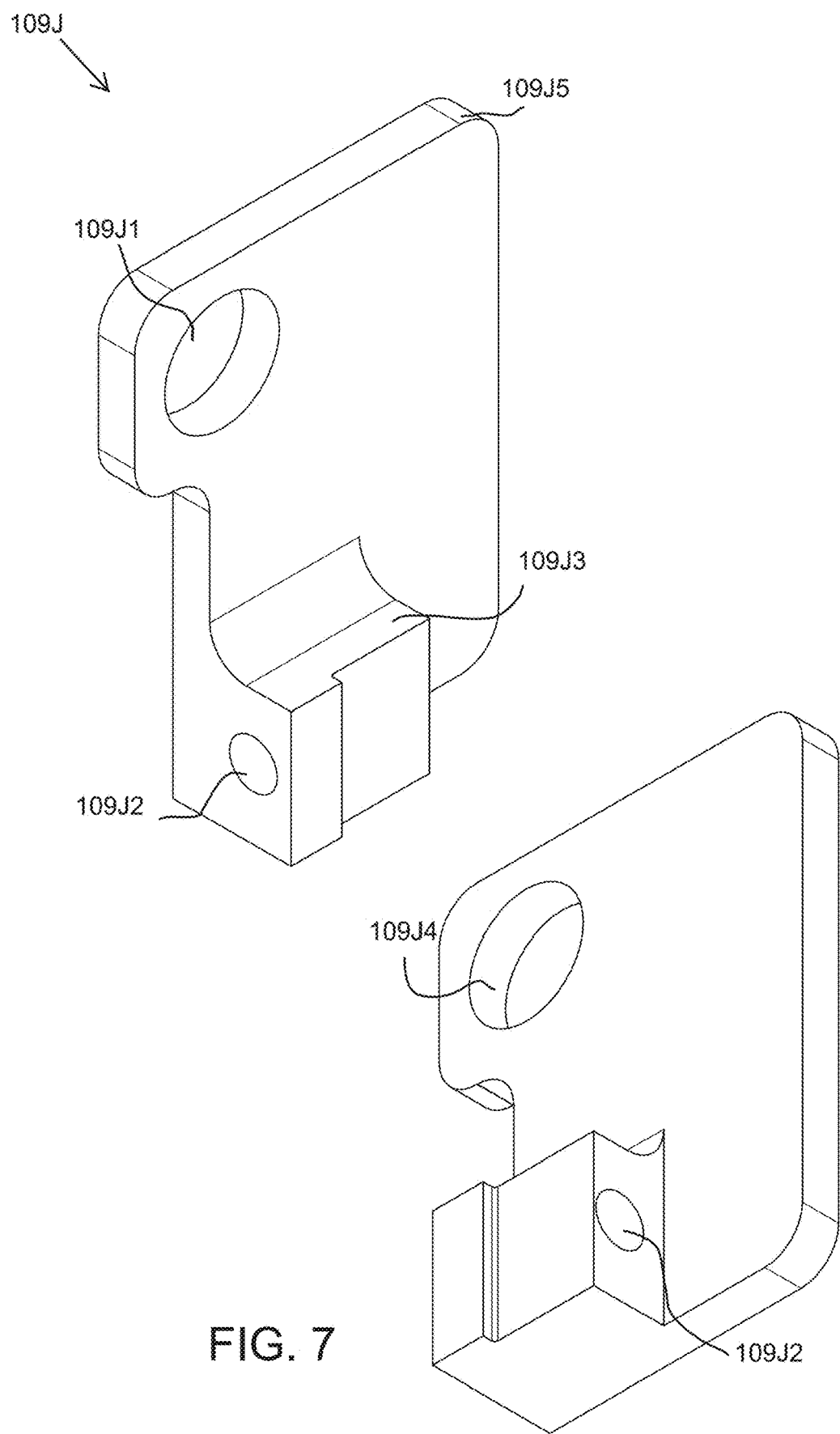
FIG. 7 is a schematic diagram of first and second views of the screw/tube guide of the present teachings.

Referring now to FIG. 7, screw/tube guide 109J can include, but is not limited to, tube cavity 109J1, fastener cavity 109J2, and shaped structure 109J3. Screw/tube guide 109J can optionally include at least one bearing (not shown) within tube cavity 109J1, for example, along tube cavity wall 109J4, for grasping tube 109B (FIG. 6A). Shaped structure 109J3 can be molded to conform with baseplate side 109F (FIG. 6A), and can be fastened to baseplate side 109F (FIG. 6A) through fastener cavity 109J2, which can be any size and shape to accommodate any type of fastener.

Referring now to FIG. 8, ball nut 109C can include, but is not limited to including, first ball nut cavity 109C2, ball nut threads 109C1, ball nut body 109C3, ball nut end taper 109C4, ball nut end 109C5, and second ball nut cavity 109C6. First ball nut cavity 109C2 and second ball nut cavity 109C6 can form a single hollow core accommodating ballscrew 107A (FIG. 15). In some configurations, ball nut 109C can include, for example, five ball nut threads 109C1, although any number and size of threads can be used. Ball nut 109C can be installed into baseplate side 109F (FIG. 6A) through ball nut threads 109C1. Ball nut body 109C3 can be any size and thickness, and can be constructed of any material with characteristics including, but not limited to, rigidity and durability. Ball nut 109C can include ball nut chamfer 109C4 to ball nut end 109C5. Ball nut taper 109C4 can be any angle, and ball nut end 109C5 can be any size, forming the thickness of ball nut walls 109C3.

Figure 15A:
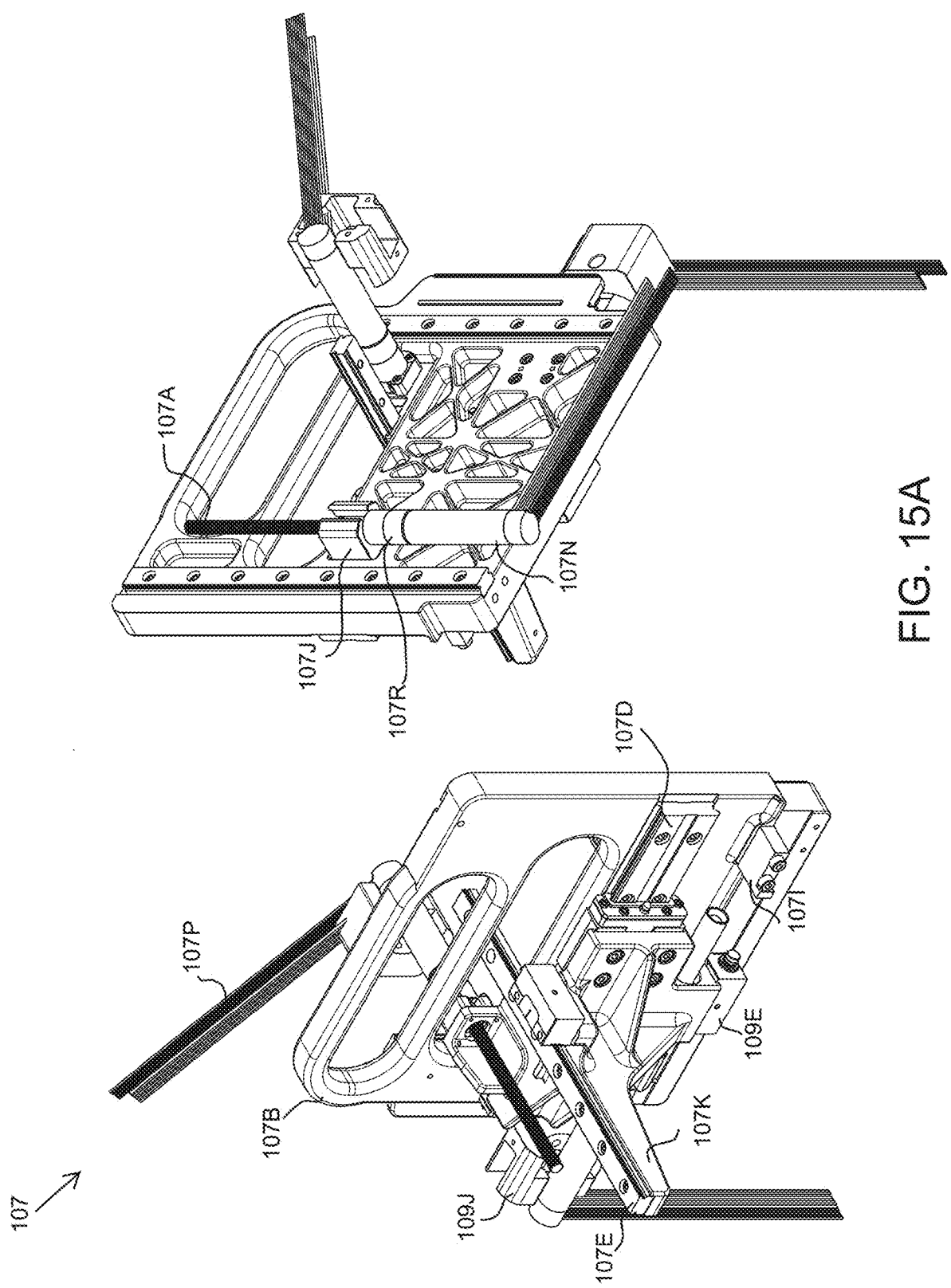
FIG. 15A is a schematic diagram of first and second views of the moving assembly of the present teachings.

Referring now to FIG. 9, screw cover tube 109B can include, but is not limited to including, tube end cap 109B1 and tube body 109B2. In some configurations, tube body 109B2 can include tube body cavity 109B7 that can, together with end cap cavity 109B6, form a continuous opening for lead/ball screw 107A (FIG. 15A). Tube body 109B2 can be joined to tube end cap 109B1 at thread relief face 109B3 which can be, but is not limited to being, recessed relative to both tube body 109B2 and tube end cap 109B1. In some configurations, tube end cap 109B1 can enable snap-on installation of tube body 109B2.

Figure 10:
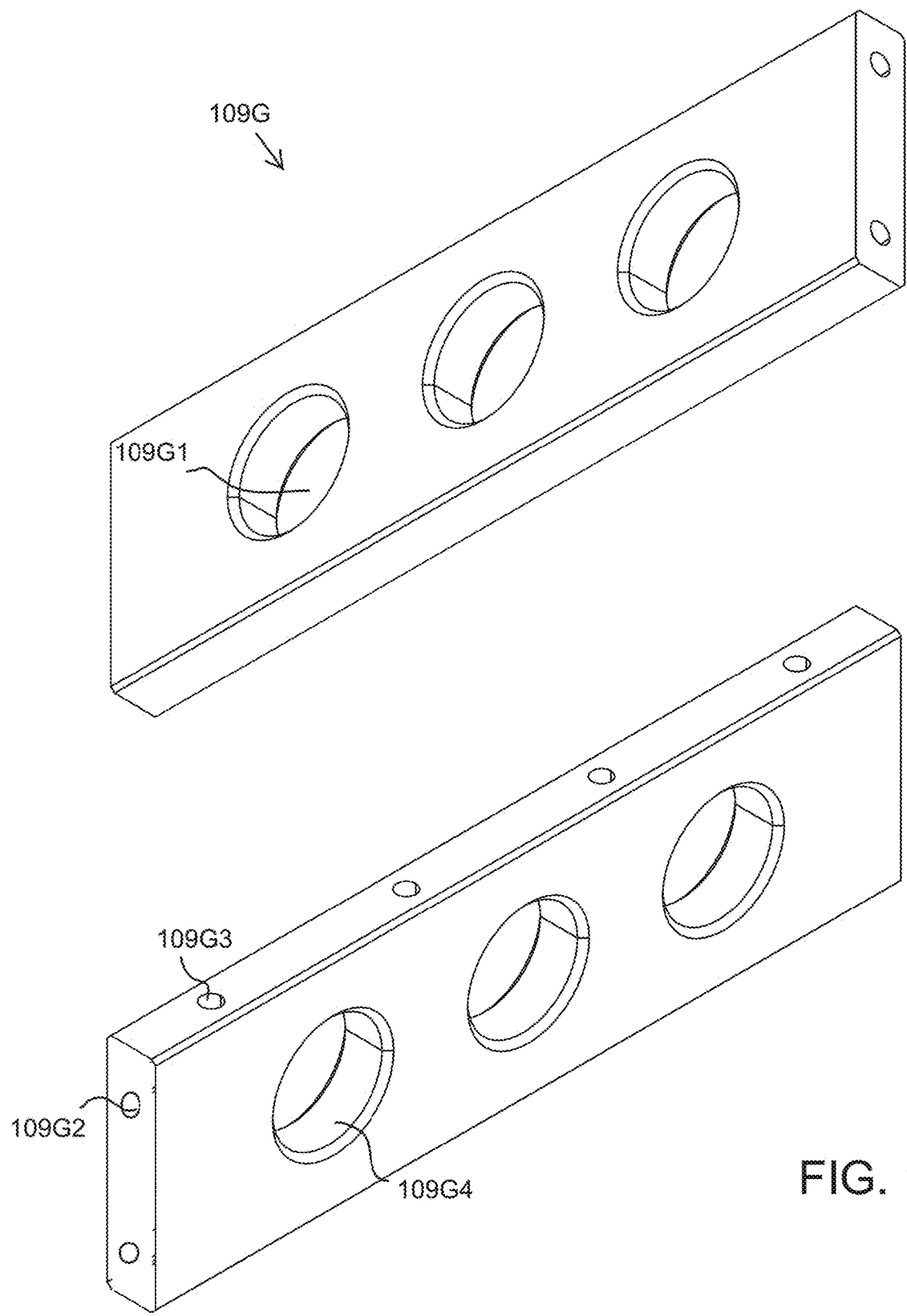
FIGS. 10 and 11 are schematic diagrams of first and second configurations of the mount crossbar of the present teachings.
Figure 11:
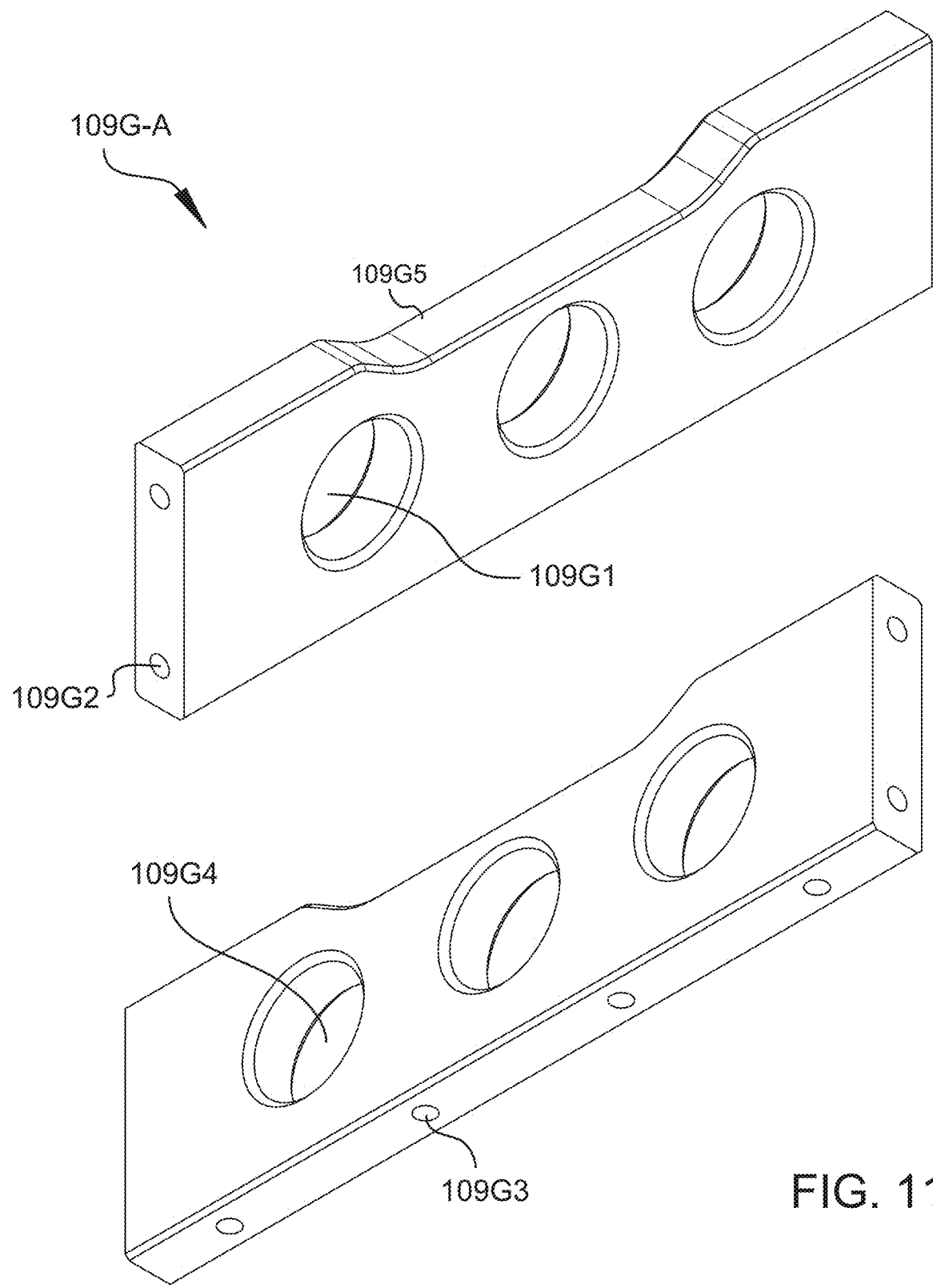

Referring now primarily to FIGS. 10 and 11, mount crossbars 109G and 109G-A can include, but are not limited to including, crossbar cavities 109G4, end fastener cavities 109G2, and side fastener cavities 109G3. In some configurations, mount crossbar 109G can be shaped to support and be fastened to, through end fastener cavities 109G2, rails 109A-C1/C2/C3 (FIGS. 4B/5B/6B). Mount crossbar 109G can be any height and length, depending on the distance between rails 109A-C1/C2/C3 (FIGS. 4B/5B/6B) and the height of rails 109A-C1/C2/C3 (FIGS. 4B/5B/6B). In some configurations, a particular depth for mount crossbar 109G can be chosen based on factors such as material used to construct mount crossbar 109G and stability requirements. Side fastener cavities 109G3 can accommodate fasteners that can be used to attach mount crossbar 109G to microscope plate adapter first side 109H1 (FIG. 4A). There can be any number and size of end fastener cavities 109G2 and side fastener cavities 109G3 that can accommodate any type, size, and shape of fastener, within the constraints of structural stability. Crossbar cavities 109G4 can be any size and shape, and can be completely absent in some configurations. When present, crossbar cavities 109G4 can enable weight reduction and provide cable runs. Crossbar 109G-A can include recess 109G5 that can accommodate other features of printer 100.

Figure 12:
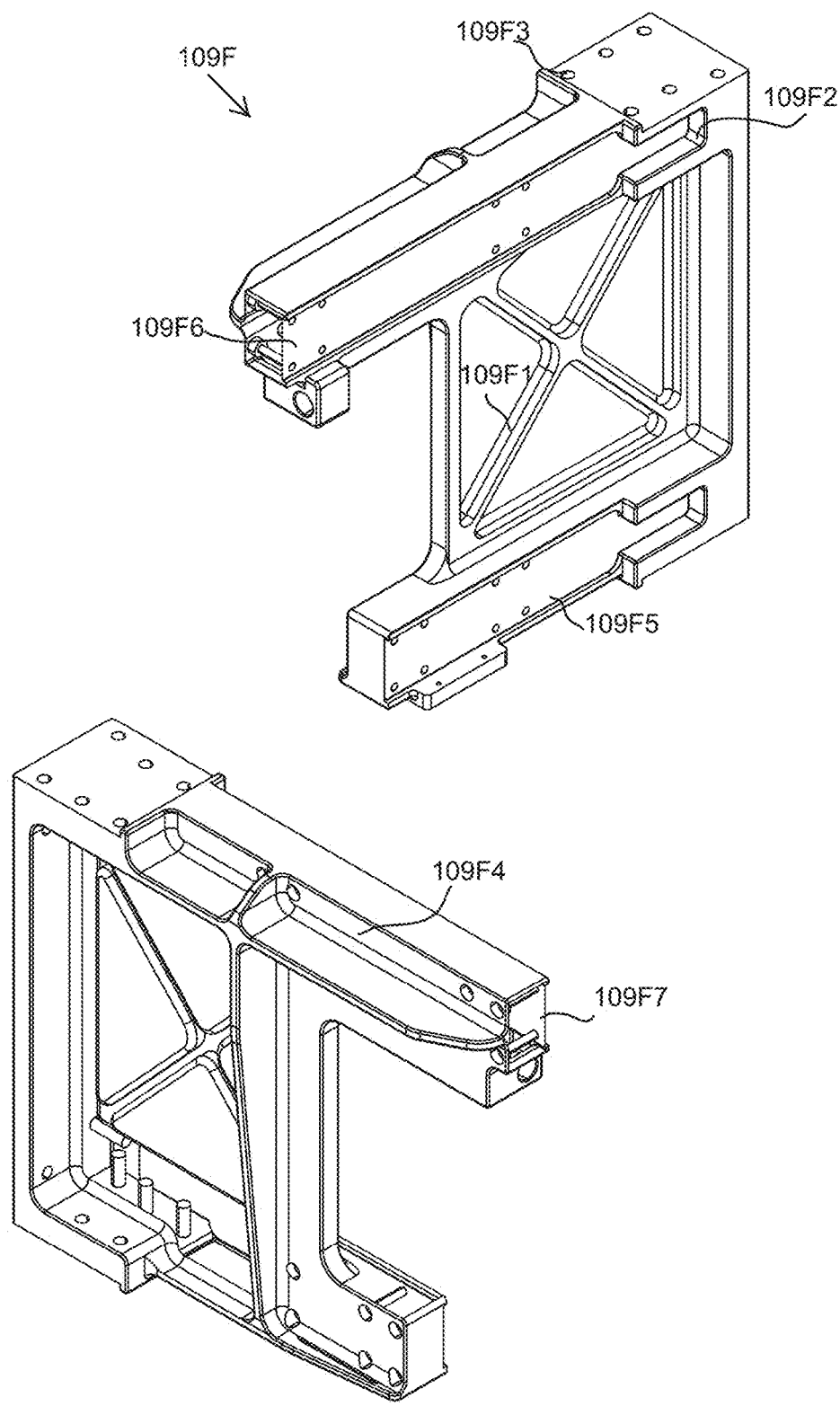
FIG. 12 is a schematic diagram of first and second views of the baseplate side of the present teachings.
Figure 16:
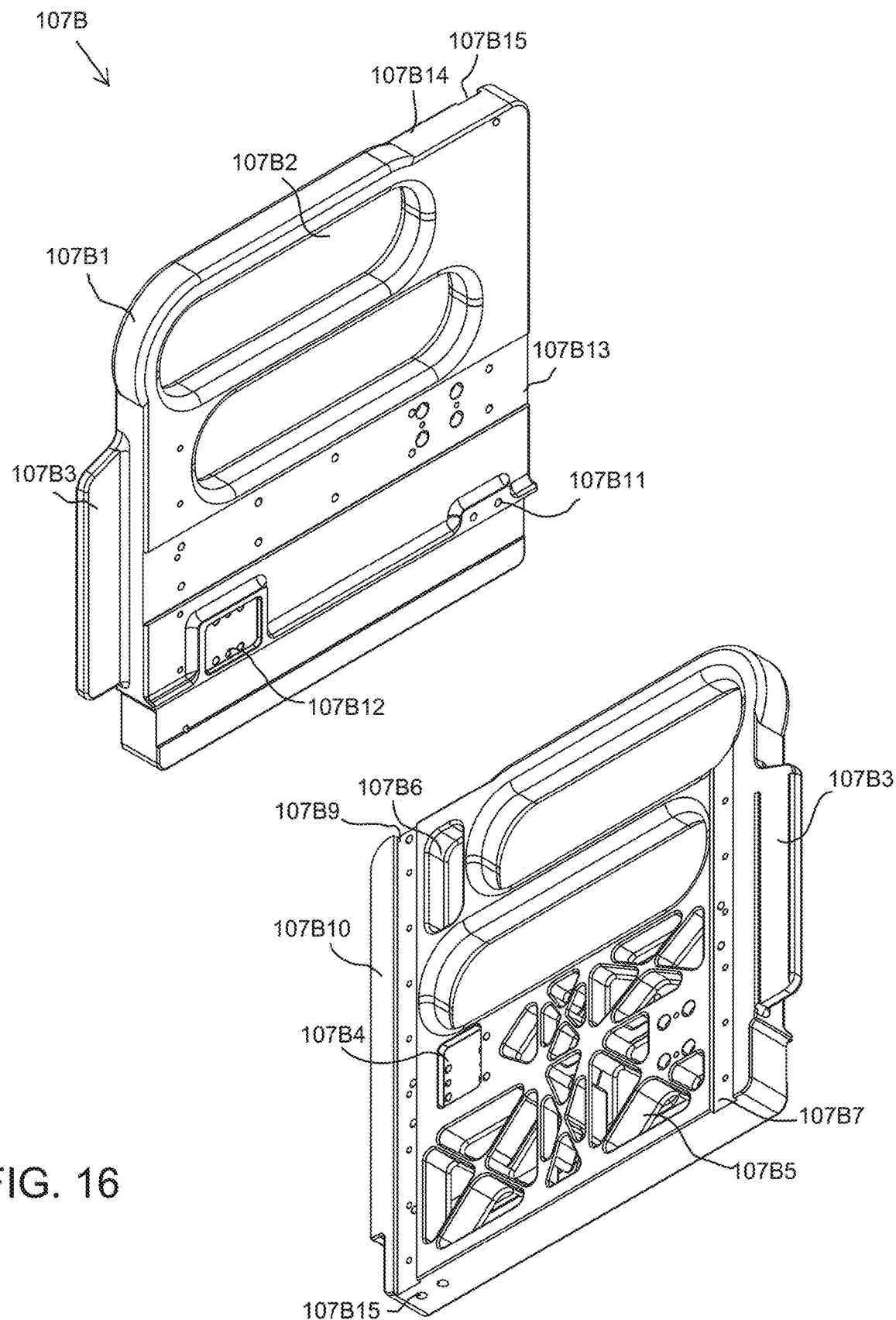
FIG. 16 is a schematic diagram of first and second views of the x-axis baseplate of the present teachings.
Figure 17:
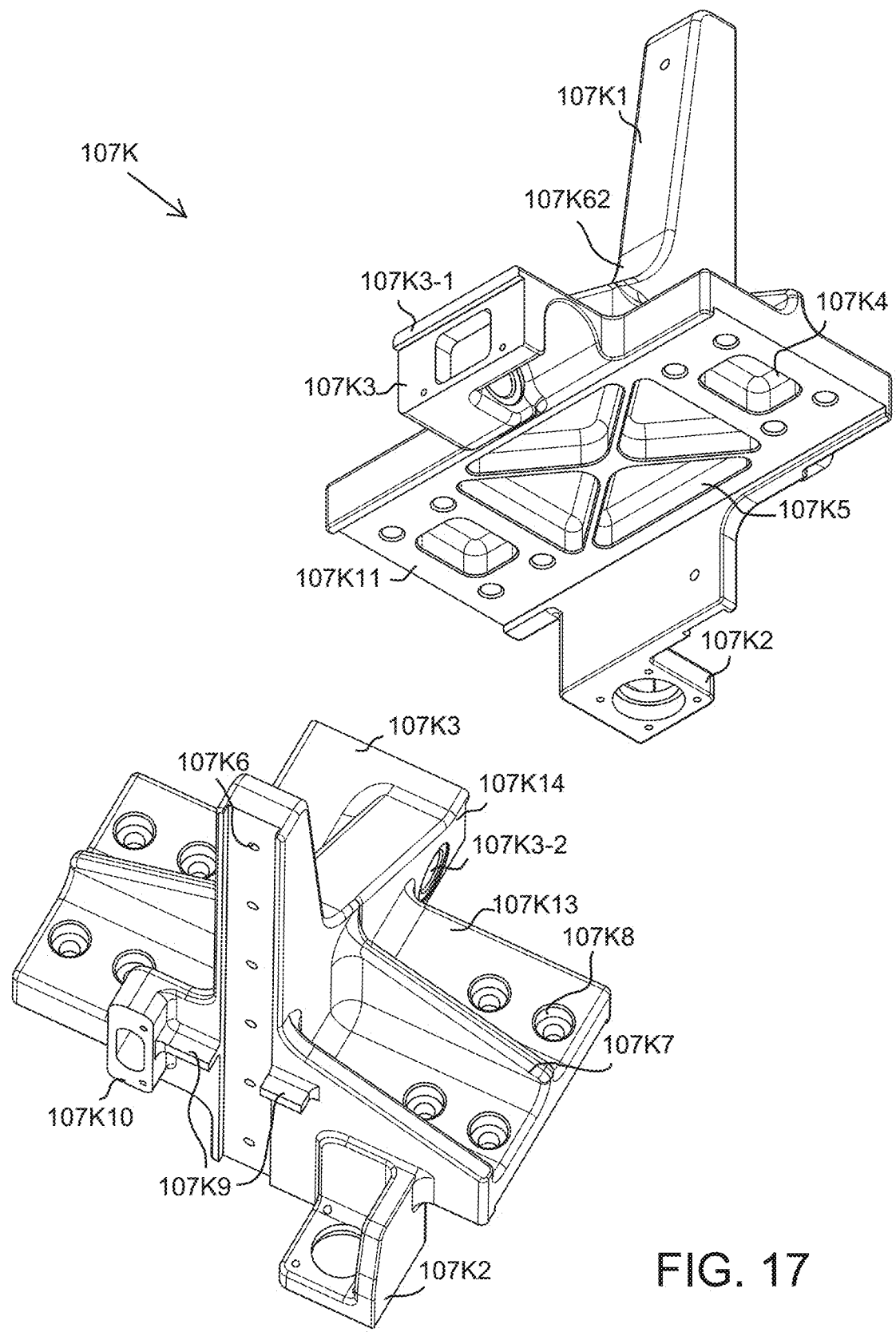
FIG. 17 is a schematic diagram of first and second views of the x-axis block of the present teachings.

Referring now to FIG. 12, baseplate side 109F can provide rail runs that can interconnect z-axis baseplate 109 (FIG. 1C) with x-axis block 107K (FIG. 17). Baseplate side 109F can include, but is not limited to including, first rail run 109F5 that can enable mounting of first rail 107M (FIG. 18A), that can interconnect with second rail indent 107B7 (FIG. 16). Baseplate side 109F can include second rail run 109F6 that can enable mounting of second rail 107E (FIG. 18B) that can interconnect with second rail indent 107B9 (FIG. 16). Baseplate side 109F can include baseplate ribs 109F1, screw run indent 109F2, fastener cavities 109F3, and structural indents 109F4. Baseplate ribs 109F1 can be any shape, size, and depth, and can provide stiffening, while allowing for reduced (with respect to a non-ribbed structure) weight, to baseplate side 109F. In some configurations, baseplate ribs 109F1 may not be present, and instead baseplate side 109F can include a solid plate in the place of baseplate ribs 109F1. In some configurations, solid plates can be interleaved among baseplate ribs 109F1. Screw run indent 109F2 can be any shape and size, and can accommodate ballscrew 107A (FIG. 15). Structural indents 109F4 can accommodate functional features of printer 100 (FIG. 2A) and/or can enable weight reduction. Baseplate side 109F can be constructed of any material and can be any size, shape, and depth. In some embodiments, baseplate side 109F can include characteristics that can enable stability as printer 100 (FIG. 2A) operates.

Referring now to FIG. 12A, z-axis stop bearing 107F7-1 can be mounted at stop bearing mounting point 109F7. Z-axis stop bearing 107F7-1 can include, but is not limited to including, mount point 107F7-1A for screw cover tube 109B (FIG. 9), fastening cavity 107F7-1B to fasten z-axis stop bearing 107F7-1 to z-axis baseplate 109F (FIG. 12), and contoured features such as, for example, but not limited to, edge filet 107F7-1C to streamline printer 100 (FIG. 1A).

Referring now primarily to FIG. 13, microscope plate adapter 109H can include, but is not limited to including, plate adapter first side 109H1, plate adapter second side 109H2, and plate adapter dish cavity 109H3. Microscope plate adapter 109H can also include at least one fastening cavity 109H4 and 109H5 (FIG. 5A). Fastening cavities 109H4 and 109H5 (FIG. 5A) can be used for any purpose such as, for example, but not limited to, cable runs. In some configurations, rails 109A-C1/C2/C3 (FIGS. 4A/5A/6A) can be attached to plate adapter first side 109H1 with fasteners accommodated by, for example, fastener cavities 109H4. In some configurations, mount crossbar (FIG. 10) can be attached to plate adapter first side 109H1 with fasteners accommodated by, for example, fastener cavities 109H4. In some configurations, baseplate side 109F (FIG. 12) can be attached to plate adapter first side 109H1 with fasteners accommodated by, for example, fastener cavities 109H4. In some configurations, microscope top plate (FIG. 3) can be attached to microscope plate adapter second side 109H2.

Figure 14A:
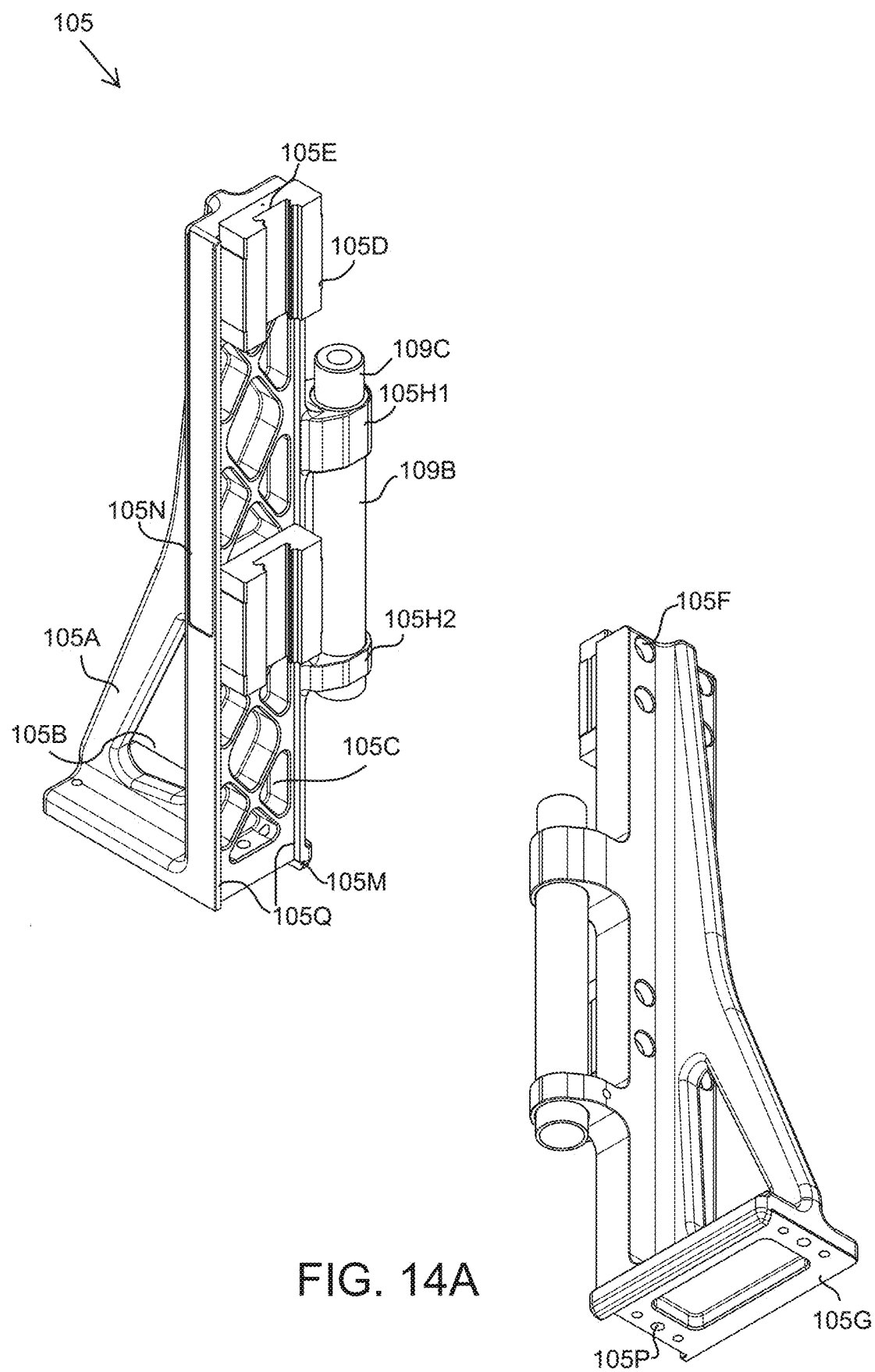
FIGS. 14A and 14B are schematic diagram of various views of the y-axis block of the present teachings.
Figure 18A:
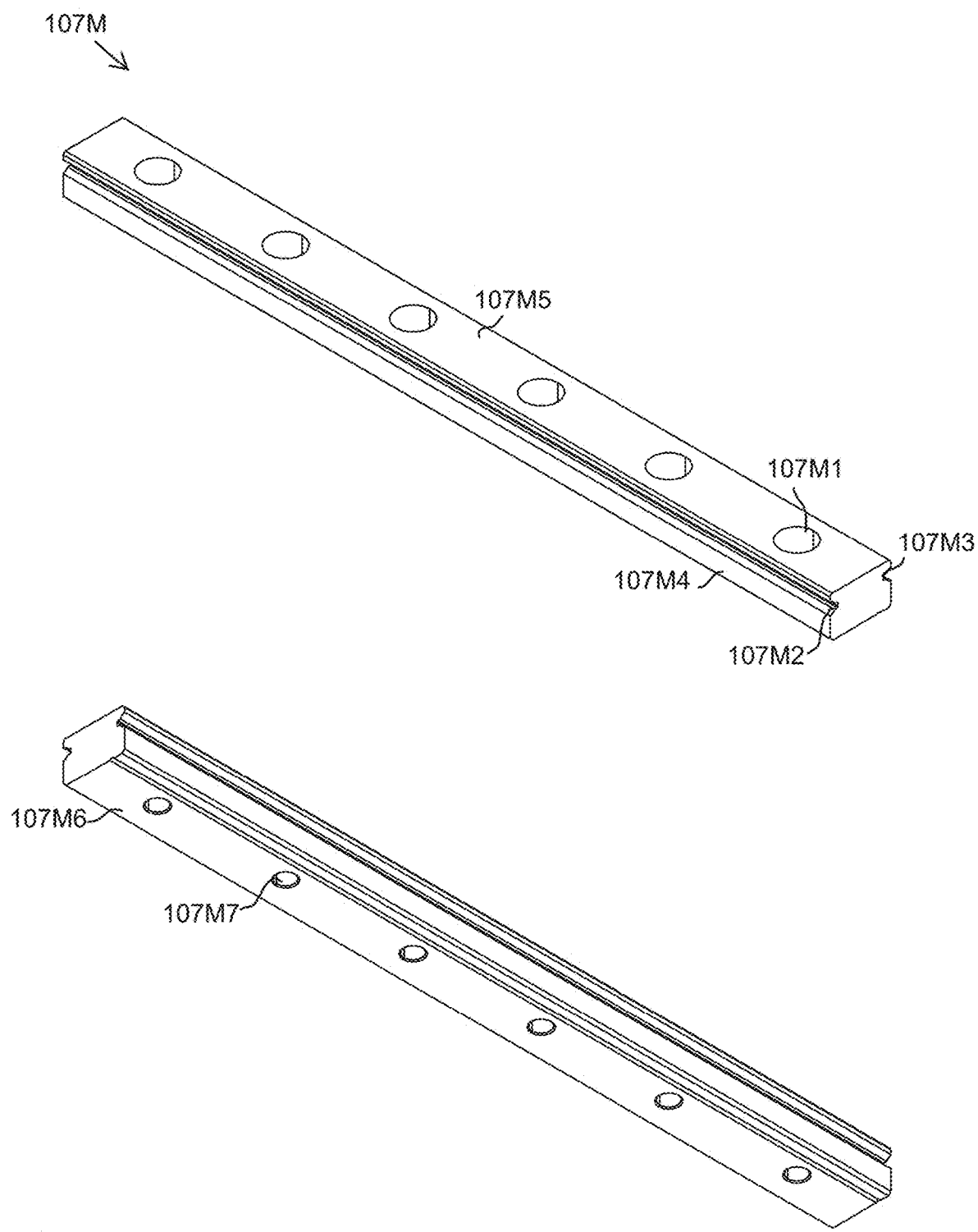
FIG. 18A is a schematic diagram of first and second views of the first rail of the present teachings.

Referring now primarily to FIG. 14A, y-axis block 105 can direct movement of delivery system 103 (FIG. 1C). Y-axis block 105 can be coupled with delivery system 103 (FIG. 1C) along y-block base 105G with, for example, but not limited to, fasteners compatible with fastener cavities 105P. Y-axis block 105 can be coupled with delivery system 103 (FIG. 1C) in any way including, but not limited to, using screws, bolts, nails, and hook-eye fasteners. Y-axis guide rails 105Q for y-axis guides 105D can enable movement of y-axis block 105. Y-axis guides 105D can be attached to y-axis guide rails 105Q by fasteners compatible with fastener cavities 105F. Y-axis guides 105D can include guide slots 105E that can be sized to accommodate, for example, first rail 107M (FIG. 18A). Y-axis guides 105D and guide slots 105E can be any size, shape, and depth. Y-axis block 105 can include, but is not limited to including, y-block support 105A, y-block support cavities 105B/105C, y-block fastener cavities 105P, and y-block lip 105M. Y-block support 105A can provide stability to y-axis block 105, and can include y-block cavity 105B to adjust the weight of y-axis block 105. Y-block cavities 105B/105C can be any size and shape, can be completely absent from y-axis block 105, and can include partial cut-outs in which y-block cavities 105B/105C extend partly into the depth of solid features of y-axis block 105. Y-block lip 105M can provide additional stability in the coupling between y-axis block 105 and delivery system 103 (FIG. 1C), and can include a datum surface or indexing face by which subsequent assemblies can be aligned and installed. Y-block lip 105M can enable maintenance of orthogonal installation and can constrain the position in which the extruder subassembly can be installed. Scale application surface 105N can provide a mounting position for a linear encode scale. Y-axis block 105 can include ball nut holder 105H1 and screw tube holder 105H2 providing stable mounting for ball nut 109C (FIG. 8) and screw cover tube 109B (FIG. 9).

Figure 14B:
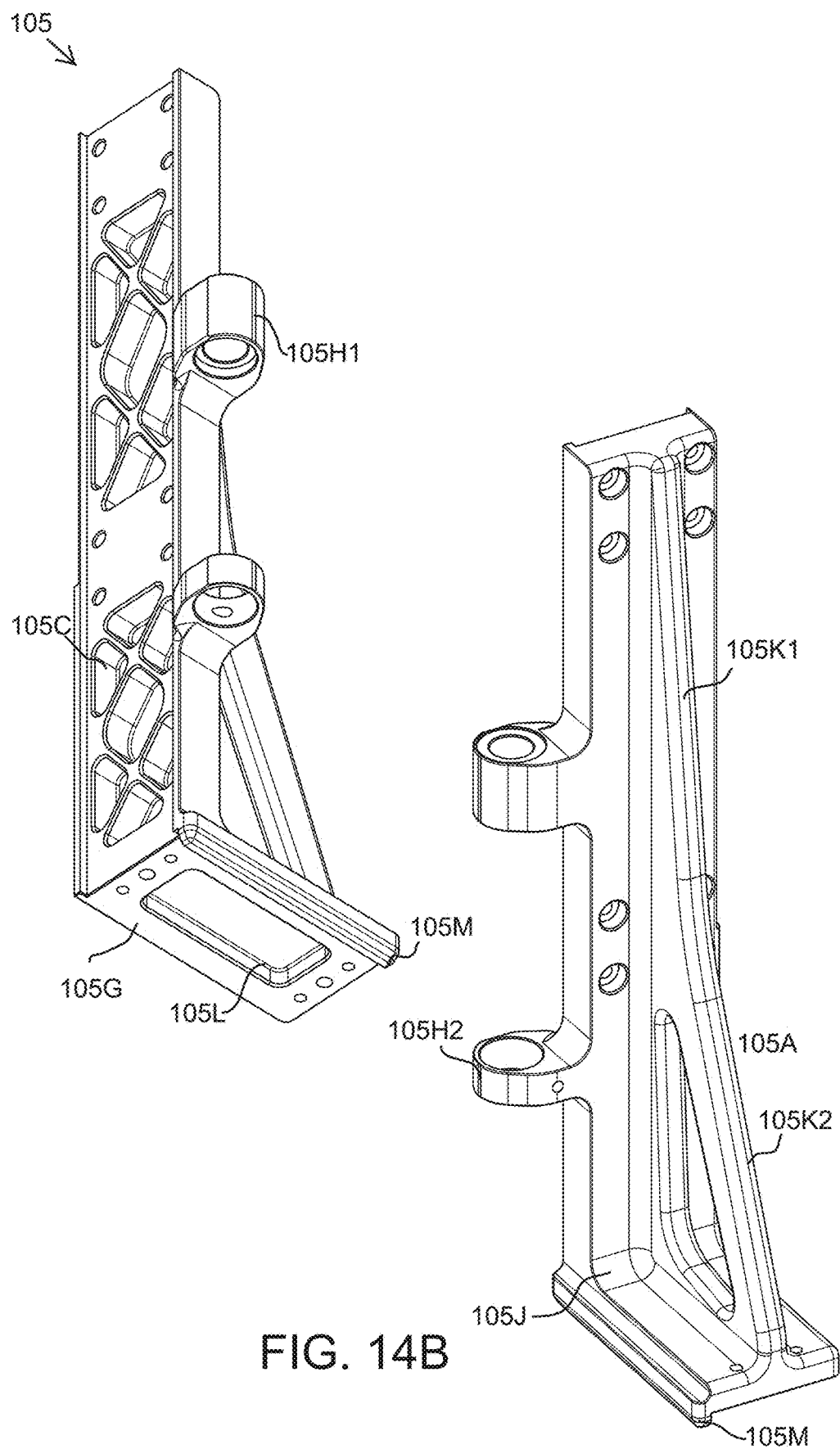

Referring now primarily to FIG. 14B, y-block support 105A can be tapered from first support end 105K1 to second support end 105K2 where first support end 105K1 can be, but is not limited to being, a different size from second support end 105K2. In some configurations, first support end 105K1 can be shaped to accommodate dimensional characteristics of x-axis block 107 (FIG. 15A). Y-block base 105G can include base indent 105L that can be any size, shape, and depth. Base indent 105L can provide weight accommodations for y-axis block 105. Various y-block filets 105J can optionally provide strength and stability to y-axis block 105.

Referring now primarily to FIG. 14C, y-axis linear bearing 105D can ride on second rail 107E (FIG. 18B) that can couple y-axis block (FIG. 14A) to x-axis block 107K (FIG. 17). Y-axis linear bearing 105D can include, but is not limited to including, guide slot 105E and guide fastener cavity 105D1. In some configurations, guide slot 105E can include first guide rail section 105E1 and second guide rail section 105E2 that can insure stable performance of the linear guide. Mounting face 105D2 can be elevated to accommodate various fastener sizes in guide fastener cavity 105D1. Mount side 105D3 can support elevated of mounting face 105D2. In some configurations, indent 105D4 can support a limit stop, for example, a compliant limit stop. In some configurations, y-axis linear bearing 105D can include any one of a variety commercially-available linear bearings.

Figure 15B:
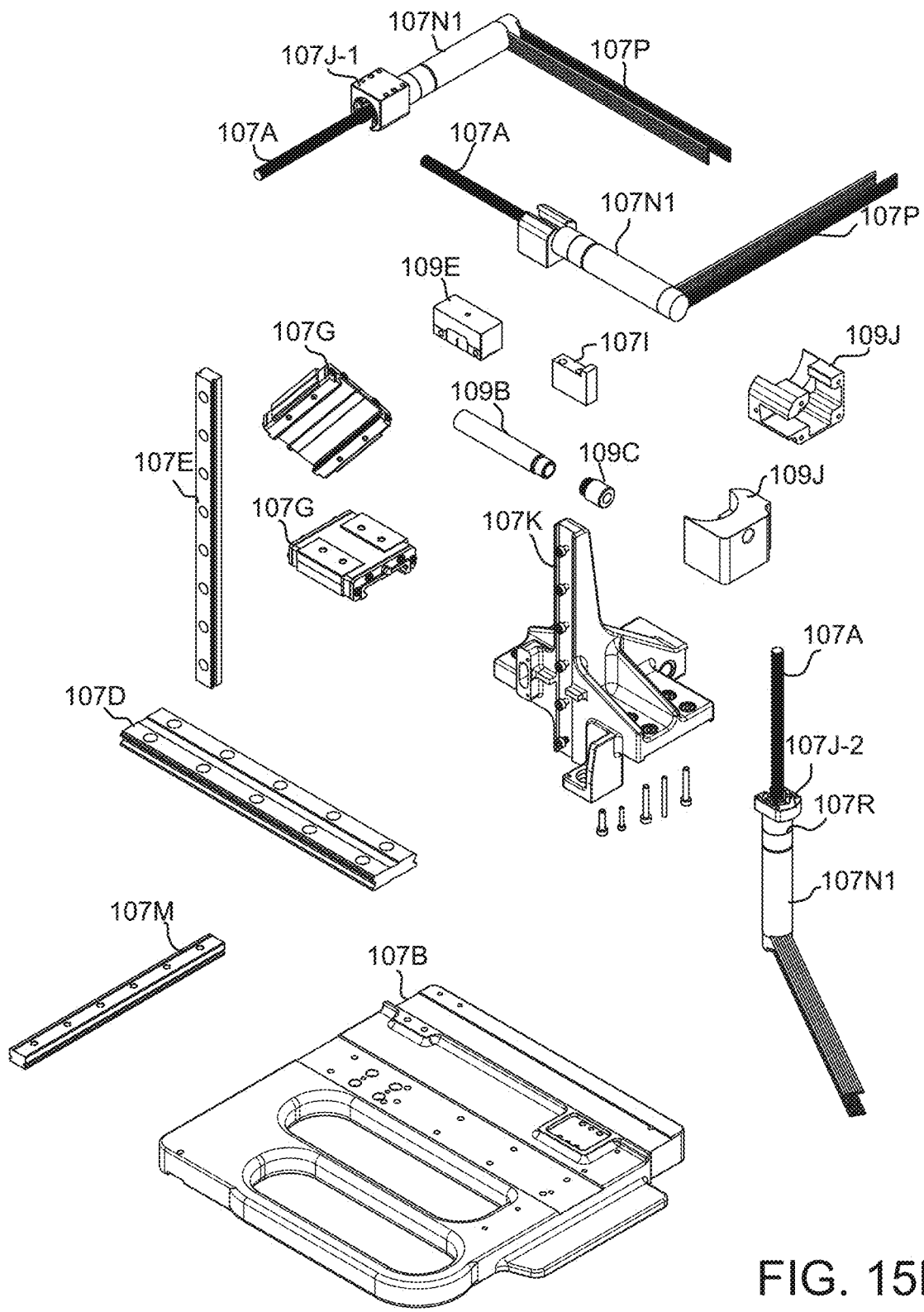
FIG. 15B is a schematic diagram of an exploded view of the moving assembly of the present teachings.

Referring now primarily to FIGS. 15A and 15B, block assembly 107 can enable movement of delivery system 103 (FIG. 1C). Block assembly 107 can include motors 107N and gears 107R, powered through cabling 107P, that can power movement of separate ballscrews 107A in x, y, and z directions as directed by a print head controller 61. Block assembly 107 can include, but is not limited to including, x-axis baseplate 107B and x-axis stability structure 107K. Block assembly 107 can couple with y-axis block 105 (FIG. 14A) through, for example, rail 107E and rail guides 105D (FIG. 14A) which can provide coupling with delivery system 103 (FIG. 1C).

Referring now to FIG. 16, x-axis baseplate 107B can provide a mounting and stability platform for various elements of printer 100 (FIG. 1A). X-axis baseplate 107B can be mounted, using, for example, mounting fastening indents 107B15 and fasteners, onto z-axis baseplate 109 (FIG. 1C). X-axis baseplate 107B can be structured to fit within supports such as, for example, support rails 109A-C1 (FIG. 4A), 109A-C2 (FIG. 5A), and/or 109A-C3 (FIG. 6A). Features such as, for example, mount 107B3 for optical encoder 109E (FIG. 11) can also provide stability through static coupling with support rails 109A-C1 (FIG. 4A), 109A-C2 (FIG. 5A), and/or 109A-C3 (FIG. 6A). Indented edge 107B10 can also statically couple with support rails 109A-C1 (FIG. 4A), 109A-C2 (FIG. 5A), and/or 109A-C3 (FIG. 6A) to provide vertical stability. X-axis baseplate 107B can be lightened and lifted by features such as cavities 107B2 and indents 107B4/107B5/107B6, and can be streamlined by positioning elements of printer 100 (FIG. 1A), filet 107B1, and cables within cavities 107B2. X-baseplate first mount 107B12 and x-baseplate second mount 107B4 can provide a mounting locations for spindle adapters 107J, x-baseplate second mount 107B11 can provide a mounting location for fastening spot for x-axis stopper 107I, and x-baseplate third mount 107B14 can provide a mounting location for stop bearing 107B20 (FIG. 16A). X-axis baseplate 107B can include indentations that can accommodate ballscrew rails. For example, first rail indent 107B7 can accommodate first rail 107M, second rail indent 107B9 can accommodate second rail 107F, third rail indent 107B13 can accommodate third rail 107D. Stop bearing 107B20 (FIG. 16A) can be mounted at bearing mount point 107B15.

Referring now to FIG. 16A, block z-axis stop bearing 107F7-2 can be mounted at block stop bearing mounting point 107B14. Block z-axis stop bearing 107F7-2 can include, but is not limited to including, mount point 107F7-2A for screw cover tube 109B (FIG. 9), fastening cavity 107F7-2B to fasten block z-axis stop bearing 107F7-2 to x-axis block 107B (FIG. 16), and contoured features such as, for example, but not limited to, edge filet 107F7-2C to streamline printer 100 (FIG. 1A).

Referring now primarily to FIG. 17, x-axis block 107K can provide support for y-axis block 105 (FIG. 14A), and can provide mounting cavities for various elements of printer 100 (FIG. 1A). X-axis block 107K can couple with y-axis block 105 (FIG. 14A) by mounting fourth rail 107E in guide slots 105E (FIG. 14A). Side tabs 107K9 can provide an integrated y-axis hard stop. In some embodiments, fastener indents 107K6 and associated fasteners can be used to couple fourth rail 107E (FIG. 16) with x-axis block 107K. X-axis block 107K can couple with x-axis baseplate 107B (FIG. 16) through rail guide 107K11 third rail indent 107B13 (FIG. 16) for mounting third rail 107D (FIG. 18C). X-block y-axis support 107K1 can include filet 107K62 to improve strength and stability, and can be tapered to possibly accommodate streamlined printer feature placement. X-axis block 107K can be coupled to linear bearings 107G (FIG. 15B) at carriage indents 107K4 and through fastening indents 107K8 and associated fasteners. Linear bearings 107G (FIG. 15B) can be, but are not limited to being, commercial products such as, for example, associated with the THK® KR1501B linear actuator. First x-block mounting cavity 107K2 and second x-block mounting cavity 107K3-2 can provide passages for ballscrews 107A (FIG. 15B). X-block optical encoder mounting 107K3 can provide a mounting location for optical encoder 109E (FIG. 11), and lip 107K3-1 can provide an indexing face to aid in optimal alignment/calibration of optical encoder 109E (FIG. 11). Support fins 107K7 can provide structural support for mounting flange 107K13 that can be coupled to linear bearings 107G (FIG. 15B) and thus third rail 107D (FIG. 18C) through fastener indents 107K8 and associated fasteners.

Referring now primarily to FIG. 18A, first rail 107M can operably couple z-axis baseplate first side run 109F5 (FIG. 12) with x-axis baseplate 107B (FIG. 16) at first rail indent 107B7 (FIG. 16). First rail 107M can include first side fastening cavities 107M1 on first rail first side 107M5 that can penetrate through first rail 107M to first rail second side 107M6 through second side fastening cavities 107M7. First rail 107M can include any number of first side fastening cavities 107M1, for example, but not limited to, six, and can be any length, width, and depth. First rail 107M can also include first rail slot 107M3, second rail slot 107M2, side face 107M4 that can enable locking and stable interconnection with z-axis carriages 109D1 (FIGS. 4A/5A/6A).

Figure 18B:
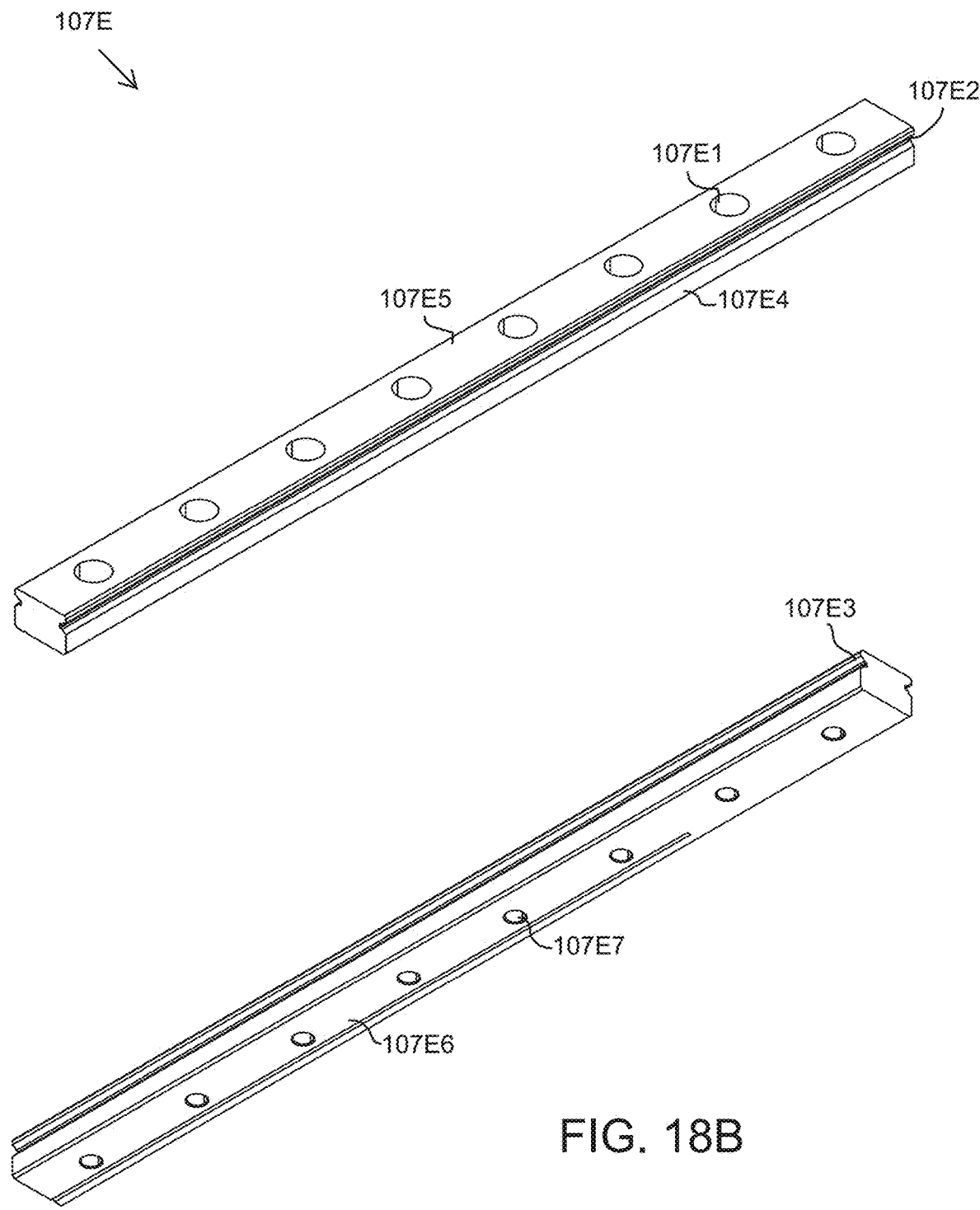
FIG. 18B is a schematic diagram of first and second views of the second rail of the present teachings.
Figure 18C:
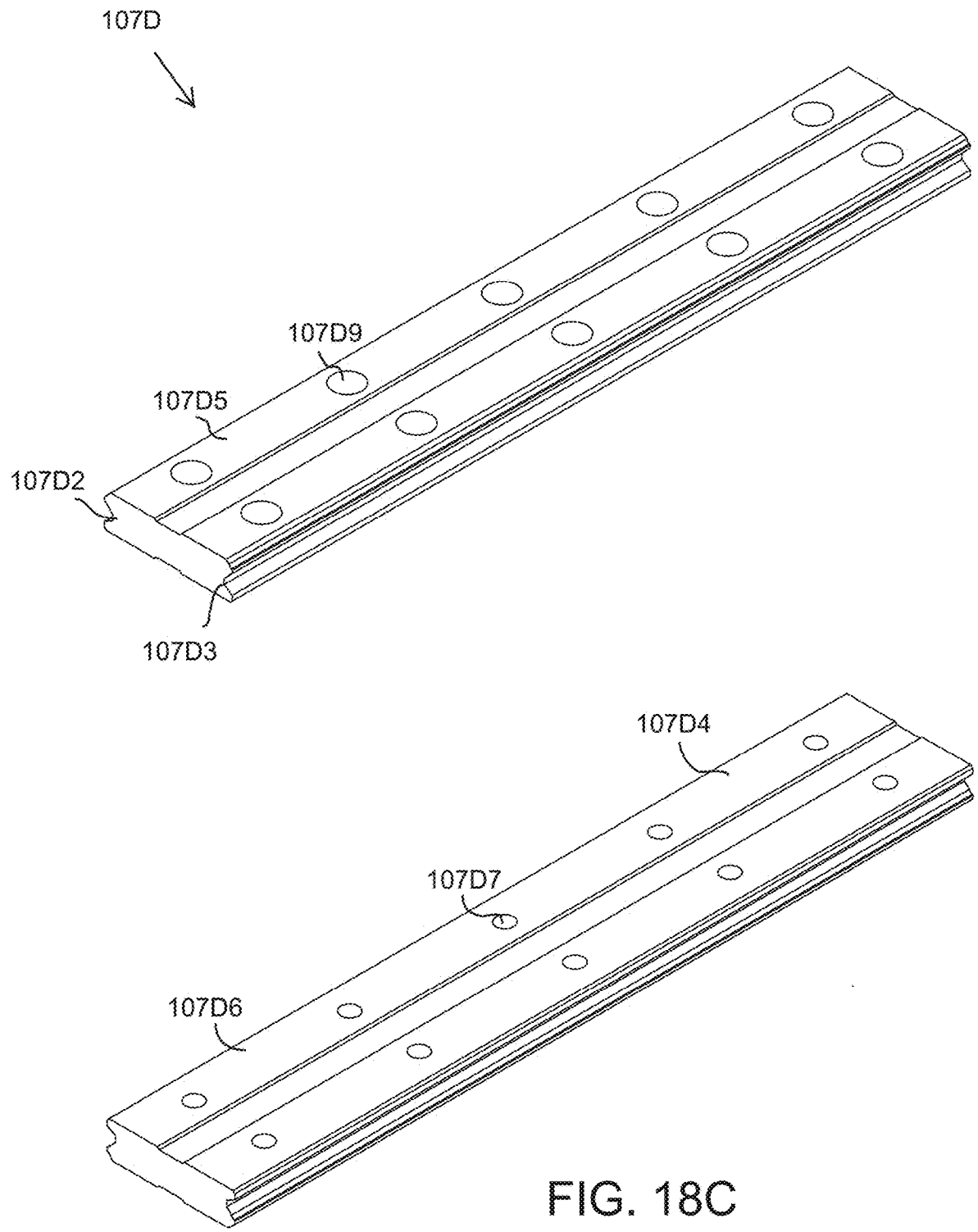
FIG. 18C is a schematic diagram of first and second views of the third rail of the present teachings.

Referring now primarily to FIG. 18B, second rail 107E can operably couple z-axis baseplate second side run 109F6 (FIG. 12) with x-axis baseplate 107B (FIG. 16) at second rail indent 107B9 (FIG. 16). Second rail 107E can include first side fastening cavities 107E1 on second rail first side 107E5 that can penetrate through second rail 107E to second rail second side 107E6 through second side fastening cavities 107E7. Second rail 107E can include any number of first side fastening cavities 107E1, for example, but not limited to, eight, and can be any length, width, and depth. Second rail 107E can also include second rail slot 107E3, second rail slot 107E2, side face 107E4 that can enable locking and stable interconnection with z-axis carriages 109D (FIGS. 4A/5A/6A).

Referring now primarily to FIG. 18C, third rail 107D can operably couple x-axis block 107K (FIG. 17) with x-axis baseplate 107B (FIG. 16) at third rail indent 107K11 (FIG. 17). Third rail 107D can include first side fastening cavities 107D9 on third rail first side 107D5 that can penetrate through third rail 107D to third rail second side 107D6 through second side fastening cavities 107D7. Third rail 107D can include any number of first side fastening cavities 107D9, for example, but not limited to, ten, and can be any length, width, and depth. Third rail 107D can include third rail slot 107D3, third rail slot 107D2, and side face 107D4 that can enable locking and stable interconnection with linear bearing 107G (FIG. 15B).

Figure 19:
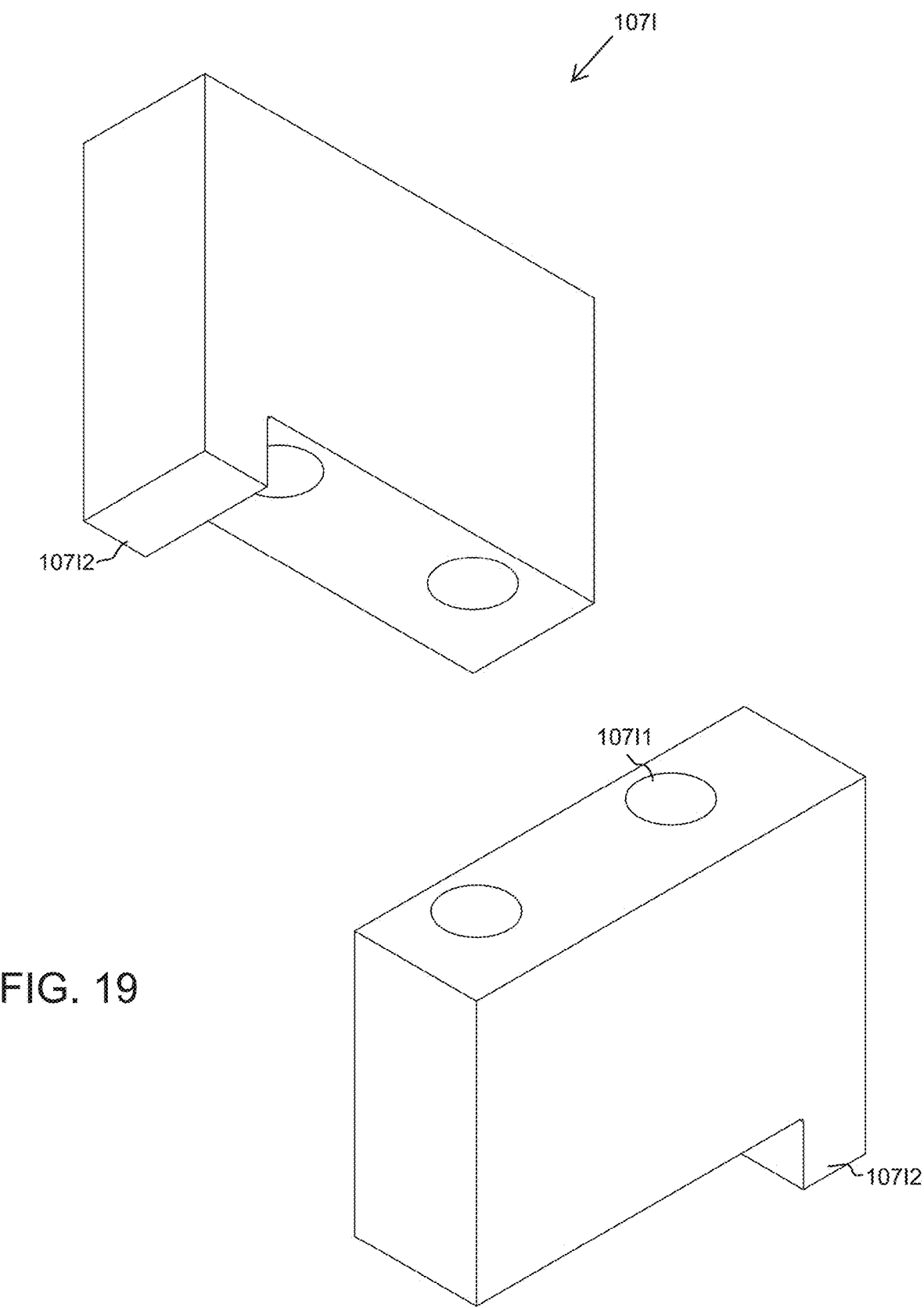
FIG. 19 is a schematic diagram of first and second views of the x-axis stop of the present teachings.

Referring now primarily to FIG. 19, y-axis stop 107I can stop the progress of ballscrew 107A (FIG. 15A) and optical encoder 109E (FIG. 11) by resting in the path of y-axis block 107K (FIG. 17). Y-axis stop 107I can be mounted at stop mounting 107B11 (FIG. 16). Y-axis stop 107I can include, but is not limited to including, fastening cavities 10711 and stop extension 10712. Fastening cavities 10711 and associated fasteners can couple y-axis stop 107I with x-axis baseplate 107B (FIG. 16). In some configurations, stop extension 10712 can be sized to accommodate the size of mounting edge 107K14 (FIG. 17). Y-axis stop 107I can be constructed any material, and in any size, shape, and depth.

Figure 25A:
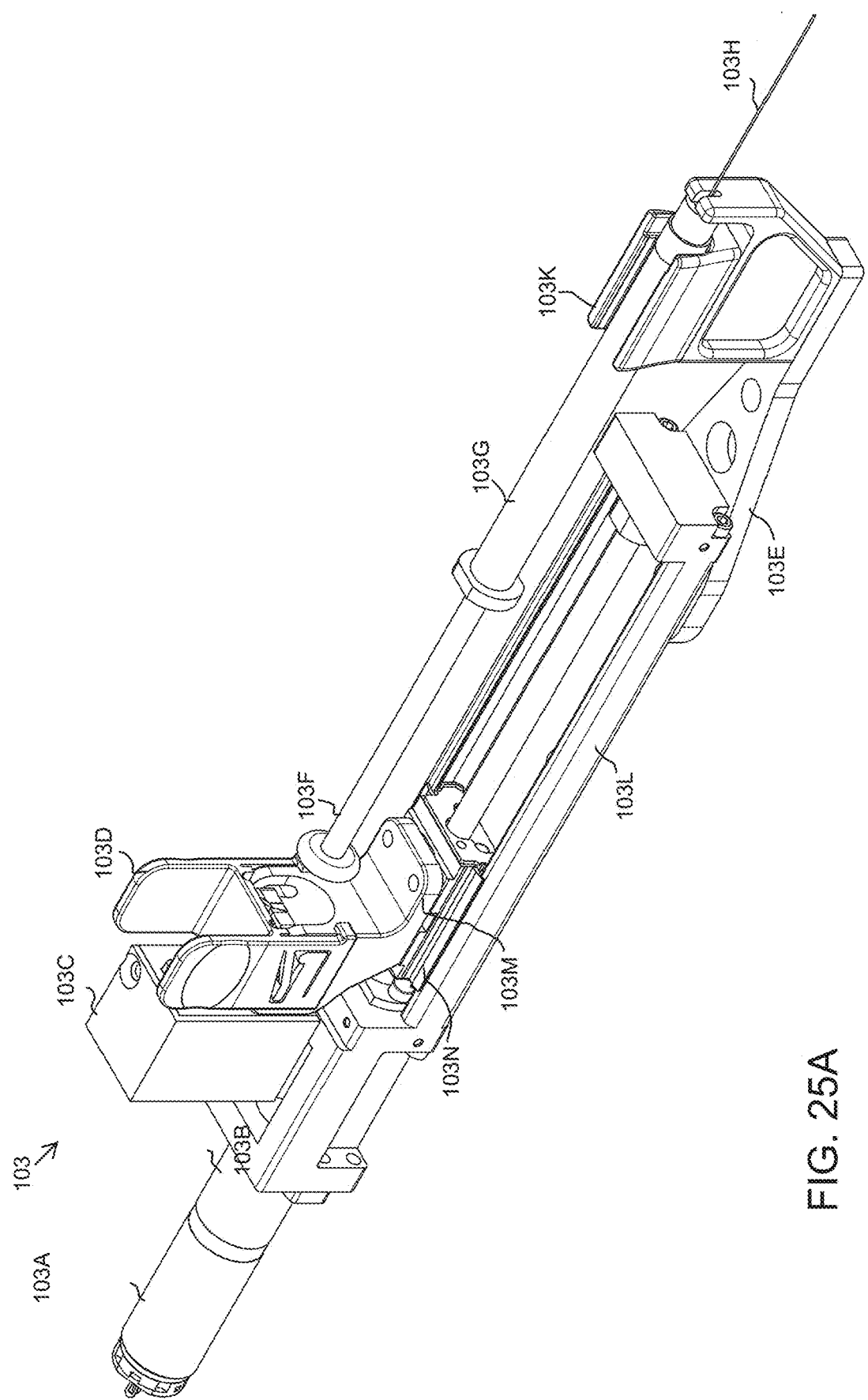
FIGS. 25A and 25C are schematic diagrams of various views of the delivery system of the present teachings.

Referring now primarily to FIG. 20, motor junction box 109J can surround motors 103A (FIG. 25A). In some embodiments, motor 103A (FIG. 25A) can rest in motor recess 109J1, and can be secured with through fastening cavities 109J6 and associated fasteners. Motor 103A (FIG. 25A) can be powered through wires that can be channeled through motor junction box 109J at various locations including first wire recess 109J4, second wire recess 109J8, and third wire recess 109J8. Motor junction box 109J can include any number of wire recesses and wire channels such as, for example, but not limited to, wire channel 109J2. Junction box indents 109J3 can be used to attach motor junction box 109J to any fixture. Junction box indents 109J3 can proceed through the length of motor junction box 109J, or can proceed some fraction of the length of motor junction box 109J. Motor junction box 109J can be constructed of any material suitable for junction box use such as, for example, but not limited to, plastic and stainless steel.

Referring now primarily to FIG. 21A, x-axis linear bearing 107G can ride on third rail 107M (FIG. 18C) that can couple x-axis block 107K (FIG. 17) to x-axis baseplate (FIG. 16). X-axis linear bearing 107G can include, but is not limited to including, guide slot 107G3 and guide fastener cavity/indent 107G4. In some configurations, guide slot 107G3 can include guide rail holder 107G2 that can insure stable performance of the linear guide. X-axis linear bearing 107G can optionally include bumper 107G1 that can buffer possible impacts when sliding on first rail 107M (FIG. 18C).

Referring now primarily to FIG. 21B, bumper 107G1 can include, but is not limited to including, nib 107G1-1, mount stopper 107G1-2, and mounting peg 107G1-3. Nib 107G1-1 can provide impact buffering, and can be constructed of any relatively flexible material. Mounting peg 107G1-3 can securely engage nib 107G1-1 with x-axis carriage 107G (FIG. 21A), and mount stopper 107G1-2 can provide a depth of engagement for nib 107G1-1. In some configurations, optical encoder non-contact limit magnets can buffer travel impacts, as well as hard stops that can be placed on any of the axes.

Figure 22A:
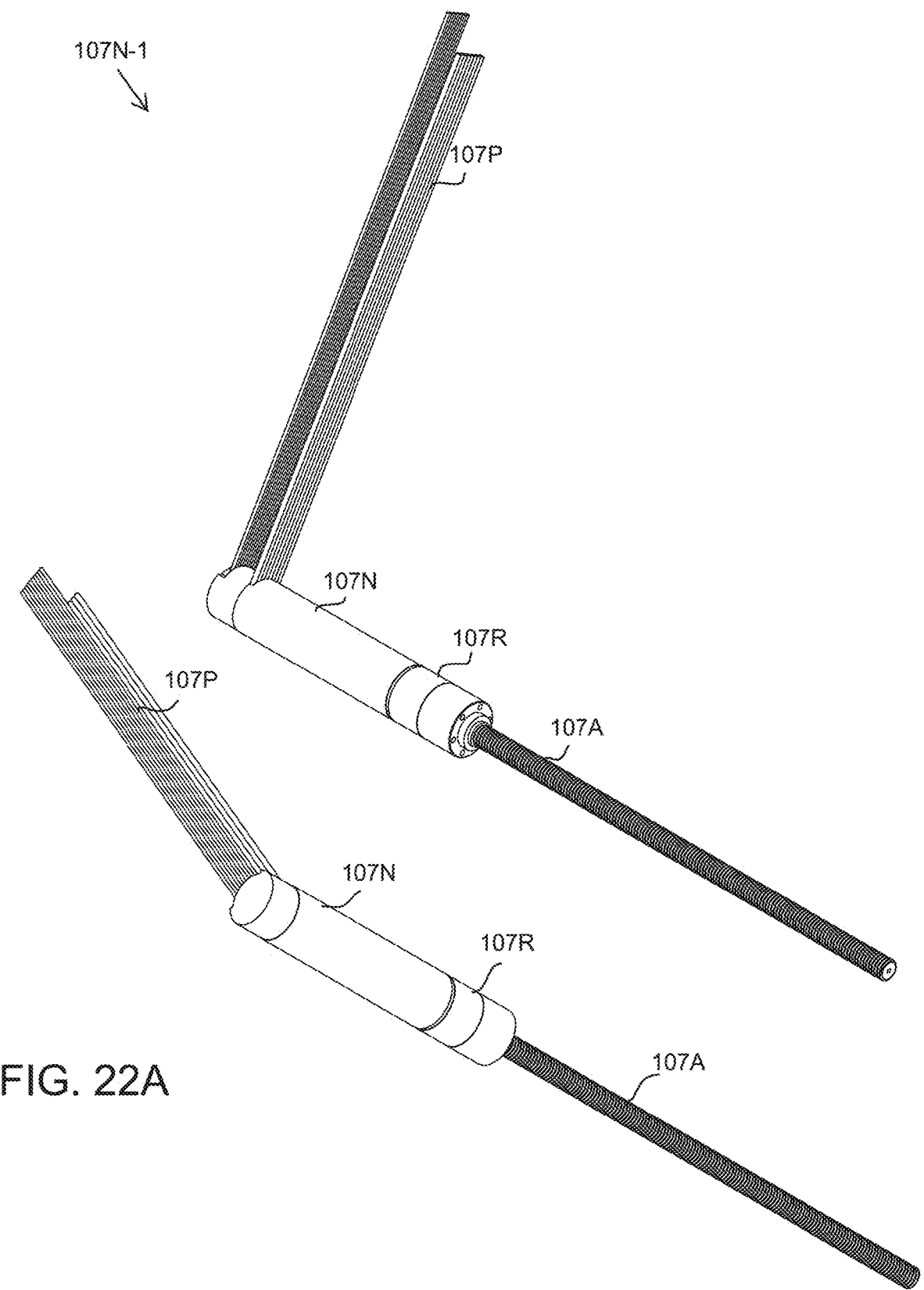
FIG. 22A is a schematic diagram of first and second views of the gearmotor/ballscrew first configuration of the present teachings.
Figure 22B:
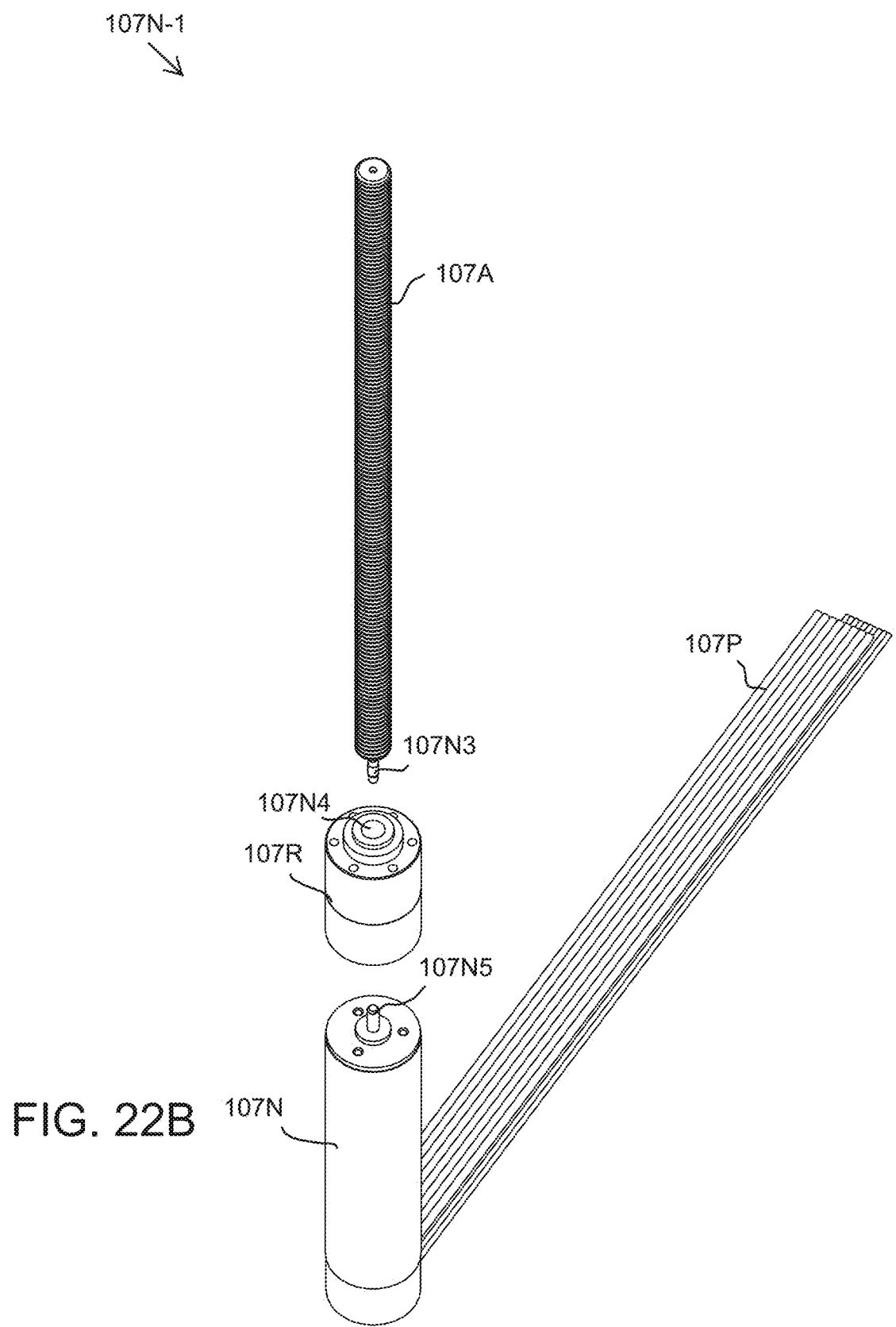
FIG. 22B is a schematic diagram of an exploded view of the gearmotor/ballscrew first configuration of the present teachings.

Referring now primarily to FIGS. 22A and 22B, gearmotor/ballscrews 107N can enable linear motion in x, y, and z directions by propelling x-axis block 107K (FIG. 17), y-axis block 105 (FIG. 14A), and z-axis baseplate 109 (FIG. 1C). Gearmotor/ballscrew 107N-1 can include, but is not limited to including, power wires 107P, motor 107N, gearbox 107R, and ballscrew shaft 107A. Motor 107N can be, but is not limited to being, a 60 W brushless DC servo gearmotor that can be purchased commercially from, for example, but not limited to, Maxon Motor. Other types of motors can be used, for example, but not limited to, linear motors with or without air bearing linear guides. The linear motors can be, but are not limited to being any type of magnetic linear motor including, but not limited to, synchronous, induction, and homopolar types. Gearbox 107R can be, but is not limited to being, a 16 mm spindle drive that can be purchased commercially from, for example, but not limited to, Maxon Motor. Gearbox 107R can include, but is not limited to including, a planetary gear. Ballscrew shaft 107A can include screw shaft interface 107N3 that can enable coupling with gearbox 107R through gearbox engagement 107N4. Gearbox 107R can engage with motor 107N through motor engagement 107N5.

Figure 23A:
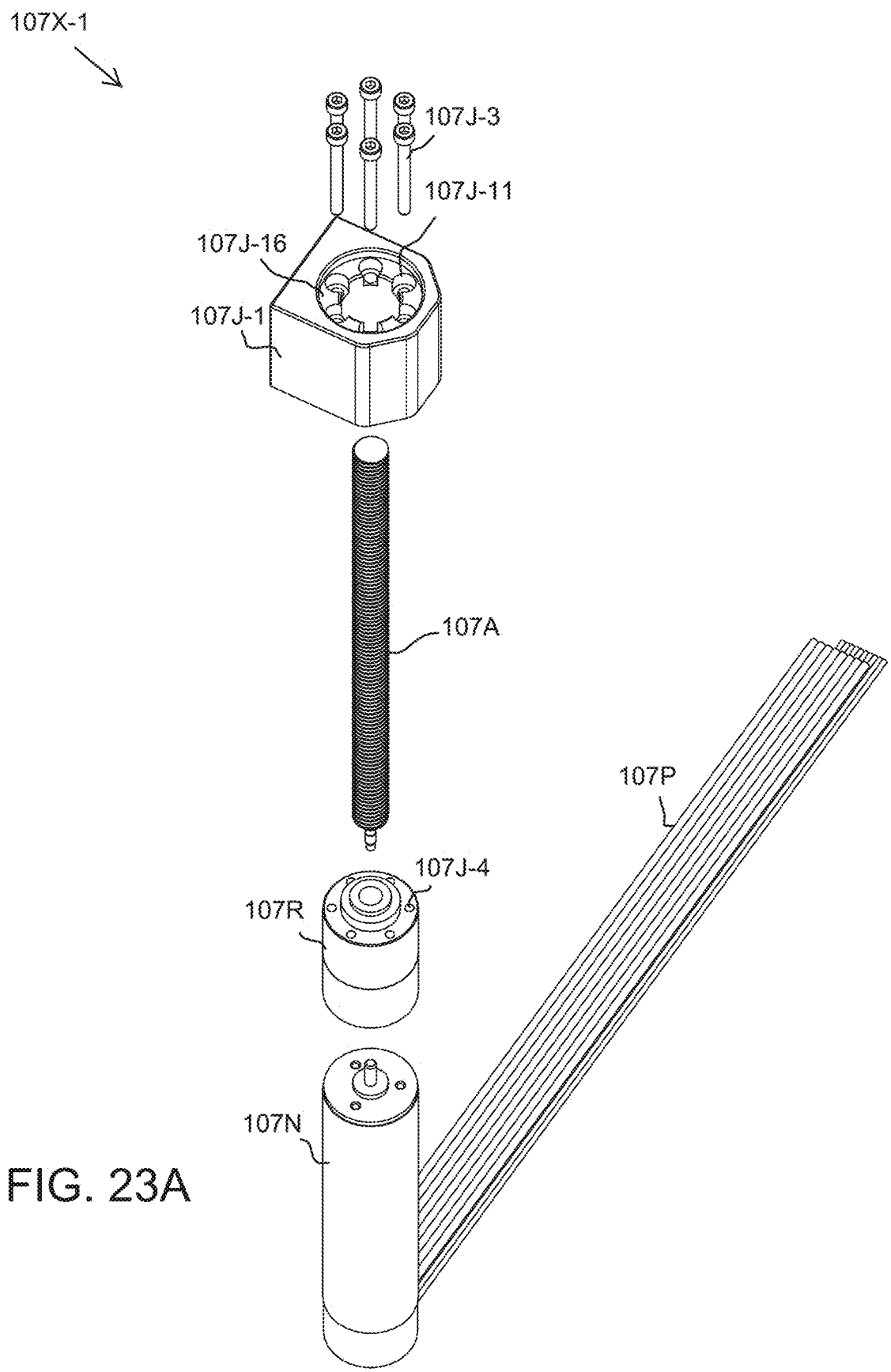
FIG. 23A is a schematic diagram of first and second views of the gearmotor/ballscrew second configuration of the present teachings.

Referring now primarily to FIG. 23A, gearmotor/ballscrews 107X-1 can include gearbox 107R that can be fitted with spindle adapter 107J-1 to enable an interface with ball nut 109C (FIG. 8). Spindle adapter 107J-1 can include spindle adapter recessed opening 107J-16 that can enable flushed mounting of spindle adapter fasteners 107J-3. In some configurations, spindle adapter 107J-1 can form a closed loop and can be fastened to gearbox 107R by fasteners 107J-3 that can fit into spindle fastener cavities 107J-11 and gearbox cavities 107J-4. In some configurations, spindle adapter 107J-1 can be open-ended which can streamline the profile of printer 100 (FIG. 1A).

Figure 23B:
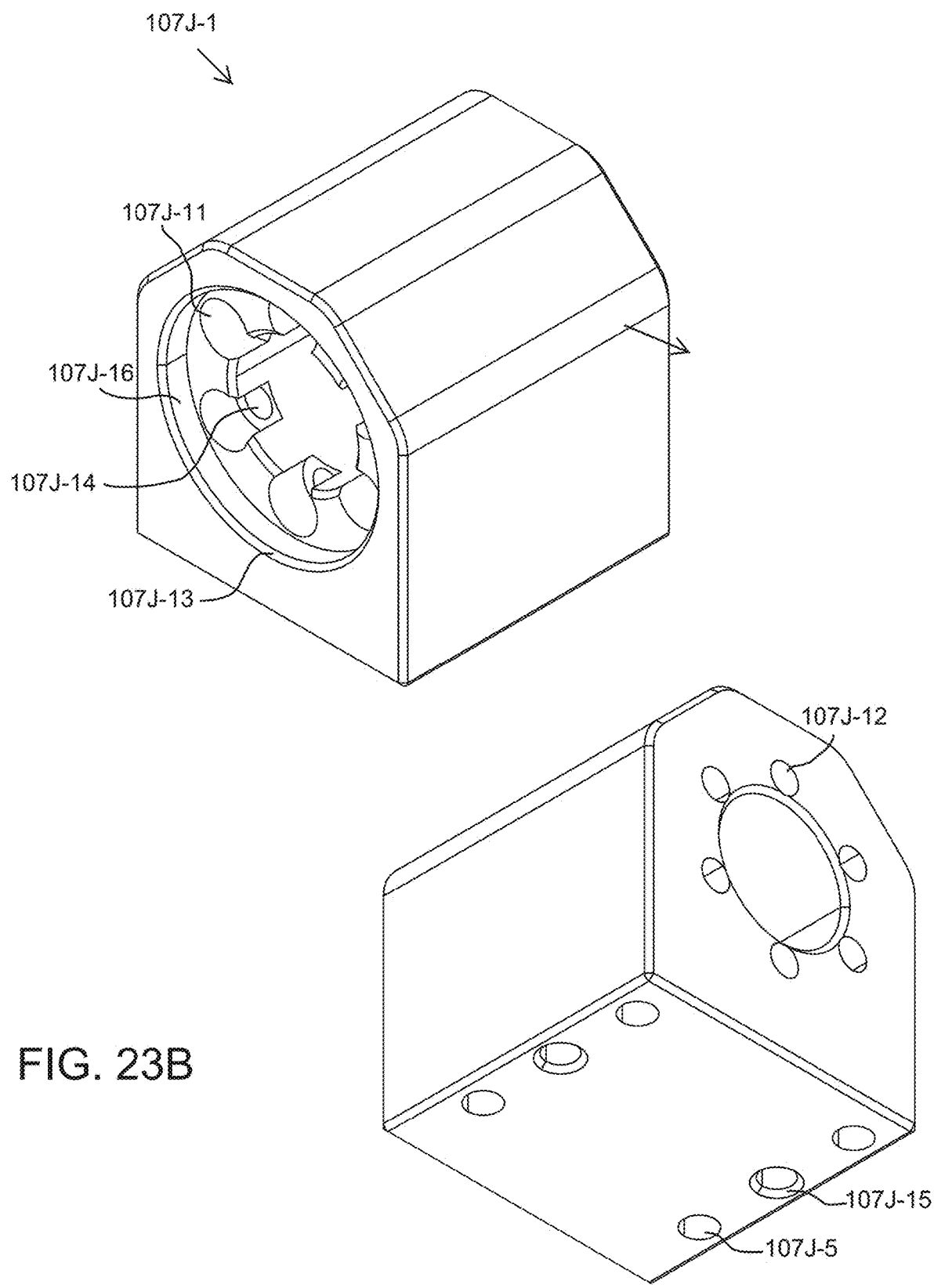
FIG. 23B is a schematic diagram of first and second views of the spindle adapter first configuration of the present teachings.

Referring now primarily to FIG. 23B, spindle adapter first configuration 107J-1 can be mounted onto, for example, but not limited to, x-axis baseplate 107B (FIG. 16) at baseplate first mount 107B12 (FIG. 16) using, for example, tapped hole array 107J-5 and associated fasteners. Tapped hold array 107J-5 can enable screw to be installed through the back of x-axis baseplate 107B. Dowel pin bores 107J-15 can accommodate dowel pins that can be used, for example, to achieve a high level of parallelism between the ballscrew and the railways. Gearbox interface cavities 107J-12 can accept fasteners 107J-3 (FIG. 23A), and can enable flush mounting of spindle adapter 107J-1 with gearbox 107R (FIG. 23A). Spindle fastener cavities 107J-11 can include recessed fastener cavities 107J-14. Spindle adapter recessed opening 107J-16 can include beveled edges 107J-13 to enable, for example, secure coupling.

Referring now to FIG. 23C, spindle adapter second configuration 107J-1-1 can include an open-ended assembly motor mount. Spindle adapter second configuration 107J-1-1 can be mounted onto, for example, but not limited to, x-axis baseplate 107B (FIG. 16) at baseplate first mount 107B12 (FIG. 16) using, for example, tapped hole array 107J-5 and associated fasteners. Dowel pin bores 107J-15 can accommodate dowel pins that can be used, for example, to achieve a high level of parallelism between the ballscrew and the railways. Gearbox interface cavities 107J-12 (FIG. 23B) can accept fasteners 107J-3 (FIG. 23A), and can enable flush mounting of spindle adapter second configuration 107J-1-1 with gearbox 107R (FIG. 23A). Spindle fastener cavities 107J-11 can include recessed fastener cavities 107J-14. Spindle adapter recessed opening 107J-16 can include beveled edges 107J-13 to enable, for example, secure coupling. Open end 107J-1-2 can enable different mounting options from spindle adapter 107J-1 (FIG. 23B).

Figure 24A:
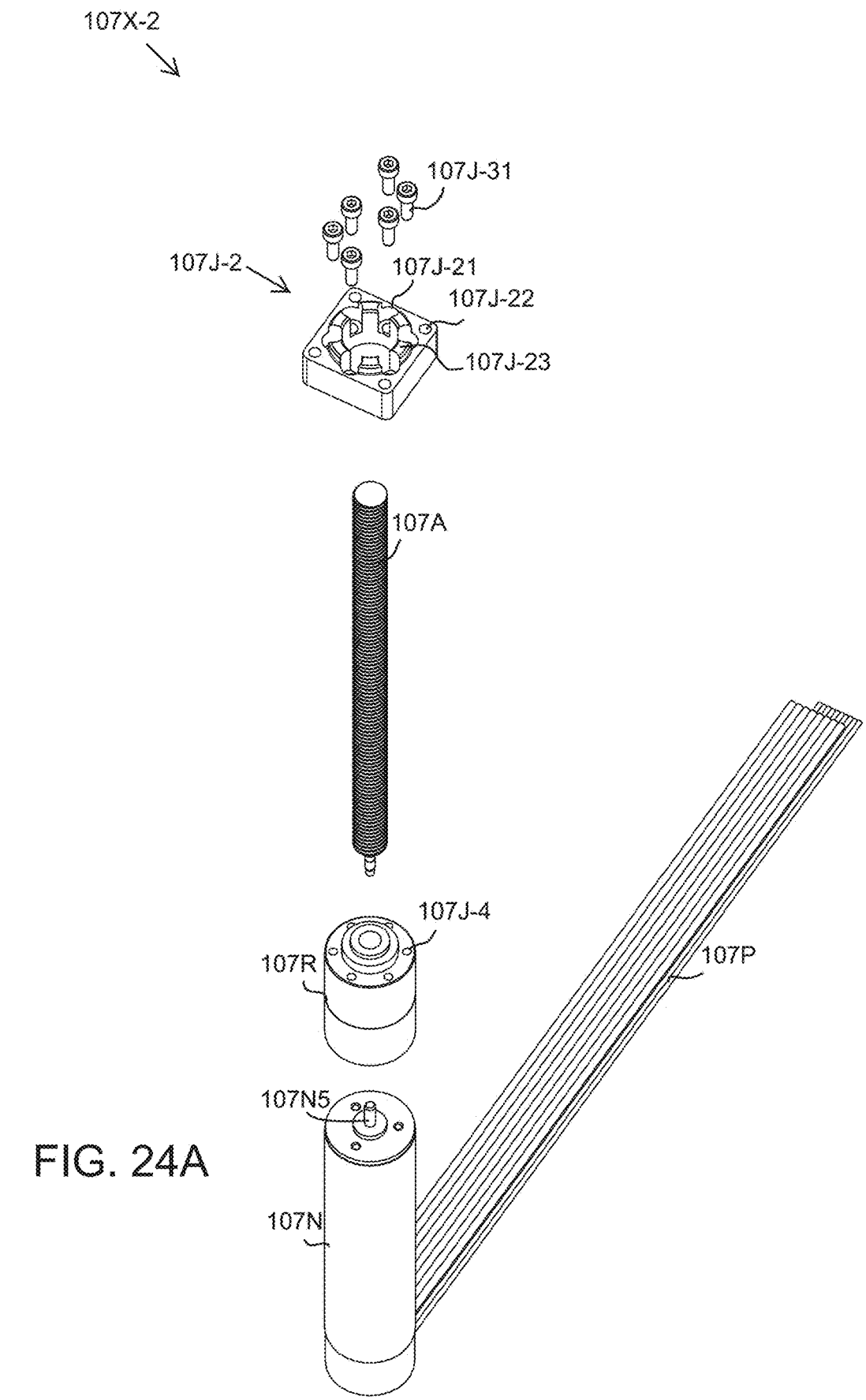
FIG. 24A is a schematic diagram of the gearmotor/ballscrew third configuration of the present teachings.

Referring now primarily to FIG. 24A, gearmotor/ballscrew third configuration 107X-2 can include gearbox 107R that can be fitted with spindle adapter 107J-2 to enable an interface with ball nut 109C (FIG. 8). Spindle adapter 107J-2 can include adapter protrusions 107J-23 that can provide a slip fit that can aid in the concentric alignment of the motor adapter to the ball nut positioning feature. In some configurations, spindle adapter 107J-2 can form a closed loop and can be fastened to gearbox 107R by fasteners 107J-31 that can fit into spindle fastener cavities 107J-21 and gearbox cavities 107J-4. In some configurations, spindle adapter 107J-2 can be open-ended which can streamline the profile of printer 100 (FIG. 1A).

Figure 24B:
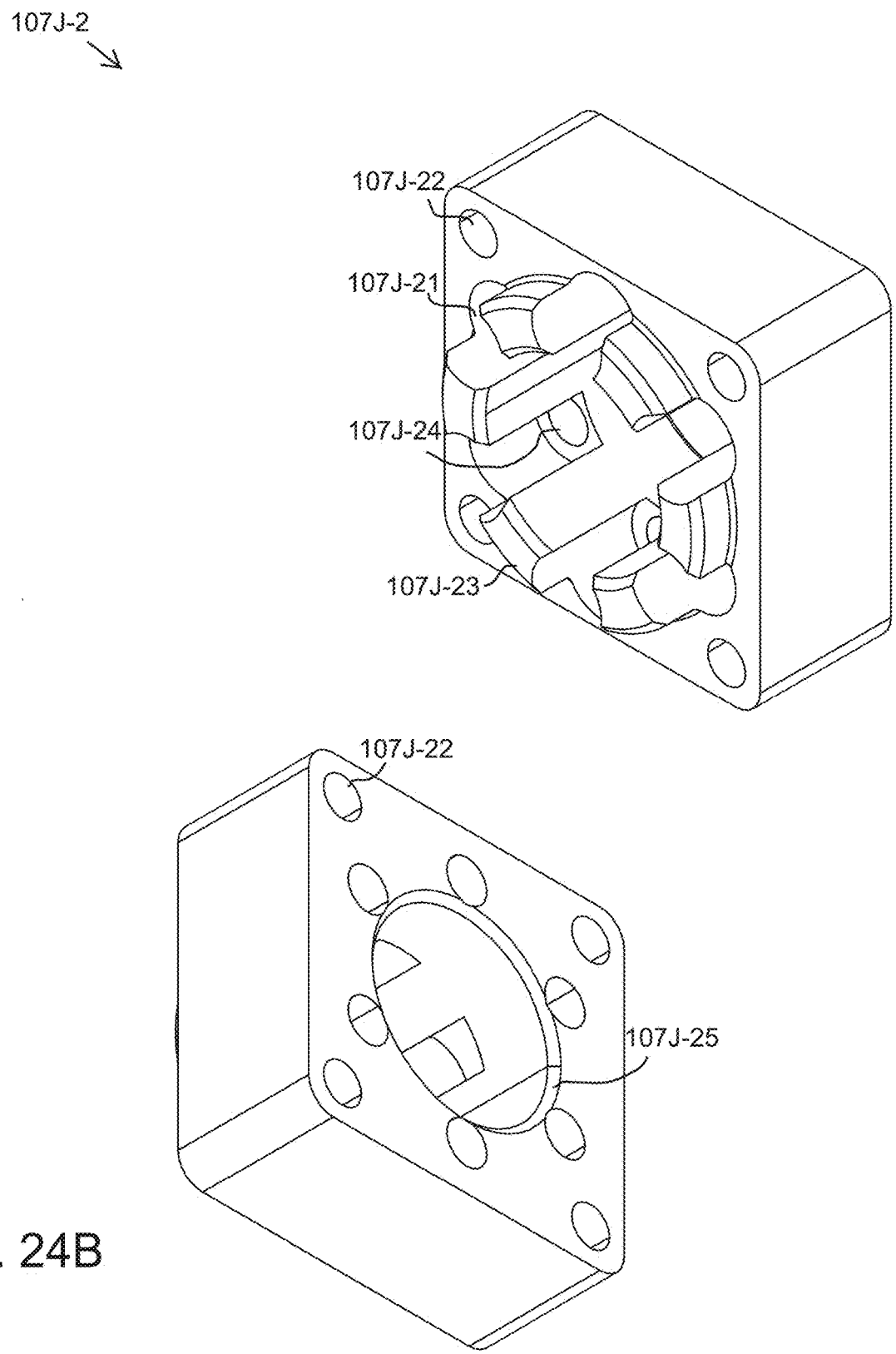
FIG. 24C is a schematic diagram of first and second views of the spindle adapter third configuration of the present teachings.

Referring now primarily to FIG. 24B, spindle adapter third configuration 107J-2 can be mounted onto, for example, but not limited to, x-axis block 107K (FIG. 16) at first x-block mounting cavity 107K22 (FIG. 17) using, for example, spindle mounting cavities 107J-24 and associated fasteners. Gearbox interface cavities 107J-22 can accept fasteners 107J-31 (FIG. 24A), and can enable flush mounting of spindle adapter 107J-2 with gearbox 107R (FIG. 24A). Spindle fastener cavities 107J-21 can include recessed fastener cavities 107J-14.

Referring now to FIG. 24C, spindle adapter fourth configuration 107J-2-1 can include, for example, but not limited to, open-ended assembly motor mount 107J-2-1A. Spindle adapter fourth configuration 107J-2-1 can be mounted onto, for example, but not limited to, x-axis block 107K (FIG. 16) at first x-block mounting cavity 107K22 (FIG. 17) using, for example, spindle mounting cavities 107J-22 and associated fasteners. Gearbox interface cavities 107J-24 can accept fasteners 107J-31 (FIG. 24A), and can enable flush mounting of spindle adapter 107J-2-1 with gearbox 107R (FIG. 24A). Spindle fastener cavities 107J-21 can include recessed fastener cavities 107J-14.

Figure 25B:
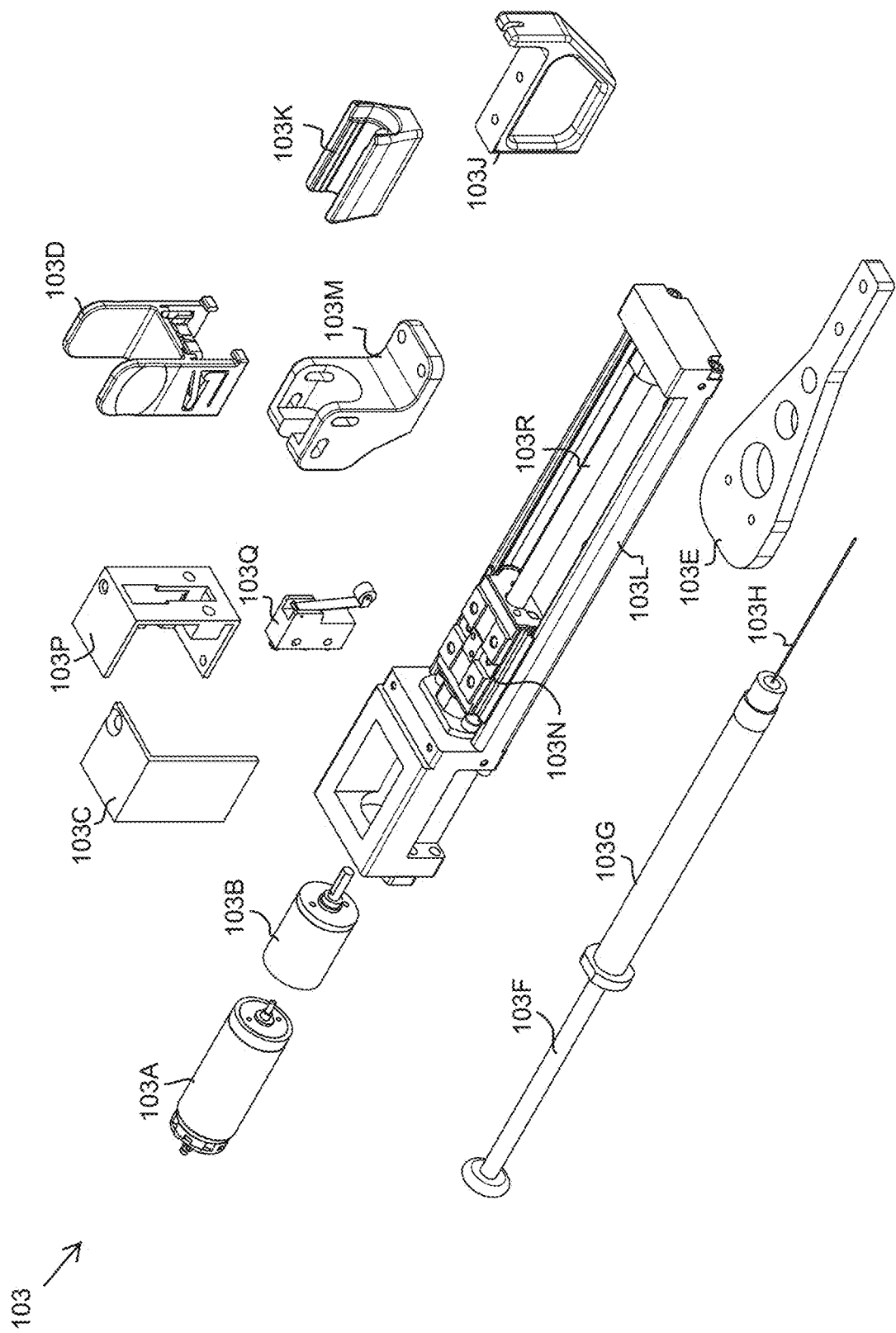
FIG. 25B is a schematic diagram of an exploded view of the delivery system of the present teachings.
Figure 25C:
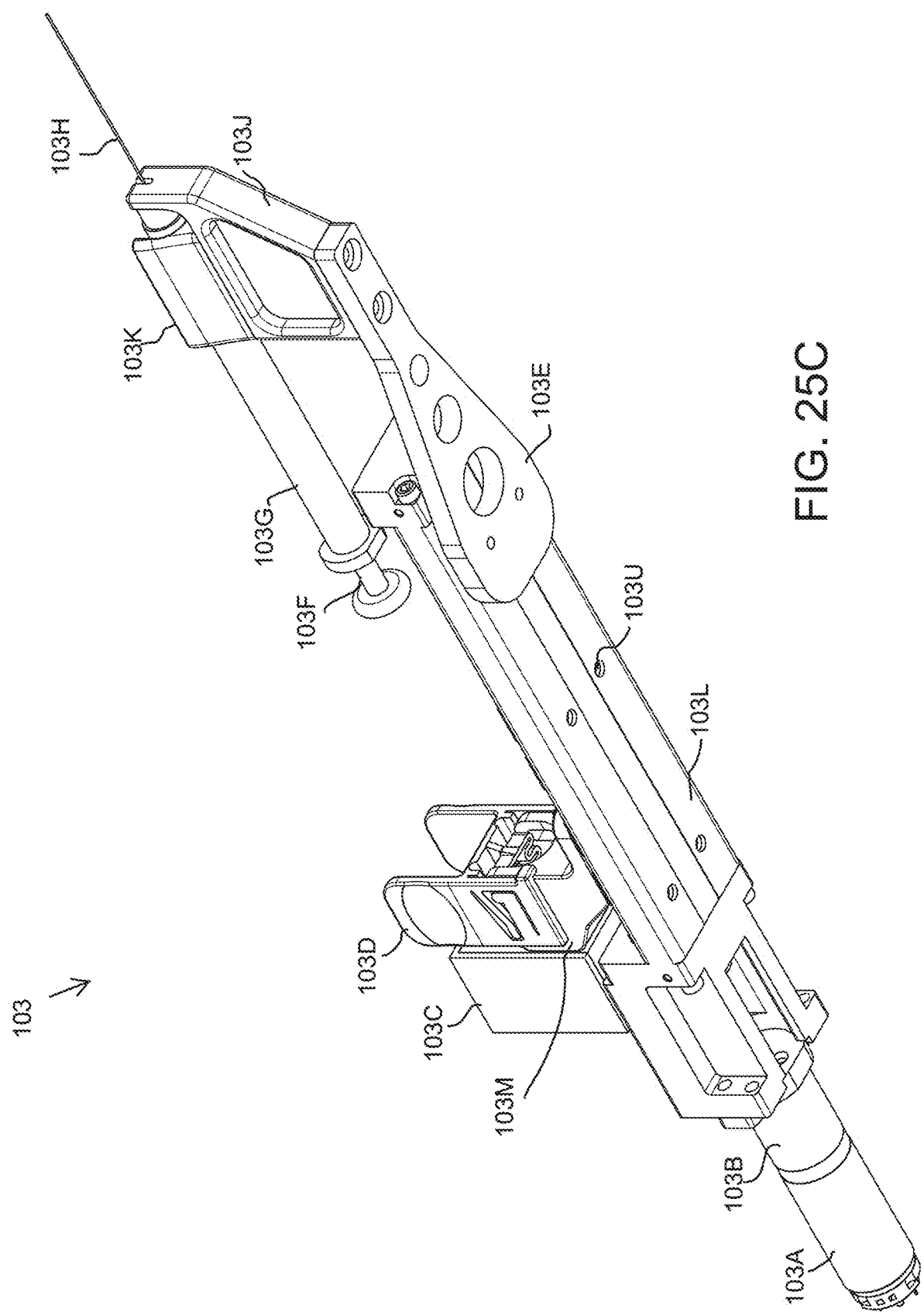
Figures 1, 25C:
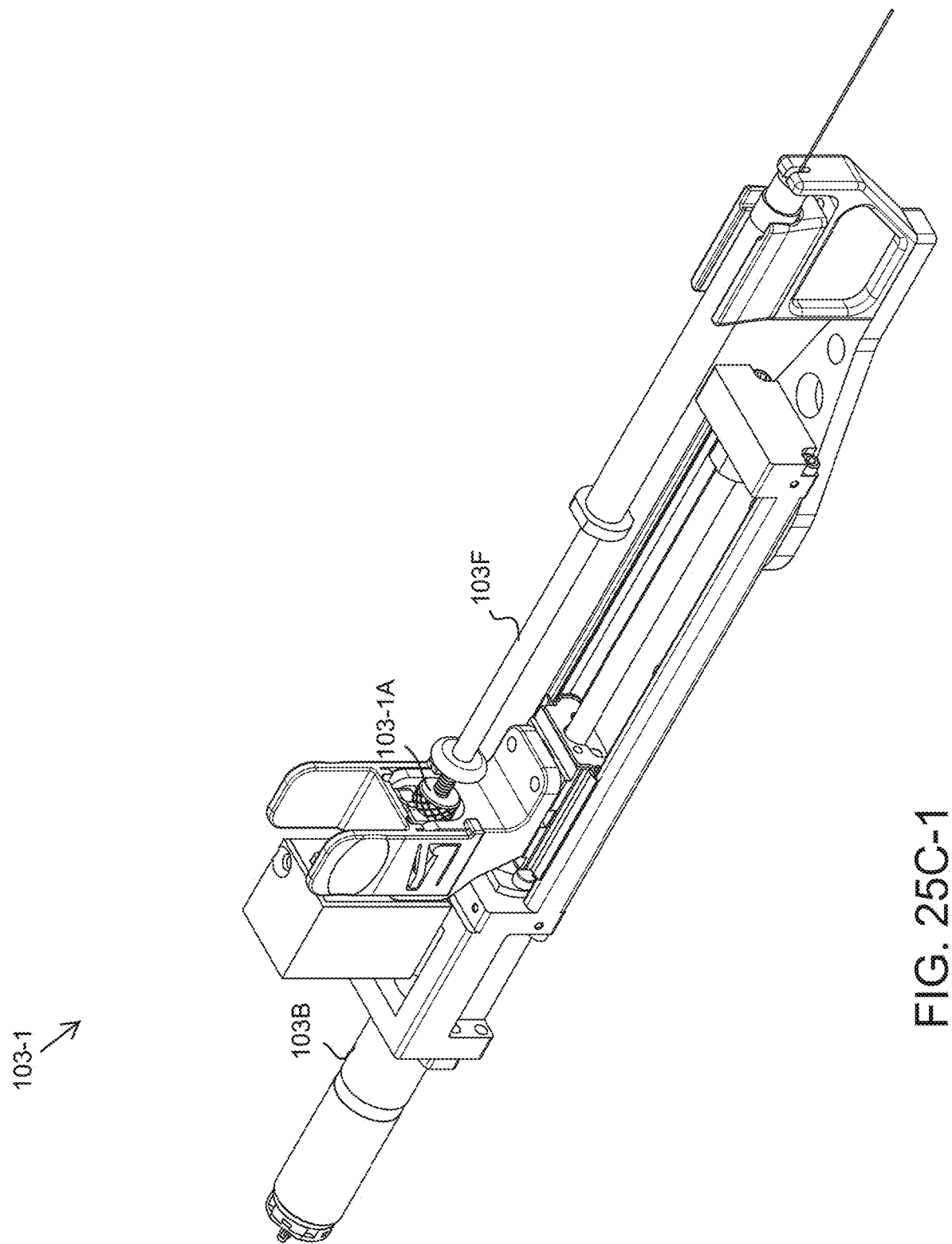
Figure 25C:
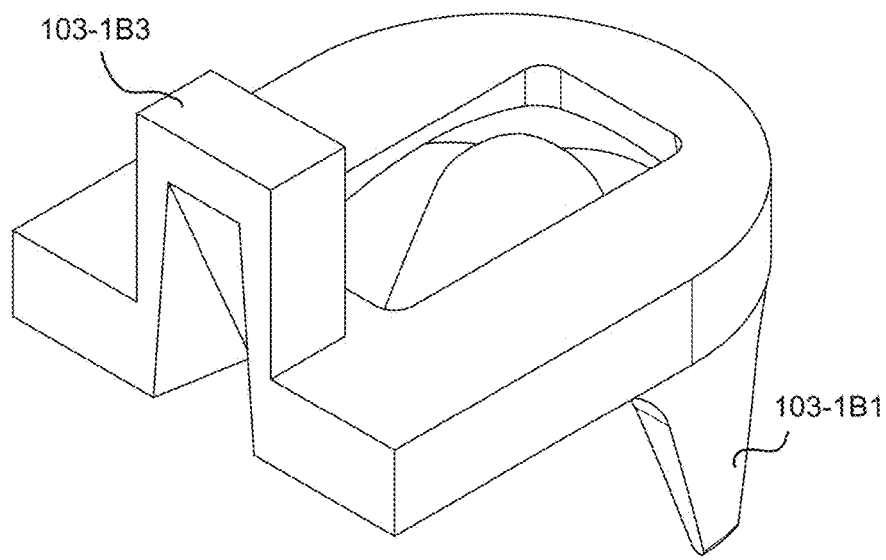
Figure 1A:
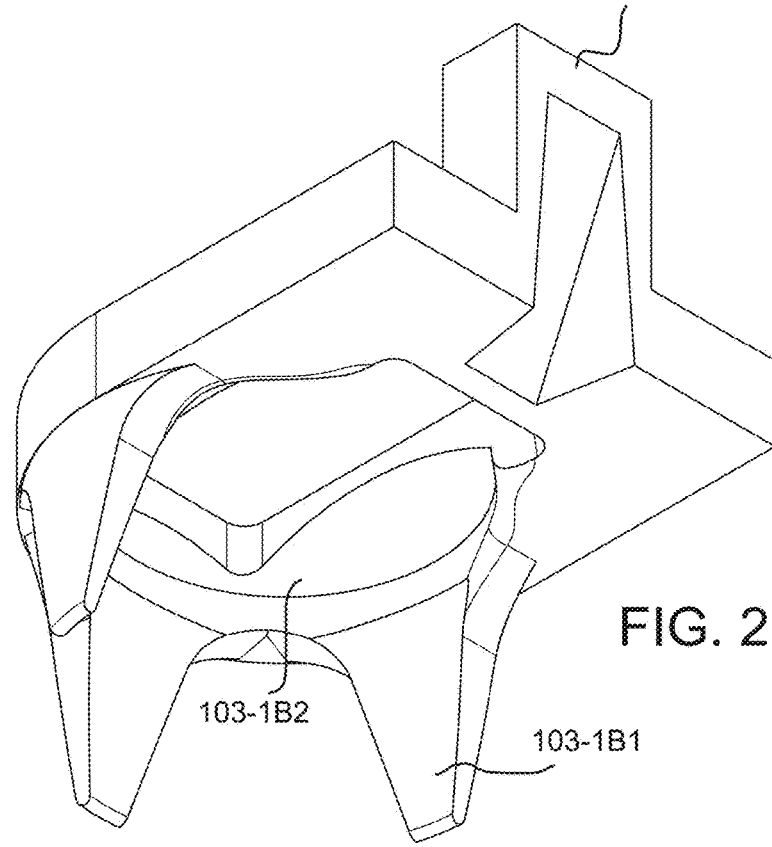
Figures 2, 25C:
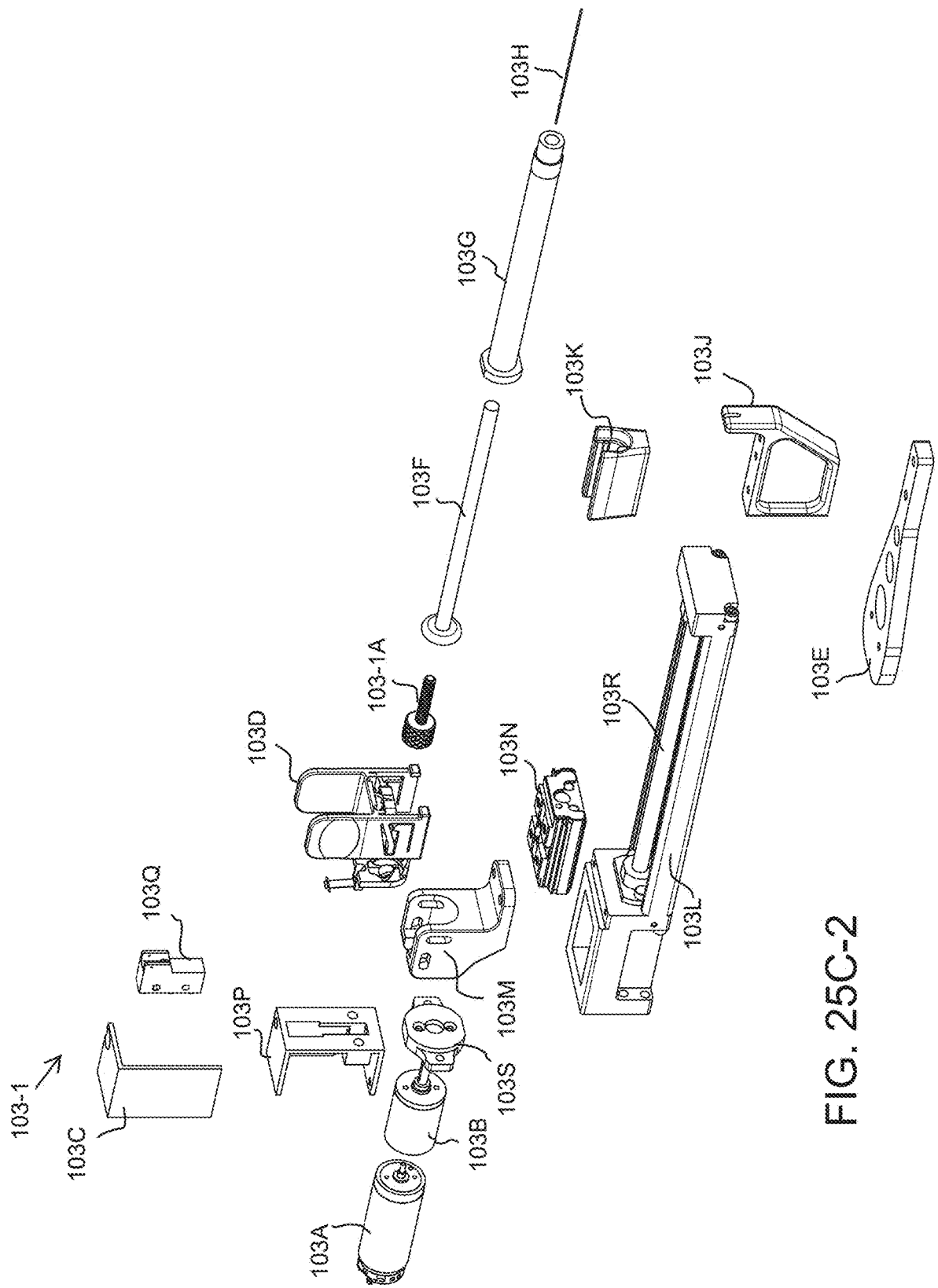
Figure 26:
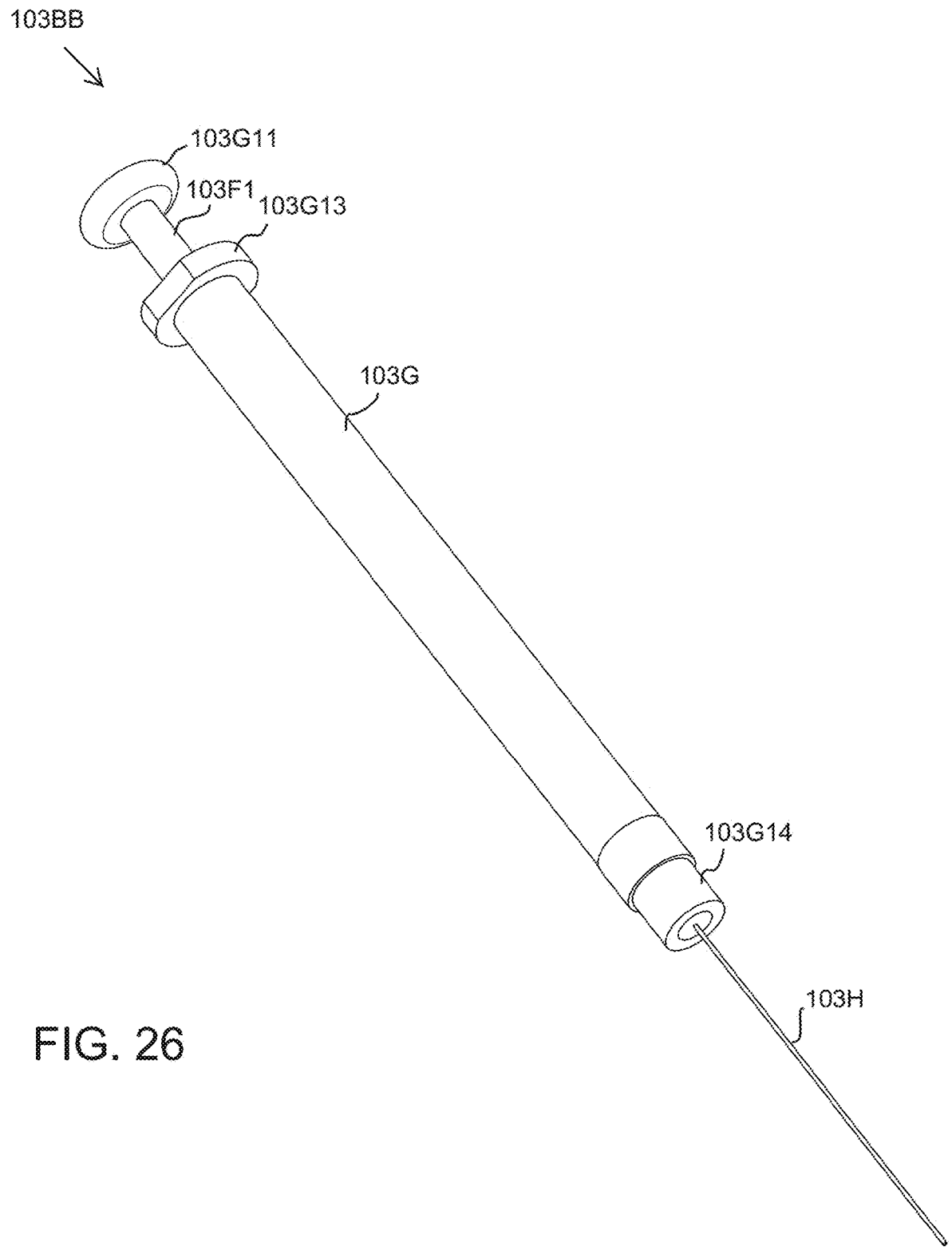
FIG. 26 is a schematic diagram of the syringe system of the present teachings.

Referring now primarily to FIGS. 25A, 25B, and 25C delivery system 103 can deliver at least one first material to a receptacle holding at least one second material. In some embodiments, the receptacle can include tissue enclosure 101 (FIG. 1A). Delivery system 103 can include, but is not limited to including, gear box 103B and motor 103A moving delivery system 103 within the at least one second material in tissue enclosure 101 (FIG. 1A) to specific positions based on at least one motion command 73 (FIG. 39). Syringe barrel 103G can rest in syringe holder 103K, which can rest upon needle guide 103J that can provide a cavity for needle 103H. Syringe system connector 103E can couple needle guide 103J and linear actuator 103L, and can also couple delivery system 103 with mount crossbar 109G (FIG. 10) and y-axis block 105 (FIG. 14A) at y-block base 105G (FIG. 14A). Linear actuator 103L can include at least one actuator linear bearing 103N (FIG. 25A) upon which plunger drive 103M can be mounted. Linear actuator 103L can be operably coupled with y-axis block at, for example, fastener indents 103U (FIG. 25C) using associated fasteners. The geometry of each configuration of delivery system described herein can include geometries that can enable retraction of syringe 103G1 (FIG. 26), and can disable backlash. Motor 103A can drive linear actuator 103T (FIG. 36A) with the efficiency and speed required of syringe system 103G1 (FIG. 26). Motor 103A can be, for example, AC or DC, and can be brushless or not. Motors such as, for example, but not limited to, the MAXON® RE16-118705, can be used in some configurations. Gearbox 103B (FIG. 29) can be operably coupled with motor 103A at motor end 103A2.

Figure 2A:
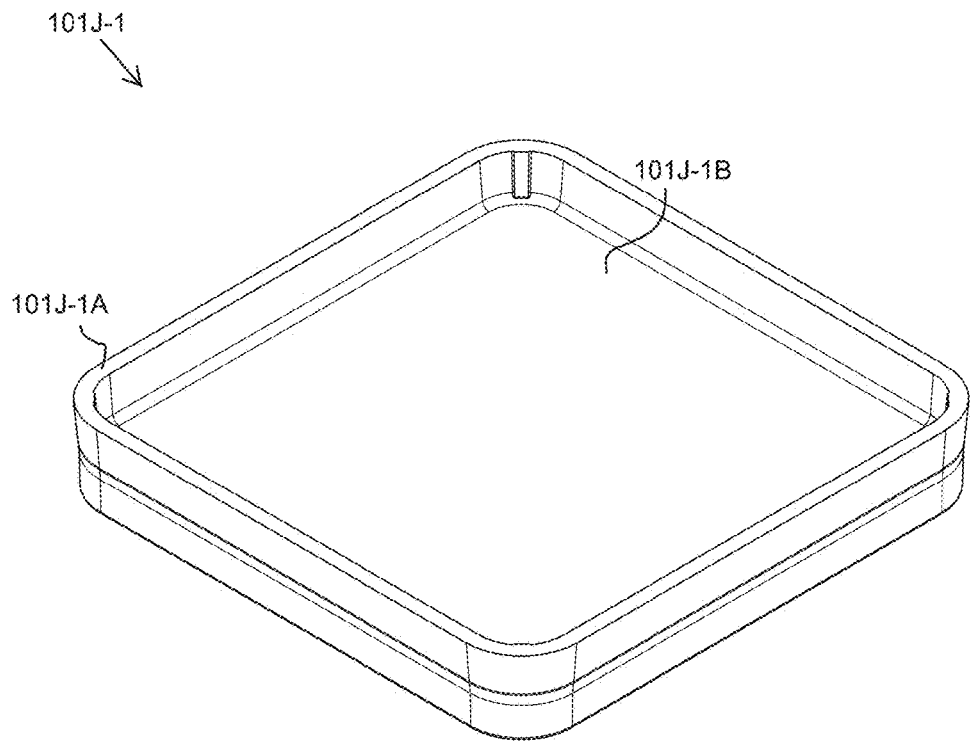
Figure 2:
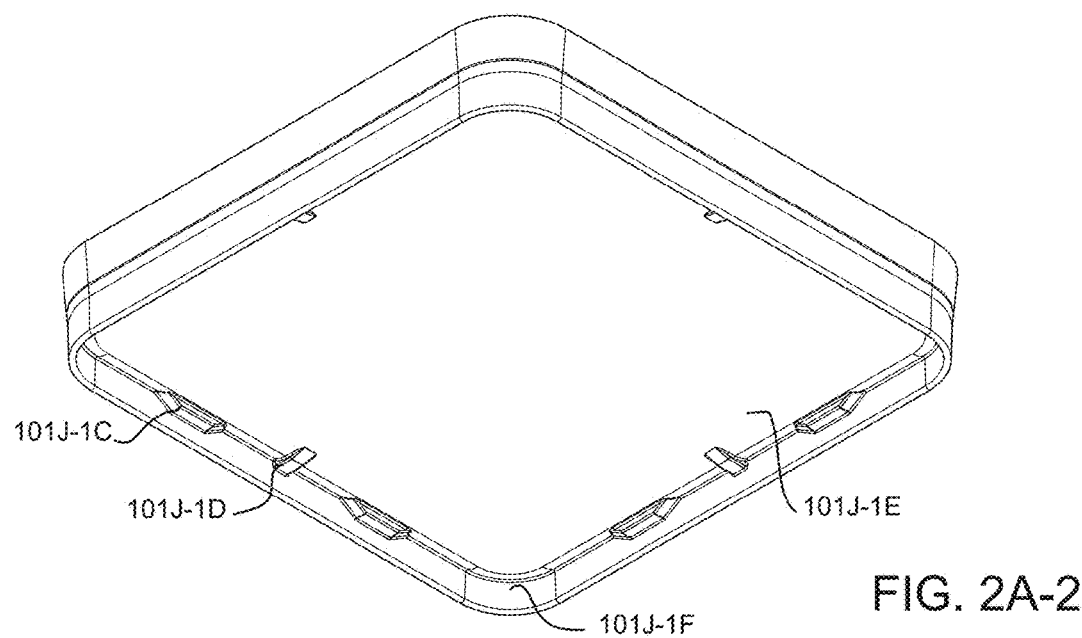

Referring now to FIGS. 25C-1 and 25C-2, delivery system second configuration 103-1 can include plunger extension 103-1A that can include a knurled head thumb screw with a shoulder, for example. Plunger extension 103-1A can include a threaded portion that can operably couple with plunger 103F. Plunger extension 103-1A can also include a head that can rest in the assembly of plunger fit 103-1B (FIG. 25C-1A), barrel slide clip 103D (FIG. 31A), and plunger drive first configuration 103M (FIG. 32), or a sub-assembly including some of the parts.

Referring now to FIG. 25C-1A, plunger fit 103-1B can provide an adaptable and secure seat, for example, for plunger extension 103-1A (FIG. 25C-1). Any type of plunger extension can be accommodated. Plunger fit 103-1B can include extension seat 103-1B2 surrounded by seat stabilizing legs 1031B1. Plunger fit 103-1B can operably couple with first configuration plunger drive 103M (FIG. 32) at drive coupling mount head 103-1B3.

Figure 25D:
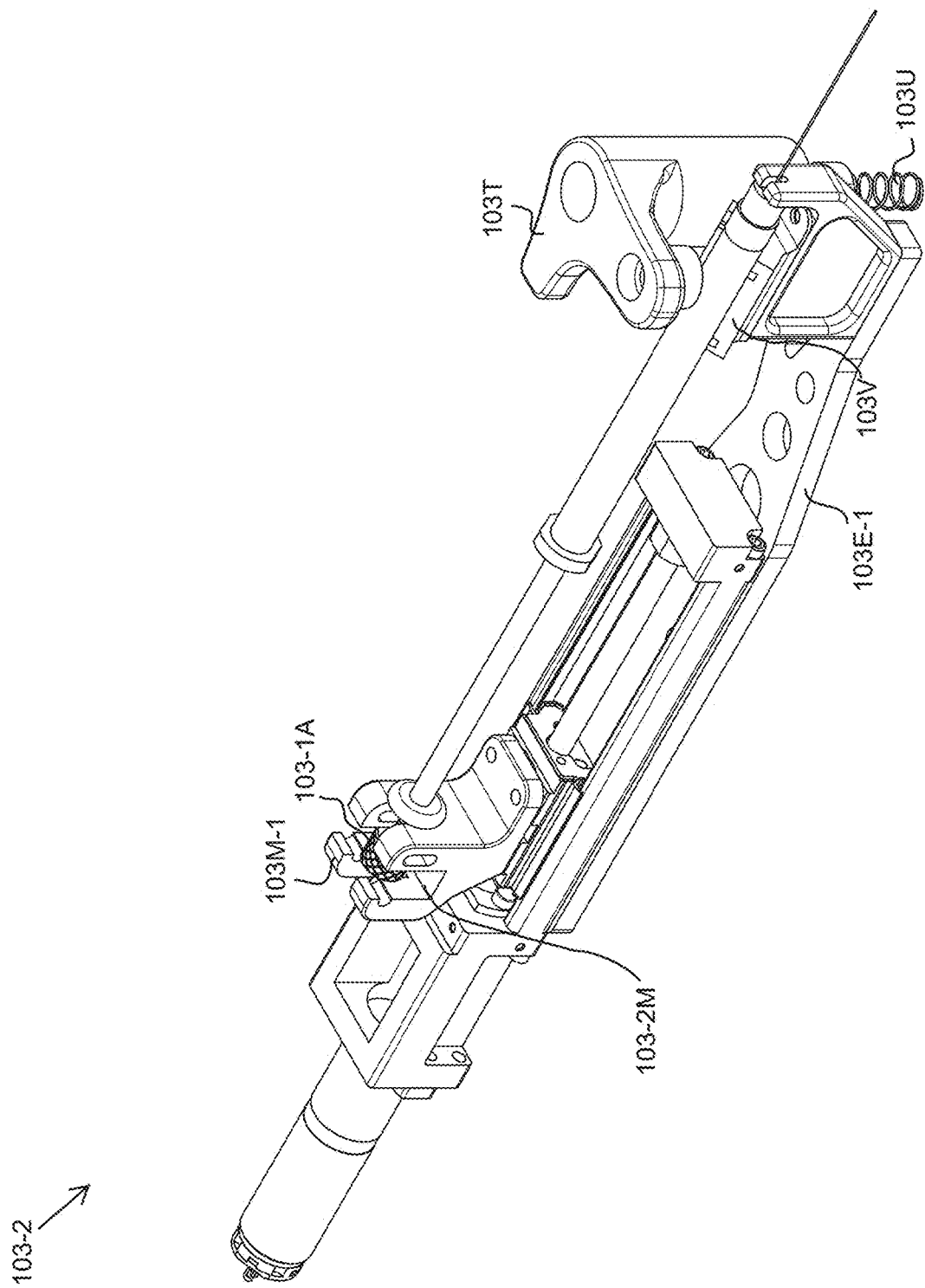
FIG. 25D is a schematic diagram of the delivery system third configuration of the present teachings.
Figure 25E:
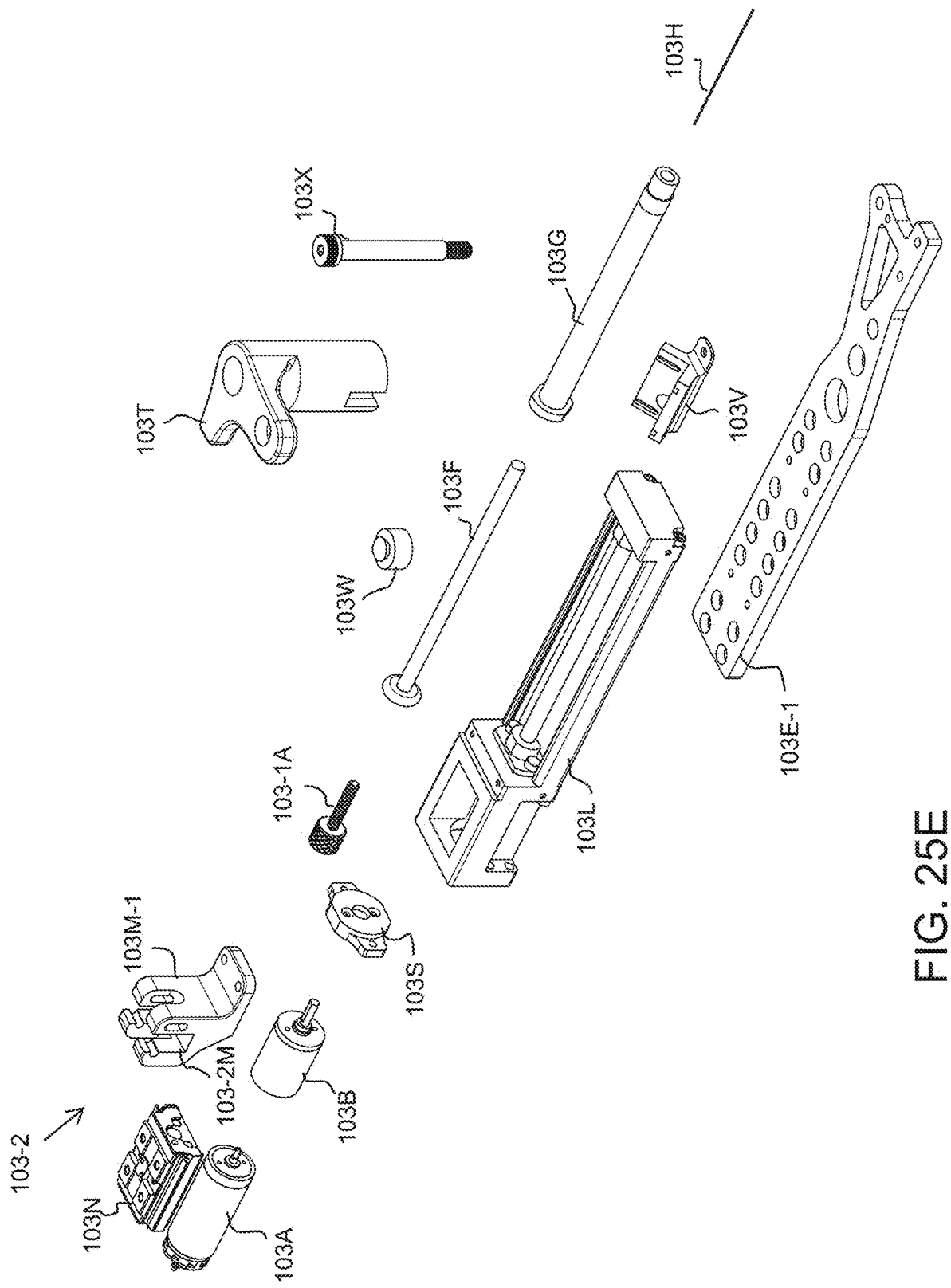
FIG. 25E is a schematic diagram of an exploded view of the delivery system third configuration of the present teachings.

Referring now to FIGS. 25D and 25E, delivery system third configuration 103-2 can include plunger extension 103-1A that can include a knurled head thumb screw with a shoulder, for example. Plunger extension 103-1A can include a threaded portion that can operably couple with plunger 103F. Plunger extension 103-1A can also include a head that can rest in second configuration plunger drive 103M-1. Second configuration plunger driver 103M-1 can include, but is not limited to including, at least one cut-out 103-2M that can accommodate various sizes of plunger extension 103-1A. Third configuration delivery system 103-2 can also include syringe swing clamp (FIG. 25F-2) that can, coupled with bumper 103W (FIG. 25F-3), retain the position of syringe 103EE (FIG. 26C) in second configuration syringe holder 103V (FIGS. 35A/35B). Syringe swing clamp (FIG. 25F-2) can include pressure-controlled positioning through the assembly of spring mount 103X and spring 103Y.

Figure 25F:
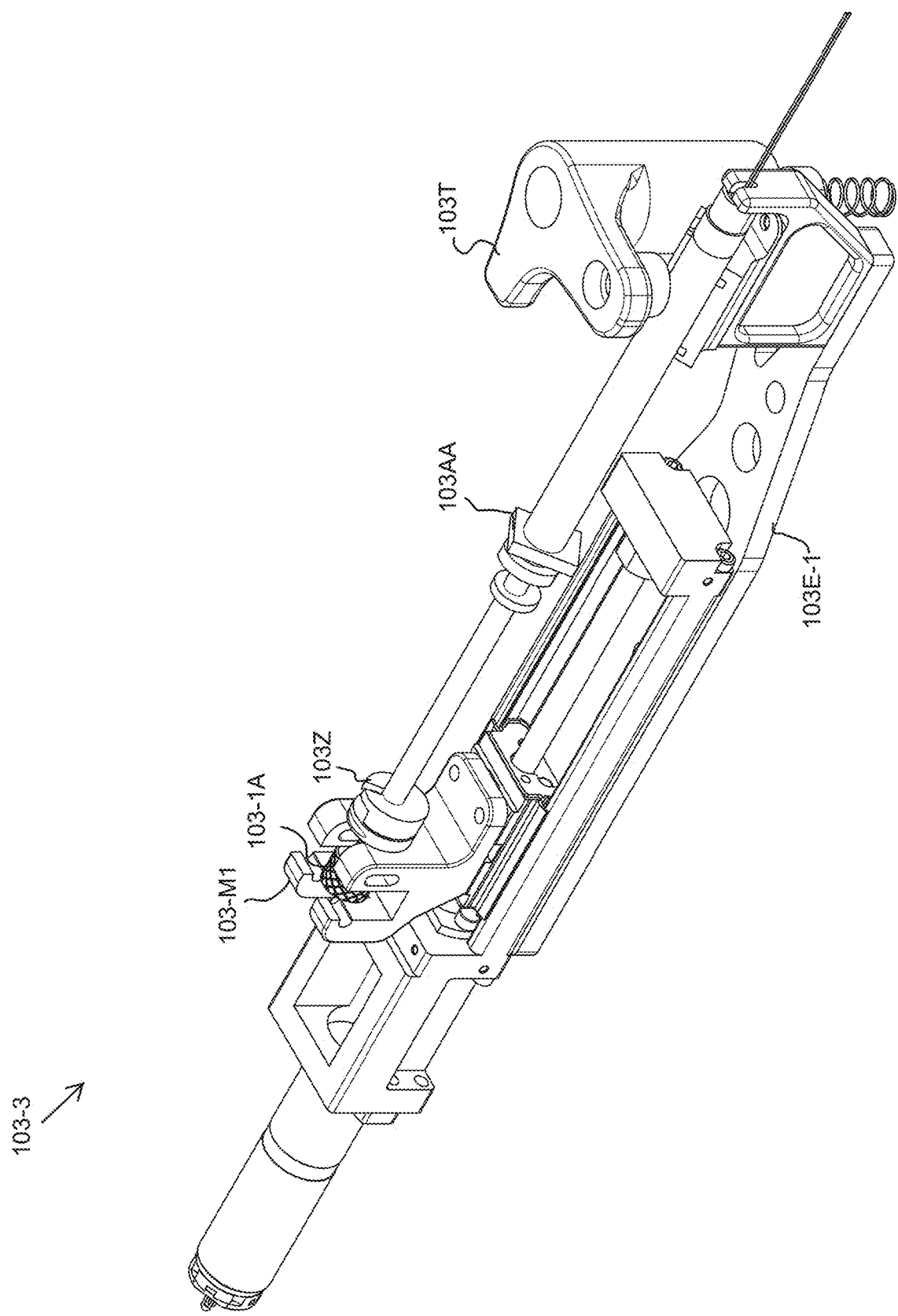
FIG. 25F is a schematic diagram of the delivery system fourth configuration of the present teachings.
Figure 25F:
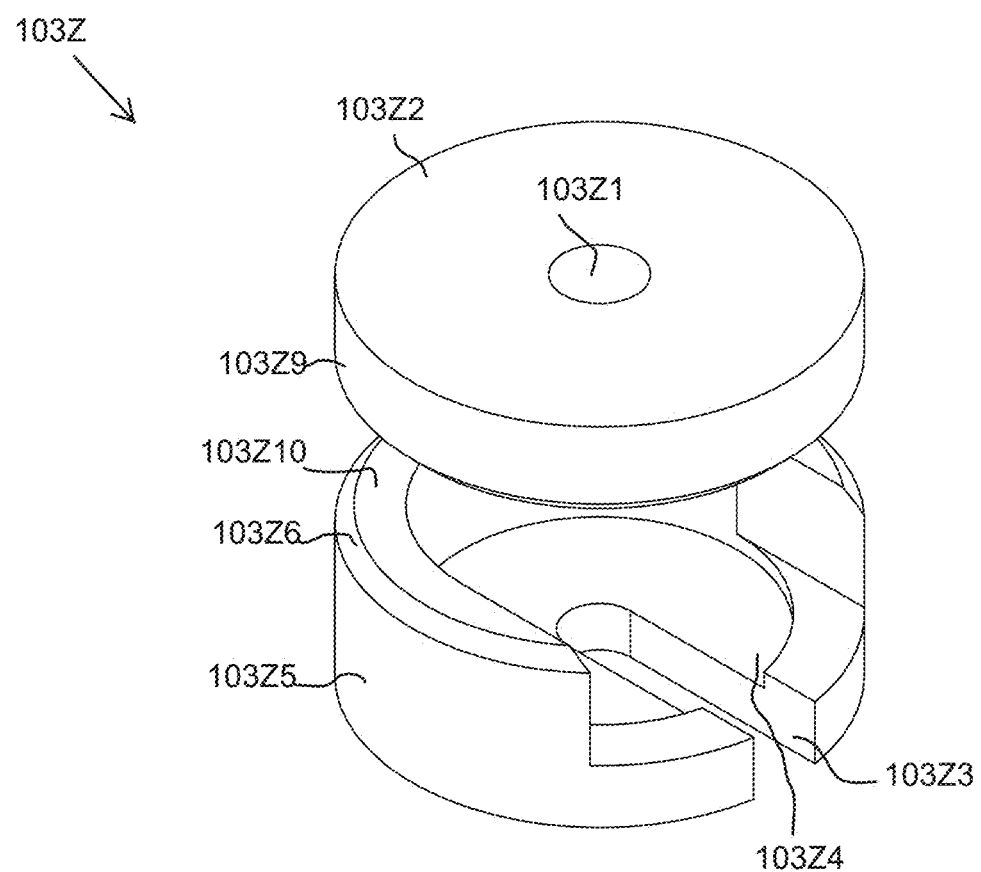
Figure 1A:
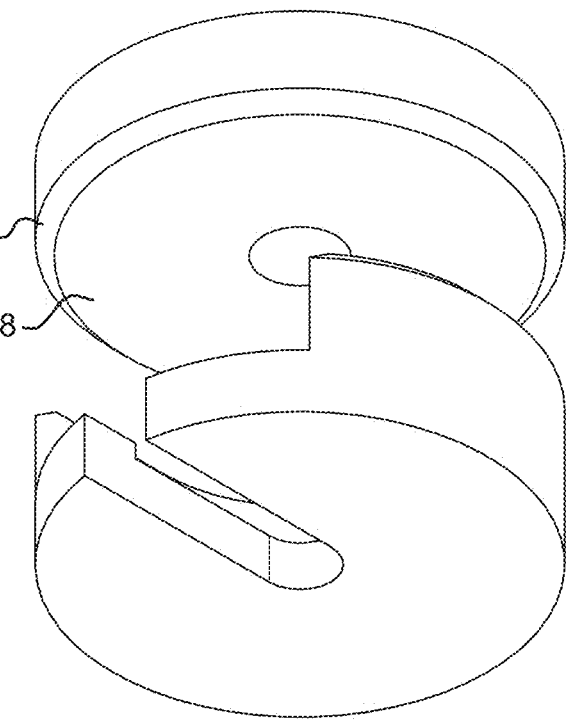
Figure 25F:
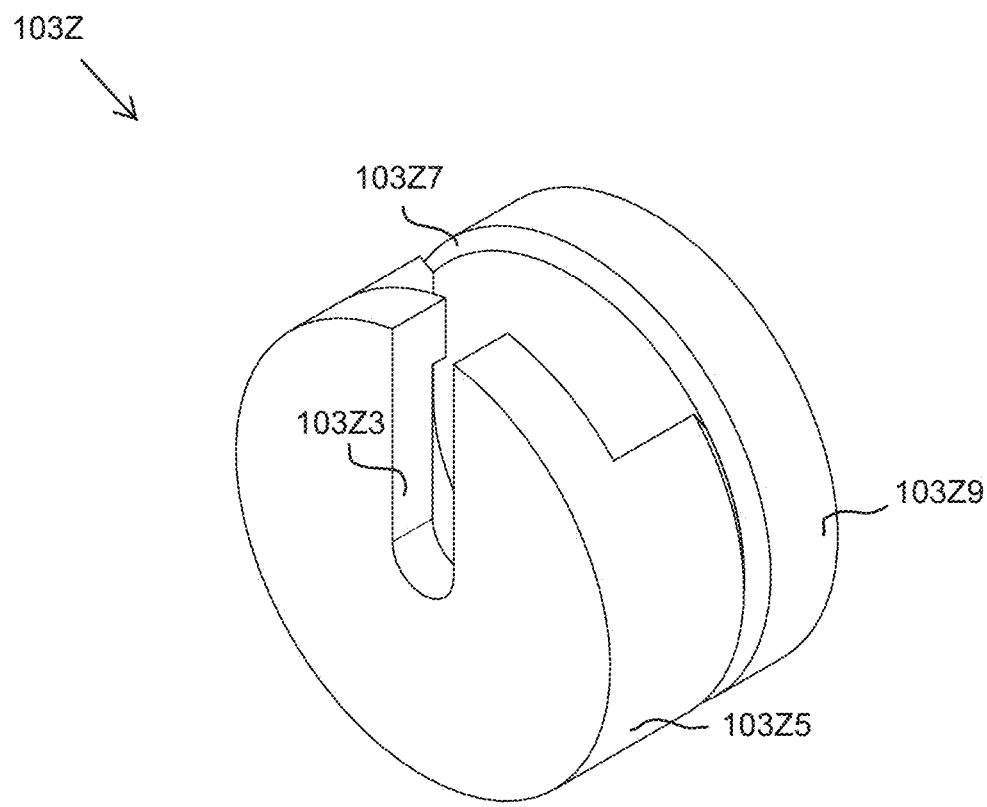
Figure 1B:
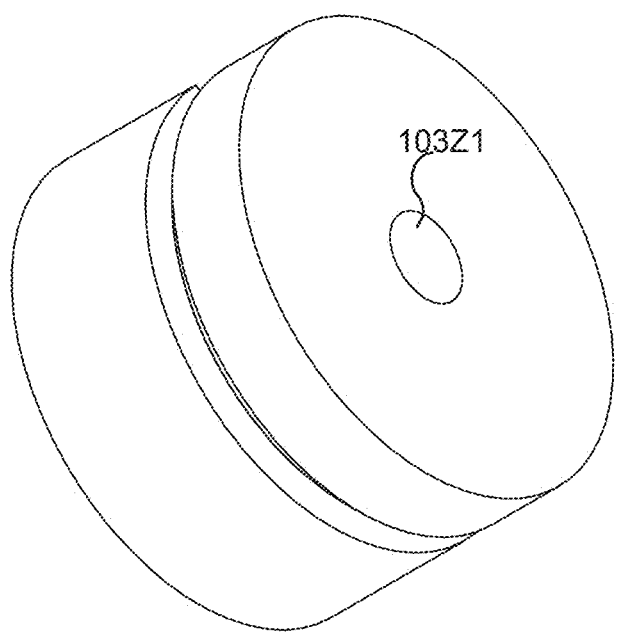
Figure 25F:
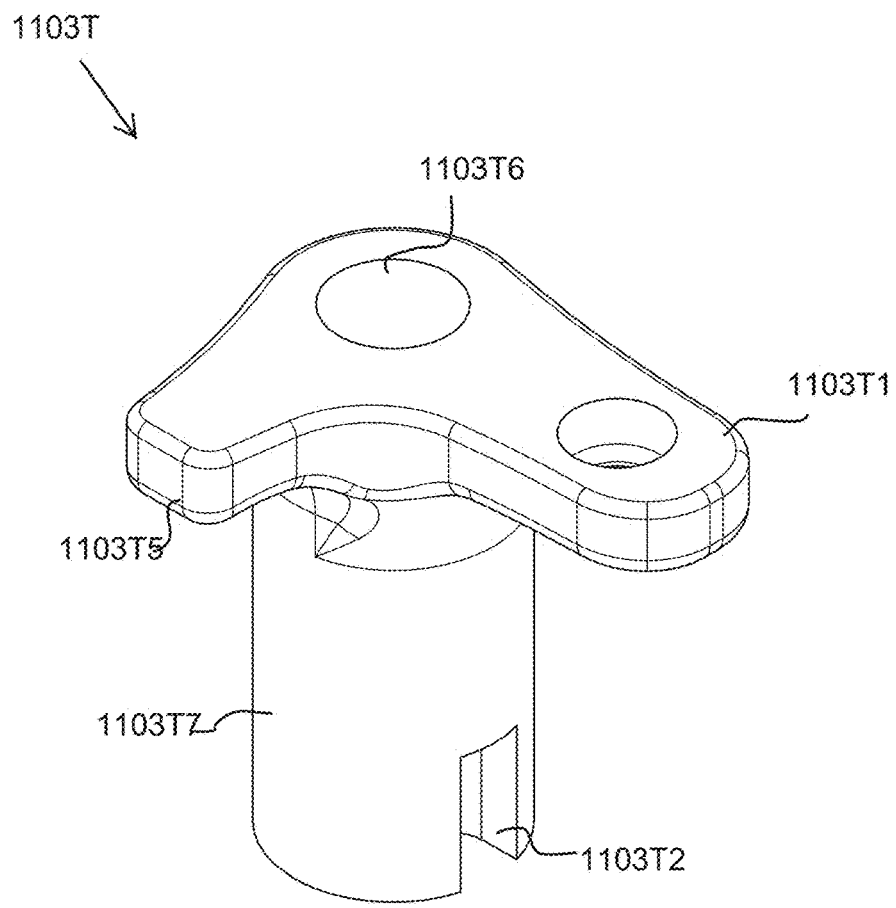
Figure 2:
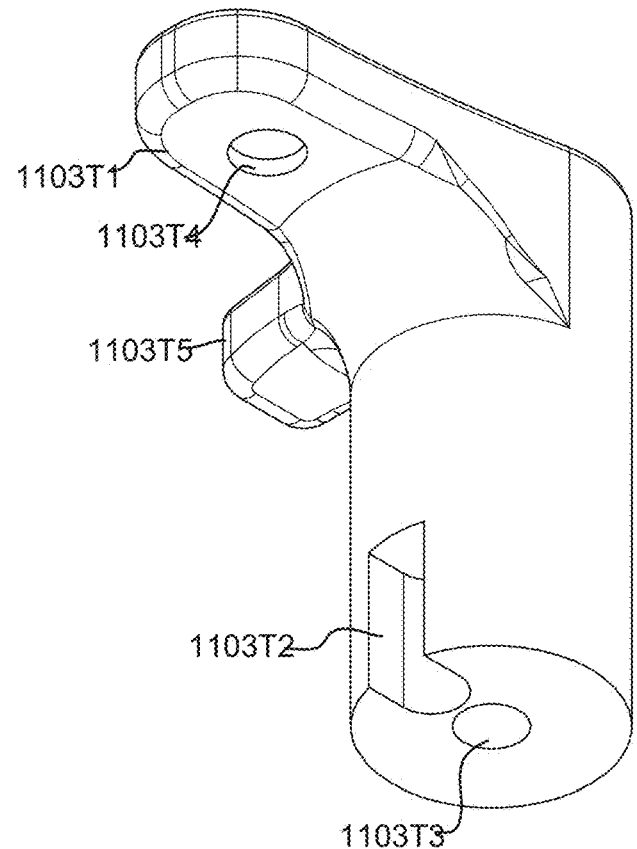
Figure 25F:
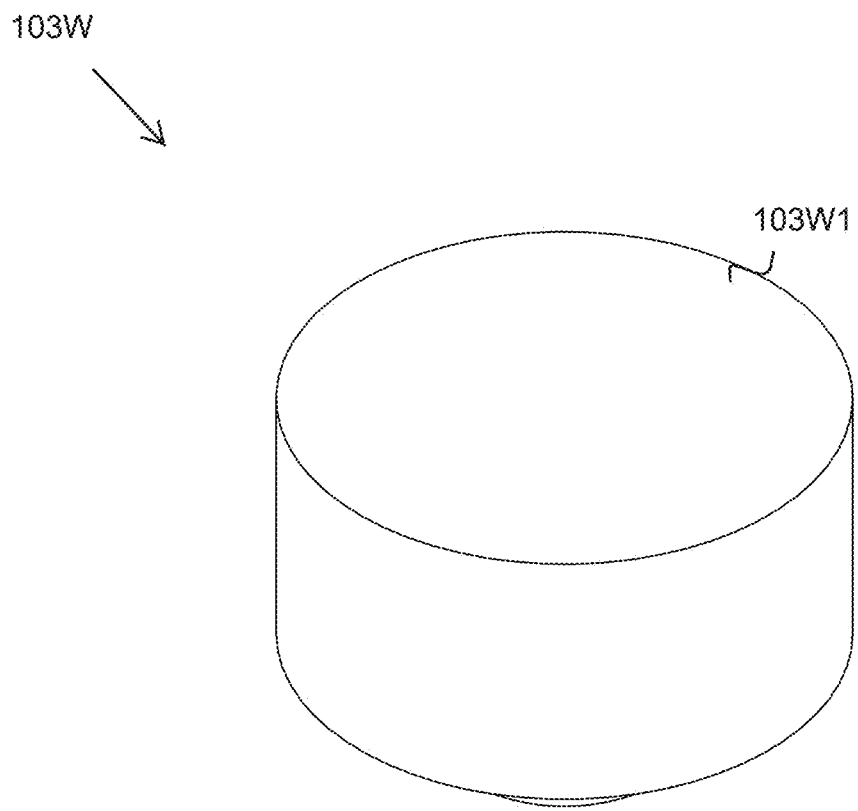
Figure 3:
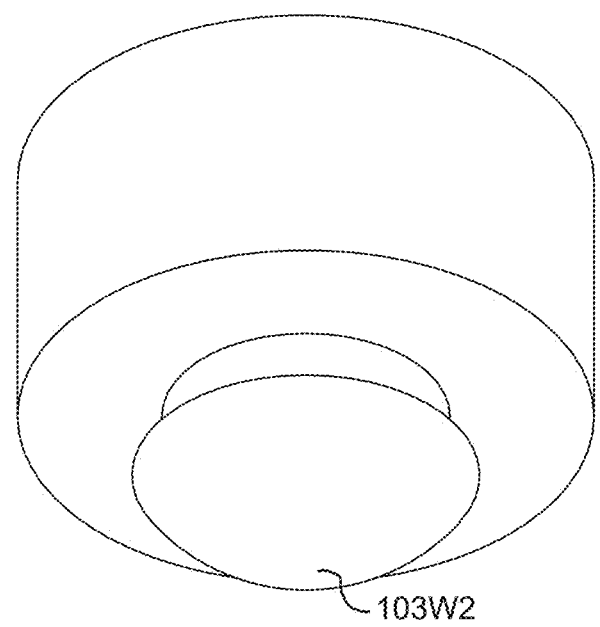
Figure 25G:
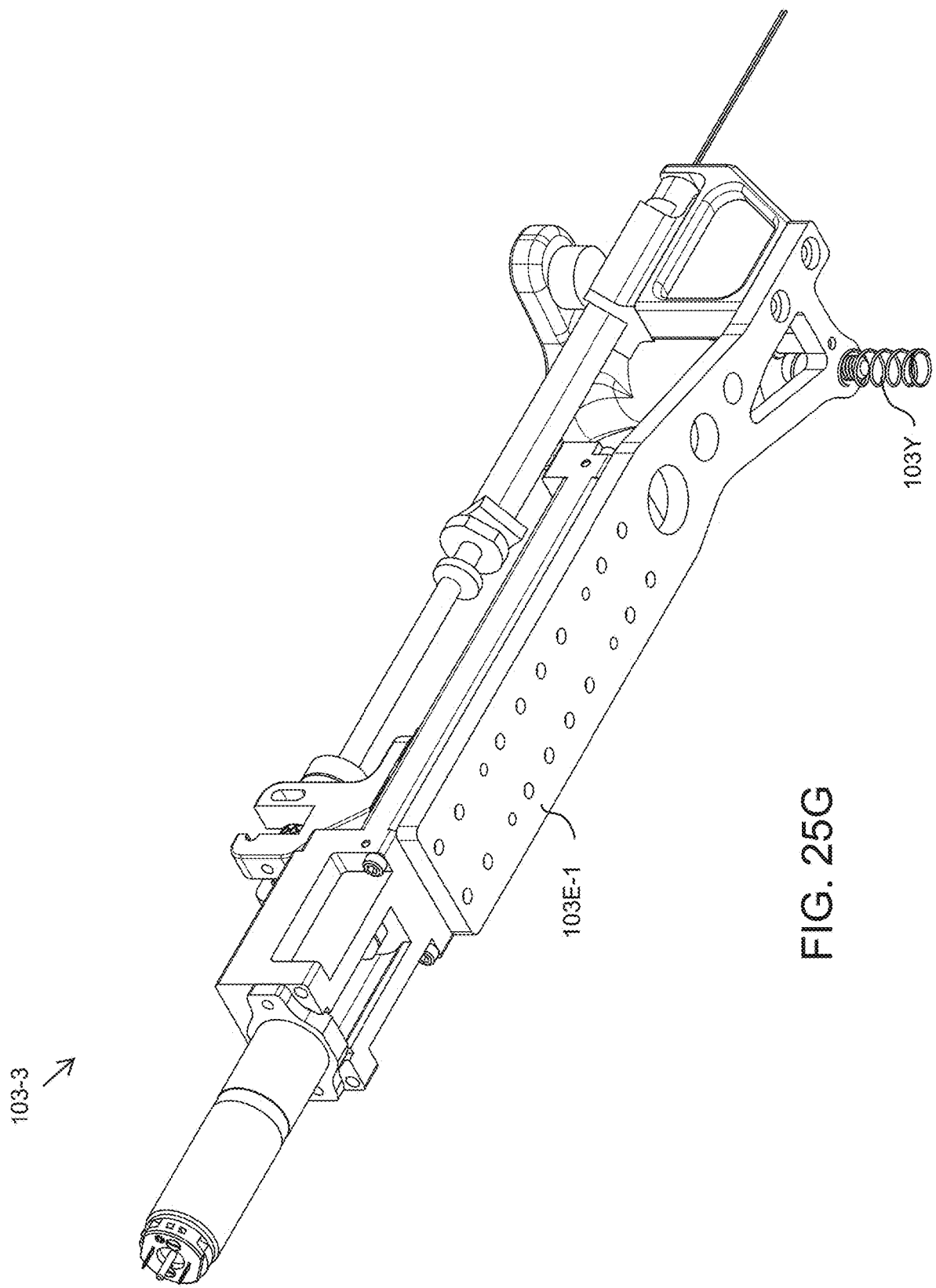
FIG. 25G is a schematic diagram of the delivery system fourth configuration of the present teachings.

Referring now to FIGS. 25F and 25G, delivery system fourth configuration 103-3 can include plunger extension 103-1A that can include a knurled head thumb screw with a shoulder, for example. Plunger extension 103-1A can include a threaded portion that can operably couple with plunger 103F. Plunger extension 103-1A can also include a head that can rest in second configuration plunger drive 103M-1. Delivery system fourth configuration 103-3 can include syringe swing clamp (FIG. 25F-2) that can, coupled with bumper 103W (FIG. 25F-3), retain the position of syringe 103FF (FIG. 26E) in second configuration syringe holder 103V (FIGS. 35A/35B). Syringe swing clamp 103T (FIG. 25F-2) can include pressure-controlled positioning through the assembly of spring mount 103X (FIG. 25E) and spring 103Y. Delivery system fourth configuration 103-3 can include plunger coupler 103Z (FIGS. 25F-1A/25F-1B) that can securely engage plunger head 103G11 (FIG. 26) while providing a means for adapting plunger head 103G11 (FIG. 26) to operably mount with plunger extension 103-1A.

Referring now to FIGS. 25F-1A and 25F-1B, plunger coupler 103Z can include, but is not limited to including, extension connector cavity 103Z1 that can house plunger extension 103-1A (FIG. 25F-1) and adapter first side 103Z2 towards second configuration plunger drive 103M-1 (FIG. 25F-1). Plunger coupler 103Z can include plunger head recess 103Z4 that can accept plunger head 103G11 (FIG. 26). Plunger head recess 103Z4 can be generically-sized to accommodate different shapes and sizes of plunger head 103G11 (FIG. 26), can include flexible material to accommodate different shapes and sizes of plunger head 103G11 (FIG. 26), and can be sized specifically for a particular size range of plunger head 103G11. Receiving cavity 103Z3 can accept and possibly position plunger body 103F1 (FIG. 26), and can be sized and shaped generically to fit various sizes and shapes of plunger body 103F1 (FIG. 26), and/or can be sized and shaped for a particular size range of plunger body 103F1 (FIG. 26). Beveled edges 103Z6 and 103Z7 can accommodate operably and rigidly connecting adapter first section 103Z9 from adapter second section 103Z5. Adapter first section 103Z9 and adapter second section 103Z5 can be operably coupled magnetically and/or mechanically, for example, at an interface formed between first face 103Z8 and second face 103Z10.

Referring now to FIG. 25F-2, syringe swing clamp 1103T can securely maintain the position of syringe 103EE (FIG. 26C), for example. Syringe swing clamp 1103T can accommodate inserting and positioning of syringe 103EE (FIG. 26), for example, through the force of spring 103Y (FIG. 25E) moderated by bumper 103W (FIG. 25F-3). The force of spring 103Y (FIG. 25E) can be adjusted by adjusting spring bolt 103X (FIG. 25E) that can be mounted in clamp cavity 103T6. Bumper 103W (FIG. 25F-3) can be mounted in bumper cavity 1103T4 in pressure arm 1103T1. Spring bolt 103X (FIG. 25E) can be mounted in shaft 1103T7, and syringe swing clamp 1103T can be operably coupled to mount 103E-1 (FIG. 33A) with a fastener that can be housed within shaft 1103T7 at mount cavity 1103T2. Syringe swing clamp 1103T can include, but is not limited to including, adjustment arm 1103T5 that can be used to adjust syringe swing clamp 1103T with respect to syringe 103EE (FIG. 26), for example.

Referring now to FIG. 25F-3, bumper 103W, can clamp syringe 103EE (FIG. 26), for example, into syringe mount 103V (FIG. 35A). Bumper 103W can provide pressure on syringe 103EE (FIG. 26), for example, at bumper face 103W1, and can be mounted on syringe swing clamp (FIG. 25F-2) using bumper mount 103W2. Bumper 103W can be commercially available.

Referring now primarily to FIG. 26, syringe system 103BB can deliver at least one first material to tissue enclosure 101 (FIG. 1A). Syringe system 103BB can include, but is not limited to including, plunger 103F, syringe barrel 103G, and needle 103H. Plunger 103F can include any type and shape of plunger tip (not shown) that is compatible with the size and shape of syringe barrel 103G. In some configurations, plunger head 103G11 can receive a depression force from plunger drive 103M (FIG. 32) that can depress plunger shaft 103F1. In some configurations, plunger shaft 103F1 can continue through syringe barrel 103G until plunger head 103G11 reaches barrel head 103G13. Plunger head 103G11 can couple with barrel slide clip 103D (FIG. 31) and plunger driver 103M (FIG. 32). Plunger barrel 103G can be housed in barrel holder 103K (FIG. 35). Needle hub 103G14 can provide a mounting location for needle 103H. Needle hub 103G14 can couple needle 103H with syringe barrel 103G, and can be sized to accommodate any size needle 103H and associated needle lumen. Needle guide 103J (FIG. 34) can brace syringe barrel 103 at needle hub 103G14, and can couple barrel holder 103K (FIG. 35) with delivery system connector 103E (FIG. 33).

Figure 26A:
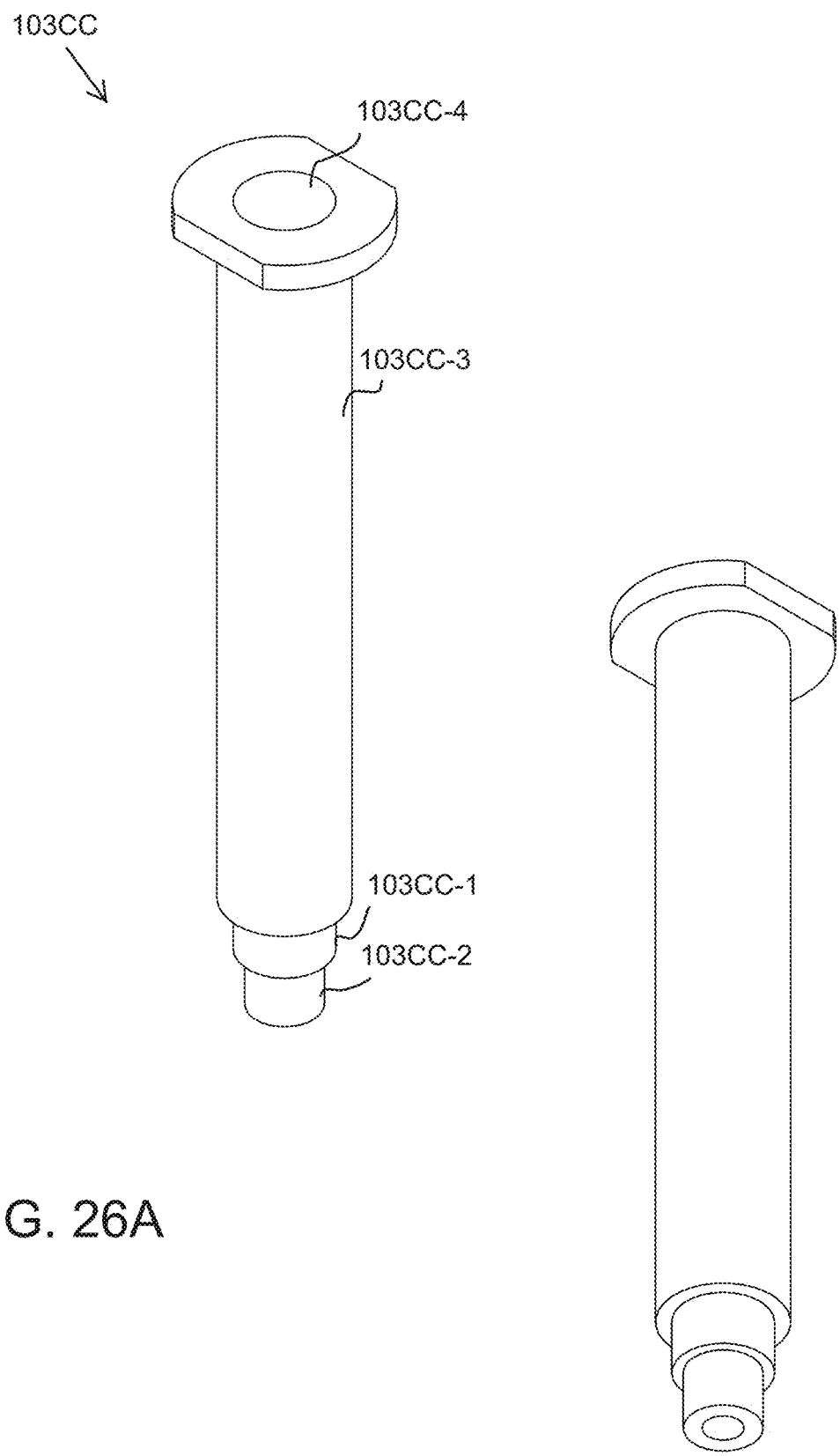
FIG. 26A is a schematic diagram of first and second views of the barrel second configuration of the present teachings.

Referring now to FIG. 26A, barrel second configuration 103CC can include, but is not limited to including, first barrel taper 103CC-2 and second barrel taper 103CC-1. First barrel taper 103CC-2 can accommodate needle 103H (FIG. 26) of any size and shape, and can provide a first size adaptation between needle 103H (FIG. 26) and barrel body 103CC-3. Depending on the size of barrel body 103CC-3 and the size of needle 103H (FIG. 26), second barrel taper 103CC-1 might be needed. Barrel second configuration 103CC can be available commercially.

Referring now to FIG. 26B, barrel third configuration 103DD can include rectangular-shaped head 103DD-1 that can facilitate mounting in, for example, but not limited to, plunger drive second configuration 103M-1 (FIG. 25F-1).

Barrel body second configuration 103DD-2 can include, but is not limited to including, needle mount cavity 103DD-3.

Figure 26C:
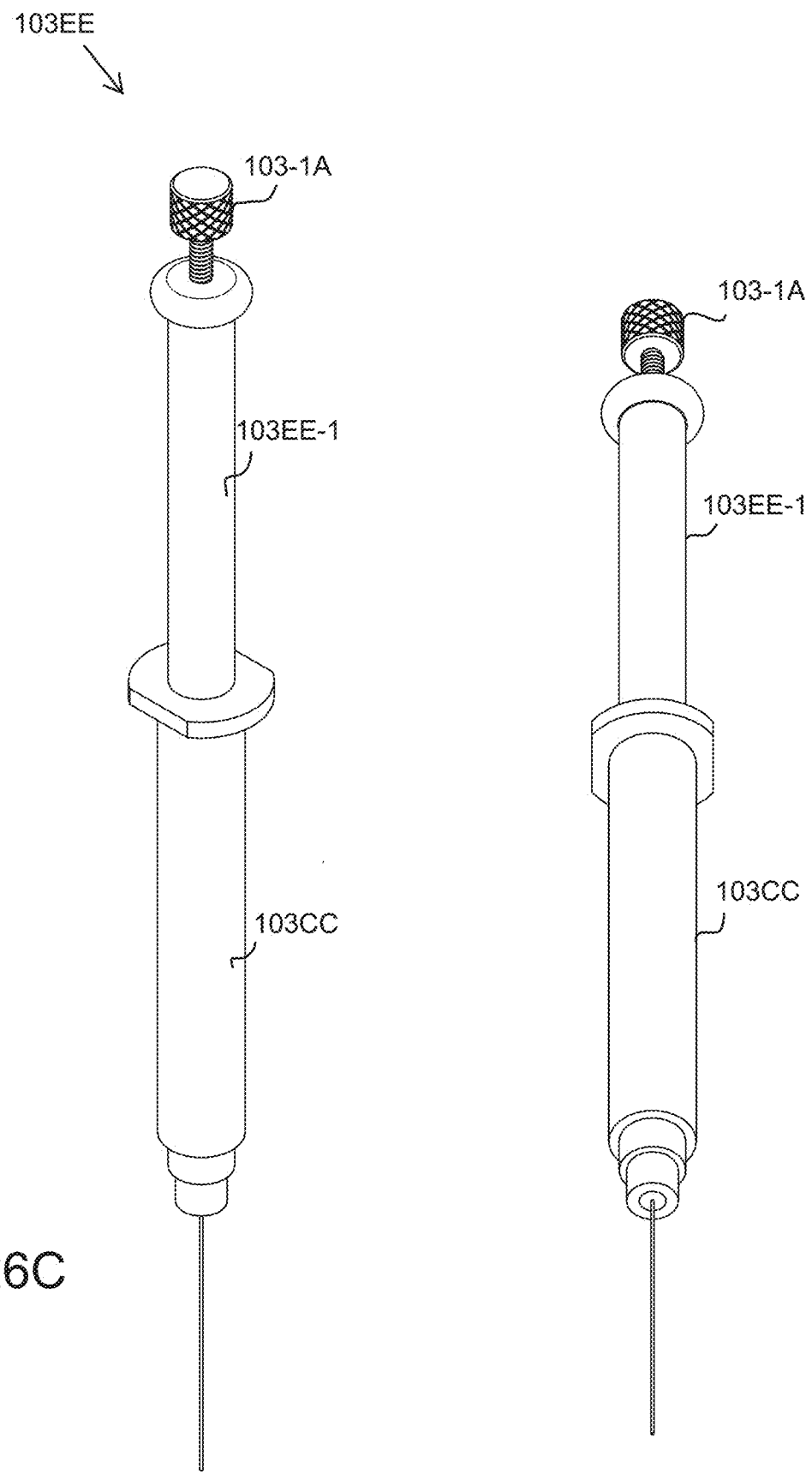
FIG. 26C is a schematic diagram of first and second views of the syringe second configuration of the present teachings.

Referring now to FIG. 26C, syringe second configuration 103EE can include barrel second configuration 103CC that can accommodate plunger second configuration 103EE-1. Plunger second configuration 103EE-1 can provide a mounting cavity for plunger extension 103-1A (FIG. 25F).

Figure 26D:
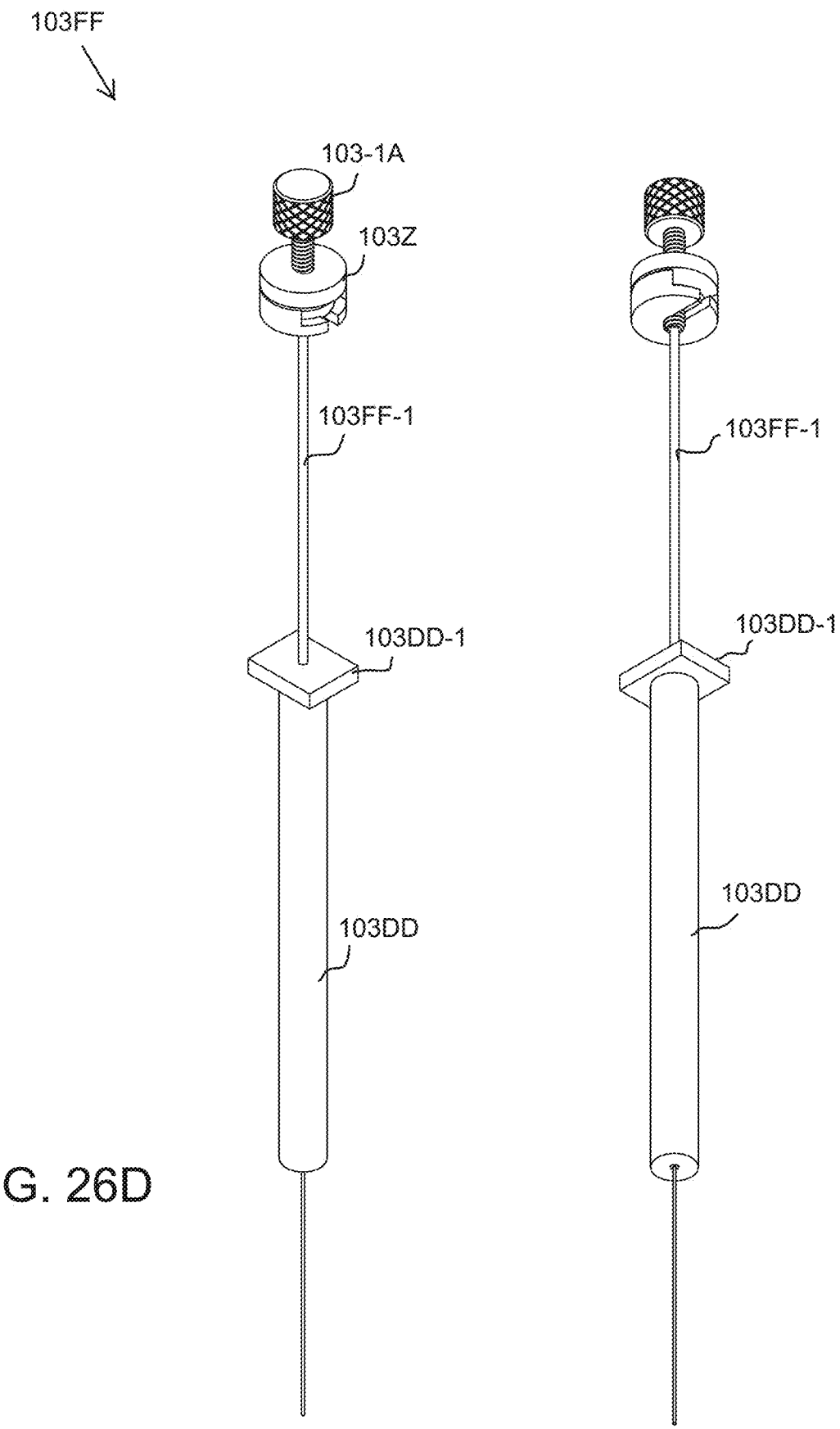
FIGS. 26D and 26E are schematic diagrams of various views of the syringe third configuration of the present teachings.
Figure 26E:
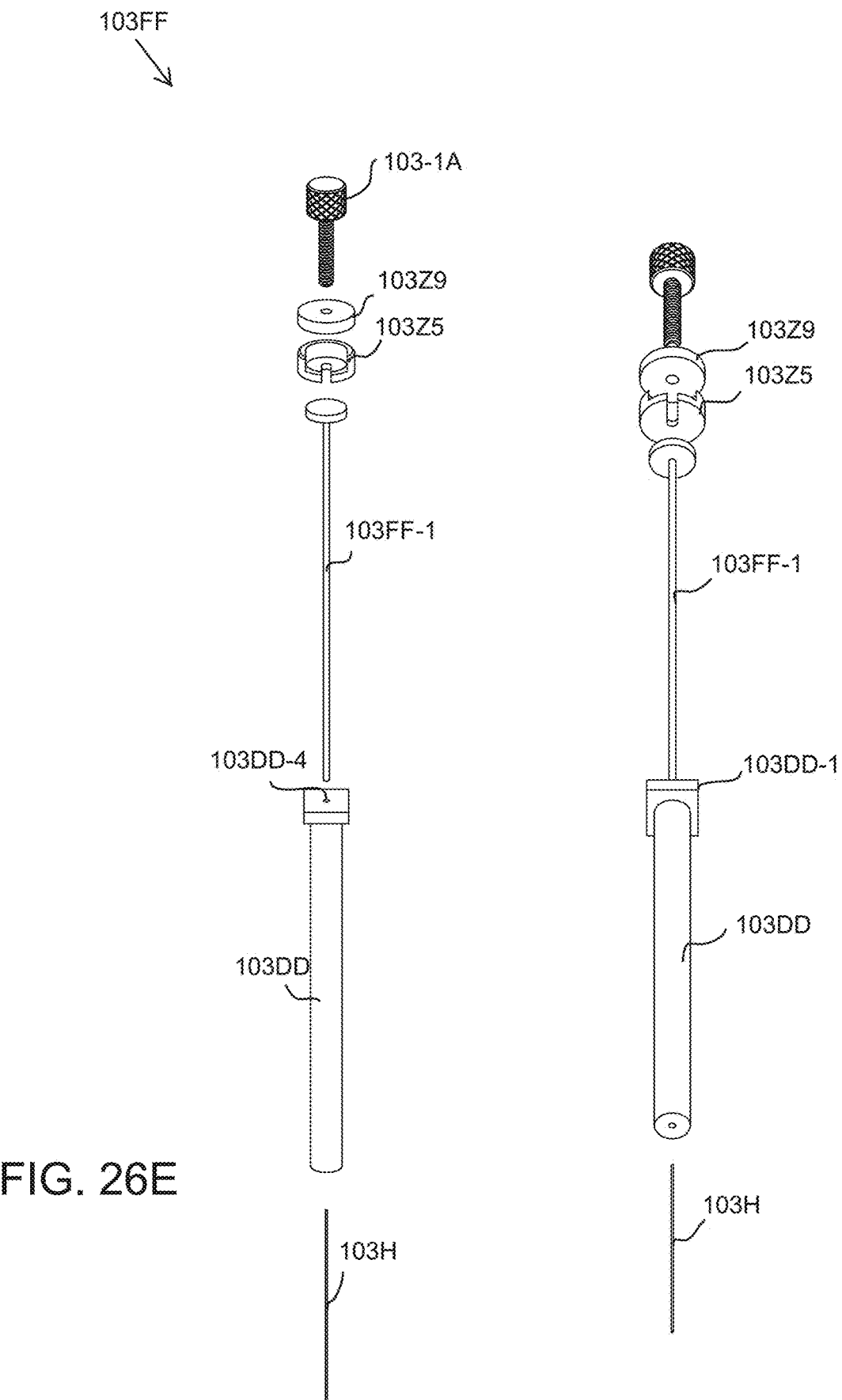

Referring now to FIGS. 26D and 26E, syringe third configuration 103FF can include barrel third configuration 103DD that can accommodate plunger third configuration 103FF-1 at plunger cavity 103DD-4 (FIG. 26B). Plunger third configuration 103FF-1 can seat into plunger coupler 103Z (FIG. 25F) that can provide a mounting cavity for plunger extension 103-1A (FIG. 25F).

Figure 26F:
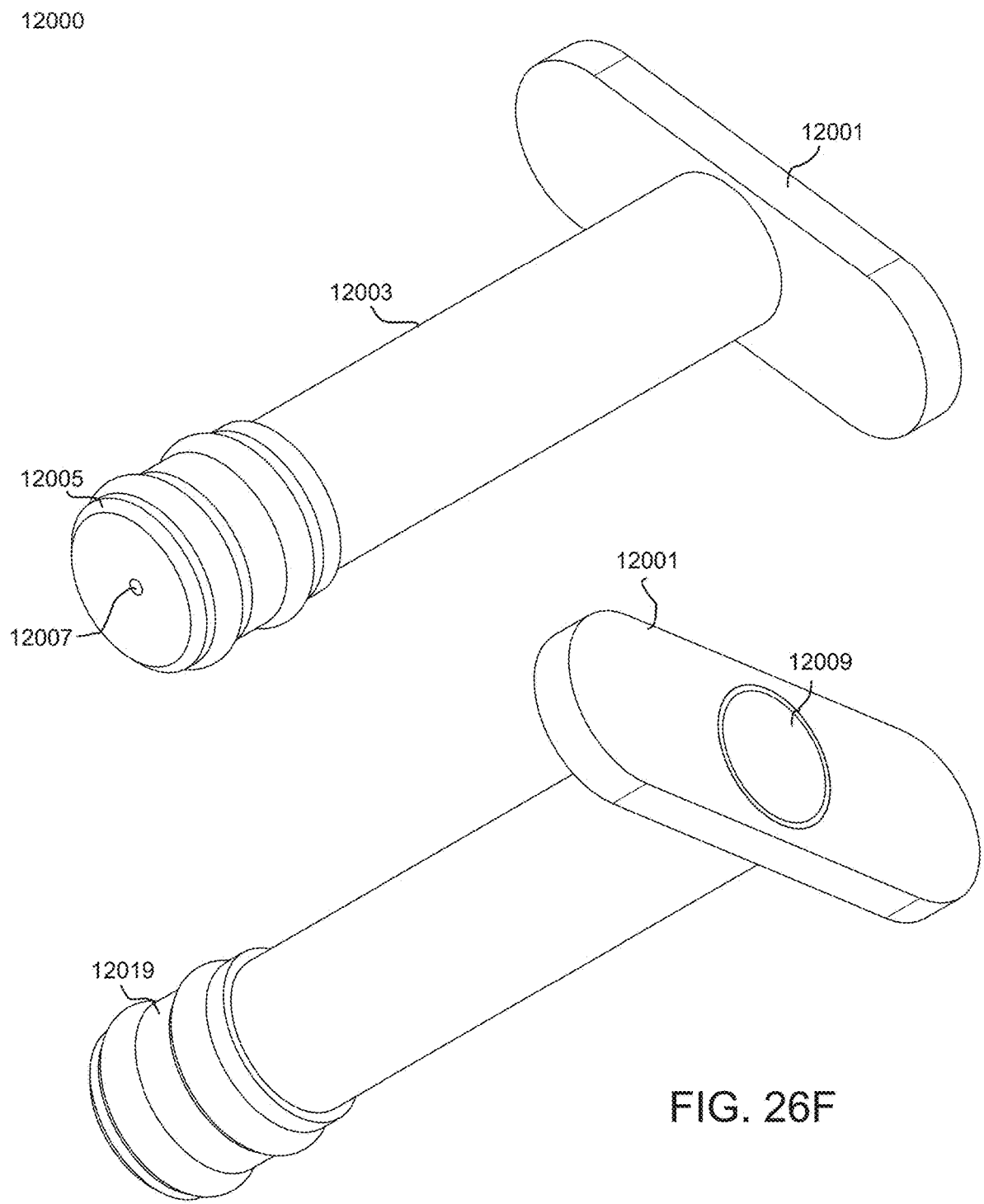
Figure 26G:
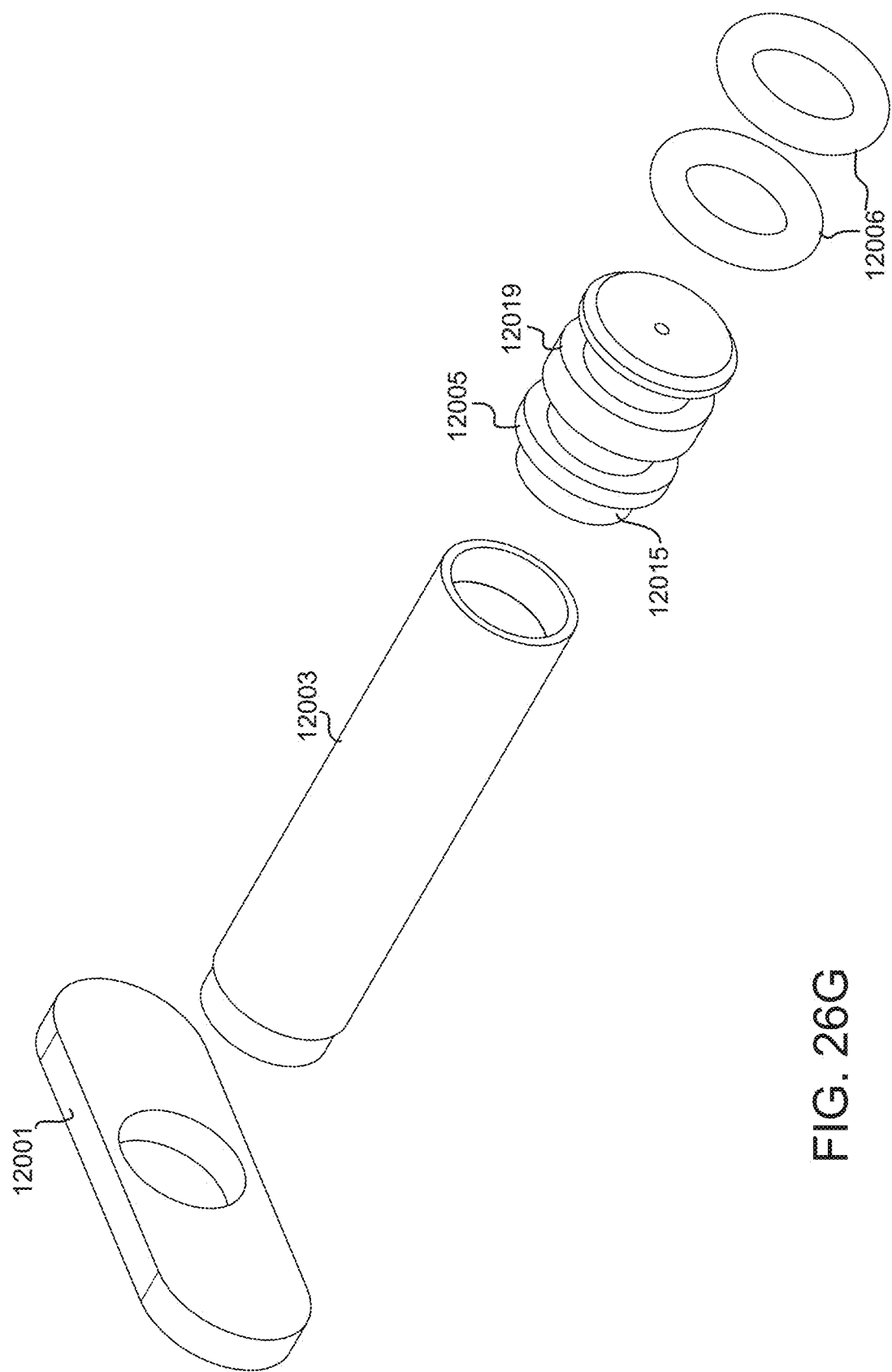
Figure 26H:
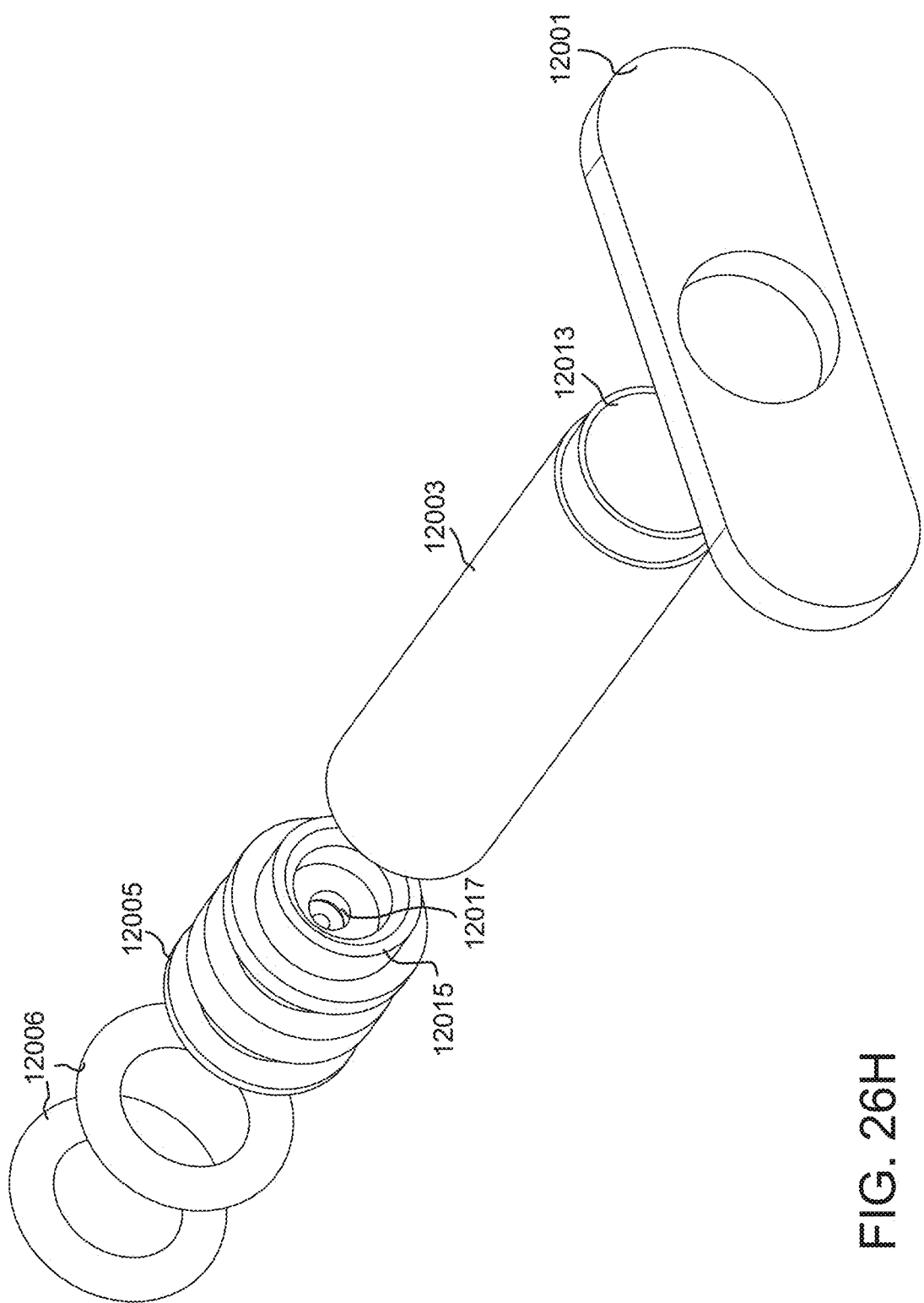
Figure 26J:
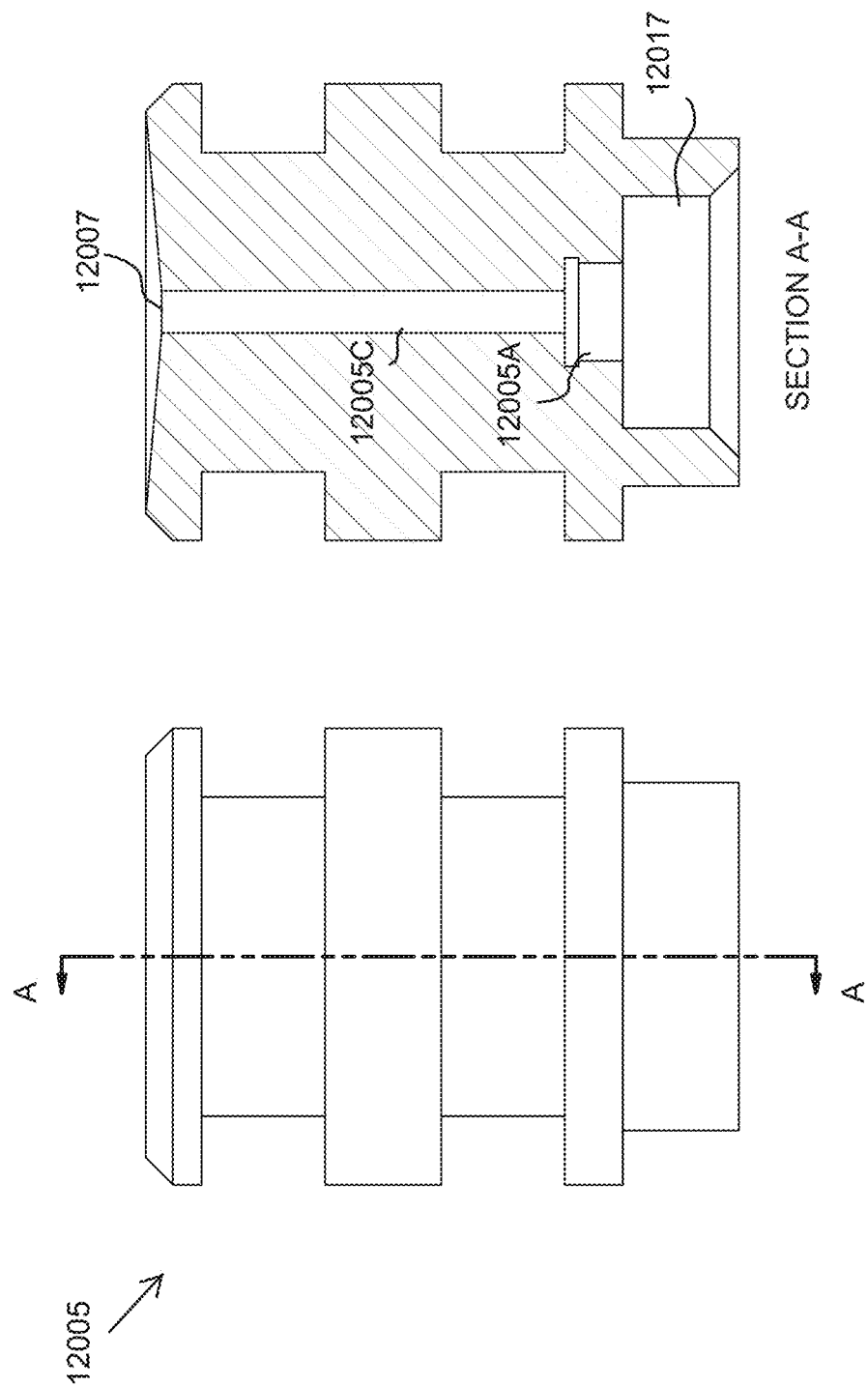

Referring now to FIGS. 26F-26H, various types and sizes of syringe barrel 103DD (FIG. 26I) can be loaded with any material suitable for extruding from a syringe using various sizes of syringe filler 12000. Syringe filler 12000 can include, but is not limited to including, flange 12001 operably coupled with filler body 12003 at flange recess 12013 (FIG. 26H). Flange 12001 can include any shape that can enable a substantially normal force to be exerted against flange 12001 to push syringe filler 12000 into a container such as container 12021 (FIG. 26I) containing material with which to load syringe barrel 103DD (FIG. 26I). Filler body 12003 can include any diameter that can accommodate syringe barrel 103DD (FIG. 26I), and can be sized according to the diameter of container 12021 (FIG. 26I). Filler body 12003 can be operably coupled with syringe coupler 12005 at coupler interface 12015 (FIG. 26G). Syringe coupler 12005 (FIG. 26J) can include threaded syringe coupling 12005A/12017 (FIG. 26J), and material tube 12005C (FIG. 26J) through which material can travel from container 12021 (FIG. 26I) to syringe barrel 103DD (FIG. 26I). Syringe coupler 12005 can include at least one protrusion 12019 that can provide at least one seating positions for at least one gasket 12006. At least one gasket 12006 can enable syringe coupler 12005 to tightly couple with container 12021 (FIG. 26I) as syringe coupler 12005 moves into container 12021 (FIG. 26I).

Referring now to FIG. 26I, in operation, syringe barrel 103DD can be loaded with any material including, but not limited to, biological gel, tissue, and growth medium. When a gel is loaded, the gel can be homogenized via, for example, but not limited to, centrifugation and/or speed mixing. To fill exemplary syringe barrel 103DD, syringe plunger 103FF-1 (FIG. 26E) can be removed, and syringe barrel 103DD can be inserted into syringe filler 12000 at syringe filler entry point 12009, and can be operably coupled with syringe coupler 12005 at syringe coupling end 12023 that can be threaded. In some configurations, syringe barrel plunger entry 12025 can protrude beyond flange 12001. Flange 12001 and syringe barrel 103DD can be depressed, into container 12021 until the material emerges from syringe barrel plunger entry 12025 which indicates that syringe barrel 103DD is full. The material within container 12021 can enter syringe coupler 12005 through opening 12007, that can be sized according to the desired flow rate of the material into syringe coupler 12005 and the desired normal force on flange 12001 required to transfer the material to syringe barrel 103DD. Syringe barrel 103DD can be removed from syringe filler 12000, syringe plunger 103FF-1 (FIG. 26E) can be replaced, and syringe filler 12000 can be removed from container 12021.

Referring now to FIG. 26K, second configuration syringe filler 12001-1 can include flange 12001A that can include, in some configurations, a circular shape. Second configuration syringe filler 12001-1 can also include second configuration filler body 12003A that can be sized according to the size(s) of the syringe(s) that can be accommodated by second configuration syringe filler 12001-1. The syringe can couple with second configuration filler body 12003A at opening 12025 that can be threaded and can be sized according to the size(s) of the accommodated syringe(s). Second configuration syringe coupler 12029 can include gasket 12031 that can enable leak-free coupling between the material container and second configuration syringe coupler 12029. The syringe can operably couple with opening 12025 in any suitable way, for example, but not limited to, threaded coupling and snap coupling. The material can enter syringe coupler 12029, and ultimately the syringe, through opening 12033.

Figure 27B:
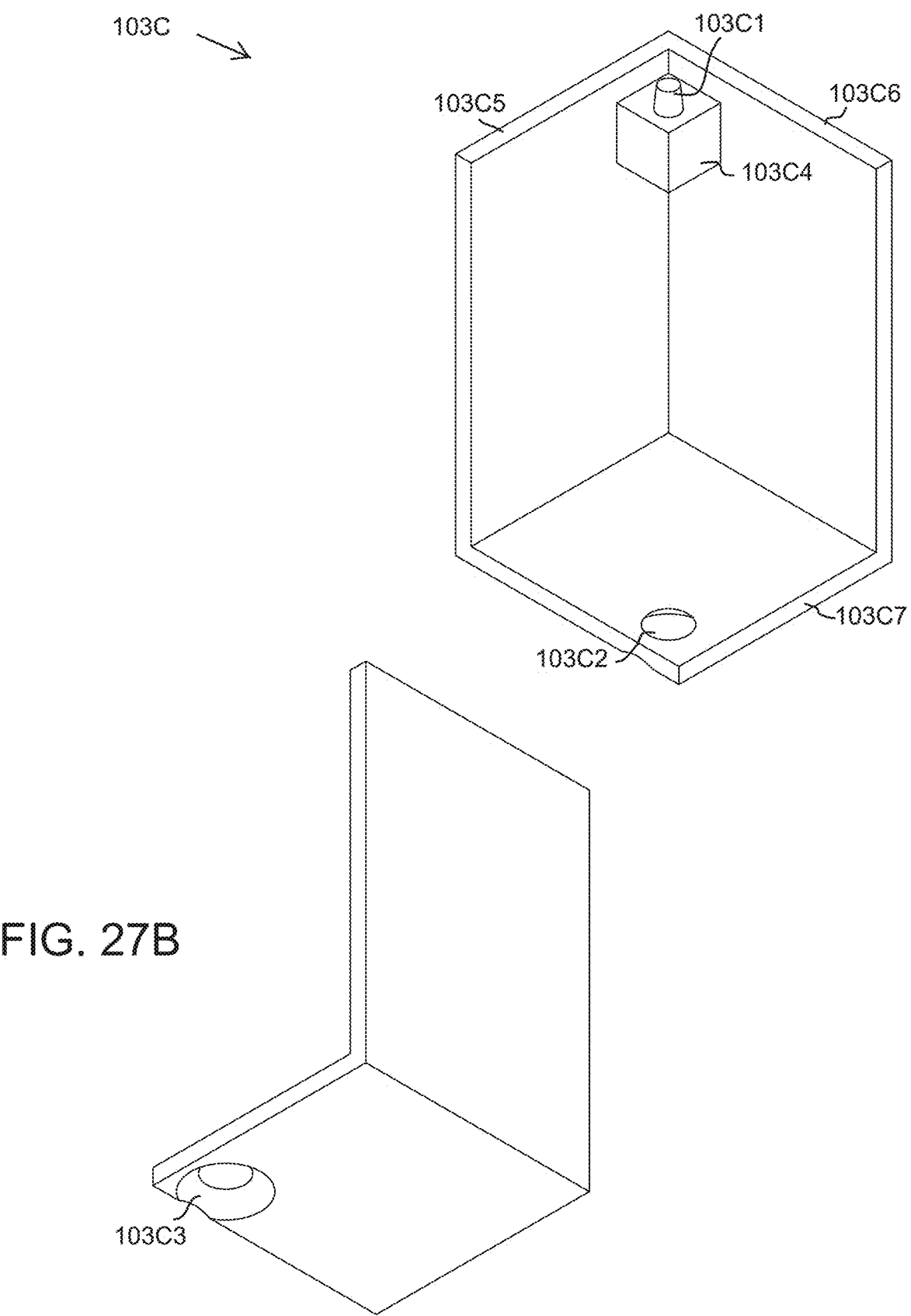
FIG. 27B is a schematic diagram of first and second views of the switch housing cap of the present teachings.
Figure 28:
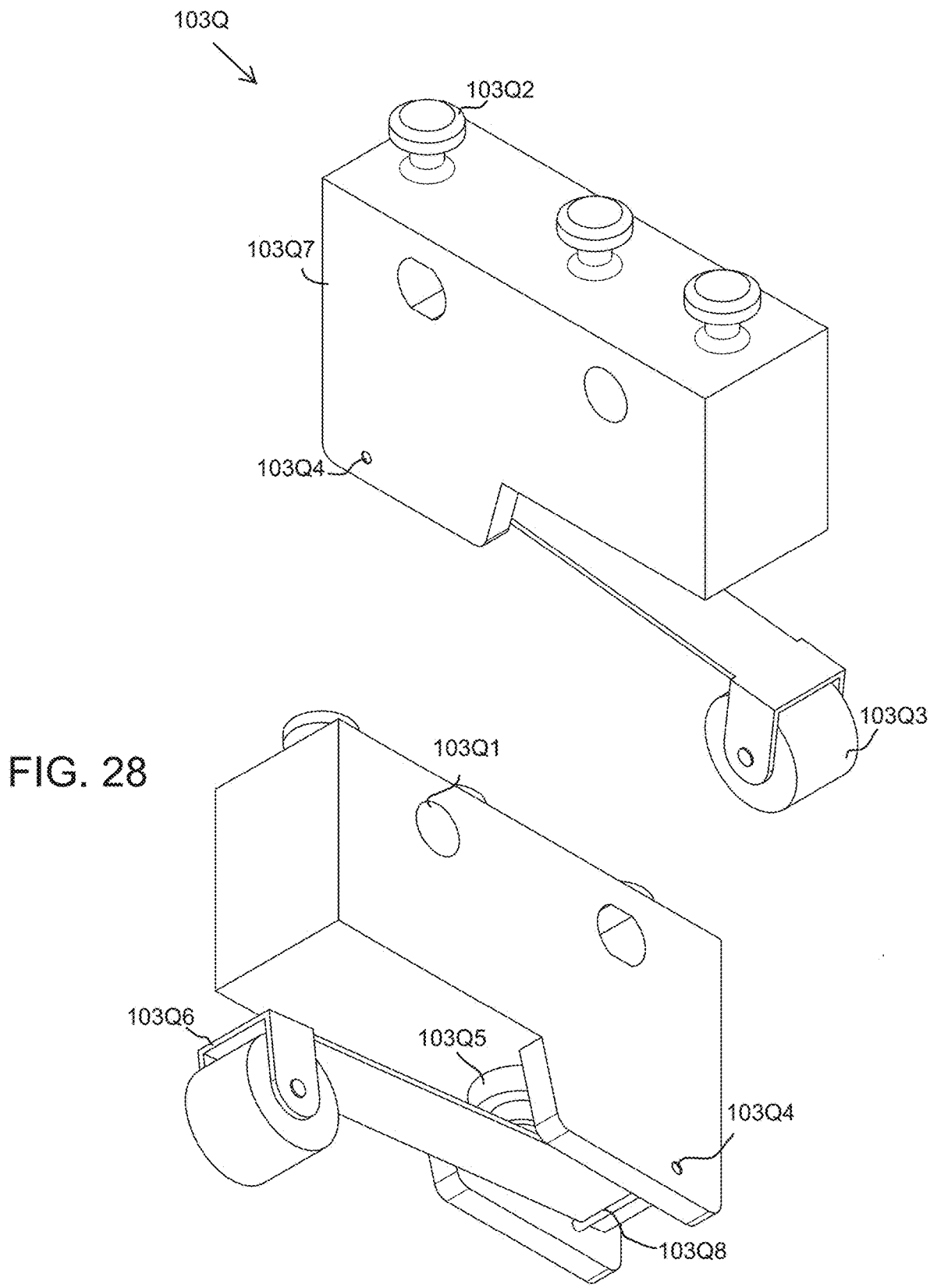
FIG. 28 is a schematic diagram of first and second views of the switch of the present teachings.

Referring now primarily to FIG. 27A, switch housing 103P can provide a protective covering for switch 103Q (FIG. 28). Switch housing 103P can provide an interface between switch 103Q (FIG. 28) and plunger drive 103M (FIG. 32), which can drive plunger 103F (FIG. 26), depending on the disposition of switch 103Q (FIG. 28), to deliver the at least one material. Switch housing 103P can include, but is not limited to including, switch opening 103P2 that can provide access for switch 103Q (FIG. 28) to barrel slide clip 103D (FIG. 31). Switch opening 103P2 can be formed into any shape that can accommodate the shape and size of switch 103Q (FIG. 28). In some embodiments, switch opening 103P21 can include multiple sizes and shapes such as, for example, but not limited to, first rectangle 103P21 and second rectangle 103P22. Switch housing 103P can include at least one connecting cavity 103P5 that can be used to connect switch housing 103P to plunger drive 103M (FIG. 32) through at least one fastener cavity 103P3 and associated fasteners. At least one connecting cavity 103P5 can be positioned to stabilize switch 103Q (FIG. 28) along at least one connecting cavity edge 103P8. Switch housing 103P can include dowel divot 103P4 that can receive, if present, cap housing dowel 103C1 (FIG. 27B). Housing fastening cavity 103P1 can include housing recessed portion 103P9 that can enable flush mounting of a fastener. Housing fastening cavity 103P1 and associated fasteners can be formed into any size and shape. Switch 103Q (FIG. 28) can be attached to switch housing using at least one switch-housing fastening cavity 103P7 mated with at least one switch fastening cavity 103Q1 (FIG. 28) and associated fasteners.

Referring now primarily to FIG. 27B, switch housing 103P (FIG. 27A) can be fastened to switch housing cap 103C at housing fastening cavity 103P1 (FIG. 27A) and cap fastening cavity 103C2. Switch housing cap 103C can include at least one side, and can partially or completely cover switch 103Q (FIG. 28) to, for example, protect switch 103Q (FIG. 28). In some configurations, switch housing cap 103C can include, but is not limited to including, cap first side 103C5, cap second side 103C6, and cap third side 103C7. In some configurations, cap third side 103C7 can include cap fastening cavity 103C2 that can include cap recessed portion 103C3. Cap recessed portion 103C3 can enable flush mounting of a fastener. Housing fastening cavity 103P1 (FIG. 27A) and cap fastening cavity 103C2 can be coupled using associated fasteners. All of housing fastening cavity 103P1 (FIG. 27A), cap fastening cavity 103C2 and associated fasteners can be formed into any size and shape. There can be multiple housing fasting cavities 103P1 (FIG. 27A) and cap fastening cavities 103C2. Cap housing dowel 103C1 can interlock switch housing 103P (FIG. 27A). Cap housing dowel 103C1 can be mounted, for example, on dowel mounting block 103C4, that can, in some configurations, be operatively coupled with cap first side 103C5 and cap second side 103C6.

Referring now primarily to FIG. 28, switch 103Q can ease installation of plunger 103F (FIG. 25B) as plunger 103F (FIG. 25B) enables the dispensing of the first at least one material 79 (FIG. 39) into tissue enclosure 101 (FIG. 2A). Switch 103Q can include, but is not limited to including, a single pole double throw (SPDT) toggle switch such as, for example, but not limited to, a MCMASTER® 7193K2 microswitch. Contact between spring 103Q5 and roller lever 103Q6 can engage roller 103Q3 with plunger head 103G11 (FIG. 26). Roller 103Q3 can become disengaged with plunger head 103G11 (FIG. 26) when spring 103Q5 and roller lever 103Q6 are not in contact with each other. In some configurations, the pressure of switch 103Q on plunger head 103G11 (FIG. 26) can be determined by, for example, but not limited to, a load sensor and/or a pressure sensor. In some configurations, a linear encoder can be included that can, for example, but not limited to, control the volume dispensed of the first at least one material 79 (FIG. 39). The linear encoder can be mounted to, for example, plunger drive 103M (FIG. 32), and a read head of the linear encoder can move with plunger 103F (FIG. 25B). Limit switches can also be included that can detect when plunger 103F (FIG. 25B) has reached a pre-selected limiting point. The limit switches can include, for example, but not limited to, magnetic, optical, and mechanical switches.

Referring now primarily to FIG. 29, gearbox 103B can include any type of gearbox that can combine with motor 103A (FIG. 25A) and provide the efficiency and speed required of syringe system 103G1 (FIG. 26), which can vary with the size and shape of syringe system 103B1 (FIG. 26). Gearboxes such as, for example, but not limited to, the MAXON® GP16A, can be used in some configurations. Gearbox 103B can be operably coupled with motor 103A (FIG. 25A) at gear end 103B2. Gear end 103B1 can be operably coupled with motor nut adapter 103S (FIG. 30) and fastened at gear fastening cavities 103B3 with associated fasteners. Gear fastening cavities 103B3 and the associated fasteners can be any size and shape.

Figure 36A:
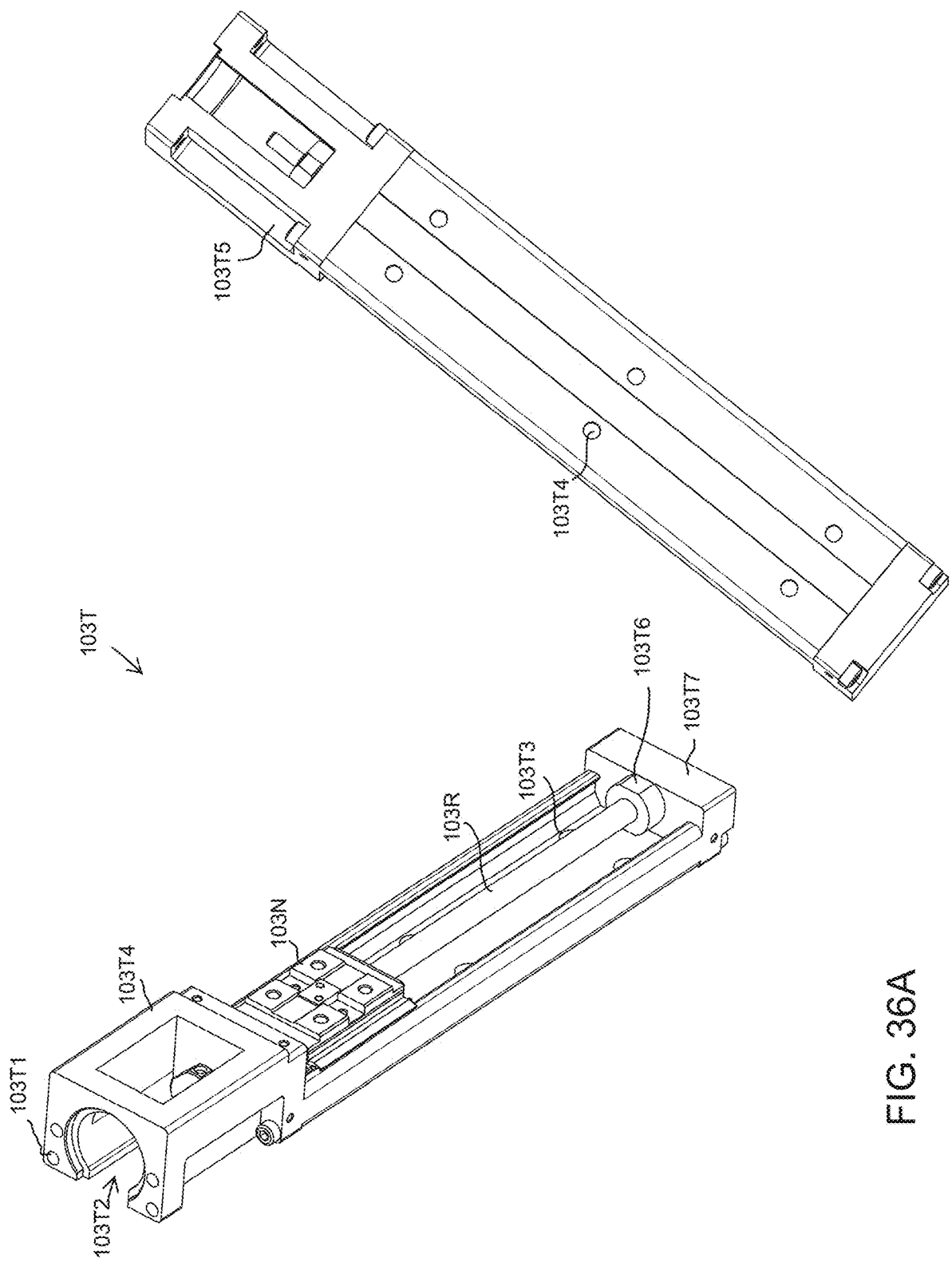
FIG. 36A is a schematic diagram of first and second views of the linear actuator of the present teachings.

Referring now primarily to FIG. 30, motor nut adapter 103S can provide a connecting interface between a motor nut and linear actuator 103T (FIG. 36A). Motor nut adapter 103S can be operably coupled with gearbox 103B (FIG. 29) at gearbox fastener cavities 103S1 and associated fasteners. Gearbox fastening cavities 103S1 and the associated fasteners can be any size and shape. Fastener cavities 103S1 can be recessed for flush mounting of the fasteners. Motor nut adapter 103S can include shaft cavity 103S2 through which gear shaft 103B4 can protrude. Motor nut adapter 103S can be operably coupled with linear actuator 103T (FIG. 36A) at actuator fastening cavities 103S3 with associated fasteners. Actuator fastening cavities 103S3 and the associated fasteners can be any size and shape.

Figure 31A:
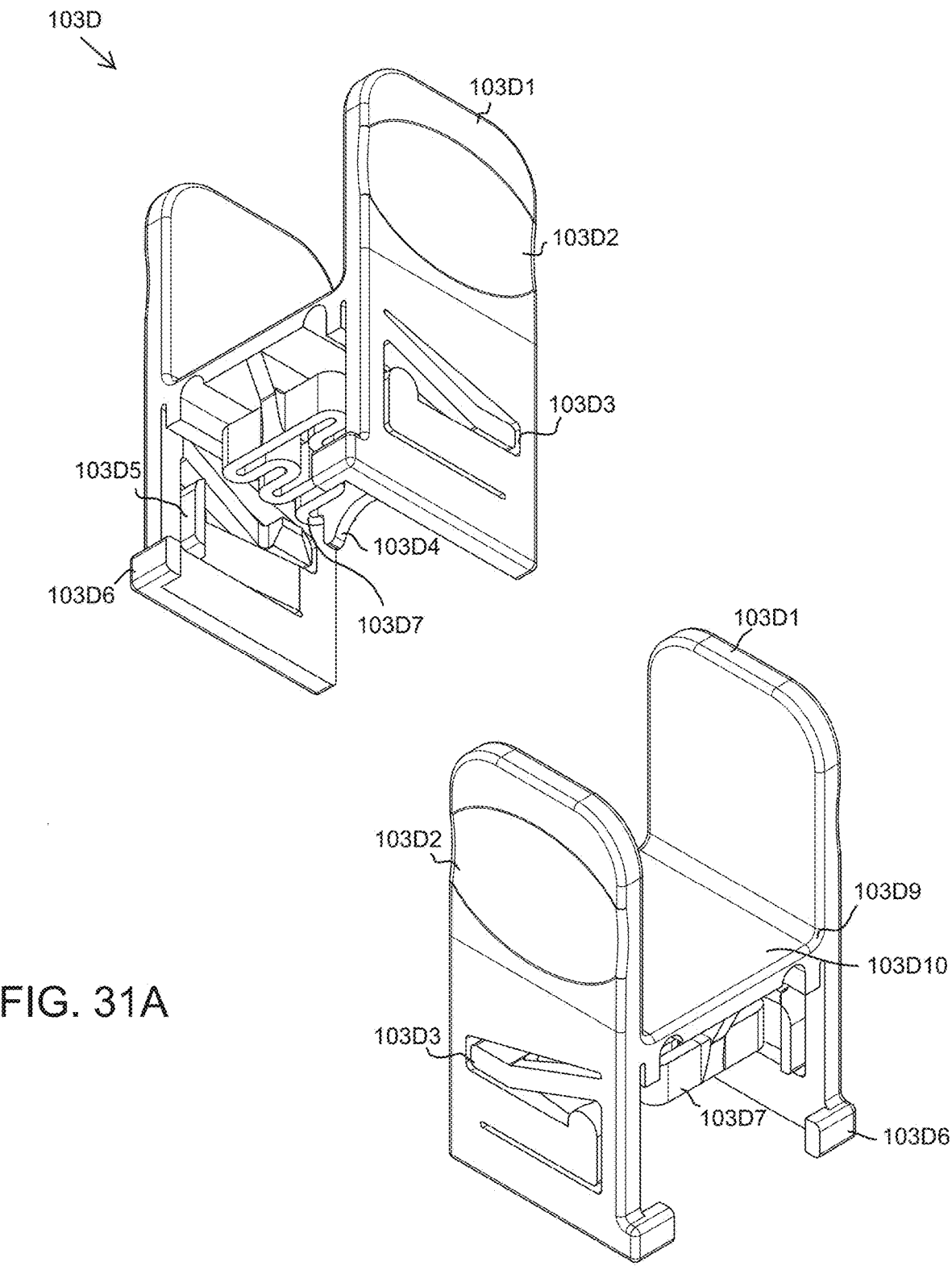
Figure 32:
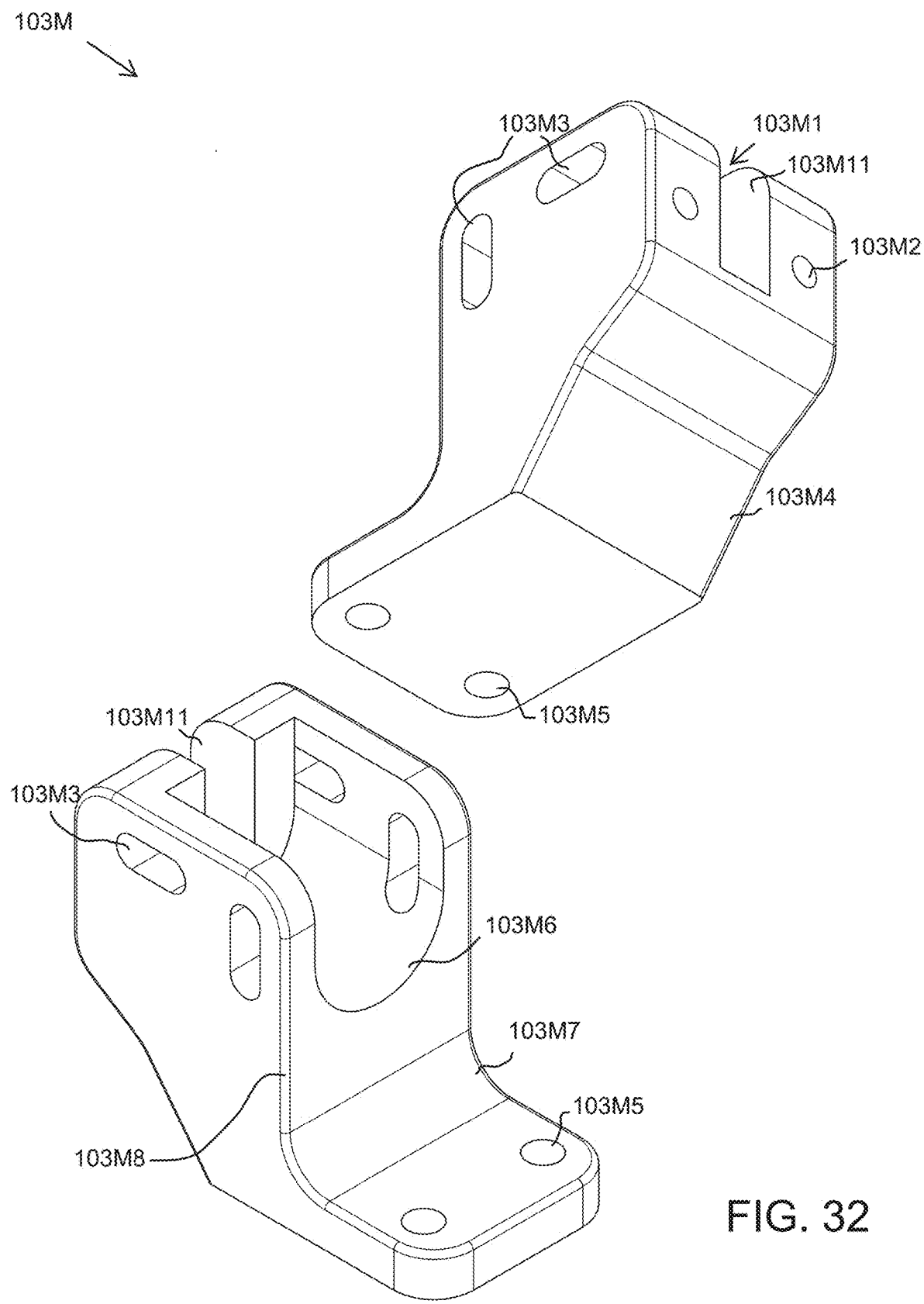
FIG. 32 is a schematic diagram of first and second views of the plunger drive of the present teachings.

Referring now primarily to FIGS. 31A and 31B, barrel slide clip 103D can include goalposts 103D1 that can be grasped at goalpost indents 103D2 to engage and disengage barrel slide clip 103D with/from plunger drive 103M. Barrel slide clip 103D can include floor 103D10 that can provide both a lever around which goalposts 103D1 can pivot when engaging/disengaging with/from plunger drive 103M, and a mounting means for barrel coil 103D7 and barrel arch 103D4. Barrel slide clip 103D can enable retraction of syringe 103G1 (FIG. 26) and can disable backlash. Syringe head 103G11 (FIG. 26) can rest at face 103D4-1 (FIG. 31B) of barrel arch 103D4. Barrel coil 103D7 can provide a spring-like pressure on syringe head 103G11 (FIG. 26) as syringe 103G1 (FIG. 26) delivers at least one first material 79 (FIG. 39) to tissue enclosure 101 (FIG. 2A). Clip anchors 103D6 can secure barrel slide clip 103D to plunger drive 103M at plunger drive side 103M8 (FIG. 32), and at least one clip notch 103D5 can secure barrel slide clip 103D to plunger drive 103M at at least one plunger drive recess 103M3 (FIG. 32).

Referring now primarily to FIG. 32, plunger drive 103M can be operably connected to actuator linear bearing 103N (FIG. 36A) at at least one driver fastening cavity 103M5. Plunger drive 103M can thus travel with actuator carriage 103N (FIG. 36B) as linear actuator 103T (FIG. 36A) causes actuator carriage 103N (FIG. 36B) to travel along screw path 103R (FIG. 36A). Plunger drive 103M can include switch cavity 103M1 that can provide a path through which roller 103Q3 (FIG. 28) can travel as it engages with plunger head 103G11 (FIG. 26). Roller 103Q3 (FIG. 28) can be positioned adjacent to roller wall 103M11. Plunger drive 103M can be connected to switch holder 103P using at least one plunger fastener cavity 103M2 and associated fasteners. At least one plunger fastener cavity 103M2 and the associated fasteners can be any shape and size. Plunger drive 103M can include tapered wall 103M4 that can provide clearance for actuator housing 103T4 (FIG. 36A). Plunger drive 103M can include plunger head cavity 103M6 that can provide space for plunger head 103G11 (FIG. 26) to enter. Plunger drive 103M can include plunger filet 103M7 that can enhance strength and stability of plunger drive 103M.

Referring now primarily to FIG. 33, delivery system connector 103E can include mount side 103E7 that can operably couple linear actuator 103T (FIG. 36A) and needle guide 103J (FIG. 34). Delivery system connector 103E can include adjacent side 103E6 that can be mounted adjacent to, but spaced from, mounting crossbar 109G (FIG. 10). At least one first connector fastening cavity 103E5, which can be recessed for flush mounting, and associated fasteners can couple delivery system connector 103E with needle guide 103J (FIG. 34). At least one second connector fastening cavity 103E4 and associated fasteners can couple delivery system connector 103E with linear actuator 103T (FIG. 36A). For reducing the weight of printer 100 (FIG. 2A) and for other optional features, delivery system connector 103E can optionally include at least one cavity 103E3, and can include a tapered profile in which connector first end 103E2 can be sized differently from connector second end 103E1.

Referring now to FIG. 33A, delivery system connector second configuration 103E-1 can include mount side 103E-1E7 that can operably couple linear actuator 103T (FIG. 36A) and needle guide 103J (FIG. 34). Delivery system connector second configuration 103E-1 can include adjacent side 103E-1E6 that can be mounted adjacent to, but spaced from, mounting crossbar 103G (FIG. 10). At least one first connector fastening cavity 103E-1E5, which can be recessed for flush mounting, and associated fasteners can couple second configuration delivery system connector 103E-1 with needle guide 103J (FIG. 34). At least one second connector fastening cavity 103E-1E4 and associated fasteners can couple delivery system connector second configuration 103E-1 with linear actuator 103T (FIG. 36A). For reducing the weight of printer 100 (FIG. 1A) and for other optional features, delivery system connector second configuration 103E-1 can optionally include at least one cavity 103E-1E3 and/or 103E-1B, and can include a tapered profile in which connector first end second configuration 103E-1E2 can be sized differently from connector second end second configuration 103E-1E1. Swing clamp 103T (FIG. 25F-1)

can be attached to delivery system connector second configuration 103E-1 at connector cavity 103E-1C.

Referring now primarily to FIG. 34, needle guide 103J can couple barrel holder 103K (FIG. 35) with delivery system connector 103E (FIG. 33). Needle guide 103J can include needle cavity 103J11 through which needle 103H (FIG. 26) can process as it deposits at least one material 79 (FIG. 39) into tissue enclosure 101 (FIG. 2A). Needle guide 103J can include contoured edge 103J7 that can bridge the space between treadle foot 103J6 and needle guide connector edge 103J8. Needle guide 103J can be operably coupled to delivery system connector 103E (FIG. 33) at at least one guide fastener cavity 103J3 using associated fasteners. In some configurations, needle guide 103J can include guide cavity 103J2 that can include at least one partial or complete recess in needle guide 103J. Needle guide 130J can include at least one filet 103J4 that can strengthen needle guide 103J. Needle guide 103J can also provide mounting and fastening of barrel holder 103K (FIG. 35) through at least one guide fastener cavity 103J5 and associated fasteners.

Referring now primarily to FIG. 35, barrel holder 103K can provide a secure mounting vehicle for barrel 103G (FIG. 26). Barrel holder 103K can retain barrel 103G (FIG. 26) in a fixed position as syringe system 103G1 (FIG. 26) moves within tissue enclosure 101 (FIG. 2A). At least one holder fastener cavity 103K3, at least one guide fastener cavity 103J5 (FIG. 34), and associated fasteners can operably couple barrel holder 103K with needle guide 103J (FIG. 34) at holder first side 103K5. At least one holder fastener cavity 103K3 can enable flush mounting through, for example, recessed sides 103K31. Holder notches 103K71 and 103K72 can lodge barrel 103G (FIG. 26) adjacent to and flush with holder wall 103K4 between holder arms 103K81 and 103K82. Barrel holder 103K can optionally include tapering between arm side 103K1 and fastener side 103K2 to reduce the size of barrel holder 103K and thus the weight of printer 100 (FIG. 2A). In particular, arm side 103K1 can be sized to accommodate barrel 103G (FIG. 26), while fastener side 103K2 can be sized to accommodate needle guide 103J (FIG. 34).

Referring now to FIGS. 35A and 35B, barrel holder second configuration 103V can provide a secure mounting area for syringe barrels of many sizes and shapes. Barrel holder second configuration 103V can itself be sized and shaped to accommodate various sizes and shapes of syringe barrels, for example, but not limited to, syringe barrel 103CC (FIG. 26A) and syringe barrel 103DD (FIG. 26B). Barrel holder second configuration can include, but is not limited to including, barrel cavity 103V2 for mounting a syringe barrel, and mounting bumper cavities 103V1 that can accommodate mounting bumpers (not shown) of any type and rigidity. Mounting bumpers can buffer the syringe from pressure effects from bumper 103W (FIG. 25F-3). At least one holder fastener cavity 103V3 and/or 103V4, at least one guide fastener cavity 103J5 (FIG. 34), and associated fasteners can operably couple barrel holder second configuration 103V with needle guide 103J (FIG. 34) at holder first side 103V7 (FIG. 35B).

Referring now primarily to FIG. 36A, linear actuator 103T can include ball or lead screw 103R and a support bearing (not shown), that combine to enable motion of syringe head 103G11 (FIG. 26). Linear actuator 103T can be a commercially available product such as, for example, but not limited to, the THK® KR1501B linear actuator. Linear actuator 103T can include at least one linear bearing 103N that can include, for example, if a ballscrew is used, ball circuits (not shown) and ballscrew nut (not shown). Actuator housing 103T4 can include an angular bearing (not shown) and motor/gearbox cavity 103T2 which can be operably coupled with actuator housing 103T4 through at least one actuator mounting cavity 103T1 and associated fasteners. Linear actuator 103T can include at least one mechanical stop 103T6 operatively coupled with actuator housing units 103T4 and 103T7. Linear actuator 103T can include rails 103L upon which at least one linear bearing 103N rests as it rides along screw 103R. Actuator fasteners 103T3 and associated fasteners can enable operable coupling among linear actuator 103T, delivery system connector 103E (FIG. 33), and y-axis block 105 (FIG. 14A). The coupling among linear actuator 103T and y-axis block 105 (FIG. 14A) can enable multidirectional movement of syringe system 103G1 (FIG. 26), thus enabling printing into tissue enclosure 101 (FIG. 2A) of CAD file 65A (FIG. 39).

Figure 36B:
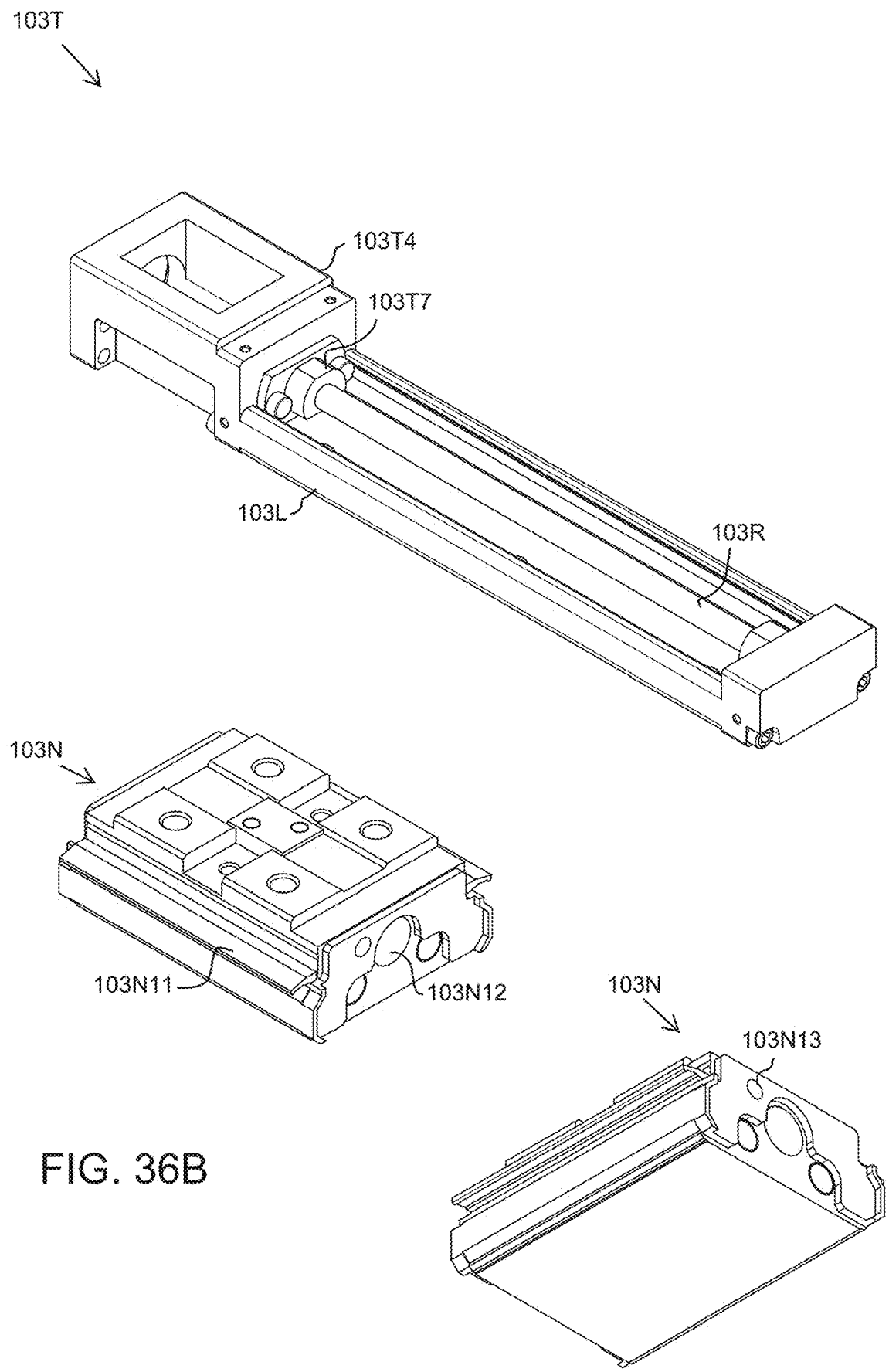
FIG. 36B is a schematic diagram of another view of the linear actuator, and first and second views of the linear bearing of the present teachings.

Referring now primarily to FIG. 36B, linear bearing 103N can include wings 103N11 that can rest on rails 103L. Linear bearing 103N can also include grease nipple 103N13 to apply lubricant to, for example, but not limited to, ball circuits (not shown).

Figure 37A:
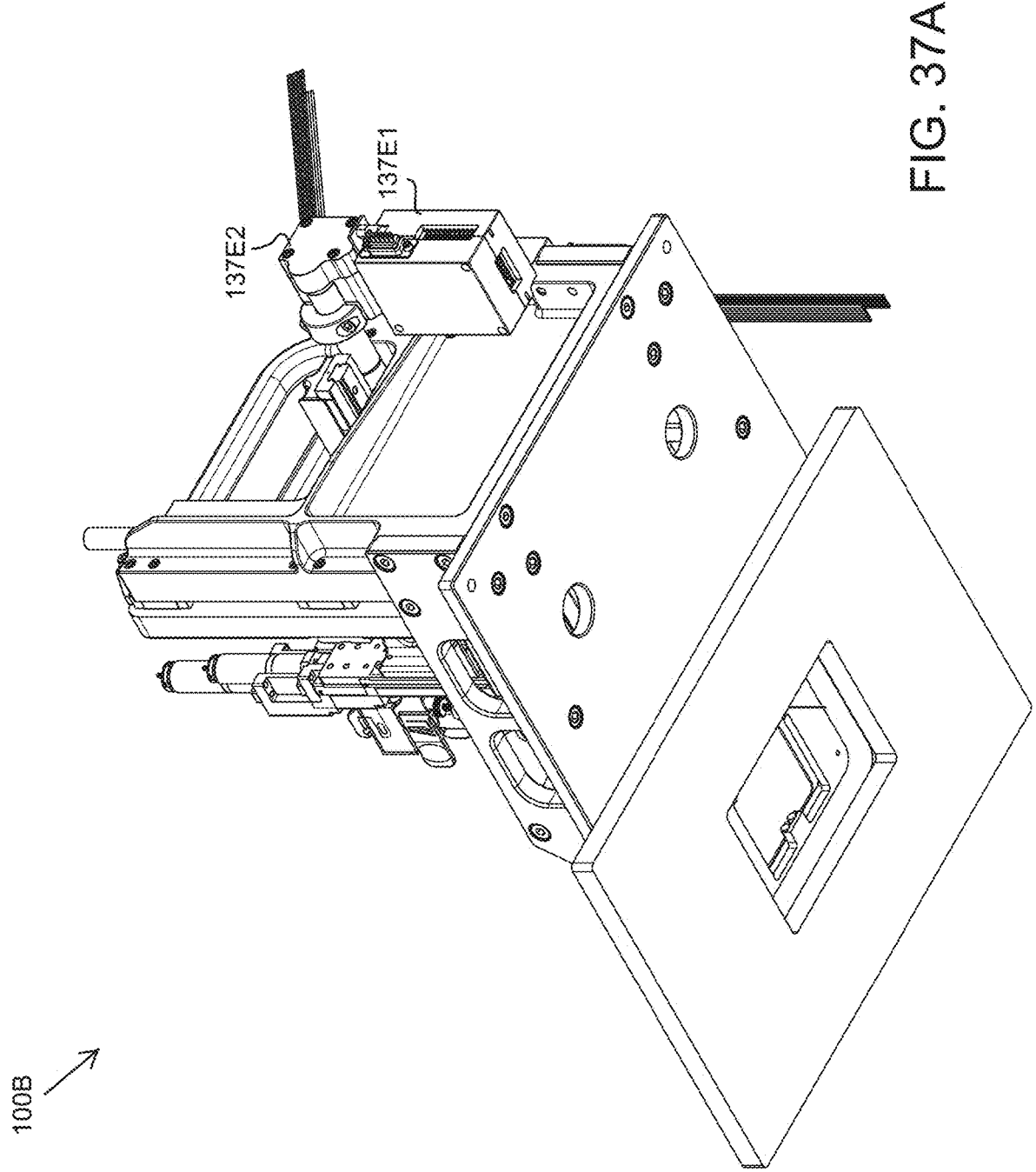
FIGS. 37A and 37B are schematic diagrams of various views of the printer third configuration of the present teachings.
Figure 37B:
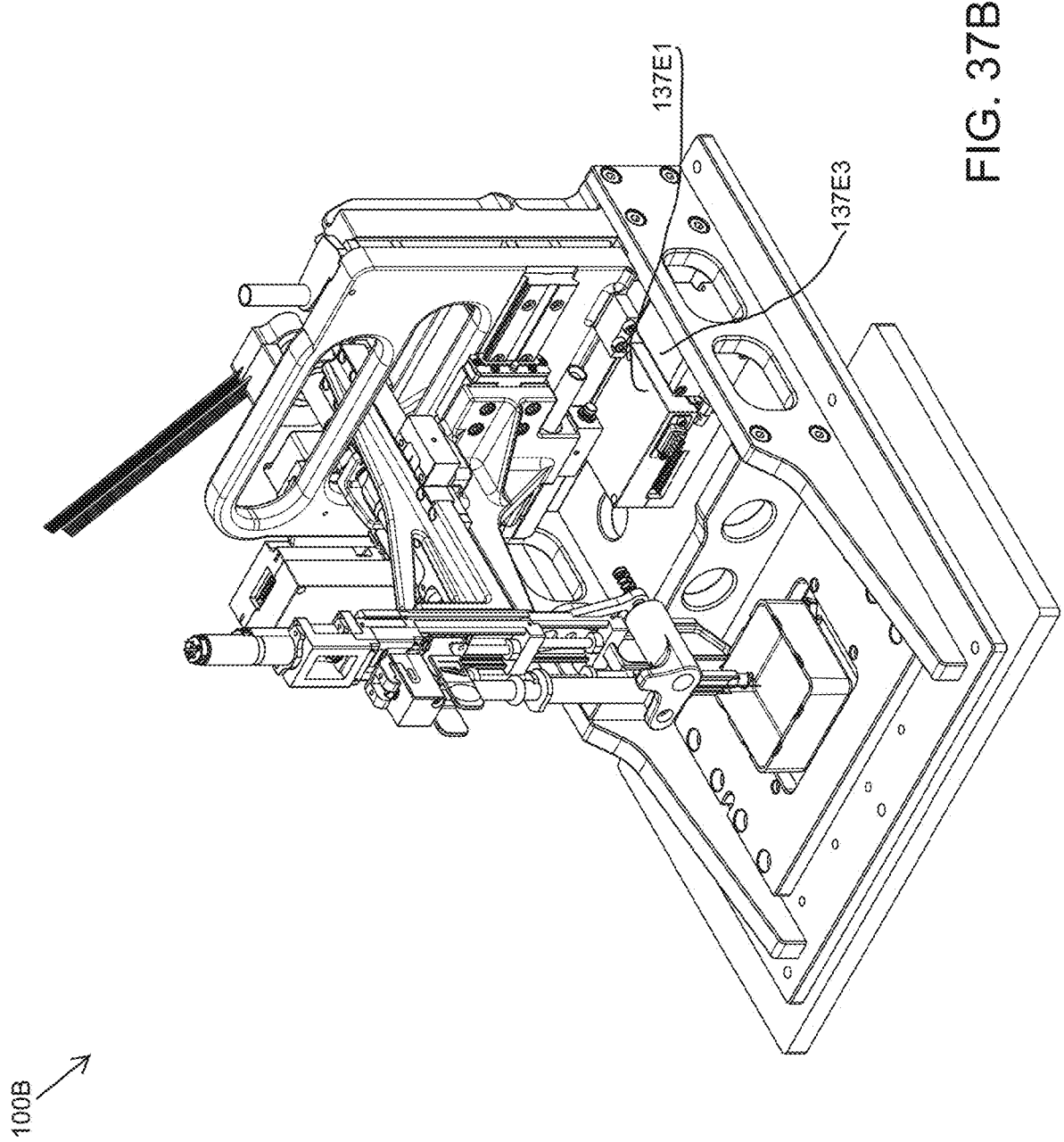

Referring now to FIGS. 37A and 37B, printer third configuration 100B can include motor junction box 137E2, shell casing junction box 137E1, and junction box lower assembly 137E3.

Figure 37C:
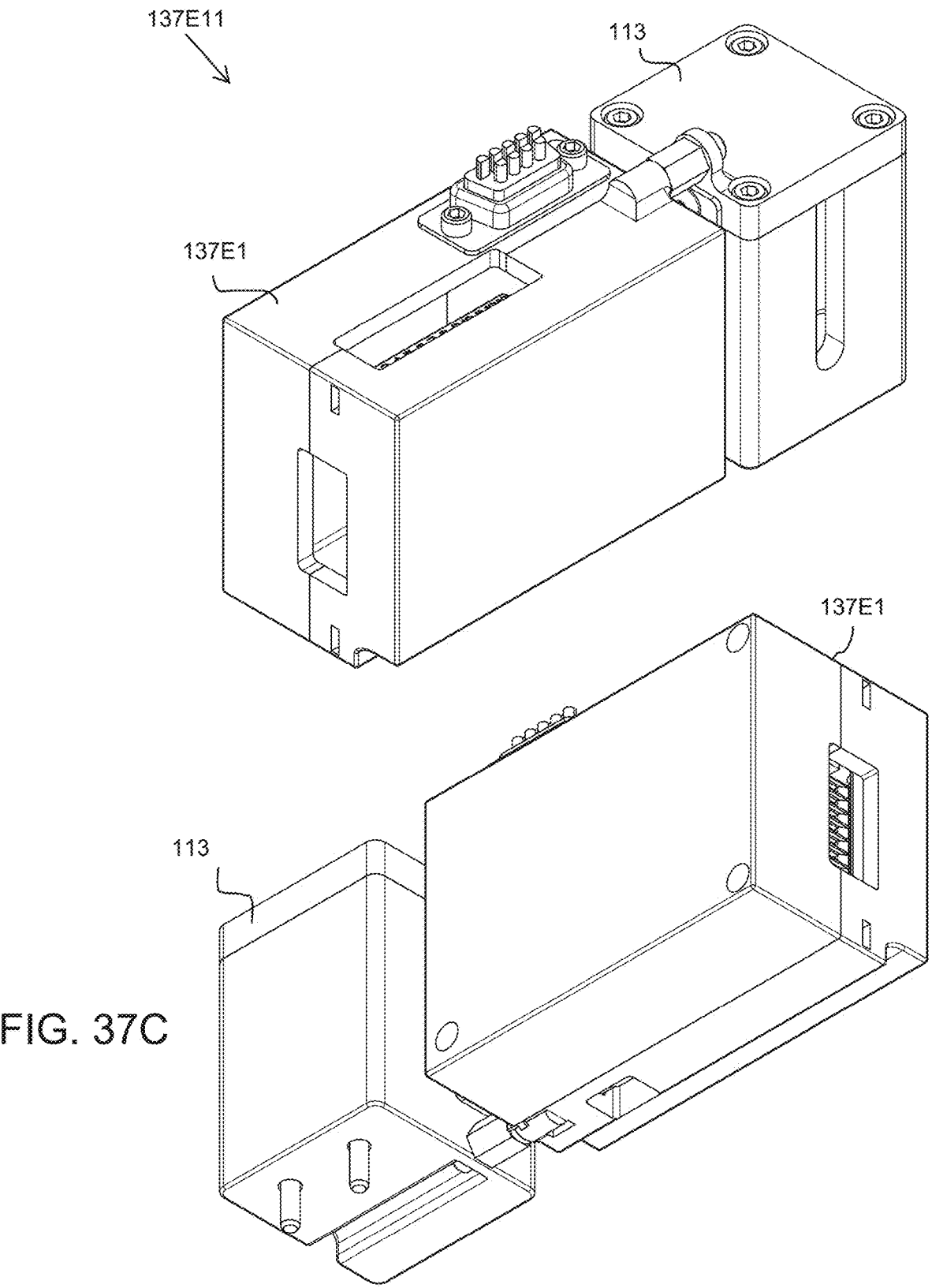
FIG. 37C is a schematic diagram of first and second views of the junction box combination of the present teachings.

Referring now to FIG. 37C, junction box combination 137E11 can include, but is not limited to including, junction box outer housing 137E1 and junction box lower assembly 113 (FIG. 37D).

Referring now primarily to FIG. 37D, junction box lower assembly 113 can be mounted upon x-axis baseplate 107B (FIG. 16) at x-baseplate second mount 107B11 (FIG. 16) at connector cavities 113G using associated fasteners, for example. Junction box lower faceplate 115 (FIG. 37B) can protect interior cabling by being mounted onto assembly face 113F at faceplate connecting cavities 113B using associated fasteners. Assembly first side 113A can include ribbon cable cavity 113J that can provide an exit point for ribbon cabling that can allow conversion of motor cabling to commercial cabling, for example, but not limited to, high flex cabling. Assembly second side 113K can include connector cavity 113H into which junction box connector 117 (FIG. 37C) can be mounted between housing arms 113D and attached by aligning box connector cavity 113L and box cavity 117D (FIG. 37C). Junction box lower assembly 113 can include beveled edges 113C that can provide for streamlined positioning in printer 100 (FIG. 1A), and connector bulges 113E to accommodate fasteners for junction box lower faceplate 115 (FIG. 37B) without protruding into the streamlined space of printer 100 (FIG. 1A).

Figure 37E:
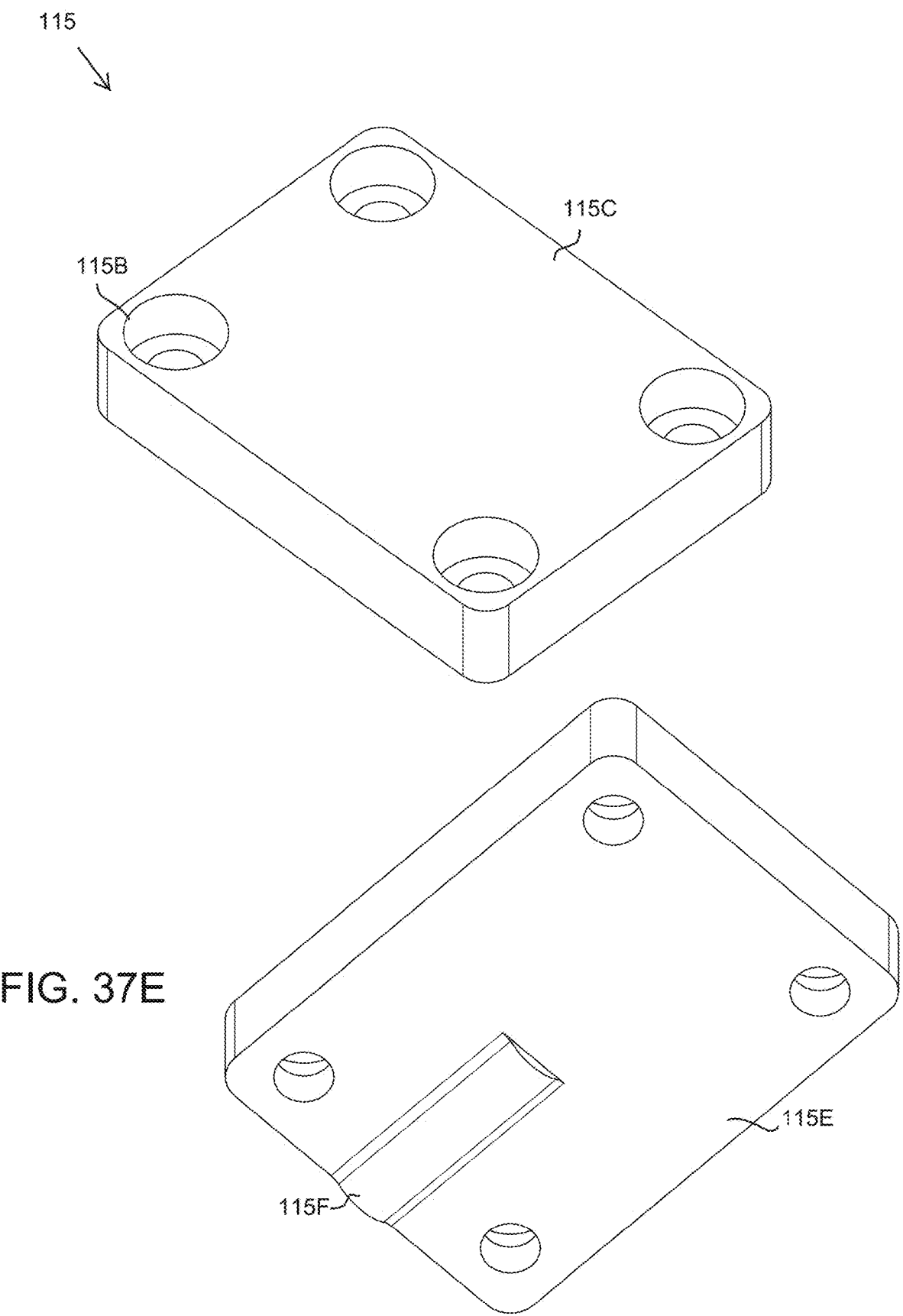
FIG. 37E is a schematic diagram of first and second views of the junction box lower faceplate of the present teachings.

Referring now primarily to FIG. 37E, junction box lower faceplate 115 can enclose junction box lower assembly 113 (FIG. 37A) by aligning faceplate connecting cavities 113B (FIG. 37A) with fastening cavities 115B and associated fasteners at first faceplate side 115C. Fastening cavities 115B can be recessed for flush mounting. Faceplate bulge 115F on faceplate second side 115E can accommodate fasteners associated with box cavity 117D (FIG. 37C) so that faceplate bulge 115F can face the interior of junction box lower assembly 113 (FIG. 37A), leaving faceplate first side 115C streamlined. Faceplate bulge 115F can increase wall thickness around fasteners associated with a junction box connector that can provide a connection to processor 55 (FIG. 39).

Referring now primarily to FIG. 38, gas spring 119 can store energy pneumatically and can retain the position of printer 100 (FIG. 2A) when printer 100 (FIG. 1A) is powered off. Gas spring 119 can include cylinder 119C, rod guide 119B, and piston rod 119A.

Configurations of the present teachings relate to a multi-dimensional printing device to be employed for printing a biological or non-biological specimen into a gel-like material. The printed specimen can be result of one or more user commands directed to the printing device through a control system. The scope of the printing device should not be limited to the configurations of the present teachings.

Figure 38B:
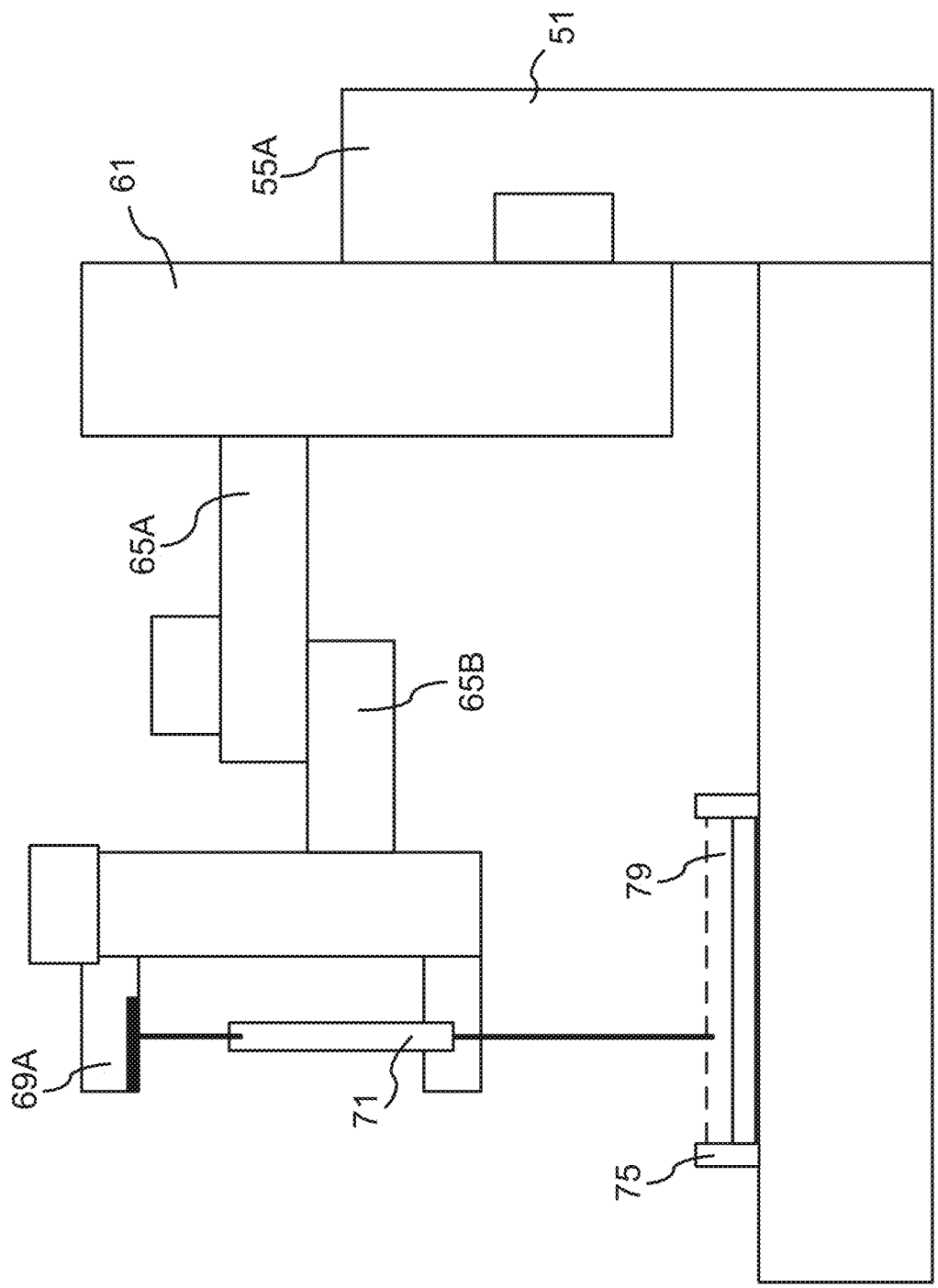
FIG. 38B is a schematic block diagram of the exemplary printing device with printing cartridge and vessel wherein printing is performed.
Figure 38C:
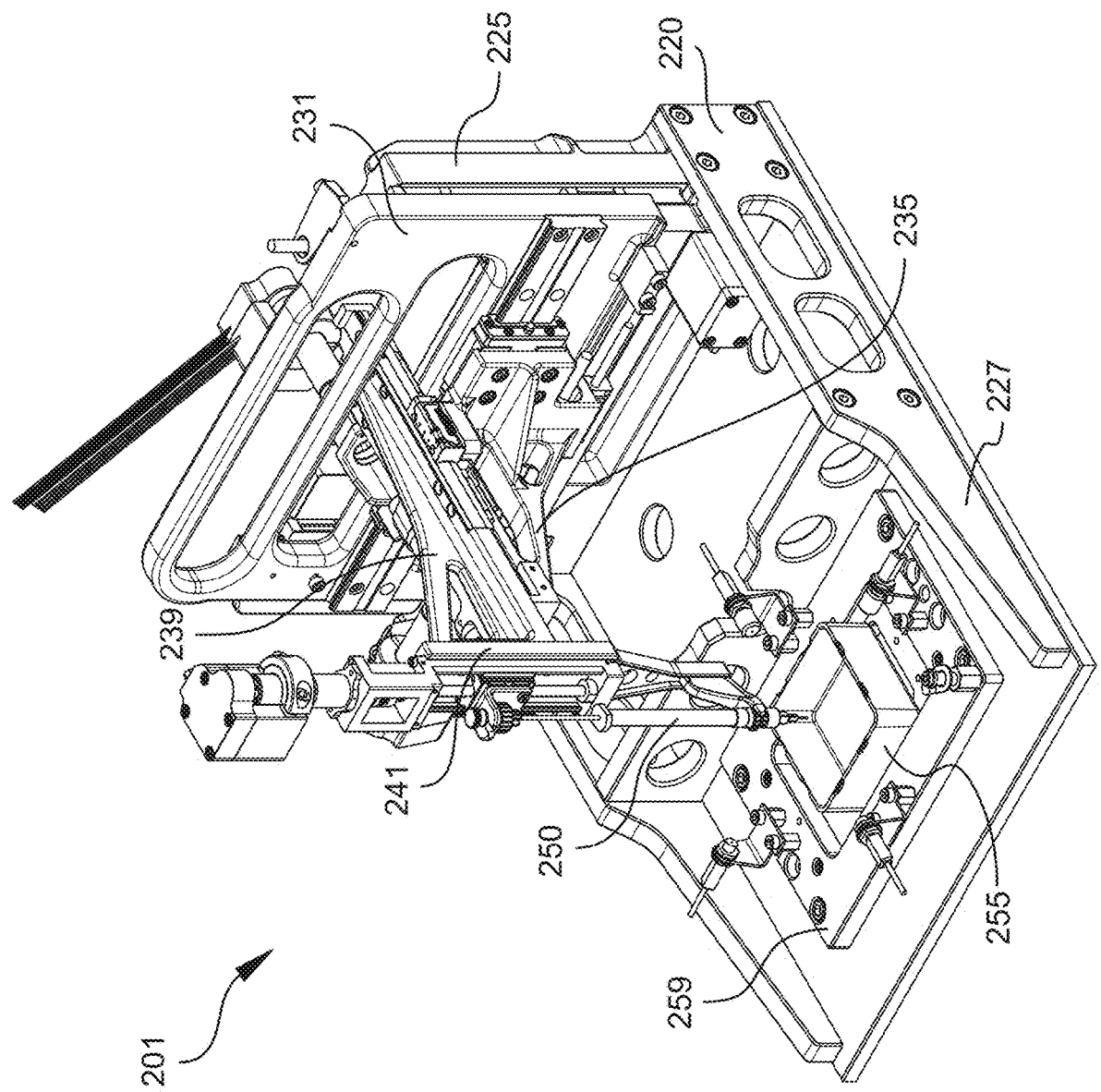
FIG. 38C is a front top right-side perspective view of the exemplary printing device with a single cartridge delivery system.
Figure 38D:
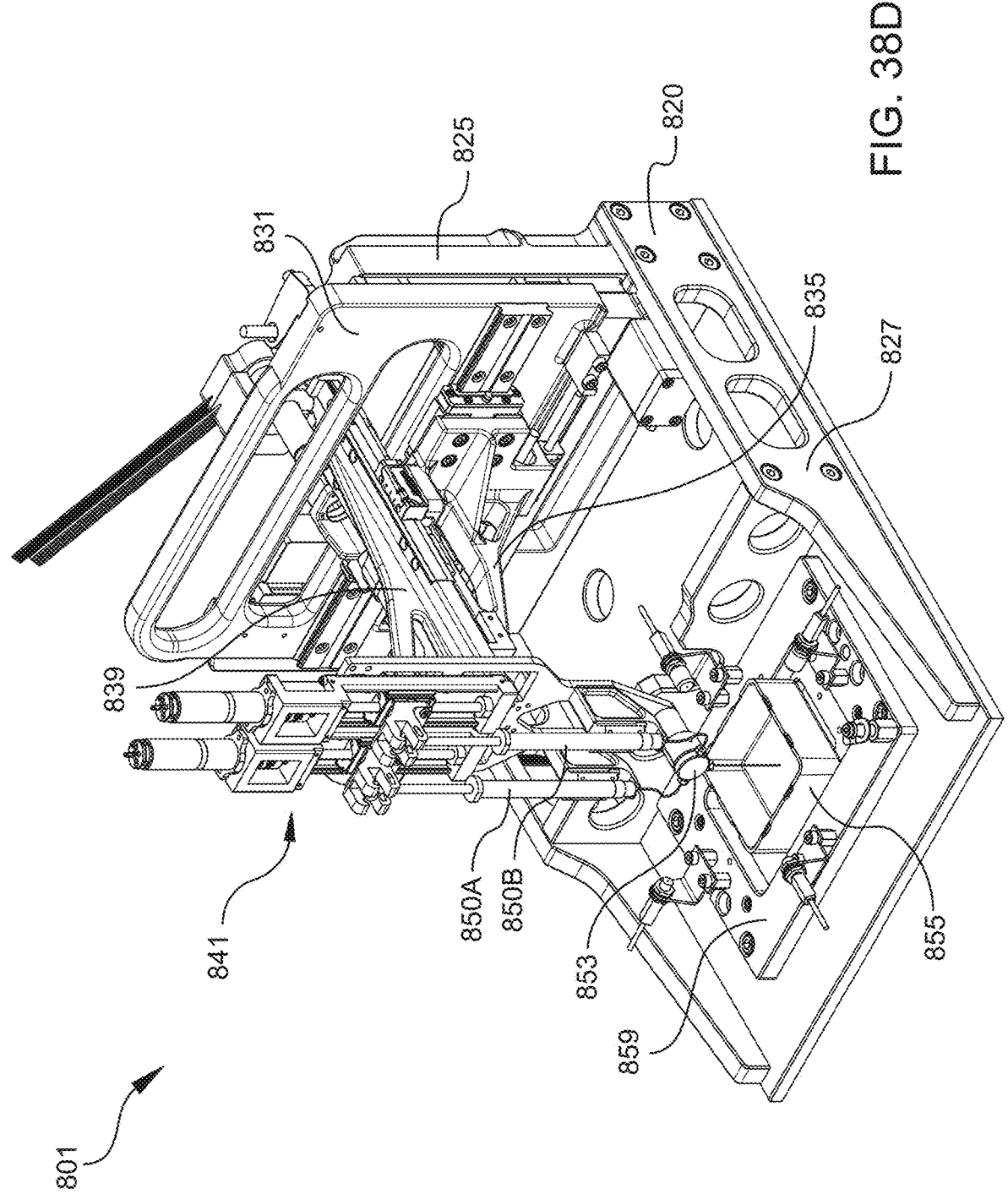
FIG. 38D is a front top right-side perspective view of the exemplary printing device with a dual cartridge delivery system.
Figures 38E, 38F:
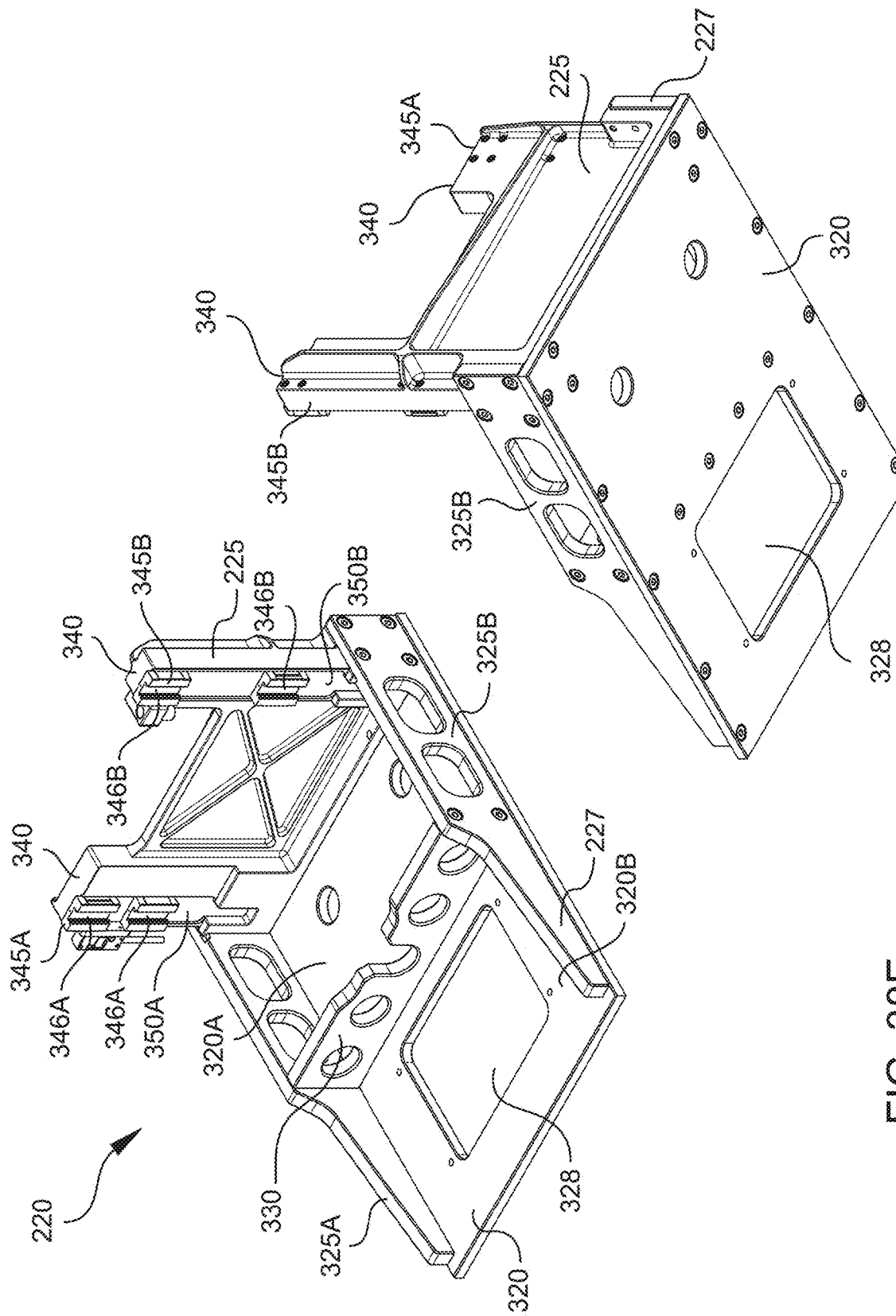
FIG. 38E is a front top right-side perspective view of a chassis belonging to the exemplary printing device.
FIG. 38F is a bottom rear left-side perspective view of a chassis belonging to the exemplary printing device.
Figure 38G:
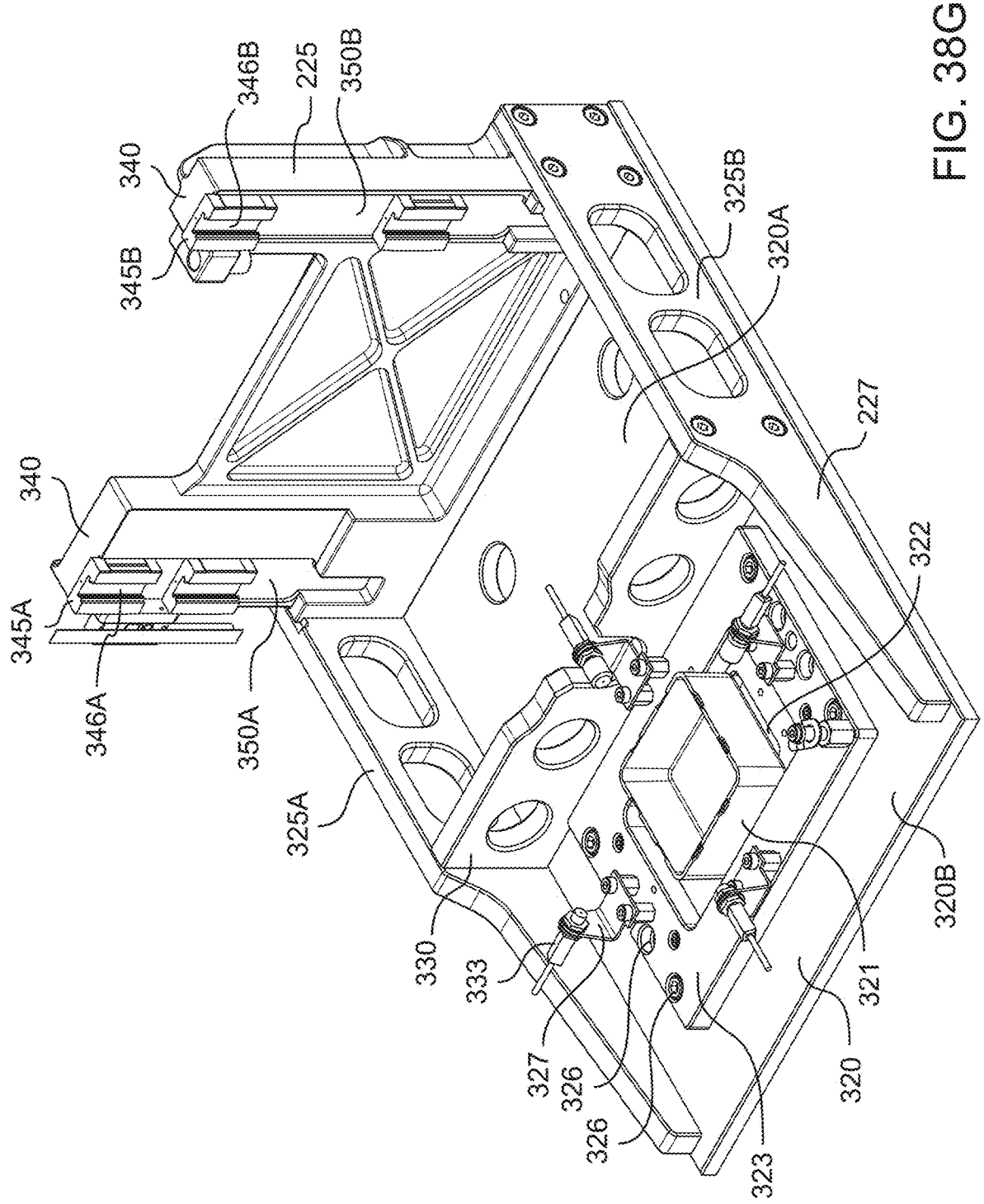
FIG. 38G is a front top right-side perspective view of the chassis of the exemplary printing device along with components wherein printing is performed.
Figure 38H:
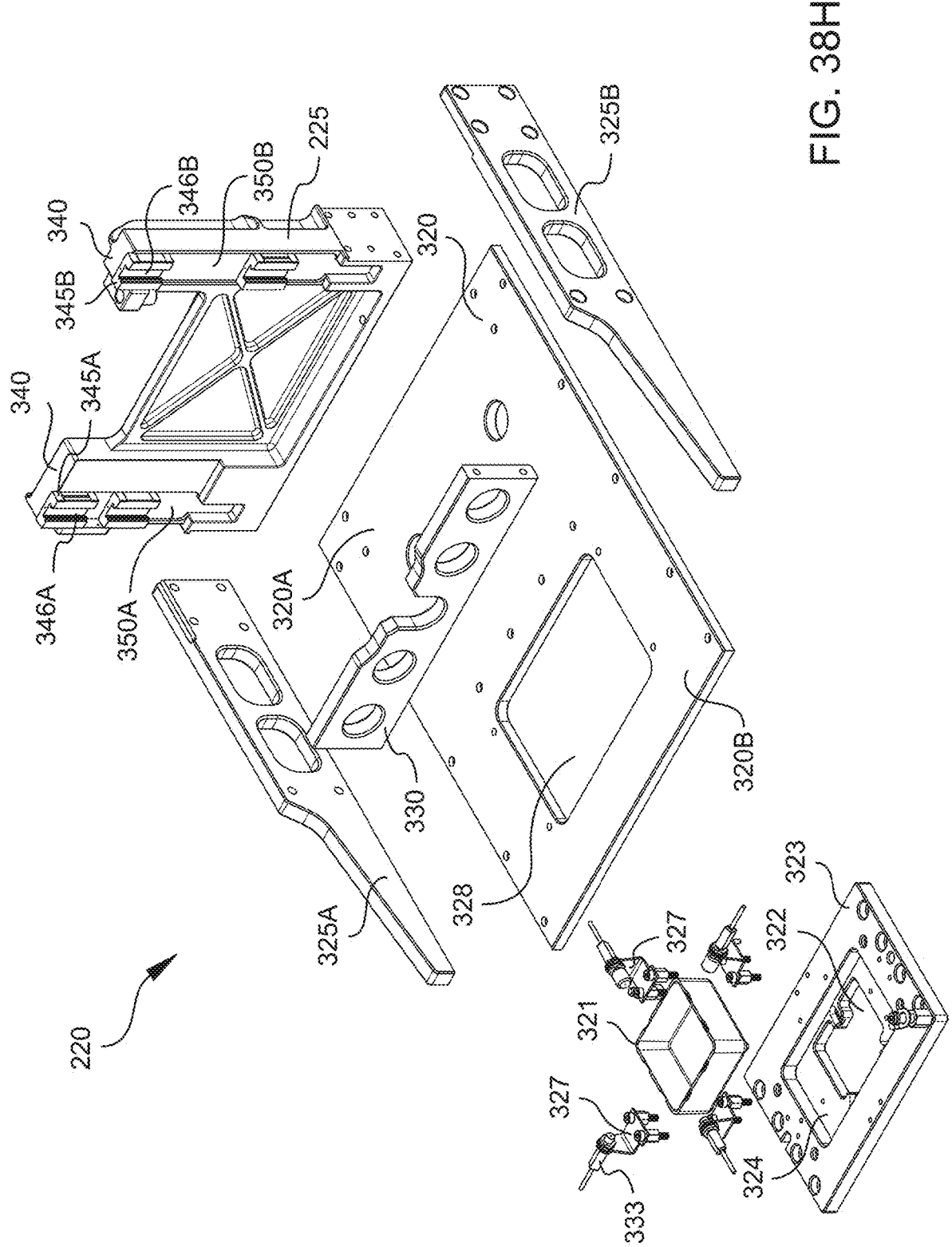
FIG. 38H is a front top right-side exploded view of the chassis of exemplary printing device along with components wherein printing is performed.
Figure 38K:
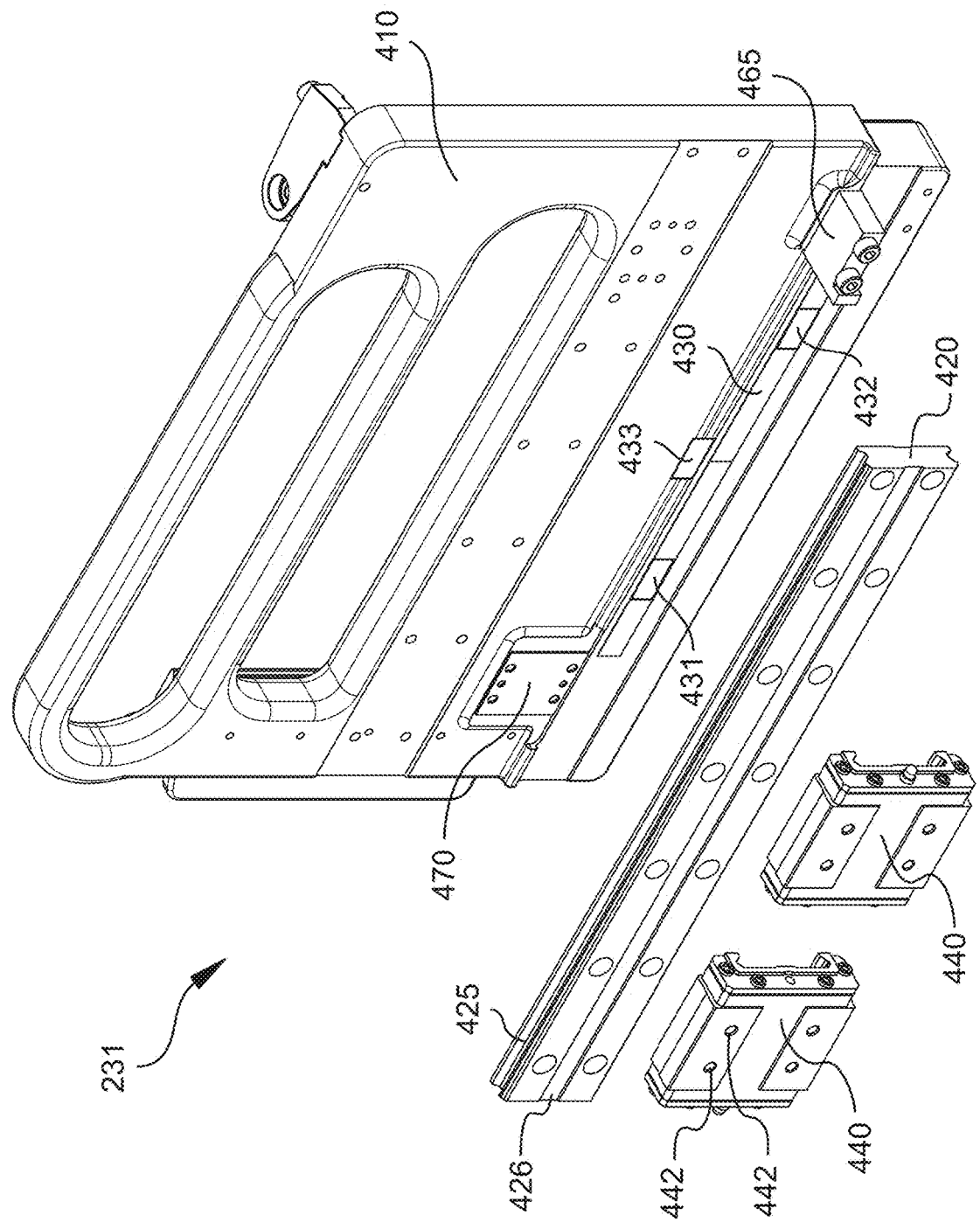
FIG. 38K is a front top right-side exploded view of primary carriage belonging to exemplary printer of the present teachings.
Figure 38M:
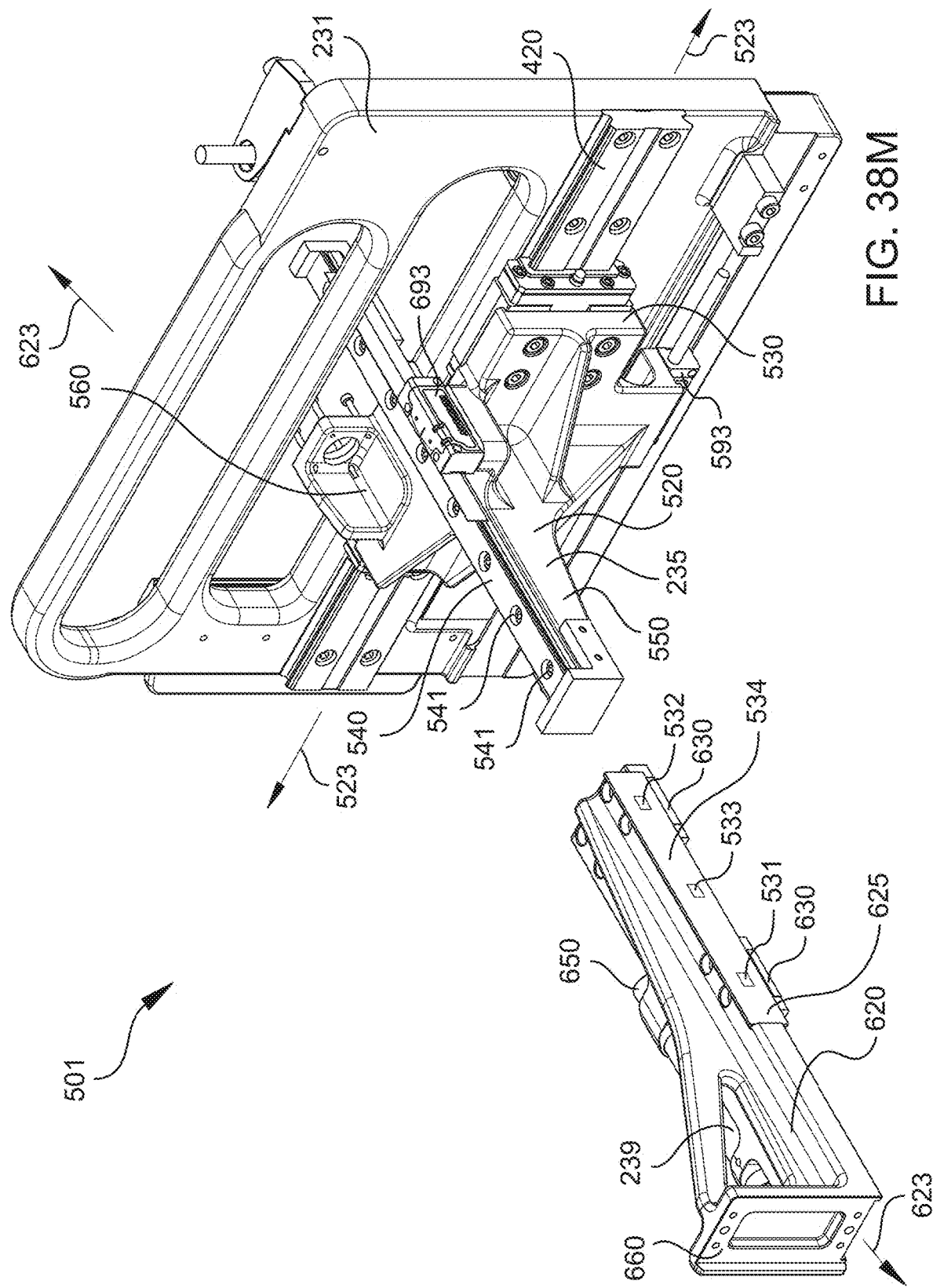
FIG. 38M is a front top right-side partially-exploded view depicting engagement of primary carriage, first sub-carriage and second sub-carriage of the exemplary printer.
Figure 38N:
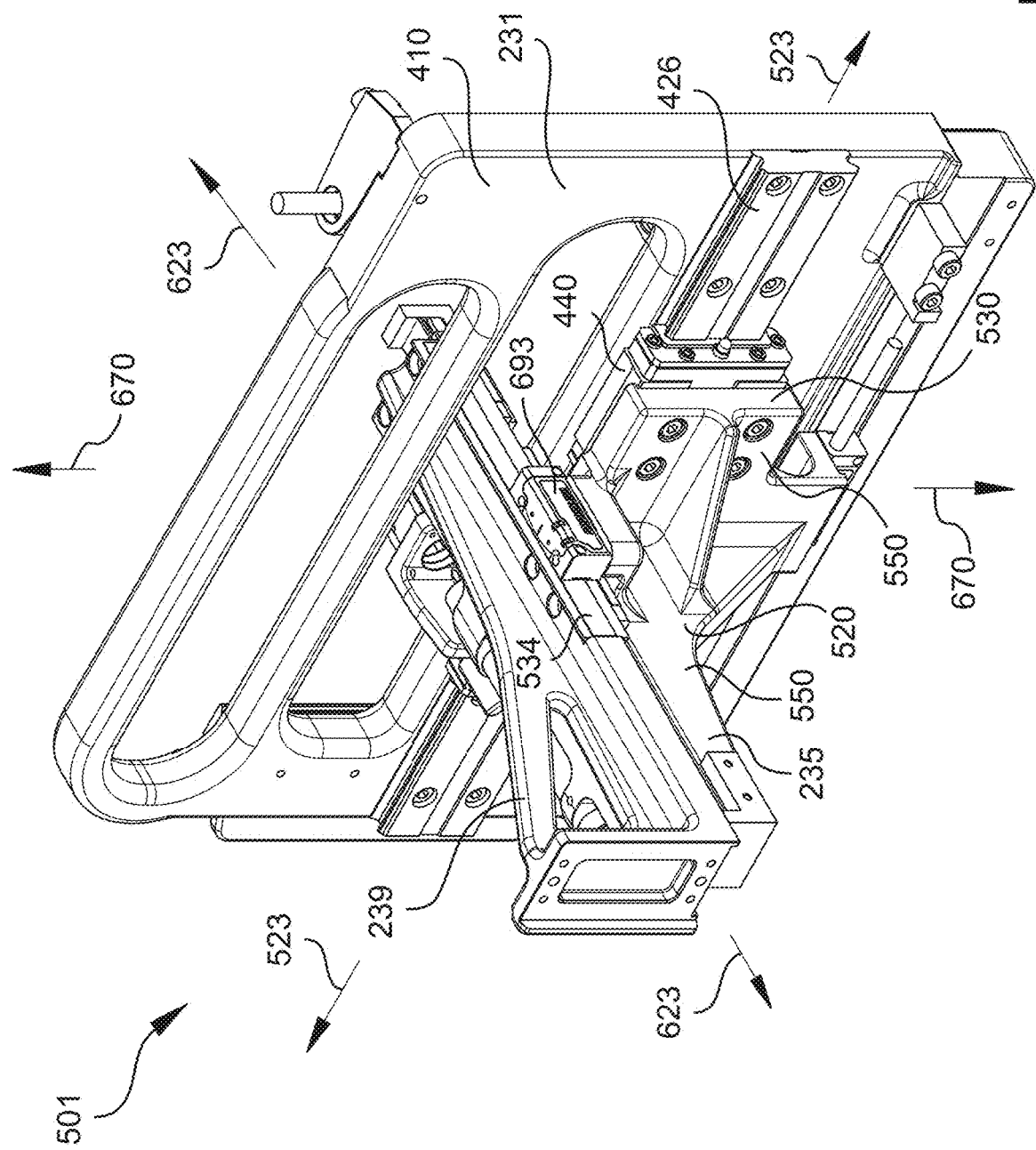
FIG. 38N is a front top right-side perspective view depicting assembly of primary carriage, first sub-carriage and second sub-carriage of the exemplary printer.
Figures 38O, 38P:
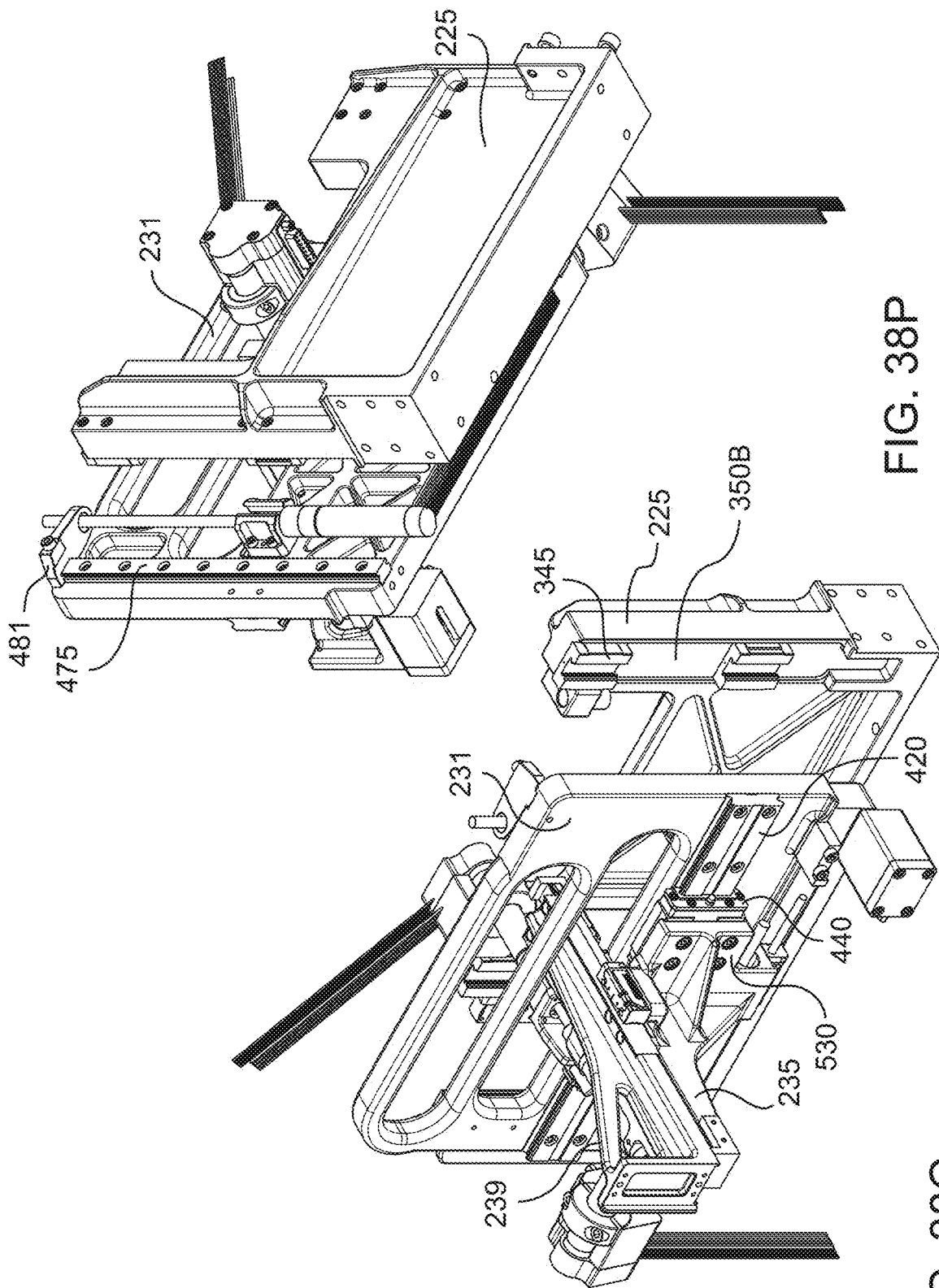
FIG. 38O depicts a front top right-side partially exploded view depicting engagement of primary carriage, first and second sub-carriages and chassis upright of the exemplary printer.
FIG. 38P depicts a rear bottom left-side partially exploded view depicting engagement of primary carriage, first and second sub-carriages and chassis upright of the exemplary printer.
Figure 38R:
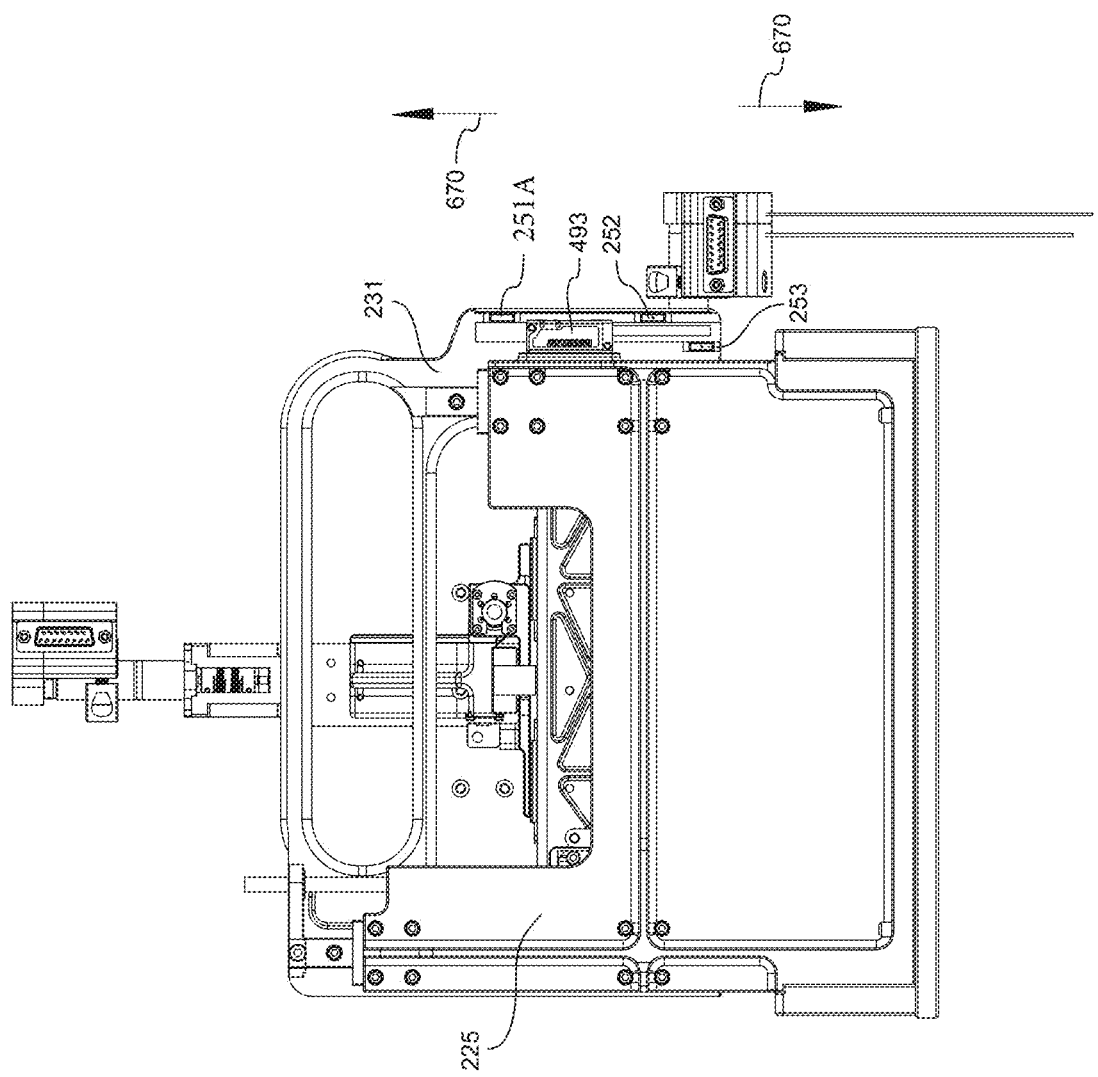
FIG. 38R depicts a rear perspective view depicting engagement of primary carriage, first and second sub-carriages and chassis upright of the exemplary printer.
Figure 38S:
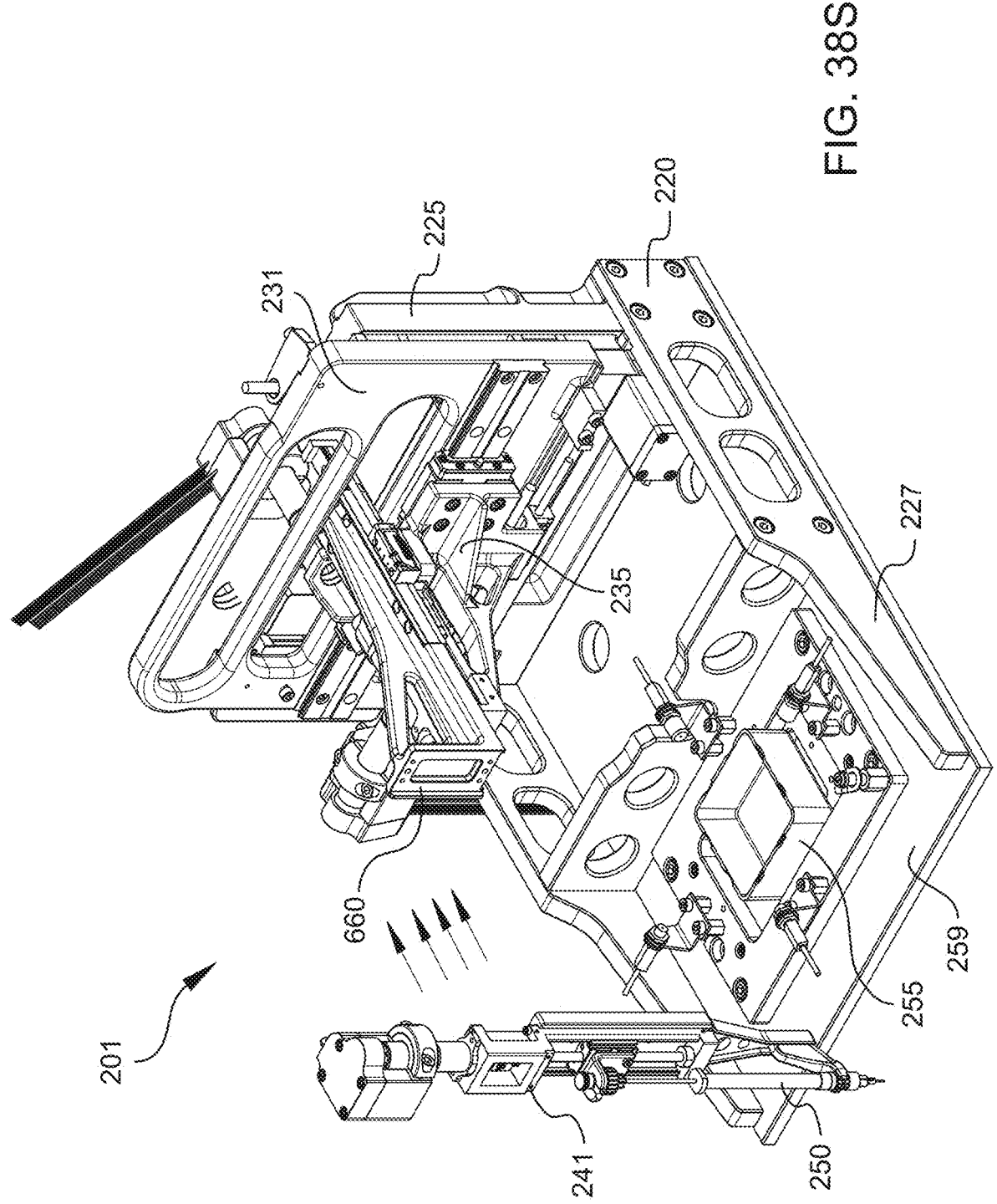
FIG. 38S is a front top right side partially assembled view depicting engagement of a single cartridge delivery system with the remainder of exemplary printer.
Figure 38T:
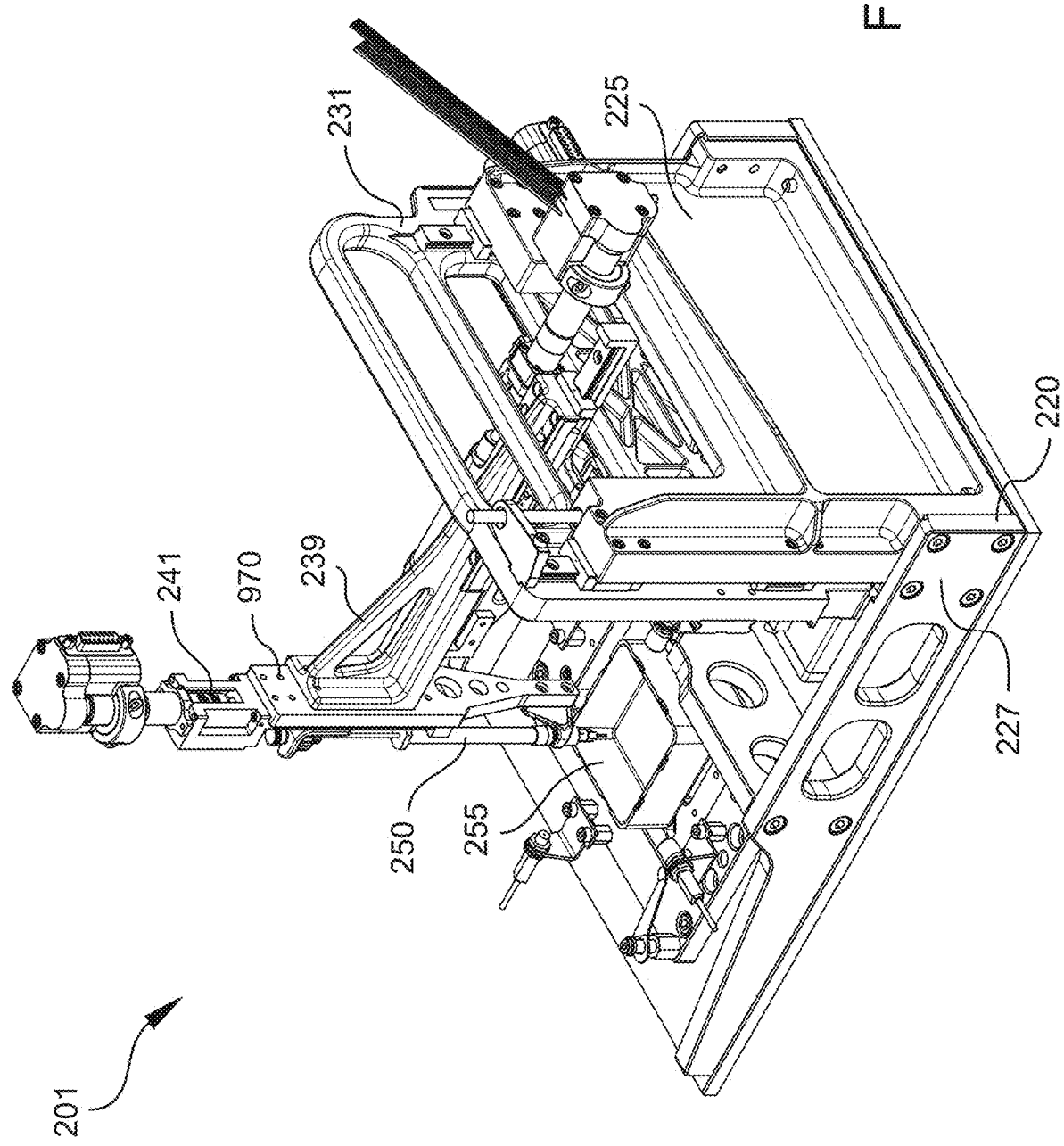
FIG. 38T is a rear top left side perspective view depicting engagement of a single cartridge delivery system with the remainder of printing device.
Figure 38W:
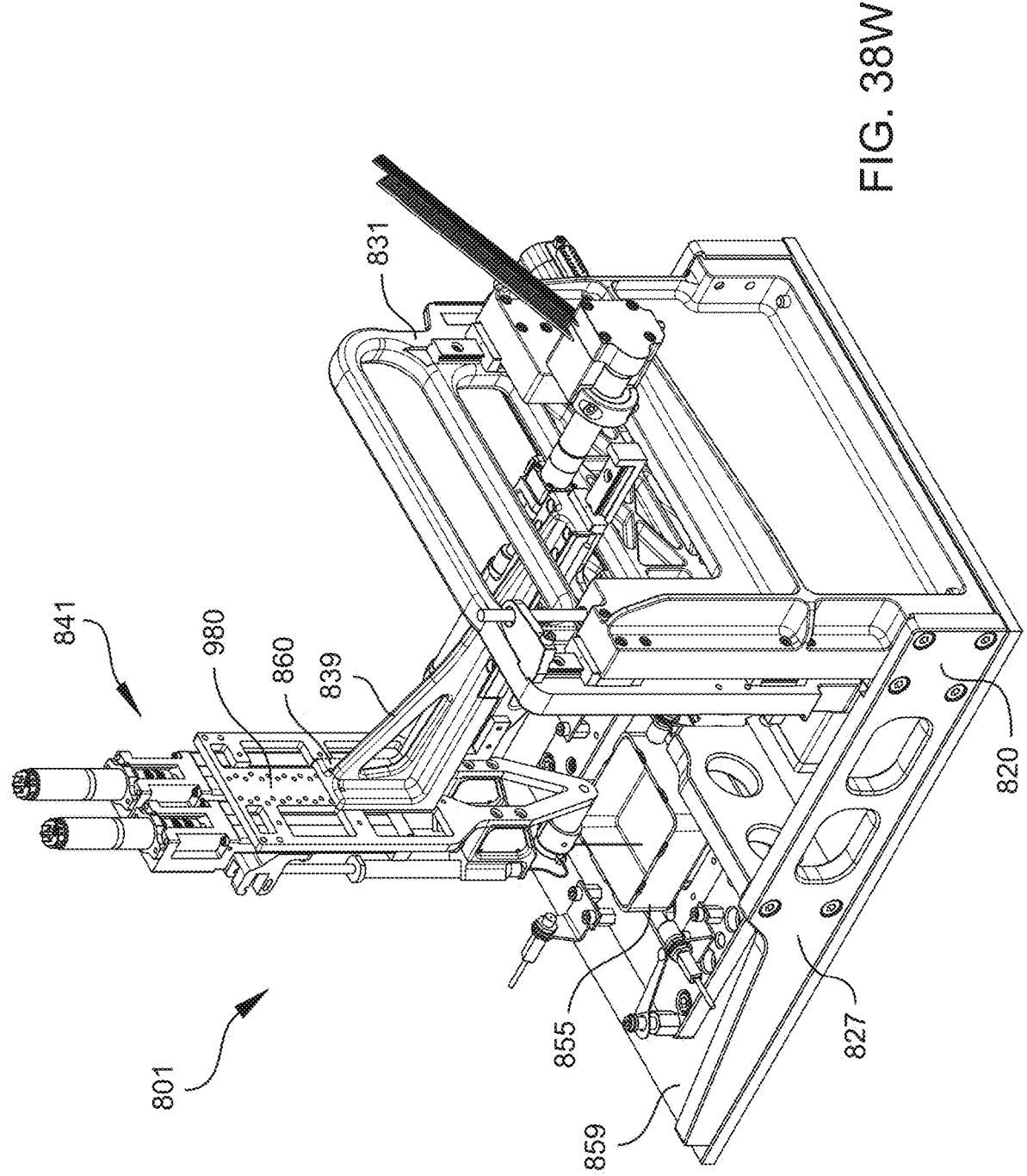
FIG. 38W is a rear top left side perspective view depicting engagement of a dual cartridge delivery system with the remainder of exemplary printing device.
Figure 38A:
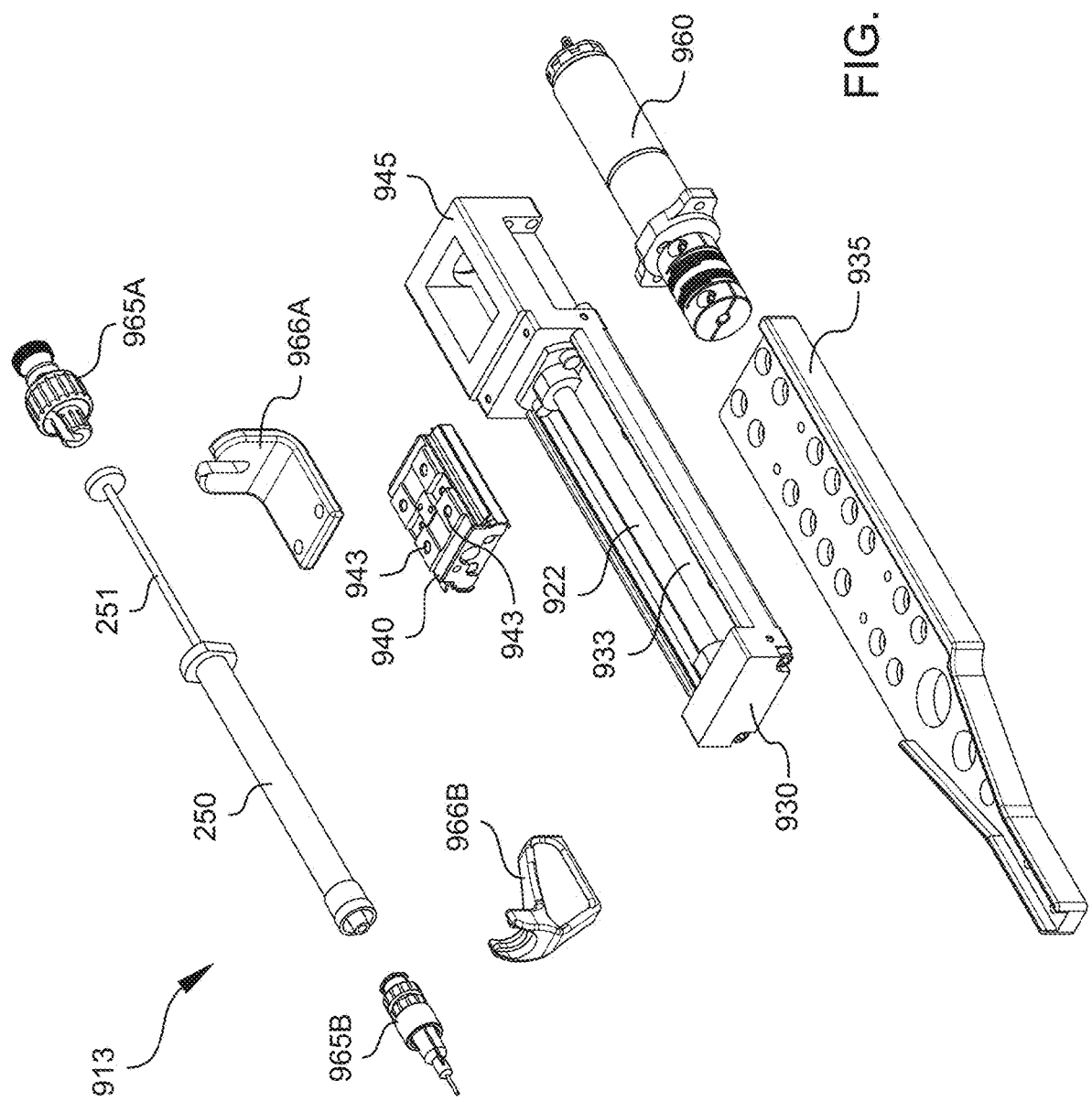
FIG. 38A is a schematic block diagram of the exemplary printing device of the present teaching.
Figure 38D:
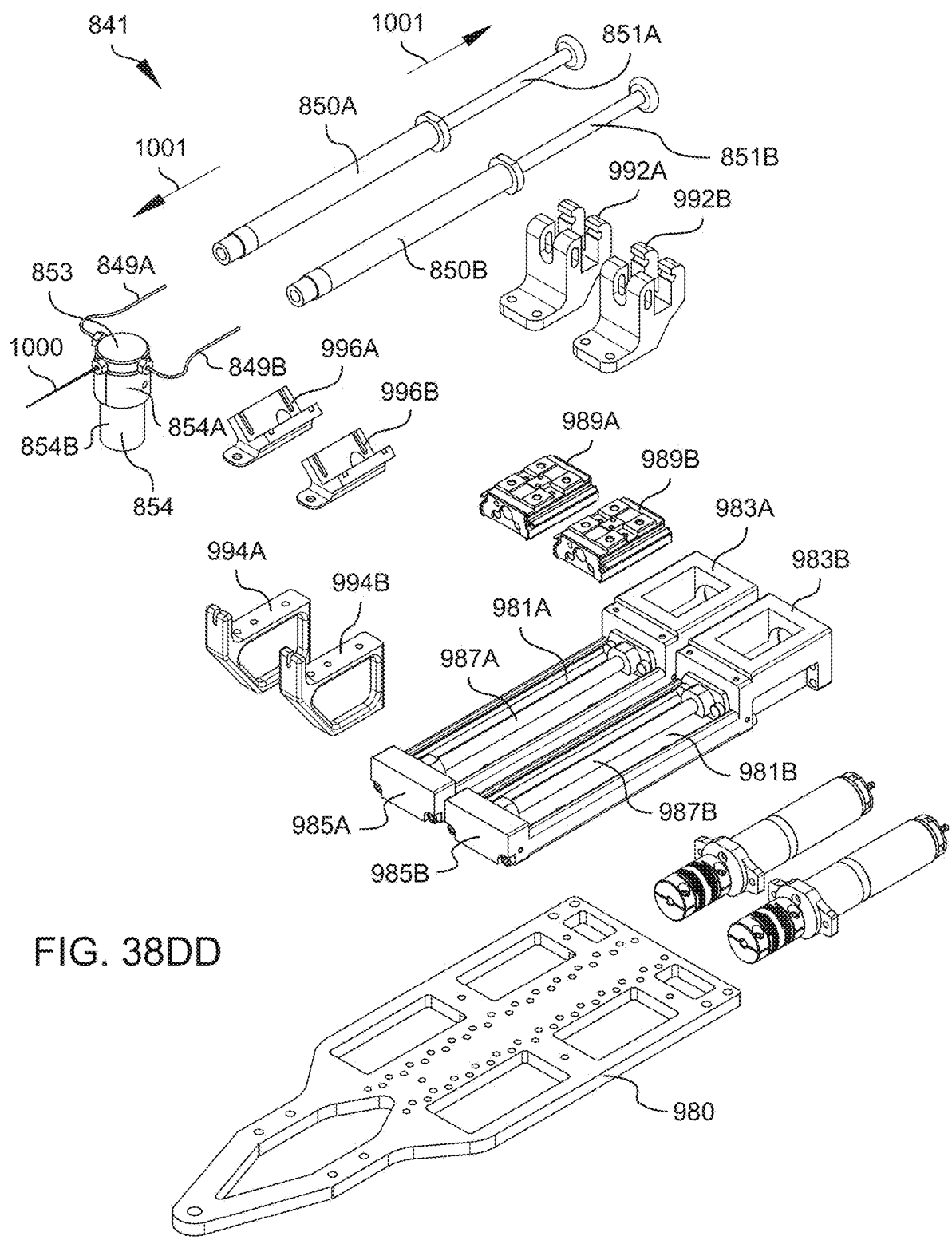
Figure 38G:
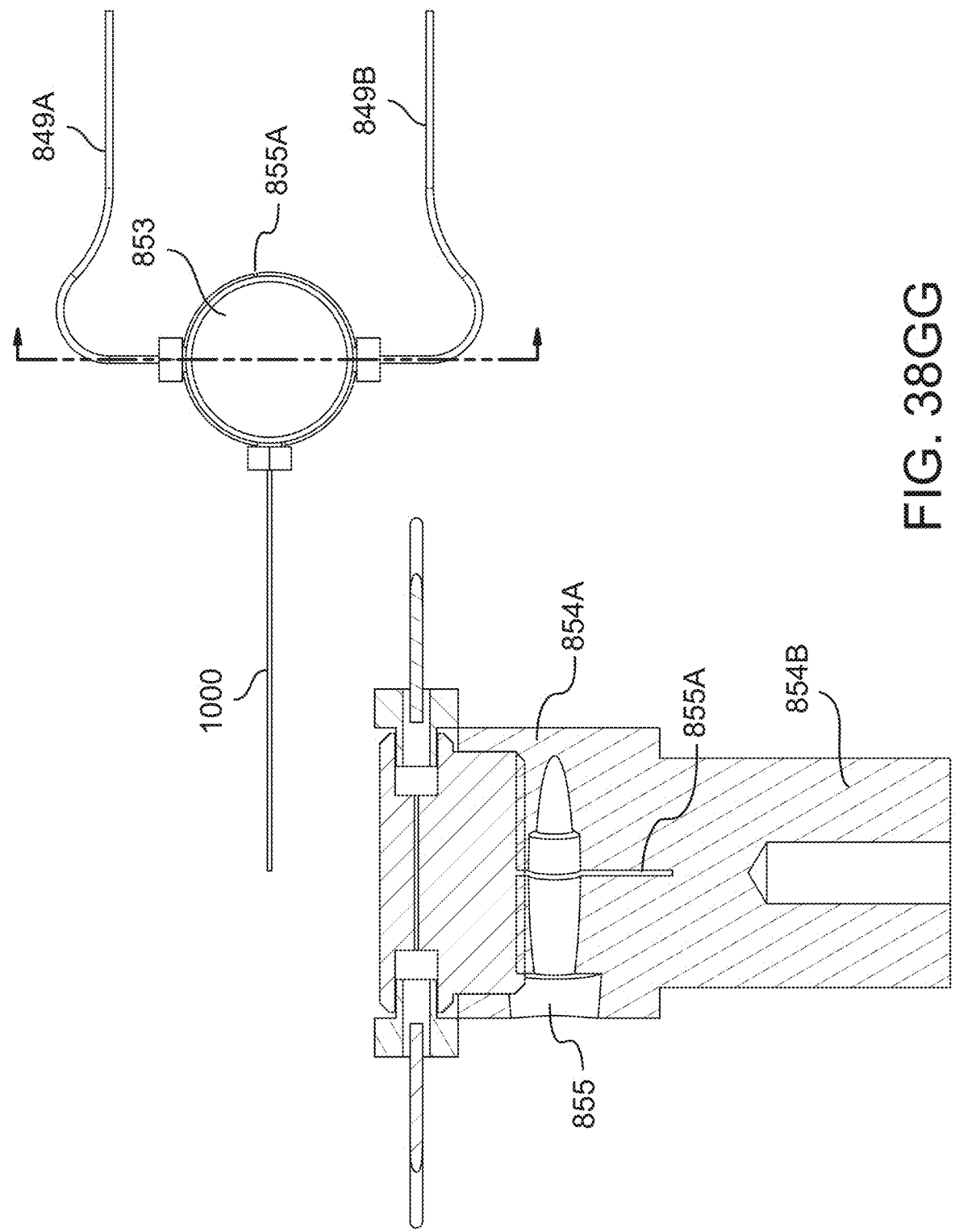

Referring now to FIGS. 38A and 38B, representative block diagrams of multi-dimensional printing device 201 (FIG. 38C) are depicted. Printing device 201 (FIG. 38C) can serve as a standalone component in a controlled environment or can contribute to a printing line with other devices working in harmony with printing device 201 (FIG. 38C). In some configurations, multi-dimensional printing device 201 (FIG. 38C) can collaboratively print with one or more printing devices similar or dissimilar to printing device 201 (FIG. 38C). Printing device 201 (FIG. 38C) of the present teachings can comprise a support structure such as a chassis 51 with at least one base 59 and at least one upright 55A. Chassis base 59 and chassis 51 can jointly support more than one moving sub-components that can lead to articulation of a print head or delivery system 69A. A calculated movement of the sub-components can cause printing of one or more desirable multi-dimensional part. The printed part/s can be a biological or a non-biological specimen of known dimensions. The printed part/s (not shown) can be printed from one or more print material/s. Chassis upright 55A can further support a primary carriage 61 that can serve as the first guided component and can further engage with subsequent guided components. Engagement between the primary carriage 61 and chassis upright 55A can be such that the primary carriage 61 can travel along the plane of chassis upright 55A.

Continuing to refer to FIGS. 38A and 38B, primary carriage 61 can serve as a support structure for additional one or more guided components such as but not limited to first sub-carriage 65. Movement of sub carriage 65 can be in conjunction with primary carriage 61 and along at least one travel path (not shown) defined by primary carriage 61. In some configurations, the sub carriage can be a combination of one or more sub-carriages that can perform guided motion to contribute to the printing process. Configurations of the present teachings can include a first sub-carriage 65A and a second sub-carriage 65B. Guided motion of first sub-carriage 65A and second sub-carriage 65B can be mutually related and can also optionally relate to guided motion of primary carriage 61. Printing device 201 (FIG. 38C) can further comprise at least one print head 69A that can be a destination of the previously discussed guided motion of the carriages. At least one cartridge 71 can be accommodated by print head 69A. Cartridge 71 can comprise at least one print material that can be of a biological or non-biological nature. Configurations of the present teachings can comprise, but are not limited to comprising a syringe as cartridge 71. Plunger of syringe or cartridge 71 can be actuated to print one or more desirable parts into a vessel 75 that can further comprise a gel-like material. In case of the printed part being a biological specimen, the gel-like material can be infused with nutrients and drive out waste for sustaining the printed biological specimen. In some configurations, vessel 75 can be but not limited to at least one petri-dish of varying sizes, at least one microplate or well plate with number of wells ranging from 6 to 1600 depending on extent of print space that exemplary printing device 201 (FIG. 38C) can cover. Printing device 201 (FIG. 38C) can be constructed to accommodate and print into microplates manufactured by Corning® and/or any other microplates or well plates configured to fulfill industry standards of a well plate. It should be noted that components of printer 201 (FIG. 38C) can be dimensionally altered to define required print space or print envelope covered by exemplary printer 201 (FIG. 38C).

Referring now to FIGS. 38C and 38D, first configuration multi-dimensional printing device 201 with a single delivery system 241 is depicted in FIG. 38C. FIG. 38D depicts a second configuration of multi-dimensional print device 801 with a multi-delivery system 850 comprising cartridges 850A and 850B. Teaching of the present configuration describe a multi-delivery system 850 with a single print head 841 and dual cartridges or syringes 850A and 850B. It should be noted that additional configurations, not described herein, can comprise multiple print head and consequently plurality of cartridges or syringes for printing.

Continuing to refer to FIG. 38C, printer 201 can be composed of a chassis 220 optionally configured to serve as a foundation of printer 201 and can further house at least one vessel 255 wherein one or more desirable parts can be printed. Chassis 220 can further comprise at least one base 227 and at least one upright 225 to support guided components therein. A first guided component, also previously referred to as a primary carriage 231 can engage with upright 225 such that the engagement can cause primary carriage 231 to travel along the plane of chassis upright 225. Guided motion of primary carriage 231 can be such that its motion optionally governs a distance between delivery system 241 vessel 255. Primary carriage 231 can further provide receptacles, discussed further, to receive or support additional guided components. These guided components can travel along surface of primary carriage 231 through travel means provided thereupon. The add-on guided components can be, but not limited to at least one sub-carriage configured to serve as a sub carriage. Configurations of the present teaching provide a first sub-carriage 235 and a second sub-carriage 239 configured to perform guided motions for positioning print head 241. First sub-carriage 235 can optionally travel along the plane of primary carriage 231 along a track and supported by travel blocks, discussed later in this application. In some configurations, first sub-carriage 235 can further provide travel means for additional guided components. Housings for electrical components to generate and drive the guided motion, can also be provided on body of first sub-carriage 235.

Continuing to refer to FIG. 38C, second sub-carriage 239 can operatively travel over body of first sub-carriage 235 to contribute in articulating print head 241. In some configurations, second sub-carriage 239 can further provide at least one engagement means to attach one or more print head/s 241. Consequently, combined guided motion of primary carriage 231, first sub carriage 235 and second sub-carriage 239 can lead to desired articulation of print head 241. At least one print cartridge such as but not limited to a syringe 250 can be housed in print head 241. Print head 241 of the present teachings can comprise mechanisms to house syringe 250 such that at least one actuating component, discussed further can apply a calculated linear displacement on the plunger of syringe 250 to release print ink for desired printing. In some configurations, guided motion of print head 241 and actuation of plunger of syringe 250 can be concurrent or asynchronous depending on part/s to be printed. Printing can be optionally performed in vessel 255 that can support by a vessel adaptor 259. Base support 227 of chassis 220 can receive vessel adaptor 259 and vessel 255 at a desirable position. It should be noted that disposition of vessel adaptor 259 and vessel 255 can be governed by, but not limited to, part/s to be printed and freedom of degree of guided motion advanced to print head 241.

Referring now primarily to FIG. 38D, printer 801 can be a multi cartridge printer and can optionally be similar to single cartridge printer 201 in mechanism related to, but not limited to advancing guided motion to print head 841. It should also noted that addition or deletion of print heads such as, but not limited to print head 841 and addition or deletion of cartridges such as, but not limited to syringes 850A and 850B can alter printer 801 in term of, factors such as and other than, dimensions and number of components of printer 801.

Continuing to refer to FIG. 38C, printer 801 can be composed of a chassis 820 optionally configured to serve as a foundation structure and can further house at least one vessel 855 wherein one or more desirable parts can be printed. Chassis 820 can further comprise at least one base 827 and at least one upright 825 to support guided components therein. A first guided component, also previously referred to as a primary carriage 831 can engage with upright 825 such that the engagement can cause primary carriage 831 to travel along plane of chassis upright 825. Guided motion of primary carriage 831 can be such that its motion optionally governs a distance between delivery system 841 of vessel 855. Primary carriage 831 can further provide receptacles or slots, discussed further, to receive or support additional guided components. These guided components can travel along surface of primary carriage 831 through travel means provided thereupon. Add-on guided components can be, but are not limited to at least one sub-carriage configured to serve as a sub carriage. Configurations of the present teaching provide a first sub-carriage 835 and a second sub-carriage 839 configured to perform guided motions for positioning print head 841. First sub-carriage 835 can optionally travel along plane of primary carriage 831 along a track and can be further supported by travel blocks, discussed later in this application. In some configurations, first sub-carriage 835 can further provide travel means for additional guided components. Housings for electrical components to drive and generate guided motion can also be alternatively provided on body of first sub-carriage 835 and/or primary carriage 831.

Continuing to refer to FIG. 38D, a second sub-carriage 839 can operatively travel over body of first sub-carriage 835 to contribute in articulating print head 841. In some configurations, second sub-carriage 839 can further provide at least one engagement means to attach one or more print head/s 841. Consequently, combined guided motion of primary carriage 831, first sub carriage 835 and second sub-carriage 839 can lead to desired articulation of print head 841. Print head 841 can be configured to house a plurality of cartridges or syringes such as, but not limited to first and second syringe 850A and 850B. A plunger actuation set-up housed in print head 841 can be devoted to each syringe 850A and 850B. Each plunger actuation set-up, discussed further can apply a calculated linear displacement on respective plunger of syringes 850A and 850B to release print ink for desired printing. In some configurations, guided motion of print head 841 and actuation of plungers of syringes 850A and 850B can be concurrent or asynchronous depending on part/s to be printed. Printing can be optionally performed in vessel 255 that can support by a vessel adaptor 259. Syringes 850A and 850B can comprise distinct print material or same print material of distinct concentrations. Respective needles, discussed herein further, of syringes 850A and 850B can serve as inlets to mixing valve 853 that can further comprise a at least one outlet. Mixing valve 853 can monitor duration and amount of print materials from syringe 850A and 850B such that a desirable print ink exits from at least one outlet of valve 853. Operation of valve 853 with inlet needles from syringes 850A, 850B and at least one outlet, is discussed further in this application.

Continuing to refer to FIG. 38D, cartridge or syringes 850A and 850B of multi-cartridge printer 801 can comprise biological and/or non-biological print material. Multi-cartridge facility can allow printing of parts composed of more than one material or of materials with different concentrations. Combination of a single print head 841 and mixing valve 853 can allow a single set of guided components to articulate each cartridge or syringe 850A and 850B, thereby allowing printer 801 to be cost effective and efficient. Base support 827 of chassis 820 can receive vessel adaptor 859 and vessel 855 at a desirable location. It should be noted that disposition of vessel adaptor 859 and vessel 855 can be governed by, but not limited to, part/s to be printed and freedom of degree of guided motion advanced to print head 841.

Referring again to FIG. 38C, description henceforth, until stated otherwise, discusses mechanical structure of chassis and guided components of single cartridge printer 201. It should be noted that chassis and guided components of single cartridge printer 201 and multi-cartridge printer 801 can be substantially similar with respect to teachings of the present configuration. However, alteration of these components can depend on, but are not limited to depending on, type and amount of print material and part/s being printed thereof.

Referring now to FIGS. 38E and 38F, chassis 220 of printer 201 (FIG. 38C) can support printing components or guided components and components wherein printing can be performed. Base 227 can be composed of at least one platform 320 that can be further fenced by at least one upright 225 and rails 325A, 325B on sides of platform 320 and adjacent to upright 225. Side rails 325A, 325B and upright 225 can define an area of chassis 220 wherein printing components perform a guided motion and wherein printing is undertaken. Base platform 320 can be further partitioned into regions 320A and 320B through barrier 330. Region 320A can confine a space wherein printing components can perform their respective guided motions, whereas printing can be performed in region 320B. As a result, region 320B can house components such as, but not limited to vessel 225 (FIG. 38C) and vessel adaptor 259 (FIG. 38C). Region 320B can further provide a cavity 328 configured to engage vessel adaptor 259 (FIG. 38C) and vessel 255 (FIG. 38C)

Continuing to refer to FIGS. 38E and 38F, upright 225 can comprise pillars 340 that can be optionally disposed at intersecting edges between base 227 and upright 225. Pillars 340 can further comprise a first travel path 350A and second travel path 350B. Travel blocks 345A and 345B can be provided on first and second travel paths 350A, 350B, respectively. In some configurations, travel blocks 345A and 345B can be affixed over travel paths 350A and 350B. Travel means such as but not limited to, one or more linear bearings (no shown) can be accommodated into recesses 346A and 346B of respective blocks 345A and 345B. Travel means (not shown) can enable a travel rail that can be provided on a component mating with upright 225 and discussed further herein, to slide through recesses 346A and 346B of blocks 345A and 345B. It should be noted that travel means can operate such that travel rail/s and travel blocks 345A, 345B move relatively to one another.

Referring now primarily to FIGS. 38G and 38H, second region 320B of base platform 320 can accommodate one or more components wherein printing can be performed. Cavity 328 of second region 320B can house at least one vessel adaptor 323 that can further provide at least one vessel space 322 to house vessel 321. Vessel adaptor 323 can further comprise mounting features 326 to allow vessel adaptor 323 to be retained within cavity 328 of base platform 320. Vessel adaptor 323 can further comprise a plurality of brackets 327, each bracket 327 can be configured to support one or more laser emitters 333. Position of needle (not shown) belonging to cartridge 250 (FIG. 38C) can be located through location monitors such as but not limited to, laser emitters 333.

Referring now to FIG. 38G, accurate printing and revisiting the printed structure require both a reproducible positioning of the tissue enclosure and calibration of the delivery device location with respect to the tissue enclosure. Sensors can be located in proximity to the tissue enclosure and can be used to determine an origin point of the delivery device. The origin point can be provided to the motion controller so that any positions to which the motion controller moves the delivery device can be located when the printed structure is to be accessed again. The origin point can be determined by an automatic process and/or by a semi-automatic process. The process of enabling reproducible positioning can include positioning tissue enclosure 101 (FIG. 1C) within kinematic mount 102 (FIG. 1C). Tissue enclosure 101 (FIG. 1C) can be empty or can include the medium into which printing can occur. Emitter/receiver pairs of sensors can be enabled, and printer 100 (FIG. 1A) can be enabled to jog each of the x, y, and z actuators in first directions until first limit switches for each of the x-, y-, and z-axes are encountered. In the case of the z-axis, the first direction can be chosen so that the delivery device moves away from tissue enclosure 101 (FIG. 1C). Printer 100 (FIG. 1A) can further jog the x and y actuators in second directions until second limit switches for x- and y-axes are encountered. An absolute reference origin position can be selected and provided to the motion controller as, for x- and y-axes, the point halfway between first and second limit switches, and for the z-axis, a point that is a preselected amount displaced from the first limit switch for the z-axis, for example, but not limited to, about 5 mm. The printer can command the delivery device to move to the absolute reference origin position provided to the motion controller.

Continuing to refer to FIG. 38G, the y-axis can be calibrated by (a) commanding the delivery device to move to a pre-selected location, for example, a few millimeters from the reference origin in the y plane, and a few millimeters from the reference origin in the z plane, based upon the length of the delivery device. These values can be built into the system, or can be supplied in any appropriate way. The delivery device can be (b) commanded to jog the y actuator towards the sensor beam until the sensor beam is crossed. If the sensor beam is not crossed after a pre-selected displacement, the process can be discontinued and an error can be reported. If the sensor beam is broken, the delivery device can be (c) commanded to continue to jog in the same direction that it is currently traveling until the sensor beam is no longer broken. In some configurations, a minimum distance can be traveled before determining if the sensor beam is no longer broken. When it is determined that the sensor beam is no longer broken, the delivery device can be (d) commanded to jog in the reverse direction at a relatively slower speed to accommodate the location of sensor beam edges, recording the y positions when the sensor beam is broken and then when the sensor beam is no longer broken. The delivery device can then be commanded to (e) move to the mid-point of the recorded y positions, and to (f) define the current position as the zero y position. The z actuator can be (g) jogged in the positive Z direction until the sensor beam is no longer broken, and record the z position to be used to return to the height of the delivery device where the sensor beam had been broken. Steps (b)-(g) of the y-axis calibration process can be (h) repeated using a reduced search window of a pre-selected amount until the beam can no longer be found. The pre-selected amount can be related to the amount of bend that can be tolerated in the delivery device. The process can continue by (i) commanding the delivery device to move to the zero y position, and (j) jogging the z actuator towards the tissue enclosure until the sensor beam is broken. The position at which the sensor beam is broken can be defined as the new zero z position. If the sensor beam is not crossed after a pre-selected displacement, the process can be discontinued and an error can be reported. Steps (b)-(f) of the y-axis calibration process can be repeated at a relatively slower speed to define the final zero y position.

Continuing to refer to FIG. 38G, the x-axis can be calibrated by repeating steps (a)-(k) of the y-axis calibration process substituting the x-axis and x actuators for the y-axis and the y actuators. The delivery device can be commanded to move to the newly-determined origin, and these coordinates can set as the origin. To determine if a sensor beam has been broken, a threshold percent of the sensor beam received with no obstruction can be chosen such that below the threshold percent, the beam can be considered broken.

Referring now to FIGS. 38I, 38J, and 38K, primary carriage 231 can operatively engage with upright 225 (FIG. 38C) of chassis 220 (FIG. 38C). Front surface 410 of primary carriage 231 can provide means for engagement and guided motion for subsequent carriages, discussed herein later. Rail 426 with at least one grooved surface 425 can be provided on front surface 410 of primary carriage 231. Fastening features 427 can enable engagement between rail 420 and front surface 410 of primary carriage 231. A second set of travel blocks 440 can engage with rail 426 such that they travel along length of rail 426. Gliding motion of travel blocks 440 can be achieved through linear bearings (not shown) disposed within travel blocks 440 to cause reduced friction between surface of travel blocks 440 that interface with grooved surface 425 of rail 426, while travelling. Additional carriages can engage with travel blocks 440 through connection points 442. Front surface 410 can further comprise receptacles for electrical such as, but not limited to motors, gear motors, encoders or holder for such electrical and their extensions, that generate and monitor guided motion of primary carriage 231 and/or additional carriages, discussed herein further. A first receptacle 470 can engage one or more of above discussed electrical/s. Protrusion 465 can serve as a hard stop for sub-carriages, discussed further, that engage with and travel through travel blocks 440. Engagement of first upright 410 with rail 425 and travel blocks 440 can be better depicted through explosions in FIG. 38K.

Continuing to refer to FIGS. 38I, 38J and 38K, back surface 415 can comprise travel means to complement travel blocks 345A, 345B (FIG. 38G) of chassis upright 225 (FIG. 38G). Such travel means can be, but not limited to rails 475 that can operatively engage with travel blocks 345A, 345B (FIG. 38G) and allow primary carriage 231 to perform a guided motion along plane of chassis upright 225. As previously discussed, disposition and motion of travel blocks 345A, 345B (FIG. 38G) can be relative to rails 475.

In some configurations, rails 475 can be provided on upright 225 (FIG. 38G) while travel blocks 345A,345B (FIG. 38G) can be provided on back surface 415 of primary carriage 231. A second receptacle 478 can be configured to engage at least one or part of at least one electrical component that can generate and monitor guided motion, discussed previously. A third receptacle 481 can operate in conjunction with receptacle 478 to support additional electrical components and/or extensions of electrical components held by receptacle 478. It should be noted that position and number of receptacles or supports for electrical components of printer 201 (FIG. 38C) are not limited to number and positions depicted by configurations of the present teachings.

Referring now to FIGS. 38L, 38M, and 38N, assembly 500 can comprise primary carriage 231 and a first sub-carriage 235 configured to engage with primary carriage 231. First sub-carriage 235 can jointly serve as one of many guided components for printing in printer 201 (FIG. 38C). Body 520 of first sub-carriage 231 can comprise a mounting area 530 and a raised area 550. Mounting area 530 can be constructed to operatively engage with travel blocks 440 of primary carriage 231. Spaces or pockets such as pocket 530A thereof can accommodate or support one or more electrical/s such as but not limited to an encoder or linear encoder 593 engaged therewith. Encoder 593 can be configured to monitor guided motion of first sub-carriage 235. Pocket 530A can also be positioned to allow an obstruction free mating of mounting area 530 and travel blocks 440. Primary carriage 231 can comprise a first reference strip 430 configured to embed referencing features therein and stretching along direction 523. Exemplary printer/s 201, 801 can provide one or more magnets to serve as referencing features on one or more reference strip provided thereupon. However, it should be noted that alternative referencing features and/or combination of such referencing feature/s can be employed to monitor guided motion of carriage 231 and sub-carriages 235, 239. First reference strip 430 can comprise limit magnets 431, 432 that can be positioned on two ends of strip 430. First reference strip 430 can also optionally provide a reference magnet 433 positioned midway between limit magnets 431 and 432. Encoder 593 can travel along or in close proximity to reference strip 430 to deliver information related to position of first sub-carriage 235 along rail 420 on primary carriage 231.

Continuing to refer to FIGS. 38L, 38M and 38N, positioning of rail 420 on primary carriage 231 and operative engagement of first sub-carriage 235 therewith can allow first sub-carriage 235 to travel in a direction 523 (FIG. 38M). It should be noted that direction of travel of first sub-carriage 235 can be determined and hence altered based on position of rail 420. Raised area 550 can comprise a second rail 540 to accommodate additional guided components that can travel along said rail 540. Receptacle/s such as receptacle 560 can form part of raised area 550 and accommodate one or more electrical components and/or extension of such electrical components responsible for guided motion of at least one of the sub-carriages therein.

Referring now primarily to FIGS. 38M and 38N, assembly 501 can comprise primary carriage 231, first sub-carriage 235 and a second sub-carriage 239 configured to jointly operate in advancing guided motion to print head 241 (FIG. 2A). Second sub-carriage 239 can comprise a body 620 with mating portion 625 configured to engage with at least one of primary carriage 231 and/or first sub-carriage 235. Receptacle 650 of second sub-carriage 239 can serve to accommodate one or more electrical components or extensions thereof such as, but not limited to, motors, gear motors, shafts and encoders. Second sub-carriage 239 can further interface with assembly 500 (FIG. 38L) by optionally mating with first sub-carriage 235. This engagement can be achieved by provision of travel means such as but not limited to rail 540 on first sub-carriage 235 and corresponding travelling means such as but not limited to travel blocks 630 of second sub-carriage 239. Rail 540 can further provide a plurality of linking points 541 to engage and also provided more than one engagement state between rail 540 and travel blocks 630. Rail and travel block engagement mechanism can allow second sub-carriage 239 to establish a freedom of linear motion in direction 623 along rail 540. As a result, exemplary assembly 501 can jointly travel in directions 670, 623 and 523. Alteration in placement of rail and travel block engagement mechanisms between primary carriage 231, first sub-carriage 235 and second sub-carriage 239 can alter directions of travel of assembly 501.

Continuing to refer to FIGS. 38M and 38N, guided motion of second sub-carriage 239 in direction 623 can be monitored by providing a combination of referencing features with position determining features thereof. Exemplary configuration of second sub-carriage 239 can comprise a second reference strip 534 configured to house referencing features such as but not limited to limit magnets 531, 532 and reference magnet 533. Encoder 693 optionally provided to engage with first sub-carriage 235 and configured to read position of second sub-carriage 239 as it travels along rail 540. Consequently, encoder 593 in combination with second reference strip 534 and magnets 531, 532 and 533 can aid in determining location of second sub-carriage 239 and monitoring its motion. Placement of second reference strip 534 and corresponding read head or encoder 693 can be interchanged in some configurations.

Referring now to FIGS. 38O, 38P, and 38Q, printer assembly 201 (FIG. 38C) can be achieved by bringing together chassis 220 (FIG. 38C) and printing components, such as but not limited to, primary carriage 231, sub carriage/s 235, 239 (FIG. 38C), print head 241 (FIG. 38C) and print cartridge or syringe 250 (FIG. 38C). It should be noted that sequence of assembling above discussed components can vary from one exemplary printer to another. Chassis upright 225 can operatively accommodate primary carriage 231. At the time of such assembly, primary carriage 231 may or may not be engaged with exemplary sub-carriages 235, 239. Configuration of FIGS. 38O, 38P and 38Q depict assembling of primary carriage 231 with chassis upright 225 such that primary carriage 231 engages sub-carriages 235 and 239 during such this assembly. Above discussed engagement can be achieved by housing rail/s 475 of primary carriage 231 within recess 346A, 346B of travel blocks 345A and 345B, respectively. Rail/475—and travel-blocks 345A, 345B interface can allow primary carriage 231 to travel along travel paths 350A, 350B (FIG. 38H) in direction 670. Consequently, sub carriages 235 and 239 travel in direction 670. Motion of sub-carriages 235, 239 can optionally be limited to an extent to which primary carriage 231 travels. Additionally, travel direction of primary carriage 231 and subsequent travel of sub-carriages 235 and 239 can alter as per disposition of rail/s 475 and corresponding travel blocks 345A, 345B.

Referring now to FIG. 38R, engagement between primary carriage 231 and chassis upright 225 can allow primary carriage 231 to travel in direction 670. Motion of primary carriage 231 can be monitored by providing at least one third reference strip 250A comprising limit magnets 251A, 252 and reference magnet 253. Corresponding encoder 493, such as but not limited to linear encoder, can be positioned on chassis upright 225 such that it can read reference strip 250A and magnets 251A, 252, and 253 and comprehend position of primary carriage 231 along direction 670. It should be noted that placement of team of reference strip 250A, magnets 251A, 252, 253 and encoder 493 can be interchangeable.

Referring now to FIGS. 38S and 38T, in some configurations, single cartridge or single syringe print head 241 can be assembled unconnected and can engage with remainder portion of printer 201, thereafter. Sub-components of printhead 241 and assembly of these sub-components are discussed further in this application. Engagement of first exemplary print head 241 and remainder of printer 201 can be at a junction featuring complementing attachment features provided a first set of which can be provided on print head 241 and a second set provided on remainder of printer 201. Configuration of the present teachings provides a connecting platform 660 belonging to second sub-carriage 239. Connecting platform 660 can be configured to accept a complementing platform 970 that can be provided on interfacing plate 950A. A variety of fastening features can be employed to achieve engagement of connecting platform 660 and complementing platform 970. Connecting platforms 660 and 970 can further provide a plurality of engaging levels such that distance of cartridge or syringe 250 and vessel 255 can be maintained and altered, as required. In other configurations, placement of complementing connecting platforms 660 and 970 can be altered to engage print head 241 with one or more other carriage/s or sub-carriage/s distinct from second sub-carriage 239. Alternatively, print head 241 can further connect with an intermediate component (not shown) configured to engage with primary carriage and/or sub-carriages of printer 201. Earlier discussed engagements between primary carriage 231, first sub-carriage 235 and second sub-carriage 239 can enable print head 241 and hence, cartridge and/or syringe 250 to be articulated to a calculated position in vessel 255. Printer configuration 201 of the present teachings can articulate print head in directions 623, 523 and 670.

Referring now to FIGS. 38V, 38W, and 38X, multi-cartridge or multi-syringe printer 801 can comprise a contact junction wherein one or more connecting plates of print head 841 can mate with remainder of printer 801. First sub-carriage 839 can provide a connecting surface 860 configured to completely or partially accept a complementing connecting plate 980 of print head 841. As previously discussed, print head 841 can accommodate a plurality of cartridges or syringes such as, but not limited to syringes 850A and 850B. These plurality of syringes can be supported by a common connecting plate such as connecting plate 980 to associate print head 841 with remainder of printer 801 through above discussed engagement. In other configurations, each syringe 850A, 850B of print head 841 can own their respective connecting plate, similar or dissimilar to plate 980. These plates can distinctly associate with connecting surface such as surface 860 of sub-carriage 839. Connecting surface 860 and/or plate/s 980 can further provide a plurality engaging levels such that distance of cartridge/s or syringe/s 850A, 850B and vessel 855 can be maintained and altered, as required. Earlier discussed engagements between primary carriage 831, first sub-carriage 835 and second sub-carriage 839 can enable print head 841 and hence, cartridge and/or syringe 850A, 850B to be articulated to a calculated position in vessel 855. Required position of print head 841 can be achieved by guiding motion of printer configuration 801 in directions 623, 523 and 670.

Referring now to FIGS. 38Y, 38Z, and 38AA, Single cartridge or syringe delivery system 913 can comprise at least one base plate 935 and corresponding partially or completely overlapping actuation plate 930. Accommodation of cartridge or syringe 250 can be optionally shared between base plate 935 and actuation plate 930 such that needle end of syringe 250 can be captured by one or more fixtures provided on base plate 935 and corresponding plunger 251 can be operatively held by one or more fixtures provided on actuation plate 930. Such cartridge or syringe holding hardware can allow bi-directional fluid control. Fixtures or exemplary actuation plate 930 can comprise a travel path 933 configured to house a screw 922. Travel block 943 can operatively couple with screw 922 such that they can travel along length of screw 922. Portion of travel block 943 that operatively couples with portion of screw 922 can comprise travel aides such as but not limited to bearings, more specifically ball bearings. Driving components for above discussed guided motion can be one or more motor/s 960 and motor extensions such as but not limited to gear motors, that can be housed in motor mount 945. In some configurations, motor mount 945 can be engaged with actuation plate 930 or can be a continuous part thereof. Driving components 960 can interact with screw 922 to allow motion of travel block 940 along length of screw 922. Plunger 251 of cartridge or syringe 250 can be partially or completely captured on travel block 940. This engagement of plunger 251 can be achieved by trapping plunger 251 within first set of hub component/s 965A that can be in turn accommodated by bracket 966A of travel block 940. Needle end of syringe 250 can be trapped by second set of hub components 965B such that needle end can rigidly rest in a pocket 967 of yoke 966B engaged with base plate 935. Above discussed engagement of syringe 250 with base plate 935 and actuation plate 930 can enable syringe plunger 251 to be actuated in direction 914 such that required amount of print material in syringe 250 can be delivered over a required duration. Drive components 960 can provide guided motion required for performing above discussed controlled actuation.

Referring now to FIGS. 38BB, 38CC and 38DD, multi-cartridge or multi-syringe delivery system can comprise a common base plate 980 to accommodate actuation plates committed to their respective syringes. A common base plate can allow a single set of guided motions to articulate all syringes engaged therewith. In some configurations, a distinct base plate can be provided for each cartridge or syringe. In such case, a distinct actuation mechanism may be required for articulation of each syringe. Configuration of present teachings depicts a dual-syringe delivery system 841 with common base plate 980 configured to support actuation mechanism committed to syringes 850A and 850B. Additionally, common base plate 980 when engaged with one or more of the carriages such as primary carriage 831 (FIG. 38D) and or sub-carriages 839, 835, can articulate both syringes 850A and 850. As predicted in FIGS. 38V and 38W, common base plate 980 can be engaged with second sub-carriage 839 through a corresponding connecting plate provided thereupon, to advance guided motion to dual-syringe delivery system 841.

Continuing to refer to FIGS. 38BB, 38CC, and 38DD, syringes 850A, 850B can be partially accommodated by common base plate 980 and respective actuation plates 985A, 985B. This engagement can allow a plunger end 851A, 851B of respective syringes to be operatively trapped by corresponding actuation plates 985A and 985B and needle ends 849A, 849B can be held over common base plate 980. Actuation plates 985A, 985B can comprise respective travel paths 981A and 981B with first screw 987A and second screw 987B thereupon, respectively. Travel blocks 989A and 989B can be engaged to travel on respective paths 981A and 981B. Such motion of travel blocks 989A and 989B can be achieved by optionally providing bearings at surfaces (not shown) on travel blocks 989A, 989B that interface first screw 987A and second screw 987B. Driving components 990A and 990B can provide calculated displacement to drive travel blocks 989A, 989B in a fashion as discussed above. These driving components 990A and 990B can be housed in compartments 983A and 983B, that can be part of or engaged with respective actuation plates 985A and 985B. Brackets 992A and 992B can serve as intermediate components to engage respective syringe ends 851A and 851B with corresponding travel blocks 989A and 989B. Needle ends 849A and 849B can be coupled with base plate 980 through respective restraining yokes 994A, 994B and support plates 996A, 996B. Restraining yokes 994A, 994B and matching support plates 996A, 996B can function jointly to allow needle end of body of syringes 850A, 850B to rest thereupon and corresponding needles 849A and 849B configured to exit from pockets to enter into mixing valve 853.

Continuing to refer to FIGS. 38BB, 38CC, and 38DD, mixing valve 853 can comprise entrances for needles 849A, 849B and a common exit needle or delivery needle 1000. Mixing valve 853 can be Vici® Mixing Tee that can be obtained off the shelf or constructed similar to Vici® Mixing Tee in case or accommodating needles in addition to needles 849A, 849B. Mixing valve 853 can allow distribution of print materials delivered from respective needles 849A, 849B and supply a desirable print material for a calculated duration through delivery needle 1000.

Referring now primarily to FIGS. 38EE, 38FF, and 38GG, stand or mount 854 can be configured to engage mixing valve 853 with common base plate 980 (FIGS. 38BB, 38CC, and 38DD) such that repository part 854A can house mixing valve 853 and stem part 854B can support valve 853 housed in repository 854A over common base plate 980 (FIGS. 38BB, 38CC, and 38DD). Repository part 854A can partially or completely accommodate valve 853 such that accommodated portion thereof can be captured within repository part 854A. Capturing of valve 853 can be achieved by providing a slit 855A in repository 854A and adjusting width of slit through at least one fastening feature such as, but not limited to a screw that can engage regions on both sides of slit 855A and can consequently forbid displacement of valve 853 in repository region 854A. Above mentioned fastening feature/s can be received into a cavity extending on either side of slit 855A. Cavity can be constructed such that tightening of fastening feature therein alters a length of cavity causing valve 853 to be secured in repository 854A. Stem part 854B can further provide one or more fixtures with at least one engaging facility to pair mount 854 with base plate 980 (FIGS. 38BB, 38CC, and 38DD) that can in turn provide a complementing engaging facility.

Referring now to FIG. 39, printer system 50 can include, but is not limited to including, printer 100, processor 55, receiving computer aided design (CAD) files 66A and other information through, for example, but not limited to, electronic communications from external applications 66, and motion controller 59. Processor 55 can provide commands to motion controller 59 that can print the structures designed and provided in CAD files 66A. Processor 55 can also receive, for example, vision data 77, hardware/sensor data 75, and user input 78, and can calculate G-code 67 based at least on a combination of one or more of CAD files 66A, vision data 77, user input 78, hardware data 75, and other information. Interpreter 57 can interpret G-code 67 and provide speed, direction, and acceleration (SDA) information 69 to motion controller 59. Motion controller 59 can compute at least one motion command 73 based at least on SDA information 69, and can provide at least one motion command 73 to printer 100 and at least one pump 66B. Printer 100 can position at least one delivery system 103 (FIG. 1A) and at least one needle 103H (FIG. 25A) based on at least one motion command 73. At least one pump 66B can provide an amount, based on at least one motion command 73, of at least one first material 79 to printer 100 to deposit into at least one tissue enclosure 101 (FIG. 1A) at the position of at least one needle 103H (FIG. 25A). Continuing to refer to FIG. 39, command interface 53 can enable user input 78 that can manually command and/or assist in automatically commanding printer 100. Command interface can include, but is not limited to including, options for adjusting the type of motion controller 59, the available electronic communications 67, and whether or not electronic communications 67 with external applications 66 is connected. Options such as, for example, printing scale, feed rate gain with respect to the commanded speed, and extruder gain with respect to extruder position commands can be adjusted through command interface 53. The structure can be viewed in a viewing window, and the G-code associated with building the structure can be displayed in a status window. The structure can be built by stepping through the G-code one line at a time. The values of the axes controlled by motion controller 59 can be shown and jogged using command interface 53. The jog function can enable free movement of the extruder module along the x, y, and z axes to accommodate maintenance and repair of printer 100.

Continuing to refer to FIG. 39, interpreter 57 can receive G-code 67 from CAD processor 56, and can transform G-code 67 into SDA information 69 that can be used by motion controller 59 to create motion commands 73 for printer 100 and pump 66B. Interpreter 57 can interface with motion controller 59 through any kind of electronic communications 67 including, but not limited to, direct wiring, Ethernet, and USB. Interpreter 57 can initiate and/or perform functions, for example in conjunction with motion controller 59, such as, for example, but not limited to, jogging individual axes by a given speed and position delta, and continuously jogging at a specified speed on an individual axis;
  moving to a target position at a specified speed;
  enabling/disabling a motor for a given axis;
  setting and clearing position offsets to specify a reference point, that is, defining a coordinate system;
  performing calibration based at least on the location of the needle tip, and setting an origin location;
  commanding the three motion axes to return to a home position;
  loading and processing G-code 67;
  saving the processed G-code 67 that can be used for example, for reference for determining start/end line numbers;
  displaying a model of the loaded G-code 67;
  displaying a model of print progress;
  panning, zooming, and rotating the model;
  adjusting the physical scale of desired structure;
  adjusting the feed rate gain for printing so that motion controller 59 can apply the gain to commanded speeds;

adjusting the extruder gain for print so that motion controller 59 can apply the gain to extruder position commands;

specifying the starting and ending line numbers of processed G-code 67 for the print;

starting printing the specified lines of processed G-code 67;

pausing printing;

stopping printing;

displaying the current line number of processed G-code 67, and commanding while print is in process;

single stepping through lines of processed G-code 67;

automatically moving the needle tip to a required starting position dictated by the starting line of G-code 67;

automatically moving the needle tip to the last known position when printing was paused enabling resuming printing after syringe swap;

configuring the extruder and motion axes encoder gains to convert from count distances to motion command 73;

configuring a maximum vector speed, vector acceleration, vector deceleration, and maximum corner speed associated with a motion segment; and monitoring and reporting the status of motion controller 59 including current position and fault conditions.

Figure 39A:
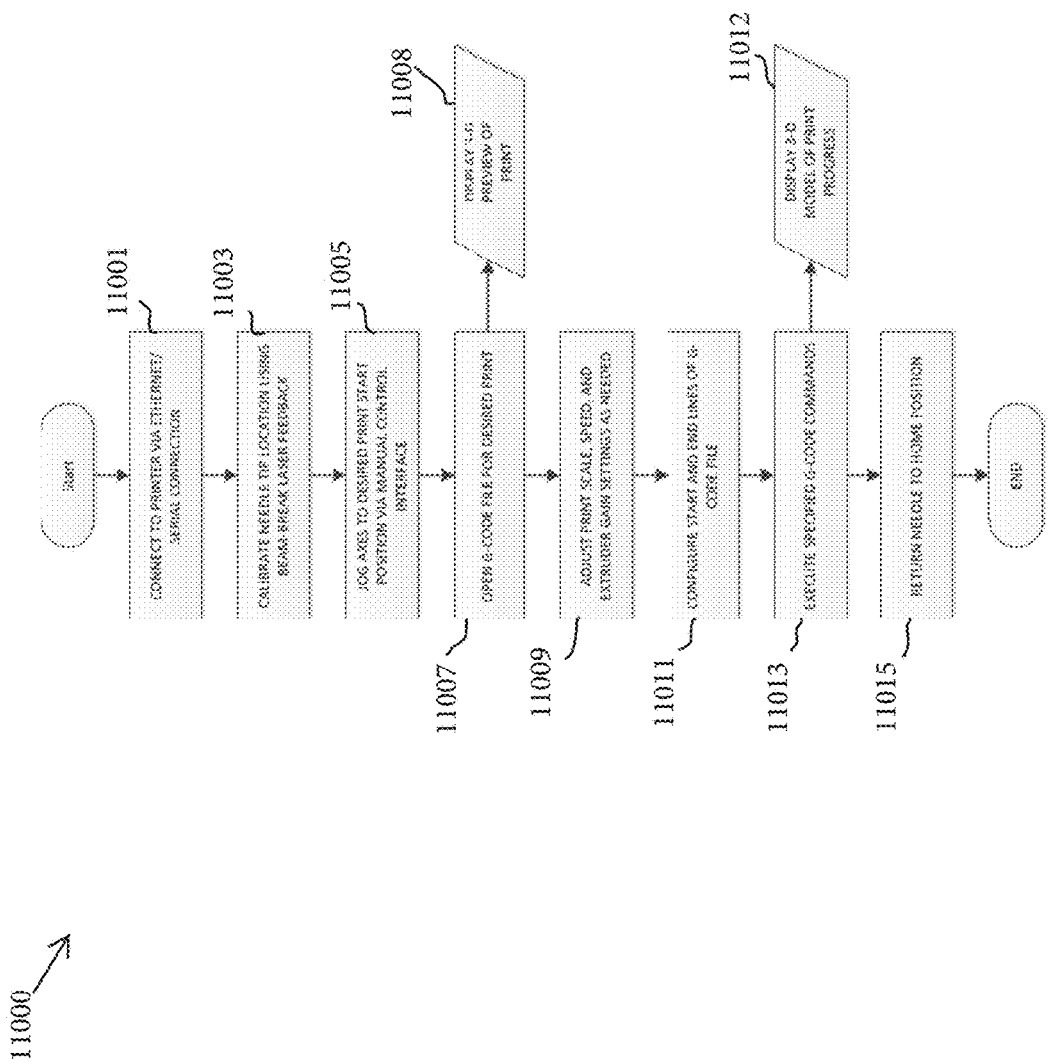
FIG. 39A is a flowchart of a first configuration of the method for interpreting G-code of the present teachings.

Referring now to FIG. 39A, method 11000 for interpreting G-code 67 by interpreter 57 can include, but is not limited to including, establishing 11001 a connection between printer 100 and processor 55, calibrating 11003 the location of the printing needle tip, jogging 11005 axes to a desired print start position, accessing 11007 G-code 67 for the structure to be printed, and displaying 11008 a preview of the structure. Method 11000 can include adjusting 11009 print scale, speed, and extruder gain settings, selecting 11011 G-code 67 between desired start and end lines, executing 11013 the selected G-code, displaying 11012 a model of print progress, and returning 11015 the needle to a home position when the end line of the selected G-code is reached. The connection between printer 100 and processor 55 can be established using Ethernet or serial technology, for example. The calibration can optionally be accomplished by beam-break laser feedback. The axes can be jogged manually or automatically. G-code 67 can optionally be stored in a file that can be opened when G-code access is desired.

Figure 39B:
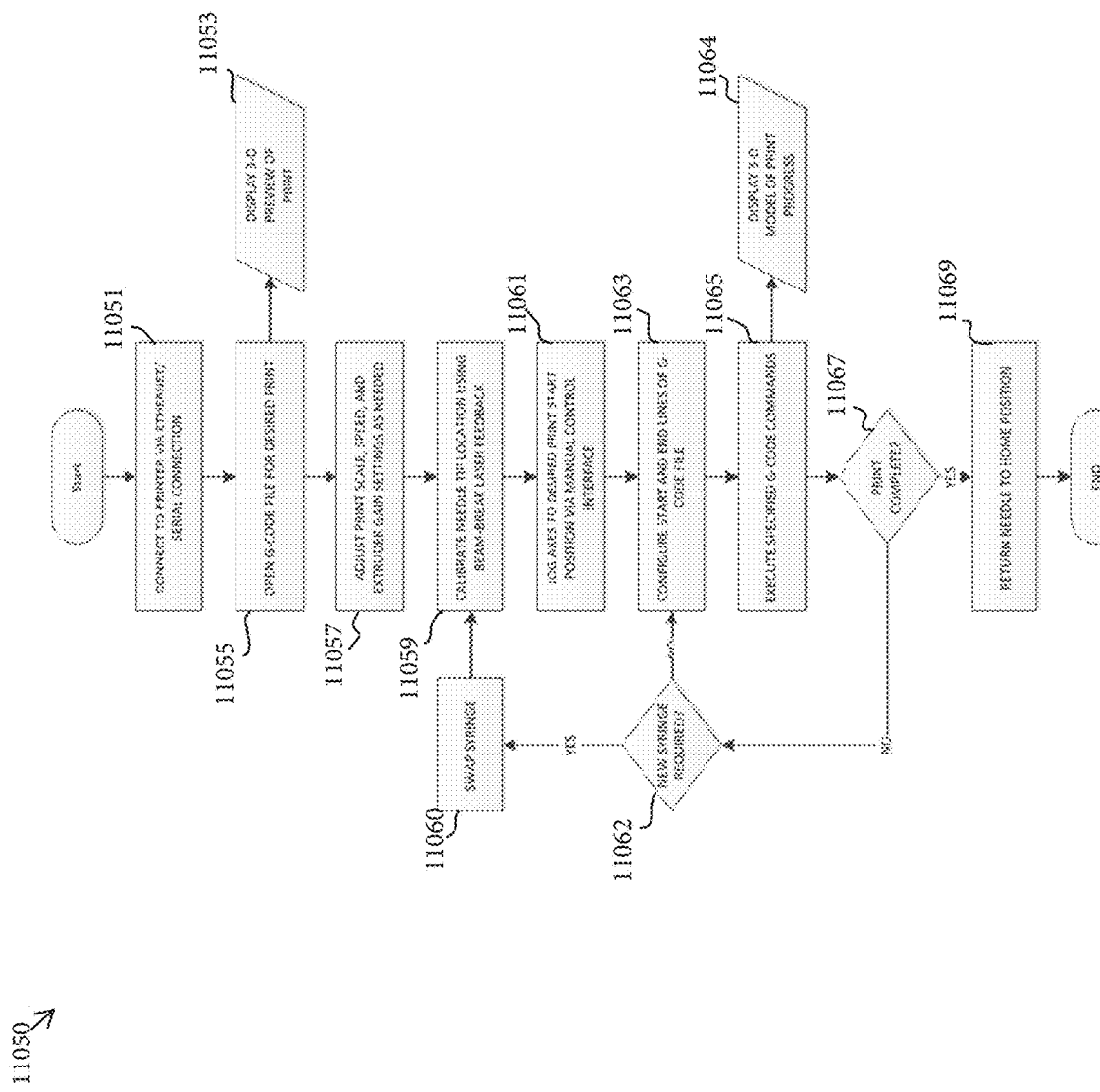
FIG. 39B is a flowchart of a second configuration of the method for interpreting G-code of the present teachings.
Figure 39C:
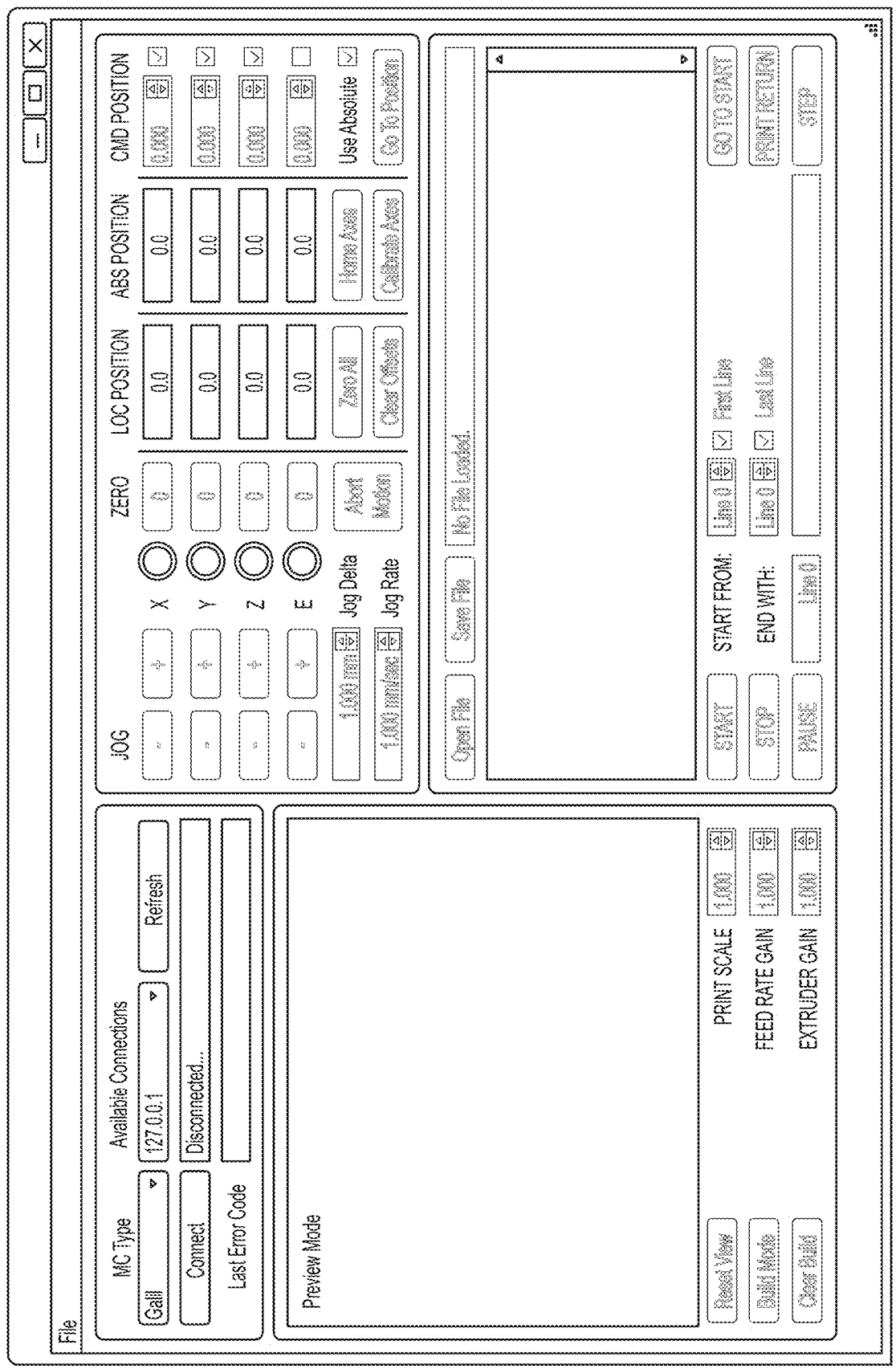
FIGS. 39C-39I are screen displays of an exemplary configuration the command interface of the present teachings.
Figure 39D:
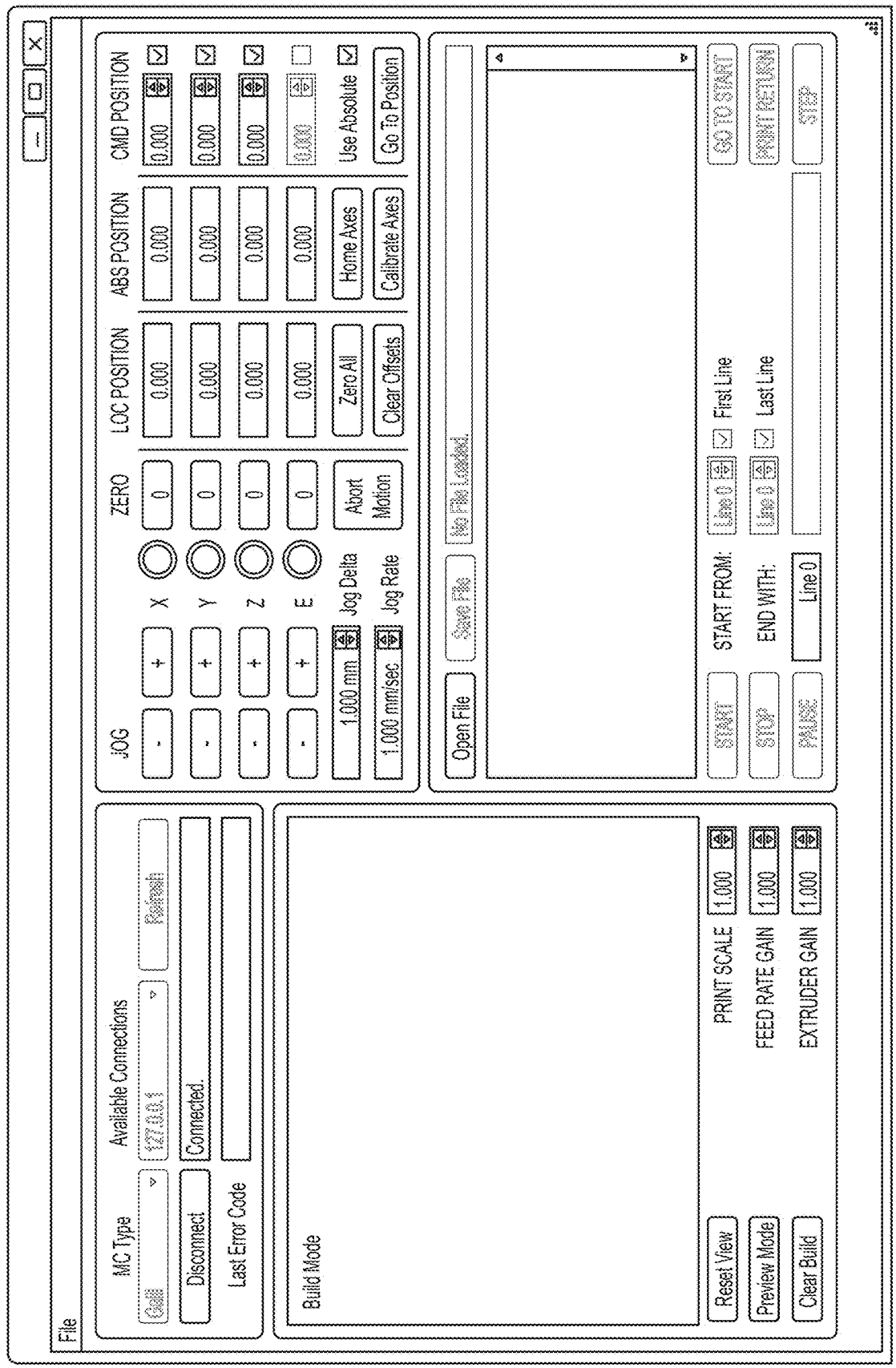
Figure 39E:
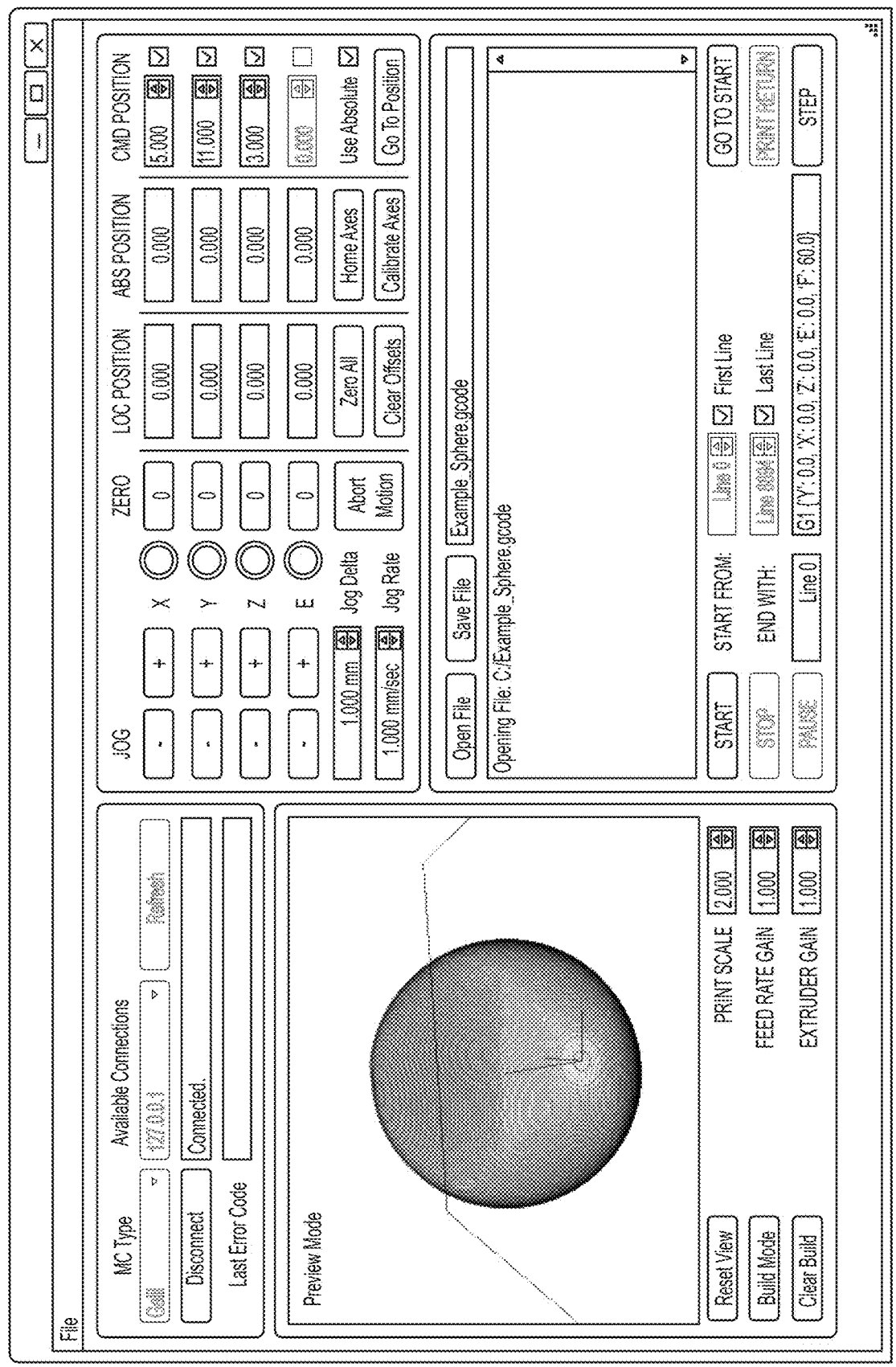
Figure 39F:
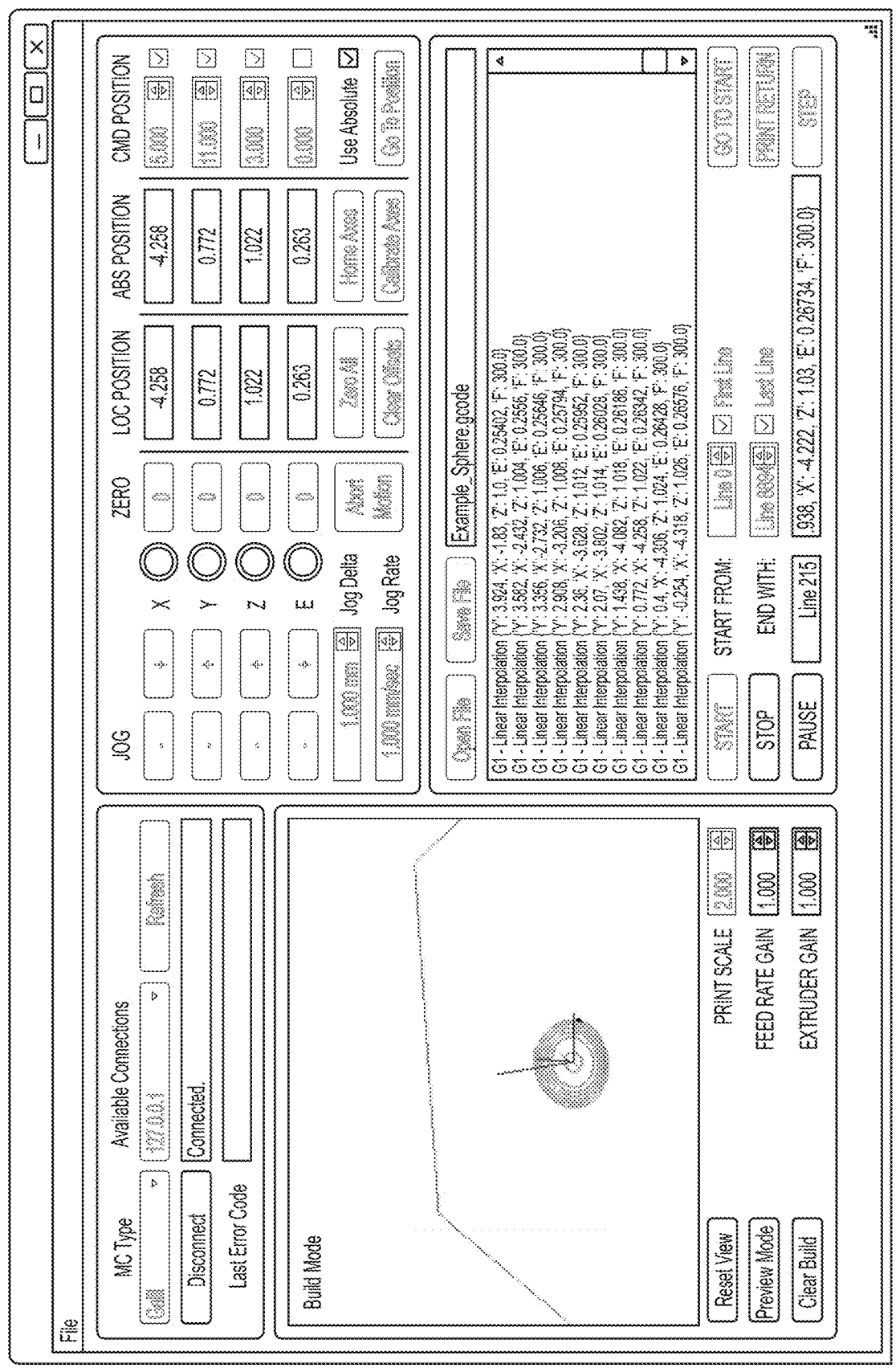
Figure 39G:
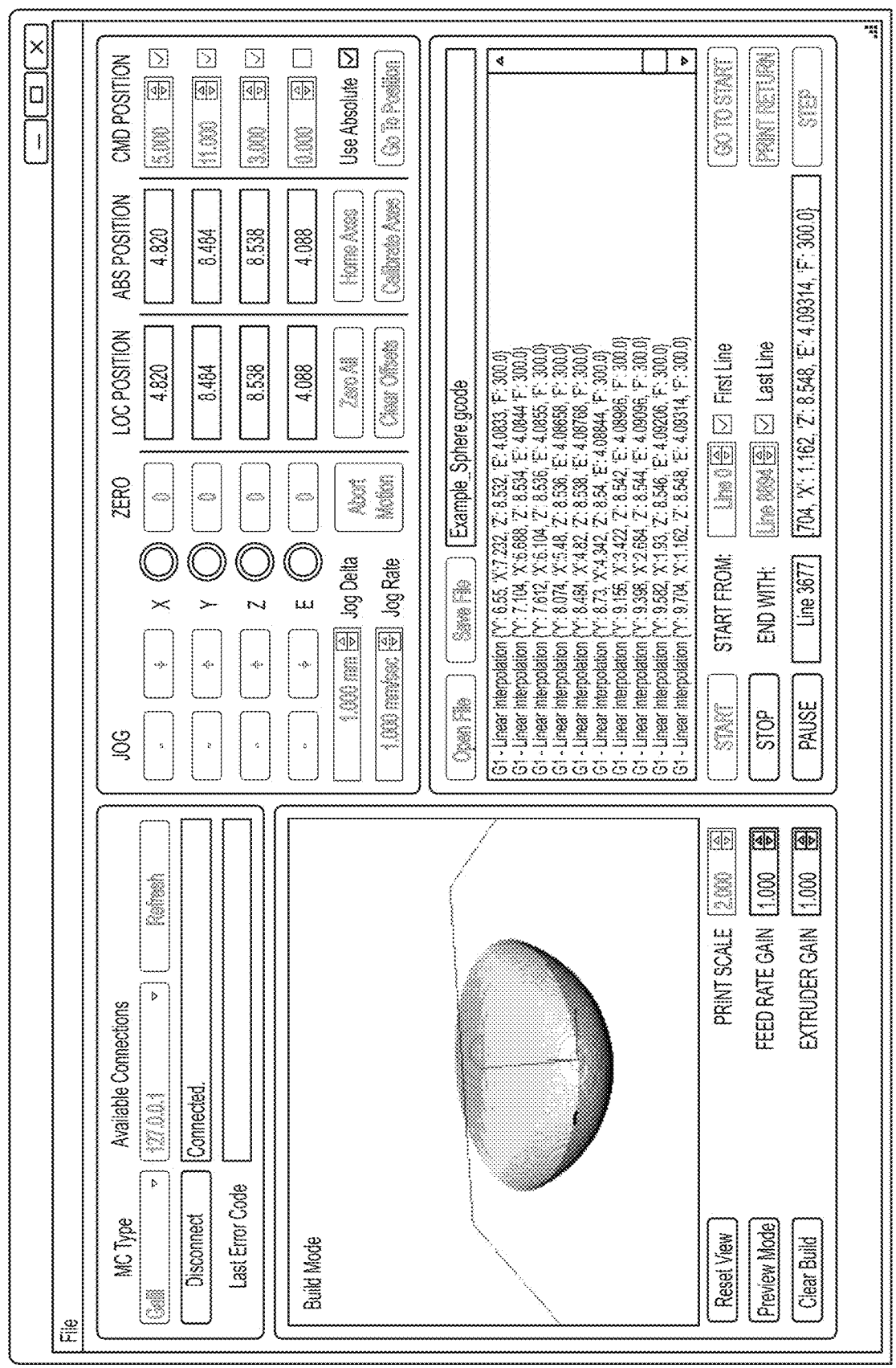
Figure 39H:
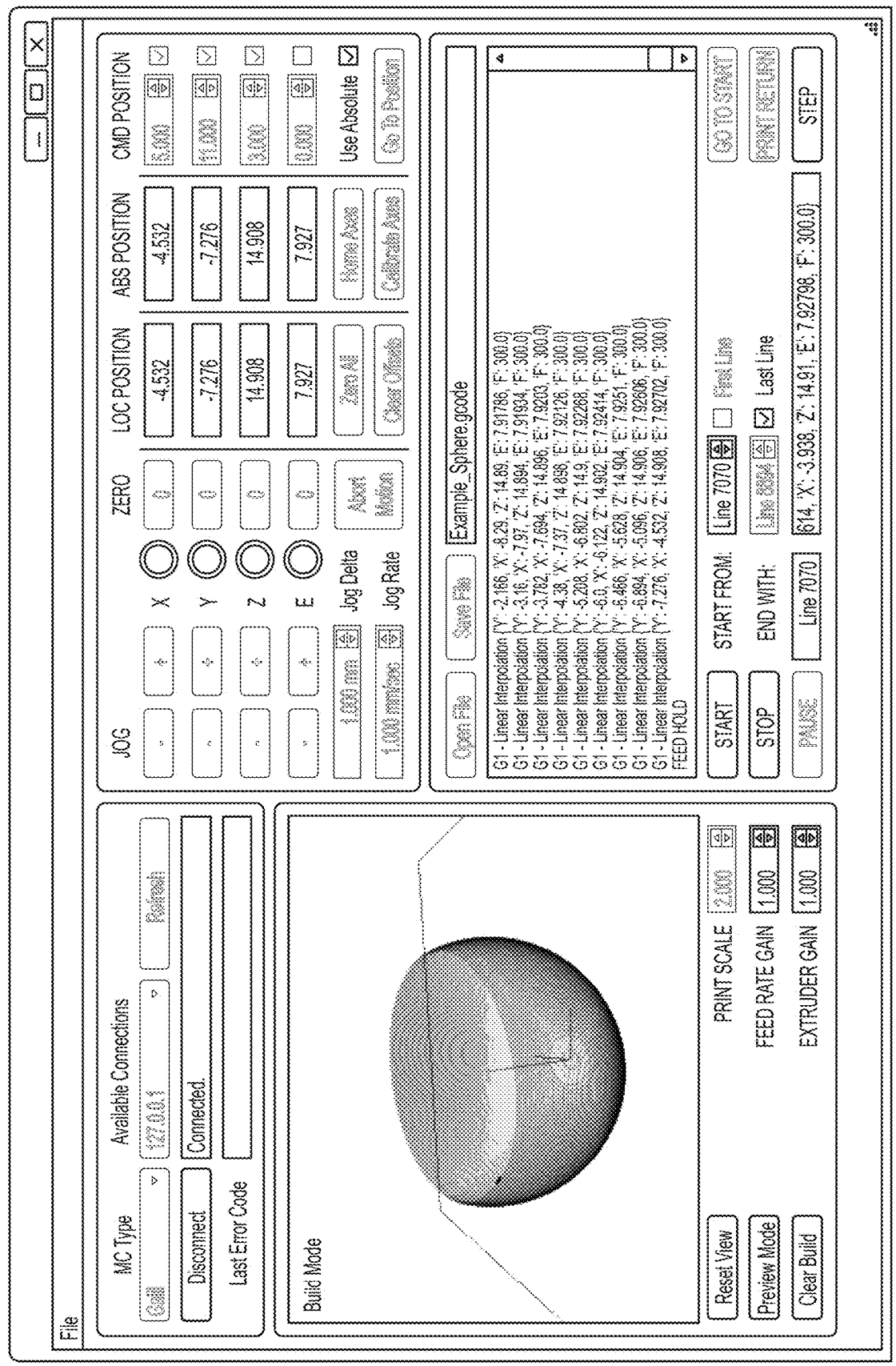
Figure 39I:
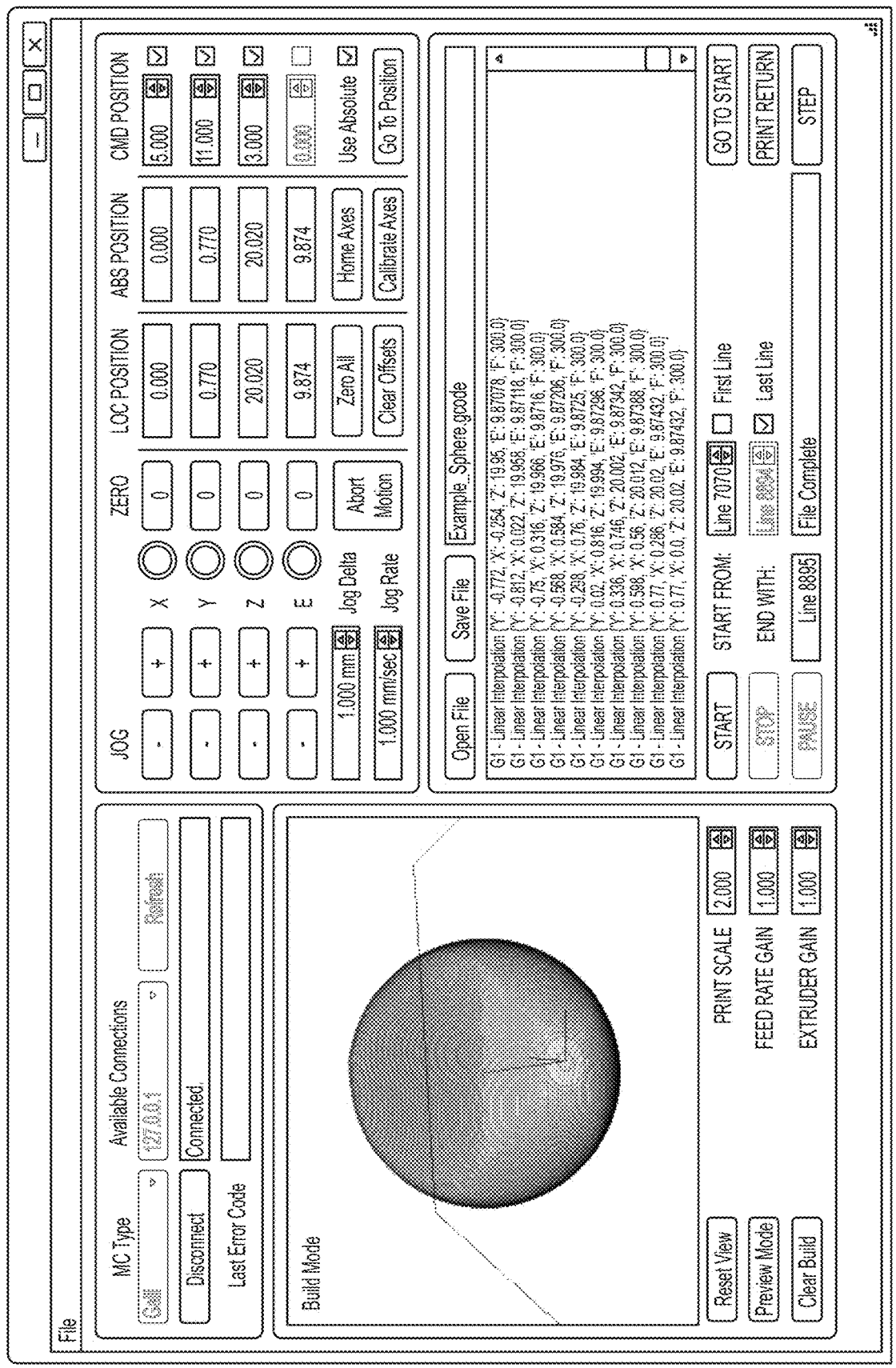

Referring now to FIG. 39B, second configuration method 11050 for interpreting G-code 67 by interpreter 57 can include, but is not limited to including, establishing 11051 a connection between printer 100 and processor 55, accessing 11055 G-code 67 for the structure to be printed, and displaying 11053 a preview of the structure. Method 11050 can include adjusting 11057 print scale, speed, and extruder gain settings, calibrating 11059 the location of the printing needle tip, jogging 11061 axes to a desired print start position, selecting 11063 G-code 67 between desired start and end lines, executing 11065 the selected G-code, and displaying 11064 a model of print progress. If 11067 printing is not complete, method 11050 can include if 11062 a new syringe is required, swapping 1160 the syringe, and continuing processing at calibrating 11059. If 11067 print is not complete, and if 11062 a new syringe is not required, method 11060 can include continuing processing at selecting 11063. If 11067 printing is complete, method 11050 can include returning 11069 the needle to a home position when the end line of the selected G-code is reached.

Referring now to FIGS. 39C-39I, a progression of the changing features of the display of a configuration of command interface 53 can be seen in screen snapshots during the creation of a structure. In some configurations, the display can begin (FIG. 39C) with a blank preview mode display and a blank status display that can invite the user to connect motion controller 59 to processor 55 through electronic communications 67. When the connection is established (FIG. 39D), a blank build mode display can await further instructions from activated radio buttons and other selection features on the display, in particular, an open file command. When a file is open and when preview mode is selected (FIG. 39E), the status display can provide the status of opening the file, and the structure display can include the structure in the opened file. Defaults for starting and ending lines of G-code can include first and last lines. When build mode is selected (FIG. 39F), the structure can be displayed as lines of G-code are executed, for example, line 215 is currently being executed. Lines of G-code that have been executed can appear in the status display. As further lines of G-code are executed (FIGS. 39G and 39H), the structure can take shape on the build mode display, and lines of G-code can be displayed as they are executed in the status area. Current needle position can also be displayed according to axis position. Eventually the last line of G-code will be executed and the structure will appear in its final shape (FIG. 39I) on the build mode display. In FIGS. 39C-39I, the local position column can include coordinates that represent the origin set point for a given structure. The absolute position column can include motion controller coordinates, and the command position column indicates a commanded position. The absolute position coordinates can indicate the origin (0,0,0) at the tip of the delivery device after calibration.

Figure 40A:
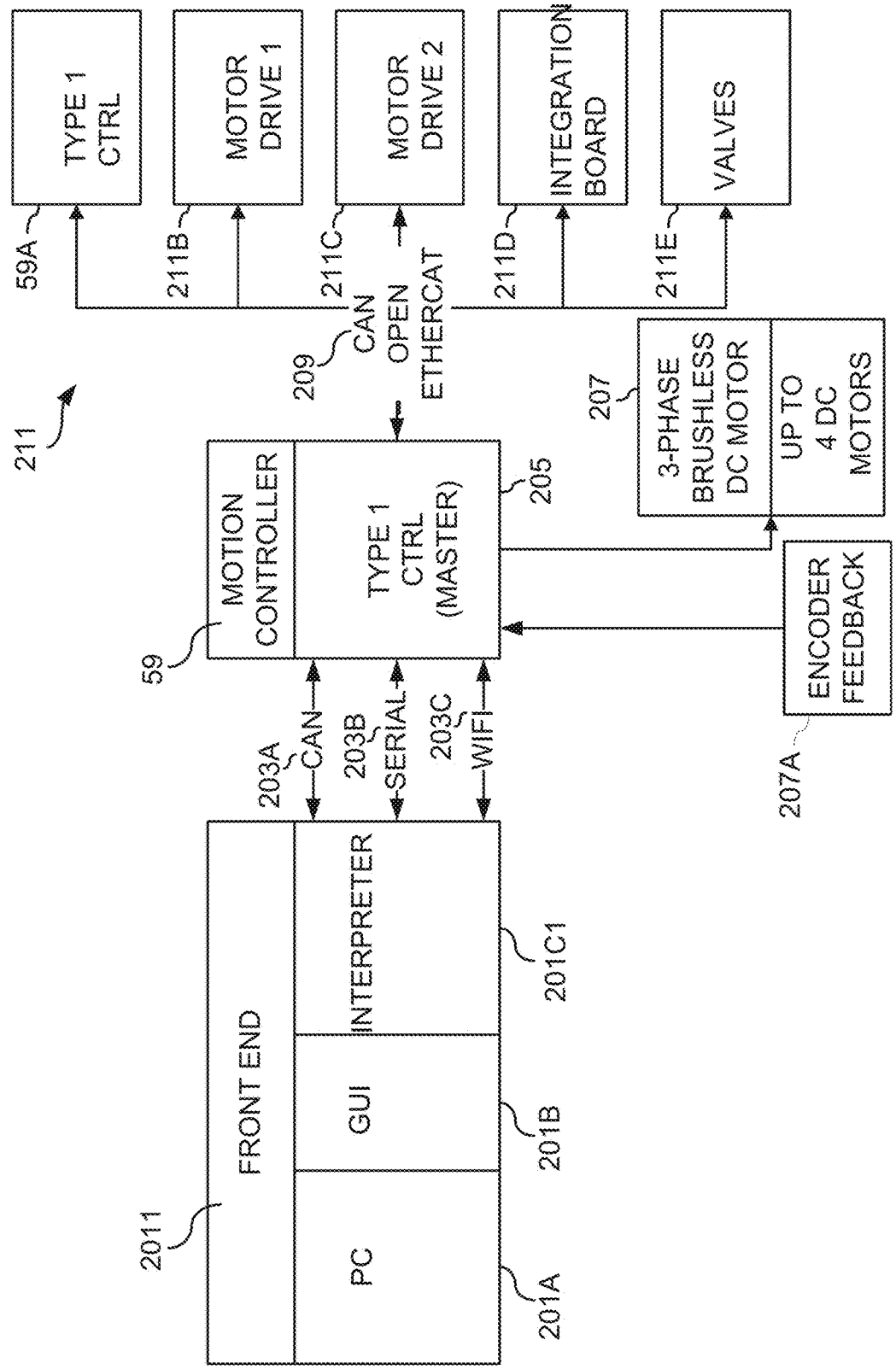
FIGS. 40A and 40B are schematic block diagrams of exemplary configurations of the control system of the present teachings.
Figure 40B:
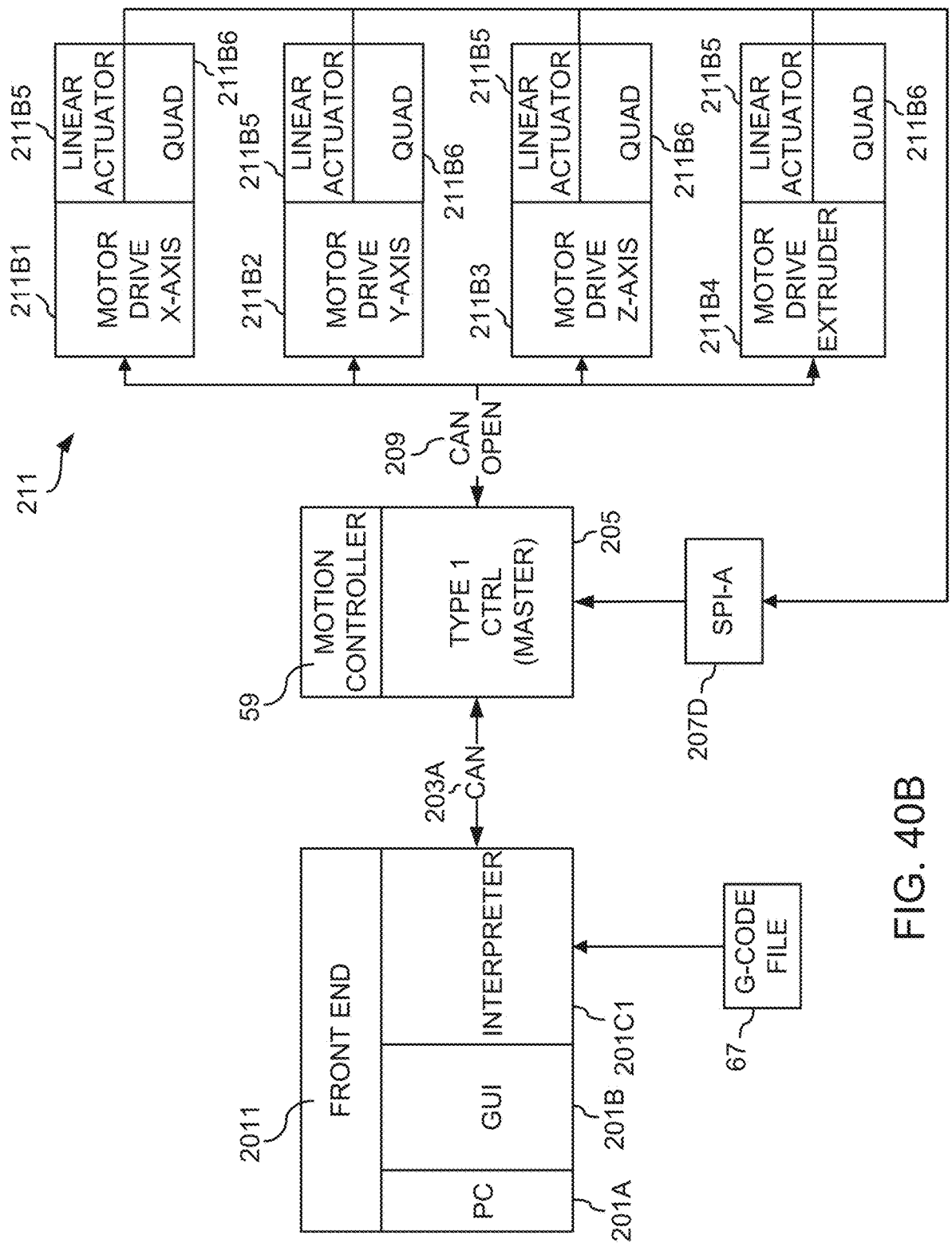

Referring now primarily to FIGS. 40A and 40B, exemplary configuration of the controller of the present teachings can include, but is not limited to including, front end 2011 that can include, but is not limited to including, computer aided design (CAD) processor 56 (FIG. 39), command interface 53 (FIG. 39), and interpreter 57 (FIG. 39). Command interface 53 (FIG. 39) can include, for example, but not limited to, graphical user interface 201B. CAD processor 56 (FIG. 39) can include, for example, but not limited to, PC 201A that can be, for example, but not limited to, a Raspberry Pi LYNX processor that can receive CAD files 66A (FIG. 39) and create G-code 67 (FIG. 40B) based on CAD files 66A (FIG. 39). Interpreter 57 (FIG. 39) can include, for example, but not limited to, G-code interpreter 201C that can compute, possibly in near real-time, SDA information 69 (FIG. 39) from G-code 67 (FIG. 39). G-code interpreter 201C can, for example, convert G-code that can be used to perform negative structure building to G-code 67 (FIG. 39) that can be used to perform positive building. SDA information 69 (FIG. 39) can be provided, possibly in near real-time, to motion controller 59 through, for example, but not limited to, CANbus 203A and/or serial communications 203B and/or wifi 203C.

Continuing to refer to FIGS. 40A and 40B, motion controller 59 can send, across, for example, but not limited to, CANopen/EtherCAT 209, an associated output signal to any of a number of hardware devices 211A. Hardware device 211A can include, for example, another type 1 controller 59A, first motor drive 211B, second motor drive 211C, integration board 211D, and valves 211E. If hardware device 211A is motor drive 211B, then first motor drives 211B can provide motor control signals through CANopen/EtherCAT 209 to motion controller 59. Motion controller 59 can provide the signals to at least one hardware device 211A (FIG. 42), such as, for example, but not limited to, at least one brushless DC motor 207. In some configurations, motion controller 59 can drive at least four motors. In some configurations, closed loop control can provide for position feedback information 207A from an encoder to be provided to motion controller 59 through serial peripheral interface (SPI-A) 207D. Motor drives 211 can include, but are not limited to including, motor drives manufactured by MAXON®, ADVANCED MOTION CONTROLS®, and/or ELMO®. Motion controller 59 can receive commands generated by front end 2011 and can coordinate hardware devices 211A (FIG. 41) in real-time.

Continuing to refer to FIGS. 40A and 40B, printer 100 (FIG. 39) can receive at least one motion command 73 (FIG. 39) to move the various parts of printer 100 (FIG. 39) in at least x, y, and z dimensions, and to extrude at least one material 79 (FIG. 39). Thus, actuator drivers 211 can include, but are not limited to including, x-axis motor drive 211B1, y-axis motor drive 211B2, z-axis motor drive 211B3, and extruder motor drive 211B4. Each of motor drives 211B1-211B4 can be associated with linear actuator 211B5 and quadrature encoder 211B6, for example, but not limited to, LS7366R manufactured by LSI Computer Systems, Inc. Quadrature encoder 211B6 can provide encoder feedback through, for example, but not limited to, SPI-A 207D. In some configurations, a parallel interface can be used. In some configurations, x-, y-, and z-axes can rely on incremental linear encoders as primary position references, and can rely on the quadrature position encoder mounted on the motor to control lash, velocity, acceleration, and driveline inertia.

Figure 41:
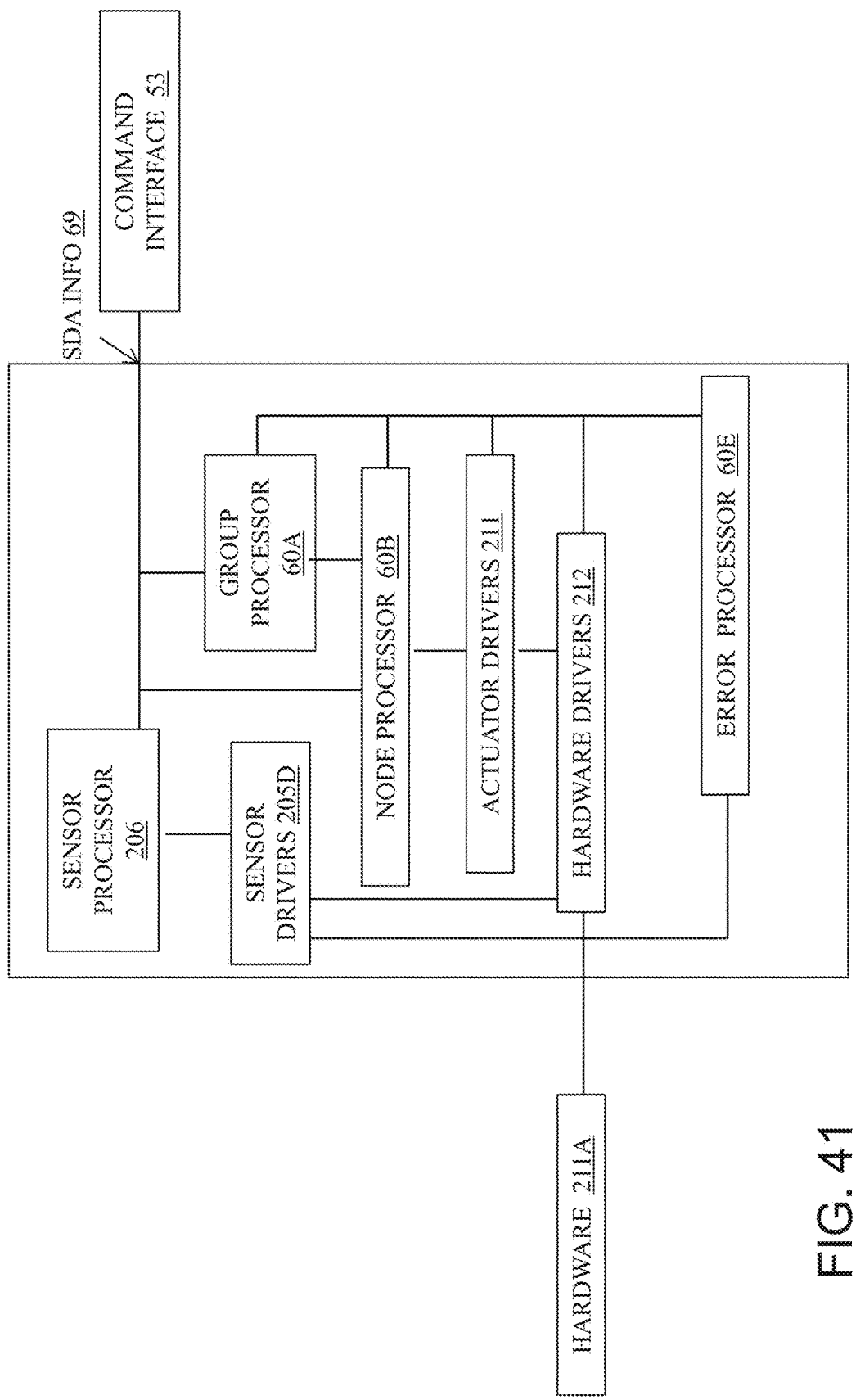
FIG. 41 is a schematic block diagram of the architecture of the motion controller of the present teachings.

Referring now to FIG. 41, motion controller 59 can provide a platform for controlling an arbitrary number of actuators in any desirable configuration. Each actuator can be controlled, for example, by one or more of several configurable control types, and can be linked to one or more sensors. Configurable control types can include, but are not limited to including, passive pass-through commands, control loops, and configurable control loops for multiple inputs. Motion controller 59 can enable configuration of nested control loops. In some configurations, motion controller 59 can include, but is not limited to including, group processor 60A, node processor 60B, sensor processor 205C, sensor drivers 205D, actuator drivers 211, hardware drivers 212, hardware 211A, and error processor 60E. Group processor 60A can manage, through node processor 60B, nodes to which actuators can be associated. Actuators can be grouped to accomplish coordinated and/or synchronized motion, and can be controlled, by actuator drivers 211, locally and/or remotely through networks that can communicate using, for example, but not limited to, standard CANbus and/or EtherCAT protocols. Actuators can control, for example rotational and/or linear motion, and can be of various types, for example, but not limited to, binary valves, pneumatic compressors, a valve apparatus, and heated elements. Sensor processor 205C can control sensors that can sense, for example, but not limited to, motor position, linear position, pressure, gyroscopic signals, accelerometer signals, and temperature. Sensors can include primary sensors that can feed into a control loop and secondary sensors that can provide feed forward information. Motion controller 59 can include options for multiple sensor inputs, and sensor limits can be used by motion controller 59 to, for example, raise warnings and/or stop motion. Types of hardware drivers 212 can include, but are not limited to including local drivers, CAN drivers, motor drivers manufactured by, for example, American Motors Corporation and/or Maxon Motor, and a modular valve apparatus.

Referring now primarily to FIGS. 42A and 42B, exemplary configurations of the architecture of the motion controller of the present teachings can include, but are not limited to including, group processor 60A (FIG. 41) that can manage N groups 205A. Each of N groups 205A can include a status that can include, but is not limited to including, the states of active and inactive. Each of the active of N groups 205A can include M nodes 205B. Both N and M can range from one to a value that can be limited by any possible hardware resource limitations. Group processor 60A (FIG. 41) can include a queue of commands derived from SDA info 69 (FIG. 41) that can include a group of commands for each of M nodes 205B of each of N groups 205A. The commands can be, for example, but not limited to, grouped sequentially. In some configurations, nodes 205B can be tightly coordinated, for example, but not limited to, in the case of 3-axis linear motion. When nodes 205B are tightly coordinated, feedback from each of nodes can be used to determine the command to its sibling nodes. In some configurations, nodes 205B can be synchronized. When nodes 205B are synchronized, feedback from a first of nodes 205B may not influence others of nodes 205B. Node processor 60B (FIG. 41) can manage nodes 205B that can represent, for example, but not limited to, actuator types described herein.

Continuing to refer primarily to FIGS. 42A and 42B, sensor processor 206 (FIG. 41), can manage at least one sensor object 205C such as, for example, but not limited to, analog-to-digital converters, general purpose input/output, accelerometer such as for example LMS303 manufactured by STMicroelectronics®, linear position sensor such as, for example, but not limited to, AS5410 manufactured by AMS®, and network input such as, for example, but not limited to, input received through CANbus and EtherCAT protocols. Each sensor object 205C has up to L values. Each can be uniquely configured, for example, but not limited to, for raw value in counts, scaled value, sensor gain, and optional filters. Each sensor object 205C can include a timestamp that can indicate the age of the sensor data. For network input, sensor object 205C can set up a CAN filter to select messages of the appropriate CAN ID and save data associated with the selected message. Update frequency for each sensor object 205C can be configurable, and can be, for example less than the control update frequency. For example, a sensor may sample at 100 Hz while the control loop cycle may be 1 kHz. At least one motion controller 59 can acquire sensor data, update communications information, and periodically process sensor data, update group data, and update node data. Sensor drivers 205D can enable sensor processor 206 (FIG. 41) to communicate with sensor hardware 211A through use of hardware driver 212. Each of sensor drivers 205D can have knowledge of the communications interface for a specific sensor object. A single instance of each of sensor drivers 205D can be used by many sensor objects 205C.

Continuing to refer to FIGS. 42A and 42B, sensor data acquisition can include updating communications interfaces such as SPI, I2C, and analog to digital converter (ADC) in parallel with constantly acquired sensor data. Incoming information can be queued and can be interrupt-driven. Available sensor data can be processed regularly, for example, when the system tick time (systick) generates an interrupt request. Actuators drivers 211 can be used by nodes 205B to communicate with at least one hardware type. Each of actuator drivers 211 can include knowledge of a communications interface for a specific type of actuator according to, for example, but not limited to, its make and model. Types of actuator drivers 211 can include, but are not limited to including, hardware driver 212, local and/or network motor drivers, another motion controller 59, and a modular valve apparatus. A single instance of each of actuator drivers 211 can be used by many of nodes 205B. For example, single group 205A can manage four nodes 205B, each of nodes 205B being associated with single sensor object 205C each. Single sensor driver 205D, can include, but is not limited to including, a driver for a quadrature encoder. Single actuator driver 205E, can include, but is not limited including, a driver for a brushless DC motor, for example, but not limited to, a MAXON® network motor driver. Hardware 211A can include a quadrature encoder and the motor/motor drive on the CANbus interface. The quadrature encoder can communicate with sensor driver 205D through hardware drivers 205F and the serial peripheral interface (SPI) communications protocol, for example. The motor can communicate with actuator driver 205E through hardware drivers 205F and the CANbus communications protocol, for example.

Referring now to FIG. 43, node configuration table 240 can enable node objects 205B to be configured, for example, through request 242A to command interface 2011. Request 242A can include, but is not limited to including, node object ID 241A, parameter index 241B, and parameter value 241C. Information about parameters associated with node object 205B can include, but are not limited to including, address offset, permissions, parameter type, and value limits.

Referring now primarily to FIGS. 44A and 44B, node processor 60B (FIG. 41) can process requests 242A (FIG. 43), 242B (FIG. 44A), and 242C (FIG. 44B) and can update a value for a requested parameter in node configuration table 240, the parameter being described in node parameter table 240A. Exemplary node parameters can include, but are not limited to including, control type, driver type, driver ID, actuator mode, sensors, gains, filter frequency, and group ID. Which node parameters appear in node parameter table 240A can depend upon the type of device that is represented by node parameter table 240A.

Referring now primarily to FIGS. 44C and 44D, sensor processor 206 (FIG. 41) can process requests 242D (FIG. 44C) and 242E (FIG. 44D) and can update a value for a requested parameter in sensor configuration table 243, the parameter being described in sensor parameter table 243A. Exemplary sensor parameters can include, but are not limited to including, sensor object, addresses, update period, and the repeated triad gain, filter, and filter frequency. Which sensor parameters appear in sensor parameter table 243A can depend upon the sensor object that is represented by sensor parameter table 243A. The same configuration scheme can be used to configure any objects, such as, for example, groups, errors, and processors.

Referring now to FIG. 45, method 11150 for controlling at least one actuator in any configuration can include, but is not limited to including, linking 11151 each of the at least one actuator to at least one sensor, controlling 11153 each of the at least one actuator in a loop, grouping 11155 the at least one actuator to accomplish coordinated/synchronized motion, and establishing 11157 communications among the at least one actuator. Communications can optionally include, but are not limited to including, network communications enabled by standard CAN and EtherCAT protocols. The at least one actuator can optionally enable rotational and/or linear motion, and can include, but is not limited to including, binary valves, pneumatic compressors, modular valves, and heating elements. The at least one sensor can optionally include, but is not limited to including, motor encoder, linear position, pressure sensor, gyroscope, accelerometer, and temperature sensor.

Referring now to FIG. 46, bioprinting system 5650 can provide constrained printing inside a tissue enclosure, for example, but not limited to, tissue enclosure 5655 (FIG. 47). Bioprinting system 5650 can include, but is not limited to including, robot 5651 operably coupled with robot tool 5657 that can provide a mounting means for needle 5755. Bioprinting system 5650 can include tissue enclosure mount sheet 5653, tissue enclosure 5655, tissue enclosure gripper 5659, and mount fastening means 5661. In some configurations, tissue enclosure 5655 can rest upon tissue enclosure gripper 5659 that can be attached to tissue enclosure mount sheet 5653. In some configurations, robot 5651 can include a 6-axis robot that can be, for example, a DENSO® VS-series 6-axis articulated robot. In some configurations, robot tool 5657 (FIG. 48) can include needle recess 5657-1 (FIG. 48) coupling needle 5755 with robot 5651, and fastening recesses 5657-2 (FIG. 48) which can couple robot tool 5657 (FIG. 48) with robot 5651. Tissue enclosure 5655 can be removably coupled with tissue enclosure gripper 5659 enabling automated removal and replacement of tissue enclosure 5655. In some configurations, tissue enclosure 5655 can include facets 5655-1 (FIG. 47) and mounting points 5655-2 (FIG. 47) that can enable repositioning of tissue enclosure 5655 to accommodate production line tissue printing and tissue maintenance. Needle recess 5657-1 can be sized according to the diameter of needle 5755. Needle 5755 can enter tissue enclosure 5655 through window 5655-3 (FIG. 47).

Referring now to FIGS. 49A and 49B, printing tissue into tissue enclosure 5655 (FIG. 47) using robot 5651 (FIG. 46) can include controlling robot 5651 (FIG. 46) to position needle 5755 (FIG. 46) according to the shape and size of a desired tissue. The design of the desired tissue can be accessible by computer 5691 (FIG. 49A), and can be, by computer 5691 (FIG. 49A), converted to coordinates that robot controller 5693 (FIG. 49A) can use to print tissue into tissue enclosure 5655 (FIG. 47). Method 5770 (FIG. 49B) for converting coordinates can include, but is not limited to including, setup 5771 (FIG. 49B) that can include, but is not limited to including, establishing robot tool offset parameters, locating control points used in pathing, and creating part points to be pathed in part space. Method 5770 (FIG. 49B) can include pathing 5773 (FIG. 49B) that can include, but is not limited to including, converting the points to robot coordinates and determining robot orientations. Method 5770 (FIG. 49B) can include data transfer 5775 (FIG. 49B) that can include, but is not limited to including, creating, in the computer, batches of binary data, sending the batches, using a communications network protocol, to robot controller 5693, and setting a pose for robot 5651 (FIG. 46) for each of the batches. Method 5770 (FIG. 49B) can include data processing 5777 (FIG. 49B) that can include, but is not limited to including, converting the binary data to robot points, approach, and orientation vector, choosing a robot figure for each path based on the desired robot position and range of motion, determining a translation data type based on the vector components and robot figure, and creating at least one motion command based on the translation data type and the robot points. Method 5770 can include motion 5779 that can include, but is not limited to including, moving, by robot controller 5693 (FIG. 49A), robot 5651 (FIG. 46) to a home position, and executing, by robot controller 5693 (FIG. 49A), at least one motion command.

Continuing to refer to FIG. 49B, in some configurations, setup 5771 can include, but is not limited to including, establishing robot tool offset parameters such that tool control point (TCP) 5753 (FIG. 50) is located where needle 5755 (FIG. 50) extends from robot end-of-arm tooling components (EOAT) 5757 (FIG. 50). Setup 5771 can include locating control points 5759 (FIG. 50) to be used in pathing in robot/world space by using needle 5755 (FIG. 50) to locate port centers 5655-3 (FIG. 47) in a configuration in which robot and world coordinate systems are coincident. Setup 5771 can include creating part points 5761 (FIG. 50) to be pathed in part space. Part points 5761 can be generated using the mathematical definitions of, for example, but not limited to, a helix and toroidal helix. A relatively large number of points, for example, thousands to tens of thousands, can be generated for each desired path.

Continuing to refer to FIG. 49B, in some configurations, pathing can include, but is not limited to including, indexing through the points to be pathed, and converting them to valid robot coordinates. Robot coordinates first require a point (a vector) to be constrained. The process of finding this point can include, but is not limited to including, choosing a control point CP 5759 (FIG. 50) through which needle 5755 (FIG. 50) will move, and transforming control point 5759 (FIG. 50) from build platform coordinates to world coordinates. Rotation data can be stored as a quaternion, Q, so that Pworld=(QplatformPplatform)+Tplatform, where Pworld is the resulting world coordinate to be determined, Qplatform is the platform coordinate system's rotation quaternion relative to world space, Pplatform is control point 5759 in platform space to be transformed, and Tplatform is the platform coordinate system's translation relative to world space. The process of finding the point (the vector) to be constrained can include choosing a point P 5761 (FIG. 50) to be reached by needle tip 5756 (FIG. 50), and transforming point P 5761 (FIG. 50) from part coordinates to world coordinates. Rotation data can be stored as a quaternion, Q, so that Pworld=Qplatform[(QpartPpart)+Tpart]+Tplatform, where Pworld is the resulting world coordinate to be determined, Qplatform is the platform coordinate system's rotation quaternion relative to world space, Qpart is the part coordinate system's rotation quaternion relative to platform space, Ppart is point P 5761 (FIG. 50) in part space to be transformed, Tpart is the part coordinate system's translation relative to platform space, and Tplatform is the platform coordinate system's translation relative to world space. The process of finding the point (the vector) to be constrained can include computing a direction vector as the difference between CP 5759 (FIG. 50) and P 5761 (FIG. 50) in world space, normalizing the direction vector so that it points from point P 5761 (FIG. 50) toward control point CP 5759 (FIG. 50). The robot tool point (in world space) is equal to P+Norm(CP−P)*(Needle Length). The process of finding the point (the vector) to be constrained can include, in some configurations, transforming the robot tool point into the robot coordinate system in a similar manner to the transforms mentioned herein. In some configurations, when the robot and world coordinate systems are coincident, so the transforming of the robot tool point may not be necessary.

Continuing to refer to FIG. 49B, in addition to the robot tool point, a valid robot coordinate includes an orientation that includes two orthogonal unit vectors that describe the approach and orientation directions of robot tool 5757 (FIG. 50). Determining the orientation of robot 5651 can include, but is not limited to including, determining robot approach vector 5751A (FIG. 50). Robot approach vector 5751A (FIG. 50) is a unit vector extending away from robot 5651 (FIG. 46), normal to the flange of robot tool 5757 (FIG. 50). Robot approach vector 5751A (FIG. 50) is the inverse of the normalized direction vector calculated herein. To calculate orientation vector 5751B (FIG. 50), an "up" vector—a unit vector that represents the approximate desired vertical direction of robot tool 5757 (FIG. 50)—is determined. The "up" vector can bear any non-equal relationship to approach vector 5751A (FIG. 50), including being non-orthogonal to approach vector 5751A (FIG. 50). The "up" vector can be set during path planning as either positive or negative vertical depending on the desired robot pose and available range of motion. The orientation, or true up vector, is finally calculated by taking the cross product of a right vector and approach vector 5751A (FIG. 50). The right vector is determined by taking the cross product of approach vector 5751A (FIG. 50) and the "up" vector. Holding the "up" vector constant can lead to unreachable robot poses as needle 5755 (FIG. 50) is moved from one port 5655-3 (FIG. 47) on tissue enclosure 5655 (FIG. 47) to another port 5655-4 (FIG. 47). To insure that robot poses are reachable, the "up" vector can be allowed to point either up or down, depending on the requirements of a particular port of tissue enclosure 5655 (FIG. 47).

Continuing to refer to FIG. 49B, in some configurations, data transfer 5775 between computer 5691 (FIG. 49A) and robot controller 5693 (FIG. 49A) can include the use of the transmission control protocol (TCP). Each individual path to be printed can be divided into a pre-selected number of points, such as, for example, but not limited to, 250 points (and orientation vectors). The points can be transferred from computer 5691 (FIG. 49A) to robot controller 5693 (FIG. 49A) in batches of binary data (one for each path). Robot controller 5693 (FIG. 49A) can convert the binary data to robot translation data before adding the robot translation data as spline paths for robot 5651 (FIG. 46) to follow. A robot pose can be set for each path. For each path sent to robot 5651 (FIG. 46), a robot point, approach vector 5751A (FIG. 50), and orientation vector 5751B (FIG. 50) can be converted into a continuous array for float-type variables. A TCP server can execute on computer 5691 (FIG. 49A), and robot controller 5693 (FIG. 49A), configured to communicate using TCP in binary mode, can connect to the TCP server and complete handshaking to begin receiving the raw binary data. When a pre-selected amount of data, such as, for example, three sets of data, have been received, robot controller 5693 (FIG. 49A) can close the connection and begin processing the data.

Continuing to refer to FIG. 49B, in some configurations, data processing 5777 can include, but is not limited to including, accessing, by robot controller 5693 (FIG. 49A) the received data as individual values, corresponding to robot point, approach vector 5751A (FIG. 50), and orientation vector 5751B (FIG. 50). The data can include, but is not limited to including, binary data, ASCII data, or any other format of data. The individual values can include, but are not limited to including, floating point values, or other numeric representations. A robot figure can be chosen for each path based on desired robot positions and range of motion. The robot figure can work with the "up" vector to constrain the motion of robot 5651 (FIG. 46). Approach vector 5751A (FIG. 50), orientation vector 5751B (FIG. 50), and the chosen figure can be transformed into a translation data type that can be used to set a robot point. Translation points from the translation data type can be added into a built-in path variable to be executed as at least one motion command.

Continuing to refer to FIG. 49B, in some configurations, motion 5779 can include, but is not limited to including, moving robot 5651 (FIG. 46) to a home position and executing at least one path. Robot 5651 (FIG. 46) can move to an approach position that can be a pre-selected distance, such as, for example, but not limited to, 100 mm away from the first point to print, and can remain in that position for a pre-selected amount of time. The pre-selected amount of time can be, but is not limited to being, based on how the ink is being dispensed. Motion 5779 can include moving robot 5651 (FIG. 46) to the first print position, and inserting needle 5755 (FIG. 46) through control point 5759 (FIG. 50 into tissue enclosure 5655 (FIG. 47). After reaching the first point, motion 5779 can include moving robot 5651 (FIG. 46) so that robot 5651 (FIG. 46) follows a spline path interpolating between the pre-selected number of path points. Motion 5779 can include retracting robot 5651 (FIG. 46) a pre-selected distance such as, for example, but not limited to, 100 mm axially to exit tissue enclosure 5655 (FIG. 47), and returning robot 5651 (FIG. 46) to the home position. Additional intermediate points can be inserted to ensure a smooth motion between the home position and the print position, avoiding collision with tissue enclosure 5655 (FIG. 47) and surroundings of robot 5651 (FIG. 46). Multiple robots 5651 (FIG. 46) can be used, and multiple needles 5755 (FIG. 46) on each robot 5651 (FIG. 46) can be used. A vision guidance system can be used to close the robot position control loop on the measured location of needle 5755 (FIG. 46), and to determine the robot tool offset. The preferred "up" vector can be determined based on which port is used. The needle tip location can be directly measured and taken into account during printing to improve accuracy. Additionally, the actual needle geometry could be respected in path planning to prevent interference with already-printed material.

Referring now to FIG. 51, a delivery system can include accommodations for print nozzles 38D-1 that can include relatively large nozzle openings 38D-3 that can reduce to relatively small nozzle openings 38D-2. This reduction can be used to prepare small amounts of bio-ink that can be used to print very fine resolution tissue features.

Referring now to FIGS. 52 and 53, a delivery system can include accommodations for second configuration print nozzle 38DA-1 that can include relatively large nozzle openings 38DA-2 that can reduce to relatively small nozzle openings 38DA-3.

Referring now to FIG. 54, when extrusion printing within medium 509 (FIG. 56), knowing the precise position of an extrusion device, for example, tip 104A of tool 104, can enable returning tip 104A to the precise position to print a continuous structure and/or to place multiple types of materials coincident with each other. Coil 1001 can be wrapped around tool 104 and a detector can sense movement of tool 104 based on the signals from coil 1001. The position tip 104A can be detected in several ways including, but not limited to, (a) a magnet/coil mounted near tip 104A, (b) a spreader/concentrator, and (c) a spreader and valve combination. Considerations for the selection of a technique can include (1) signal strength, (2) noise in the signal, and (3) resolution. The requirements for resolution can depend upon which tissue is being generated, and can be, for example, but not limited to, in the 1-10μ range.

Continuing to referring to FIG. 54, with respect to (a), source 1007 can provide voltage to driven coil 1001 that can induce current flowing through driven coil 1001 and a magnetic field 1015 can be formed. High Q resonant tank circuit coil 1003 can enhance magnetic field 1015. Driven coil 1001 can be sized to accommodate the voltage and to take into account thermal limitations of driven coil 1001 with respect to the current flowing through driver coil 1001. The amount of space along tool 104 between driven coil 1001 and high Q coil 1003 can depend upon the desired strength of magnetic field 1015. Filter 1005 can be used to filter unwanted frequencies, limit the transmit noise bandwidth, and improve resolution. Filter 1005 can include, for example, but not limited to, a crystal filter.

Referring now to FIG. 55, at least one sensor can be positioned in the vicinity of magnetic field 1015 and can sense magnetic field 1015. Sensors can include, but are not limited to including, x-y sensor 1009 and z sensor 1011, and can include anisotropic magneto-resistive (AMR) sensors. The sensors can measure magnetic fields and can convert incident magnetic fields in a sensitive axis direction to voltage output. Sensor 1009 can include, but is not limited to including, a HONEYWELL® AMR sensor HMC 1002, and Sensor 1011 can include, but is not limited to including, a HONEYWELL® AMR sensor HMC. In some configurations, noise can be limited by locking the received signal phase onto the source with at least one filter 1005, for example, but not limited to, a crystal filter. In some configurations, voltage output can be converted to vector magnitudes 1013 that can indicate the position of the tip of tool 104.

Referring now to FIG. 56, the x-y-z positions of tool tips 104A relative to a motion axis can be determined by optic sensors, for example, opposed (through beam), retro-reflective, and proximity-sensing (diffused) optic sensors which can be mounted above the printing area of tissue enclosure 700, at varying heights. A photoelectric sensor can discover the distance and presence (or absence) of the tool 104 by transmitting light from a transmitter to a receiver, the needle being detected by the absence of light at the receiver. In some configurations, a through-beam sensor could be used to take advantage of its accuracy, sensing range, and reliability. In some configurations, reflective sensors and/or diffuse sensors can be used to take advantage their features. Tissue enclosure 700 can accommodate external sensors 1011/1009. In some configurations, a sensor in the vicinity of each face of tissue enclosure 700 can accommodate sensing of magnetic field 1015. In some configurations, the number of sensors 1011/1009 that can be located in the vicinity of tissue enclosure 700 can depend upon the strength of magnetic field 1015. X-measurement line 1072A and Y-measurement line 1072B can be used by sensors 1011/1009 to capture the magnetic field strength in the x-y-z directions. Sensors 1011/1009 can be operably connected to controller 519 and can supply controller 519 with position data of tool tip 104A. Controller 519 can resolve the actual position of the tip of tool 104 based on the available sensor data as modified by corrective features that can accommodate the particular characteristics of tool 104.

Referring now to FIG. 57, in some configurations, at least one magnet 1023 can provide the source for the magnetic field. In some configurations, several permanent magnets such as, for example, but not limited to, 0.5 mm neodymium magnets grade 52, for example, can be used to create the magnetic field. Tissue enclosure 700 can accommodate external sensors 1011/1009. In some configurations, a sensor located in the vicinity of each face of tissue enclosure 700 can accommodate sensing of magnetic field 1015. In some configurations, the number of sensors 1011/1009 that can be located in the vicinity of tissue enclosure 700 can depend upon the strength of magnetic field 1015. Sensors 1011/1009 can be operably connected to controller 519 and can supply controller 519 with position data of tool tip 104A. Controller 519 can resolve the actual position of the tip of tool 104 based on the available sensor data as modified by corrective features that can accommodate the particular characteristics of tool 104.

Referring now to FIG. 58, in some configurations, sensor 1051 can be mounted on tool 104 in the vicinity of tool tip 104A. Coils 1053 can be mounted external to tissue enclosure 700. In some configurations, pulsing coils can provide noise immunity. Coils 1053 can be positioned to illuminate the area including tool 104 and generate a magnetic field. In some configurations, coils 1053 can be activated sequentially or in any random order. The magnetic field can be sensed by sensor 1053, which can return the information to controller 519 that can be used to determine the position of tool tip 104A.

Referring now to FIG. 59, calibrating the starting location of tool tip 104A can improve accuracy of the measurement of the positions of tool tips 104A as tool 104 prints into tissue enclosure 700. Tool touch-off sensors 101A can be mounted at pre-determined x-y-z locations around tissue enclosure 101 and can be used to detect the position of tool tip 104A. The pre-determined z locations can be achieved by stand-offs 101B. Tool touch-off sensors 101A can be mounted upon petri disk mounting plate 102 and/or can be mounted upon a stand-alone mounting platform at a pre-selected x-y-z distance from petri dish 102. As tool tip 104A travels towards medium 509, tool touch-off sensors 101A can detect its location and provide that information to controller 519. Tool touch-off sensors 101A can be used for calibration of the delivery device as described herein. Tool touch-off sensors can include, but are not limited to including, commercial products such as, for example, KEYENCE® laser sensors LV-S72R and LV-S72T.

Referring now to FIG. 60, distance 104B between calibration tool tip location 104H and projection point 104G can be determined during calibration.

Referring now to FIG. 61, as tool 104 moves through medium 509, tool 104 can change shape, and actual tool tip location 104I can differ from the calibration tool tip position 104H by location delta 104D. The more compliant tool 104 can be, the more likely tool 104 can change shape during printing in medium 509. Controller 519 can determine location delta 104D, and therefore actual tool tip location 104I, based on, for example, but not limited to, tool speed, tool characteristics, tool depth, and medium characteristics. Controller 519 can also determine a feed rate compensation amount based on, for example, but not limited to, tool tip speed, tool characteristics including, but not limited to, the diameter of tool tip 104A, and medium characteristics. The feed rate compensation can be applied to a bio-ink feed rate and can enable smooth deposition of bio-ink 514A (FIG. 1A).

Referring now to FIG. 62, controller 519 can anticipate when tool 104 will be changing direction with reference to axis 104E, can decelerate the speed of tool 104, and can accelerate the speed of tool 104 in a different direction for backup distance 104J. This series of actions by controller 519 can enable tool 104 to correctly position bio-ink at turning point 104F and beyond.

Referring now to FIG. 63, with respect to (b), in some configurations, dual spreader configuration 1021 can include first spreader 1054A and second spreader 1054B that can be used to concentrate the field lines from the magnetic field in tissue enclosure 700 to more readily observe the movement of tool 104. In some configurations, spreaders 1054A/1054B can include bells 1028 and spreader tips 1026. In some configurations, when the ratio between distance 1027 and bell outer diameter 1025 is honored, 1054A/1054B can be scalable. In some configurations, the ratio can be about 0.43. In some configurations, spreader 1054 can include stainless steel material that can be characterized, for example, as low carbon, high chromium, ferritic stainless steel, and can include such materials as SS-430F. In some configurations, spreader 1054 can include a nickel-iron magnetic alloy with high permeability, such as, for example, but not limited to, mu-metal. Dual spreader configuration 1021 can include sensor 1053 that can be positioned between spreader tips 1026. The spacing between spreader tips 1026 and sensor 1053 can depend upon the characteristics of the magnetic field. The magnetic field can be captured by first spreader 1054A, for example, and be concentrated towards tip 1026 in first spreader 1054A. The magnetic field can proceed through tip 1026 in first spreader 1054A, through sensor 1053, and into second spreader 1054B which can provide a conduit for the magnetic field. As the magnetic field transits through tips 1026, sensor 1053 can detect information that can be converted to the position of, for example, tool tip 104A.

Referring now to FIG. 64, at least one spreader configuration 1021 as described with respect to FIG. 63 can be located in the vicinity of tissue enclosure 700 to determine the location of tool tip 104A. Tool tip 104A can provide, for example, mounting capability for at least one magnet 1023 that can generate the magnetic field as described with respect to FIG. 57. The magnetic field can be induced in other ways including, but not limited to including, coils as described with respect to FIGS. 54, 55, and 56-58. In some configurations, spreader configurations 1021 can be located in the vicinity of each face of tissue enclosure 700. Sensors 1053 can provide information to controller 519 that can be used to determine the position of tool tip 104A.

Referring now to FIG. 65, magnetic valve 1075 can be used to improve the resolution of the location of tool tip 104A (FIG. 66). Specifically, magnetic valve 1075 can control the flow of the magnetic field induced by magnet 1023.

Referring now to FIG. 66, magnetic valve 1075 can direct the magnetic field through at least one sensor 1053 by the current in magnetic valve 1075. The coil on magnetic valve 1075 can be tuned to direct magnetic flux through the coil. The sensitivity of spreader 1021A can be controlled by the current in coil 1075 which is energized by power source 522. Coil 1075 can be large enough in diameter to accommodate at least one sensor 1053. In some configurations, spreaders 1021A and magnetic valves 1075 can be mounted in the vicinity of each face of tissue enclosure 700. At least one sensor 1053 can provide information to controller 519 that can be used to determine the position of tool tip 104A.

Referring now to FIG. 67, in some configurations, height 1075A of coil 1075 can be about 0.4 inches, inner diameter 1075B of coil 1075 can be about 0.7 inches, and outer diameter 1075C of coil 1075 can be about 0.9 inches. When coil 1075 includes these dimensions, about 0.1 A is required to generate $0.005V_s/m^2$. Magnetic valve 1075 can provide the resolution to support use of very small materials in multi-dimensional printing operations such as, for example, but not limited to, optical materials.

Referring now to FIG. 68, magnetic field 1015 induced by of magnetic valve 1075 and magnet 1023 can be funneled towards sensor 1053 by spreader 1021A. The strength of magnetic field 1015 increases in and around spreader 1021, strengthening the signal arriving at and sensed by sensor 1053.

Configurations of the present teachings are directed to computer systems for accomplishing the methods discussed in the description herein, and to computer readable media containing programs for accomplishing these methods. The raw data and results can be stored for future retrieval and processing, printed, displayed, transferred to another computer, and/or transferred elsewhere. Communications links can be wired or wireless, for example, using cellular communication systems, military communications systems, and satellite communications systems. Parts of system 50 (FIG. 39), for example, can operate on a computer having a variable number of CPUs. Other alternative computer platforms can be used.

The present embodiment is also directed to software for accomplishing the methods discussed herein, and computer readable media storing software for accomplishing these methods. The various modules described herein can be accomplished on the same CPU, or can be accomplished on a different computer. In compliance with the statute, the present embodiment has been described in language more or less specific as to structural and methodical features. It is to be understood, however, that the present embodiment is not limited to the specific features shown and described, since the means herein disclosed comprise preferred forms of putting the present embodiment into effect.

Method 2150 (FIG. 45), can be, in whole or in part, implemented electronically. Signals representing actions taken by elements of motion controller 59 (FIG. 39) and system 50 (FIG. 39) and other disclosed configurations can travel over at least one live communications network 67 (FIG. 39). Control and data information can be electronically executed and stored on at least one computer-readable medium. The systems can be implemented to execute on at least one computer node in at least one live communications network. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form, subject to appropriate licenses where necessary, including, but not limited to, Graphic Interchange Format (GIF), Joint Photographic Experts Group (JPEG), Portable Network Graphics (PNG), Scalable Vector Graphics (SVG), and Tagged Image File Format (TIFF).

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

The invention claimed is:

1. A bioprinting system for printing tissue into a tissue enclosure comprising:
   a multi-dimensional printer;
   a delivery device operably coupled to the multi-dimensional printer, the delivery device including a compliant needle, the compliant needle having a proximal end and a distal end, the delivery device delivering the tissue through the distal end;
   a motion controller configured to command the delivery device to print the tissue;
   a delivery device locating subsystem configured to return the delivery device distal end to selected locations within the printed tissue;
   at least one sensor configured for determining the position of the delivery device distal end within the tissue enclosure during operation of printing the tissue; and
   at least one delivery device fixture operably coupled with the delivery device, the at least one sensor configured to continuously determine the position of the delivery device distal end based at least on the at least one delivery device fixture.

2. The bioprinting system as in claim 1 wherein the delivery device locating subsystem comprises:
   a mounting plate including kinematic positioning features; and
   a tissue enclosure being a repository for the printed tissue, the tissue enclosure being mounted at a pre-selected orientation, the tissue enclosure including kinematic mounting features complementary with the kinematic positioning features, the kinematic mounting features matably couplable with the kinematic positioning features, the mounting features and the positioning features forcing the tissue enclosure to be mounted at the pre-selected orientation and no other orientations.

3. The system as in claim 1 wherein the motion controller comprises a sensor processor, a group processor, and a node processor, the group processor managing at least one group, the at least one group including at least one node, the at least one node associated with at least one actuator, the node processor managing the at least one actuator, the sensor processor managing at least one sensor hardware through at least one sensor driver, the sensor processor communicating the sensor data to the group processor and the node processor.

4. The system as in claim 3 wherein the motion controller comprises at least one actuator driver driving the at least one actuator, at least one hardware driver driving the at least one hardware device, and an error processor tracking errors encountered by the motion controller.

5. The bioprinting system as in claim 1 wherein the delivery device comprises:
   bi-directional fluid control between the delivery device and the tissue enclosure.

6. The bioprinting system as in claim 1 wherein the delivery device comprises:
   input means for a plurality of input materials; and
   a mixing valve receiving the plurality of input materials, the mixing valve extruding a single stream of the input materials as the printed tissue.

7. The bioprinting system as in claim 1 further comprising:
   a calibration system configured to determine origin coordinates of a reference point of the delivery device within the tissue enclosure, the calibration system providing the reference point to the motion controller.

8. The bioprinting system as in claim 1 wherein the delivery device locating subsystem comprises:
   being configured to determine location coordinates of the delivery device delivery means as the motion controller commands the delivery device to print the tissue.

* * * * *